(12) United States Patent
Pandey et al.

(10) Patent No.: US 11,891,369 B2
(45) Date of Patent: Feb. 6, 2024

(54) COMPOUNDS FOR BINDING PROPROTEIN CONVERTASE SUBTILISIN/KEXIN TYPE 9

(71) Applicant: SRX Cardio, LLC, Pittsford, NY (US)

(72) Inventors: Anjali Pandey, Fremont, CA (US); Simeon Bowers, Oakland, CA (US); Thomas E. Barta, Carrboro, NC (US); Jonathan William Bourne, Fairport, NY (US)

(73) Assignee: SRX Cardio, LLC, Pittsford, NY (US)

( * ) Notice: Subject to any disclaimer, the term of this patent is extended or adjusted under 35 U.S.C. 154(b) by 0 days.

(21) Appl. No.: 16/861,166

(22) Filed: Apr. 28, 2020

(65) Prior Publication Data

US 2021/0032214 A1 Feb. 4, 2021

Related U.S. Application Data

(63) Continuation of application No. 16/078,578, filed as application No. PCT/US2017/019189 on Feb. 23, 2017, now abandoned.

(60) Provisional application No. 62/298,920, filed on Feb. 23, 2016.

(51) Int. Cl.
| | |
|---|---|
| *A61K 31/4709* | (2006.01) |
| *C07D 295/073* | (2006.01) |
| *C07D 401/04* | (2006.01) |
| *C07D 403/04* | (2006.01) |
| *C07D 211/18* | (2006.01) |
| *C07D 211/26* | (2006.01) |
| *C07D 211/46* | (2006.01) |
| *C07D 211/54* | (2006.01) |
| *C07D 211/58* | (2006.01) |
| *C07D 295/195* | (2006.01) |
| *C07D 401/12* | (2006.01) |
| *C07D 401/14* | (2006.01) |
| *C07D 405/14* | (2006.01) |
| *C07D 407/02* | (2006.01) |
| *C07D 417/04* | (2006.01) |
| *C07D 417/14* | (2006.01) |
| *C07D 471/08* | (2006.01) |

(52) U.S. Cl.
CPC ........ *C07D 295/073* (2013.01); *C07D 211/18* (2013.01); *C07D 211/26* (2013.01); *C07D 211/46* (2013.01); *C07D 211/54* (2013.01); *C07D 211/58* (2013.01); *C07D 295/195* (2013.01); *C07D 401/04* (2013.01); *C07D 401/12* (2013.01); *C07D 401/14* (2013.01); *C07D 403/04* (2013.01); *C07D 405/14* (2013.01); *C07D 407/02* (2013.01); *C07D 417/04* (2013.01); *C07D 417/14* (2013.01); *C07D 471/08* (2013.01)

(58) Field of Classification Search
CPC ............ A61K 31/4709; C07D 401/04

USPC .................................................. 514/314, 174
See application file for complete search history.

(56) References Cited

U.S. PATENT DOCUMENTS

| | | | |
|---|---|---|---|
| 4,064,245 | A | 12/1977 | Beregi et al. |
| 5,236,934 | A | 8/1993 | Vanatten |
| 5,462,947 | A | 10/1995 | Svensson et al. |
| 5,863,903 | A | 1/1999 | Lundgren et al. |
| 5,866,513 | A | 2/1999 | Michelotti et al. |
| 7,750,012 | B2 | 7/2010 | Sandanayaka et al. |
| 8,673,850 | B2 | 3/2014 | Seidah et al. |
| 10,034,892 | B2 | 7/2018 | Barta et al. |
| 10,287,317 | B2 | 5/2019 | Muehlemann et al. |
| 10,307,433 | B2 | 6/2019 | Barta et al. |
| 10,568,882 | B2 | 2/2020 | Barta et al. |
| 10,688,114 | B2 | 6/2020 | Barta et al. |
| 10,865,185 | B2 | 12/2020 | Barta et al. |
| 10,980,801 | B2 | 4/2021 | Barta et al. |
| 2004/0082641 | A1 | 4/2004 | Rytved et al. |

(Continued)

FOREIGN PATENT DOCUMENTS

| | | |
|---|---|---|
| EP | 0378207 B1 | 7/1990 |
| EP | 1987827 | 11/2008 |

(Continued)

OTHER PUBLICATIONS

Wolff et. al., "Burger's Medicinal Chemistry and Drug Discovery," 5th Ed. Part 1, pp. 975-977 (1995). (Year: 1995).*

(Continued)

*Primary Examiner* — Jeffrey H Murray
(74) *Attorney, Agent, or Firm* — Sheppard Mullin Richter & Hampton LLP

(57) ABSTRACT

The present disclosure relates to novel compounds, methods, and compositions capable of binding to PCSK9, thereby modulating PCSK9 proprotein convertase enzyme activity, for treatment of a disease or condition mediated, at least in part, by PCSK9. The compounds of the disclosure include compounds Formula (I).

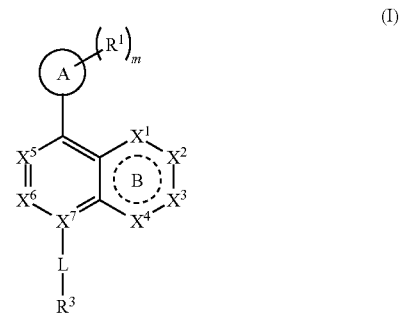

5 Claims, No Drawings
Specification includes a Sequence Listing.

(56) References Cited

U.S. PATENT DOCUMENTS

| | | |
|---|---|---|
| 2004/0254120 A1 | 12/2004 | Fogelman et al. |
| 2007/0207985 A1 | 9/2007 | Li et al. |
| 2008/0194621 A1 | 8/2008 | Lang |
| 2009/0203676 A1 | 8/2009 | Barba et al. |
| 2010/0113782 A1 | 5/2010 | Bolin et al. |
| 2013/0064825 A1 | 3/2013 | Chan et al. |
| 2014/0045854 A1 | 2/2014 | Uesugi et al. |
| 2014/0093513 A1 | 4/2014 | Milne et al. |
| 2015/0051144 A1 | 2/2015 | Pingali et al. |
| 2015/0111857 A1 | 4/2015 | Hodous et al. |
| 2018/0237381 A1 | 8/2018 | Barta et al. |
| 2018/0250291 A1 | 9/2018 | Barta et al. |
| 2019/0119236 A1 | 4/2019 | Pandey et al. |
| 2020/0207718 A1 | 7/2020 | Barta et al. |
| 2020/0253958 A1 | 8/2020 | Barta et al. |
| 2021/0309613 A1 | 10/2021 | Barta et al. |
| 2022/0047582 A1 | 2/2022 | Barta et al. |
| 2022/0267269 A1 | 8/2022 | Bowers et al. |

FOREIGN PATENT DOCUMENTS

| | | |
|---|---|---|
| EP | 1987827 A1 | 11/2008 |
| EP | 2170866 | 12/2008 |
| EP | 2170866 B1 | 12/2008 |
| WO | WO 92/02501 | 2/1992 |
| WO | WO 199500161 A1 | 1/1995 |
| WO | WO 199902502 A2 | 1/1999 |
| WO | WO 199928313 A1 | 6/1999 |
| WO | WO 01/96301 | 12/2001 |
| WO | WO 02/36123 | 5/2002 |
| WO | WO 2003/072558 | 9/2003 |
| WO | WO 2003072558 A3 | 9/2003 |
| WO | WO 2004/043929 | 5/2004 |
| WO | WO 2004043929 A1 | 5/2004 |
| WO | WO 2004060882 A1 | 7/2004 |
| WO | WO 2004069792 A1 | 8/2004 |
| WO | WO 2005/000309 | 1/2005 |
| WO | WO 2005115361 A2 | 8/2005 |
| WO | WO 2005/115361 | 12/2005 |
| WO | WO 2006049597 A1 | 5/2006 |
| WO | WO 2006125665 A1 | 11/2006 |
| WO | WO 2007009741 A1 | 1/2007 |
| WO | WO 2009/002469 | 12/2008 |
| WO | WO 2009002469 A1 | 12/2008 |
| WO | WO 2011051961 A1 | 5/2011 |
| WO | WO 2012/039660 | 3/2012 |
| WO | WO 2012154760 A1 | 11/2012 |
| WO | WO 2014101120 A1 | 7/2014 |
| WO | WO 2014101373 A1 | 7/2014 |
| WO | WO 2014105666 A1 | 7/2014 |
| WO | WO 2014/127316 | 8/2014 |
| WO | WO 2014/128198 | 8/2014 |
| WO | WO 2014127316 A2 | 8/2014 |
| WO | WO 2014/150395 | 9/2014 |
| WO | WO 2014150395 A1 | 9/2014 |
| WO | WO 2014150983 A1 | 9/2014 |
| WO | WO 2015/024016 | 2/2015 |
| WO | WO 2016/029307 | 2/2016 |
| WO | WO 2016029037 A1 | 2/2016 |
| WO | WO 2016107602 A1 | 7/2016 |
| WO | WO 2016107603 A1 | 7/2016 |
| WO | WO 2017/100726 | 6/2017 |
| WO | WO 2018026866 A1 | 8/2018 |
| WO | WO 2018165718 A1 | 9/2018 |
| WO | WO 2020252383 A2 | 12/2020 |

OTHER PUBLICATIONS

Banker, et al., (1996), Modern Pharmaceuticals, p. 596. (Year: 1996).*
Le Bourdonnec et al., Journal of Medicinal Chemistry, 49(25), 7290-7306 (2006).
European Search Report and Opinion dated Jan. 2, 2019, for EP Patent Application No. 16839887.3.
Sam et al., "Phenylisoquinolines and Hydroisoquinolines," Journal of Pharmaceutical Sciences, Jan. 1970, vol. 59, No. 1, 59-62.
International Search Report and Written Opinion in PCT/US2016/047798, dated Jan. 13, 2017.
Pubchem CID 73012351 Create Date: Mar. 7, 2014, p. 3 figure listed. Retrieved from the Internet: <URL: https://pubchem.nbci.nlm.nih.gov/compound/73012351>.
STN Registry database entry for CAS RN 769101-76-0, entry date of Oct. 26, 2004, accessed Feb. 18, 2020.
Annoura et al., "A Novel Class of Na+ and CA2+ Channel Dual Blockers with Highly Potent Ani-Ischemic Effects," Bioorganic and Medicinal Chemistry Letters 9 (1999), pp. 2999-3002.
Extended European Search Report for EP Application No. 16839890.7, dated Mar. 20, 2019.
Extended European Search Report for EP Application No. 16839893.1, dated Feb. 25, 2019.
International Search Report and Written Opinion for PCT/US2016/047816, dated Nov. 16, 2016.
International Search Report and Written Opinion for PCT/US2016/047810, dated Nov. 16, 2016.
International Search Report and Written Opinion for PCT/US2016/047798, dated Jul. 13, 2017.
Pubchem CID 14819316 Create Date: Feb. 9, 2007. Retrieved from the Internet: <URL: https://pubchem.ncbi.nlm.nih.gov/compound/14819316>.
Pubchem-CID 73012351 Date Created: Mar. 7, 2014, p. 3 figure listed. Retrieved from the Internet: URL: https://pubchem.ncbi.nlm.nih.gov/compound/73012351>.
Pubchem CID 23519490 Create Date: Dec. 6, 2007 Date Accessed: Oct. 20, 2016, p. 3, compound listed. Retrieved from the Internet: URL: https://pubchem.ncbi.nlm.nih.gov/compound/23519490/>.
Pubchem CID 28917034 Create Date: May 28, 2009 p. 3, Fig. Retrieved from the Internet: <URL: https://pubchem.ncbi.nlm.nih.gov/compound/28917034>.
STN Registry database for CAS RN 758671-90-8, entry date of Oct. 8, 2004, accessed Sep. 26, 2019.
International Search Report and Written Opinion in International Patent Application No. PCT/US2020/037591, dated Feb. 3, 2021.
Pubchem. CID 135243294. Dec. 15, 2018, pp. 1-9. Retrieved from the Internet <URL: https://pubchem.ncbi.nlm.nih.gov/compound/135243294>; p. 2, formula.
Pubchem. CID 84050476. Oct. 20, 2014, pp. 1-8. Retrieved from the Internet <URL: https://pubchem.ncbi.nlm.nih.gov/compound/84050476>; p. 2, formula.
Bowers et al., U.S. Appl. No. 17/124,357, filed Dec. 16, 2020.
U.S. Appl. No. 17/020,276, filed Sep. 14, 2020, Barta et al.
CAS Registry No. 57536-86-4; entry dated Mar. 25, 2005.
International Search Report and Written Opinion for PCT/US2017/019189 dated Jul. 24, 2017, 13 pages.
Database Registry, Chemical Abstracts Service, XP002768756, retrieved from STN Database accession No. 1770149-41-1, Jun. 1, 2015.
Database Registry, Chemical Abstracts Service, XP002768757, retrieved from STN Database accession No. 1796858-42-8, Jul. 8, 2015.

* cited by examiner

SEQUENCE LISTING

```
<160> NUMBER OF SEQ ID NOS: 1

<210> SEQ ID NO 1
<211> LENGTH: 692
<212> TYPE: PRT
<213> ORGANISM: Homo sapiens
```

<400> SEQUENCE: 1

```
Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
                20                  25                  30

Asp Glu Asp Gly Asp Tyr Glu Glu Leu Val Leu Ala Leu Arg Ser Glu
            35                  40                  45

Glu Asp Gly Leu Ala Glu Ala Pro Glu His Gly Thr Thr Ala Thr Phe
    50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
        115                 120                 125

Asp Leu Leu Glu Leu Ala Leu Lys Leu Pro His Val Asp Tyr Ile Glu
    130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
        195                 200                 205

Pro Glu Glu Asp Gly Thr Arg Phe His Arg Gln Ala Ser Lys Cys Asp
    210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
            260                 265                 270

Lys Ser Gln Leu Val Gln Pro Val Gly Pro Leu Val Val Leu Leu Pro
        275                 280                 285

Leu Ala Gly Gly Tyr Ser Arg Val Leu Asn Ala Ala Cys Gln Arg Leu
    290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
            340                 345                 350

Thr Asn Phe Gly Arg Cys Val Asp Leu Phe Ala Pro Gly Glu Asp Ile
        355                 360                 365

Ile Gly Ala Ser Ser Asp Cys Ser Thr Cys Phe Val Ser Gln Ser Gly
    370                 375                 380

Thr Ser Gln Ala Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415
```

-continued

```
His Phe Ser Ala Lys Asp Val Ile Asn Glu Ala Trp Phe Pro Glu Asp
            420                 425                 430

Gln Arg Val Leu Thr Pro Asn Leu Val Ala Ala Leu Pro Pro Ser Thr
            435                 440                 445

His Gly Ala Gly Trp Gln Leu Phe Cys Arg Thr Val Trp Ser Ala His
            450                 455                 460

Ser Gly Pro Thr Arg Met Ala Thr Ala Val Ala Arg Cys Ala Pro Asp
465                 470                 475                 480

Glu Glu Leu Leu Ser Cys Ser Ser Phe Ser Arg Ser Gly Lys Arg Arg
                485                 490                 495

Gly Glu Arg Met Glu Ala Gln Gly Gly Lys Leu Val Cys Arg Ala His
                500                 505                 510

Asn Ala Phe Gly Gly Glu Gly Val Tyr Ala Ile Ala Arg Cys Cys Leu
            515                 520                 525

Leu Pro Gln Ala Asn Cys Ser Val His Thr Ala Pro Pro Ala Glu Ala
    530                 535                 540

Ser Met Gly Thr Arg Val His Cys His Gln Gln Gly His Val Leu Thr
545                 550                 555                 560

Gly Cys Ser Ser His Trp Glu Val Glu Asp Leu Gly Thr His Lys Pro
                565                 570                 575

Pro Val Leu Arg Pro Arg Gly Gln Pro Asn Gln Cys Val Gly His Arg
            580                 585                 590

Glu Ala Ser Ile His Ala Ser Cys Cys His Ala Pro Gly Leu Glu Cys
            595                 600                 605

Lys Val Lys Glu His Gly Ile Pro Ala Pro Gln Glu Gln Val Thr Val
            610                 615                 620

Ala Cys Glu Glu Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
                645                 650                 655

Arg Ser Arg Asp Val Ser Thr Thr Gly Ser Thr Ser Glu Gly Ala Val
            660                 665                 670

Thr Ala Val Ala Ile Cys Cys Arg Ser Arg His Leu Ala Gln Ala Ser
            675                 680                 685

Gln Glu Leu Gln
    690
```

COMPOUNDS FOR BINDING PROPROTEIN CONVERTASE SUBTILISIN/KEXIN TYPE 9

CROSS REFERENCE TO RELATED APPLICATIONS

This application is a continuation of U.S. application Ser. No. 16/078,578, filed Aug. 21, 2018, which is the U.S. National Stage of International Application Number PCT/US2017/019189, filed Feb. 23, 2017, which claims the benefit under 35 U.S.C. § 119(e) of U.S. Application No. 62/298,920, filed Feb. 23, 2016, the contents of which are hereby incorporated by reference in their entirety.

SEQUENCE LISTING

The instant application contains a Sequence Listing which has been filed electronically in ASCII format and is hereby incorporated by reference in its entirety. Said ASCII copy, created on Oct. 22, 2020, is named 69TJ-227763-US_SL.txt and is 6,342 bytes in size.

FIELD

The present disclosure relates to novel compounds, methods, and compositions capable of binding to proprotein convertase subtilisin/kexin type 9 (PCSK9), thereby modulating PCSK9 proprotein convertase enzyme activity.

STATE OF THE ART

Elevated plasma levels of low density lipoprotein cholesterol (LDL-C) represent a great risk factor for the development of coronary heart disease. Clearance of LDL-C from the plasma occurs primarily by the liver through the action of low density lipoprotein receptors (LDLRs), which are cell surface glycoproteins that bind to apolipoprotein B100 (apoB100) on LDL particles with high affinity and mediate their endocytic uptake. Goldstein et al., *Annu. Rev. Cell Biol.* 1:1-39 (1985). Autosomal dominant hypercholesterolemia (ADH) is associated with mutations that reduce plasma LDL clearance that are found in genes encoding the LDLR (familial hypercholesterolemia (FH)) or apoB100 (familial defective apoB100). Hobbs et al., *Annu. Rev. Genet.* 24, 133-170 (1990); and Innerarity et al., *J. Lipid Res.* 31:1337-1349 (1990), respectively.

The low density lipoprotein receptor (LDLR) mediates efficient endocytosis of very low density lipoprotein (VLDL), VLDL remnants, and LDL. As part of the endocytic process, the LDLR releases lipoproteins into hepatic endosomes.

Proprotein convertase subtilisin/kexin type 9 (PCSK9) is an enzyme encoded by the PCSK9 gene in humans. PCSK9 is believed to play a regulatory role in cholesterol homeostasis. For example, PCSK9 can bind to the epidermal growth factor-like repeat A (EGF-A) domain of the low-density lipoprotein receptor (LDLR) resulting in LDLR internalization and degradation.

A drug that could modulate the activity of PCSK9 would be useful in controlling LDL-cholesterol levels. Therefore, there remains a need for compounds that are effective in the treatment and prevention of conditions and disorders associated with PCSK9, including hypercholesterolemia and hypocholesterolemia. The compounds provided herein bind to PCSK9, thereby modulating PCSK9 proprotein convertase enzyme activity, and can be used to treat and prevent PCSK9-associated conditions and disorders.

SUMMARY

Provided herein are compounds that are useful for binding and modulating PCSK9 enzyme activity. The disclosure also provides compositions, including pharmaceutical compositions, kits that include the compounds, and methods of using (or administering) and making the compounds. The disclosure further provides compounds or compositions thereof for use in a method of treating a disease, disorder, or condition that is mediated by PCSK9. Moreover, the disclosure provides uses of the compounds or compositions thereof in the manufacture of a medicament for the treatment of a disease, disorder or condition that is mediated, at least in part, by PCSK9.

Accordingly, in one embodiment provided is a compound of Formula (I):

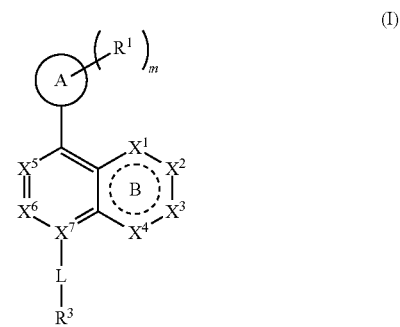

or a pharmaceutically acceptable salt, ester, prodrug, isomer, or mixture of isomers thereof;
wherein:
  m is 0, 1, or 2;
  $X^1$ is absent, $CR^2$, $CR^2R^2$, $C(O)$, N, $NR^2$, S, $SO_2$, or O;
  $X^2$, $X^3$, and $X^4$ are each independently $CR^2$, $CR^2R^2$, $C(O)$, N, $NR^2$, S, $SO_2$, or O;
  ring B is a five- or six-membered ring comprising one or more double bonds;
  $X^5$ and $X^6$ are either $CR^2$ or N;
  $X^7$ is C or N;
  ring A is selected from:

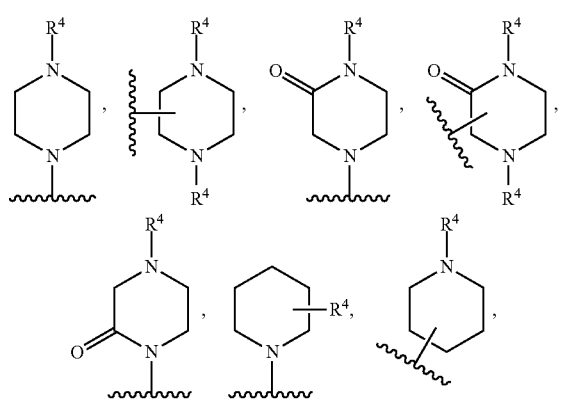

-continued

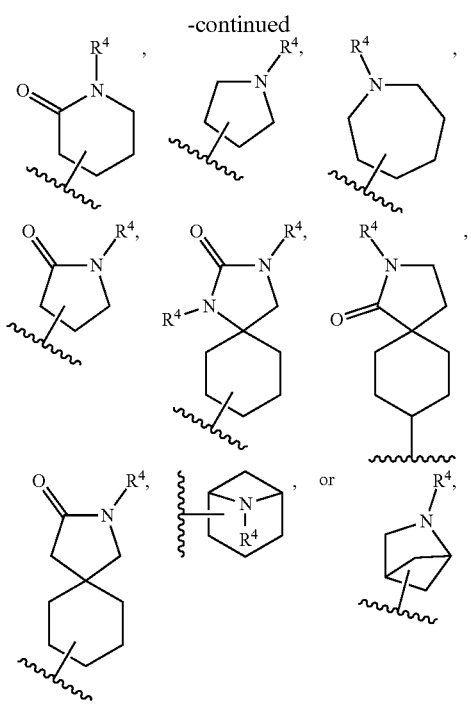

where the wavy line in ring A indicates the point of attachment to

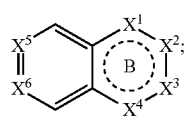

L is a bond, $C_{1-6}$-alkylene, —O—, —C(O)—, —SO$_2$—, —N(R$^a$)—, —N(R$^a$)SO$_2$—, or —SO$_2$N(R$^a$)— where R$^a$ is hydrogen, $C_{1-6}$ alkyl, or $C_{1-6}$ heteroalkyl, wherein the $C_{1-6}$ alkyl or $C_{1-6}$ heteroalkyl are optionally substituted with 1 to 3 substituents independently selected from halo, oxo, hydroxy, $C_{1-6}$ alkyl, or $C_{1-6}$ heteroalkyl;

R$^1$ in each instance is independently halo, cyano, $C_{1-6}$ alkyl optionally substituted with halo or hydroxy, $C_{3-6}$ cycloalkyl, —NR$^b$C(O)NR$^b$R$^b$, or —NR$^b$S(O)$_2$R$^b$;
wherein each R$^b$ is independently hydrogen, $C_{1-6}$ alkyl, $C_{3-6}$ cycloalkyl, or $C_{2-6}$ hydroxyalkyl;

R$^2$ in each instance is independently hydrogen, halo, $C_{1-6}$ alkyl optionally substituted with halo or hydroxy, $C_{3-6}$ cycloalkyl, $C_{2-6}$ hydroxyalkyl, cyano, —C(O)OR$^c$, or —C(O)NR$^c$R$^c$;
wherein each R$^c$ is independently, hydrogen, $C_{1-6}$ alkyl, $C_{3-6}$ cycloalkyl, or $C_{2-6}$ hydroxyalkyl;

R$^3$ is hydrogen, halo, cyano, amino, $C_{1-12}$ alkyl, $C_{1-12}$ alkenyl, $C_{1-12}$ alkynyl, $C_{3-10}$ cycloalkyl, aryl, heteroalkyl, heterocyclyl, or heteroaryl;
wherein each $C_{1-12}$ alkyl, $C_{1-12}$ alkenyl, $C_{1-12}$ alkynyl, $C_{3-10}$ cycloalkyl, aryl, heteroalkyl, heterocyclyl and heteroaryl of R$^3$ is optionally substituted with 1 to 3 substituents independently selected from halo, hydroxy, cyano, $C_{1-6}$ alkyl, $C_{1-6}$ alkenyl, $C_{1-6}$ alkynyl, $C_{1-6}$ alkoxy, acyl, $C_{3-10}$ cycloalkyl, heteroalkyl, heteroaryl, heterocyclyl, aryl, oxo, —N$_3$, —NO$_2$, —N(R$^f$)$_2$, —C(O)N(R$^f$)$_2$, —C(NR$^f$)(N(R$^f$)$_2$), —NR$^f$C(O)OR$^f$, —C(O)N(R$^f$)$_2$, —CO$_2$H, —CO$_2$R$^f$, —NR$^f$C(NR$^f$)(N(R$^f$)$_2$), haloalkyl, haloalkoxy, —N(R$^f$)N(R$^f$)$_2$, —C(NR$^f$)R$^f$, —S(O)R$^f$, —SO$_2$H, —S(O)$_2$R$^f$, —SCN, —SH, or (=S), and where each R$^f$ is independently H or $C_{1-6}$ alkyl;

or when X$^7$ is N, then L-R$^3$ is absent;

R$^4$ in each instance is independently hydrogen, $C_{1-6}$ alkyl, —C(O)NR$^d$R$^d$, —C(NR$^d$)NR$^d$R$^d$, —C(O)R$^d$, or —S(O)$_2$NR$^d$R$^d$;
wherein each R$^d$ is independently, hydrogen, $C_{1-6}$ alkyl, $C_{3-6}$ cycloalkyl, or $C_{2-6}$ hydroxyalkyl;

with the following provisos:
1) when m is 0, then both R$^4$ and L-R$^3$ cannot be hydrogen;
2) when m is 0, R$^4$ is hydrogen, X$^1$, X$^2$, X$^3$, X$^4$ are all CH, then L-R$^3$ is not CF$_3$;
3) when X$^5$ and X$^6$ are both nitrogen, then L-R$^3$ is not hydrogen, —CH$_2$-aryl, or —CH$_2$-heteroaryl;
4) when X$^1$, X$^2$, X$^3$, and X$^4$ are all CH or X$^1$ is nitrogen and X$^2$, X$^3$, and X$^4$ are all CH, then L-R$^3$ is not —SO$_2$-aryl, wherein the aryl is optionally substituted;
5) when A is attached via a carbon atom to the remainder of the molecule and m is other than 0, then R$^1$ is not appended to the same carbon;
6) the compound is not 3-bromo-8-(4-methylpiperidin-1-yl)quinoline or 4-methyl-1-(naphthalen-1-yl)piperidine; and
7) when A is piperidinyl and L-R$^3$ is hydrogen, then R$^4$ is not C(O)NH$_2$.

In certain embodiments, provided herein is a method of using a compound of Formula I or a pharmaceutically acceptable salt, ester, prodrug, isomer, or mixture of isomers thereof in the treatment of a disease or condition in a mammal that is mediated, at least in part, by PCSK9. Such diseases or conditions include cardiovascular diseases (e.g., coronary disease, hypertension, hypercholesterolemia, or atherosclerosis), a metabolic diseases (e.g., diabetes), hypocholesterolemia, a disease or condition where the mammal has elevated plasma levels of low density lipoprotein cholesterol, and a disease or condition where the mammal has suppressed plasma levels of low density lipoprotein cholesterol. Therefore, in certain embodiments, a compound of Formula I or a pharmaceutically acceptable salt, ester, prodrug, isomer, or mixture of isomers thereof are of use as a medicament for the treatment of the aforementioned diseases or conditions.

DETAILED DESCRIPTION

Before the present compositions and methods are described, it is to be understood that the disclosure is not limited to the particular compounds, compositions, methodologies, protocols, cell lines, assays, and reagents described, as these may vary. It is also to be understood that the terminology used herein is intended to describe particular embodiments of the present disclosure, and is in no way intended to limit the scope of the present disclosure as set forth in the appended claims.

1. Definitions

The following description sets forth exemplary embodiments of the present technology. It should be recognized, however, that such description is not intended as a limitation on the scope of the present disclosure but is instead provided as a description of exemplary embodiments.

As used in the present specification, the following words, phrases and symbols are generally intended to have the meanings as set forth below, except to the extent that the context in which they are used indicates otherwise.

A dash ("—") that is not between two letters or symbols is used to indicate a point of attachment for a substituent. For example, —C(O)NH$_2$ is attached through the carbon atom. A dash at the front or end of a chemical group is a matter of convenience; chemical groups may be depicted with or without one or more dashes without losing their ordinary meaning. A wavy line or a dashed line drawn through a line in a structure indicates a specified point of attachment of a group. Unless chemically or structurally required, no directionality or stereochemistry is indicated or implied by the order in which a chemical group is written or named.

The prefix "C$_{u-v}$" indicates that the following group has from u to v carbon atoms. For example, "C$_{1-6}$ alkyl" indicates that the alkyl group has from 1 to 6 carbon atoms.

Reference to "about" a value or parameter herein includes (and describes) embodiments that are directed to that value or parameter per se. In certain embodiments, the term "about" includes the indicated amount ±10%. In other embodiments, the term "about" includes the indicated amount ±5%. In certain other embodiments, the term "about" includes the indicated amount ±1%. Also, to the term "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to an unbranched or branched saturated hydrocarbon chain. As used herein, alkyl has 1 to 20 carbon atoms (i.e., C$_{1-20}$ alkyl), 1 to 8 carbon atoms (i.e., C$_{1-8}$ alkyl), 1 to 6 carbon atoms (i.e., C$_{1-6}$ alkyl), or 1 to 4 carbon atoms (i.e., C$_{1-4}$ alkyl). Examples of alkyl groups include methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl, and 3-methylpentyl. When an alkyl residue having a specific number of carbons is named by chemical name or identified by molecular formula, all positional isomers having that number of carbons may be encompassed; thus, for example, "butyl" includes n-butyl (i.e. —(CH$_2$)$_3$CH$_3$), sec-butyl (i.e. —CH(CH$_3$)CH$_2$CH$_3$), isobutyl (i.e. —CH$_2$CH(CH$_3$)$_2$) and tert-butyl (i.e. —C(CH$_3$)$_3$); and "propyl" includes n-propyl (i.e. —(CH$_2$)$_2$CH$_3$) and isopropyl (i.e. —CH(CH$_3$)$_2$).

Certain commonly used alternative chemical names may be used. For example, a divalent group such as a divalent "alkyl" group, a divalent "aryl" group, etc., may also be referred to as an "alkylene" group or an "alkylenyl" group, an "arylene" group or an "arylenyl" group, respectively. Also, unless indicated explicitly otherwise, where combinations of groups are referred to herein as one moiety, e.g. arylalkyl, the last mentioned group contains the atom by which the moiety is attached to the rest of the molecule.

"Alkenyl" refers to an alkyl group containing at least one carbon-carbon double bond and having from 2 to 20 carbon atoms (i.e., C$_{2-20}$ alkenyl), 2 to 8 carbon atoms (i.e., C$_{2-8}$ alkenyl), 2 to 6 carbon atoms (i.e., C$_{2-6}$ alkenyl), or 2 to 4 carbon atoms (i.e., C$_{2-4}$ alkenyl). Examples of alkenyl groups include ethenyl, propenyl, butadienyl (including 1,2-butadienyl and 1,3-butadienyl).

"Alkynyl" refers to an alkyl group containing at least one carbon-carbon triple bond and having from 2 to 20 carbon atoms (i.e., C$_{2-20}$ alkynyl), 2 to 8 carbon atoms (i.e., C$_{2-8}$ alkynyl), 2 to 6 carbon atoms (i.e., C$_{2-6}$ alkynyl), or 2 to 4 carbon atoms (i.e., C$_{2-4}$ alkynyl). The term "alkynyl" also includes those groups having one triple bond and one double bond.

"Alkoxy" refers to the group "alkyl-O—". Examples of alkoxy groups include methoxy, ethoxy, n-propoxy, iso-propoxy, n-butoxy, tert-butoxy, sec-butoxy, n-pentoxy, n-hexoxy, and 1,2-dimethylbutoxy.

"Alkylthio" refers to the group "alkyl-S—".

"Acyl" refers to a group —C(O)R, wherein R is hydrogen, alkyl, alkenyl, alkynyl, cycloalkyl, heterocyclyl, aryl, heteroalkyl, or heteroaryl; each of which may be optionally substituted, as defined herein. Examples of acyl include formyl, acetyl, cylcohexylcarbonyl, cyclohexylmethyl-carbonyl, and benzoyl.

"Amido" refers to both a "C-amido" group which refers to the group —C(O)NR$^y$R$^z$ and an "N-amido" group which refers to the group —NR$^y$C(O)R$^z$, wherein R$^y$ and R$^z$ are independently hydrogen, alkyl, alkenyl, alkynyl, cycloalkyl, heterocyclyl, aryl, heteroalkyl, or heteroaryl; each of which may be optionally substituted, as defined herein.

"Amino" refers to the group —NR$^y$R$^z$ wherein R$^y$ and R$^z$ are independently hydrogen, alkyl, alkenyl, alkynyl, cycloalkyl, heterocyclyl, aryl, heteroalkyl, or heteroaryl; each of which may be optionally substituted, as defined herein.

"Aryl" refers to an aromatic carbocyclic group having a single ring (e.g. monocyclic) or multiple rings (e.g. bicyclic or tricyclic) including fused systems. As used herein, aryl has 6 to 20 ring carbon atoms (i.e., C$_{6-20}$ aryl), 6 to 12 carbon ring atoms (i.e., C$_{6-12}$ aryl), or 6 to 10 carbon ring atoms (i.e., C$_{6-10}$ aryl). Examples of aryl groups include phenyl, naphthyl, fluorenyl, and anthryl. Aryl, however, does not encompass or overlap in any way with heteroaryl defined below. If one or more aryl groups are fused with a heteroaryl, the resulting ring system is heteroaryl. If one or more aryl groups are fused with a heterocyclyl, the resulting ring system is heterocyclyl.

"Carbamoyl" refers to both an "O-carbamoyl" group which refers to the group —O—C(O)NR$^y$R$^z$ and an "N-carbamoyl" group which refers to the group —NR$^y$C(O)OR$^z$, wherein R$^y$ and R$^z$ are independently hydrogen, alkyl, alkenyl, alkynyl, cycloalkyl, heterocyclyl, aryl, heteroalkyl, or heteroaryl; each of which may be optionally substituted, as defined herein.

"Carboxyl ester" refers to both —OC(O)R and —C(O)OR, wherein R is hydrogen, alkyl, alkenyl, alkynyl, cycloalkyl, heterocyclyl, aryl, heteroalkyl, or heteroaryl; each of which may be optionally substituted, as defined herein.

"Cycloalkyl" refers to a saturated or partially unsaturated cyclic alkyl group having a single ring or multiple rings including fused, bridged, and spiro ring systems. The term "cycloalkyl" includes cycloalkenyl groups (i.e. the cyclic group having at least one double bond). As used herein, cycloalkyl has from 3 to 20 ring carbon atoms (i.e., C$_{3-20}$ cycloalkyl), 3 to 12 ring carbon atoms (i.e., C$_{3-12}$ cycloalkyl), 3 to 10 ring carbon atoms (i.e., C$_{3-10}$ cycloalkyl), 3 to 8 ring carbon atoms (i.e., C$_{3-8}$ cycloalkyl), or 3 to 6 ring carbon atoms (i.e., C$_{3-6}$ cycloalkyl). Examples of cycloalkyl groups include cyclopropyl, cyclobutyl, cyclopentyl, and cyclohexyl. Further, the term cycloalkyl is intended to encompass any non-aromatic ring which may be fused to an aryl ring, regardless of the attachment to the remainder of the molecule.

"Imino" refers to a group —C(NR)R, wherein each R is independently hydrogen, alkyl, alkenyl, alkynyl, cycloalkyl, heterocyclyl, aryl, heteroalkyl, or heteroaryl; each of which may be optionally substituted, as defined herein.

"Halogen" or "halo" includes fluoro, chloro, bromo, and iodo. "Haloalkyl" refers to an unbranched or branched alkyl group as defined above, wherein one or more hydrogen atoms are replaced by a halogen. For example, where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. Examples of haloalkyl include difluoromethyl (—CHF$_2$) and trifluoromethyl (—CF$_3$).

"Haloalkoxy" refers to an alkoxy group as defined above, wherein one or more hydrogen atoms are replaced by a halogen.

"Hydroxyalkyl" refers to an alkyl group as defined above, wherein one or more hydrogen atoms are replaced by a hydroxyl group.

"Heteroalkyl" refers to an alkyl group in which one or more of the carbon atoms (and any associated hydrogen atoms) are each independently replaced with the same or different heteroatomic group. The term "heteroalkyl" includes unbranched or branched saturated chain having carbon and heteroatoms. By way of example, 1, 2 or 3 carbon atoms may be independently replaced with the same or different heteroatomic group. Heteroatomic groups include, but are not limited to, —NR—, —O—, —S—, —S(O)—, —S(O)$_2$—, and the like, where hydrogen, alkyl, alkenyl, alkynyl, cycloalkyl, heterocyclyl, aryl, heteroalkyl, or heteroaryl; each of which may be optionally substituted, as defined herein. Examples of heteroalkyl groups include —OCH$_3$, —CH$_2$OCH$_3$, —SCH$_3$, —CH$_2$SCH$_3$, —NRCH$_3$, and —CH$_2$NRCH$_3$, where R is hydrogen, alkyl, alkenyl, alkynyl, cycloalkyl, heterocyclyl, aryl, heteroalkyl, or heteroaryl; each of which may be optionally substituted, as defined herein. As used herein, heteroalkyl includes 1 to 10 carbon atoms, 1 to 8 carbon atoms, or 1 to 4 carbon atoms; and 1 to 3 heteroatoms, 1 to 2 heteroatoms, or 1 heteroatom.

"Heteroaryl" refers to an aromatic group having a single ring, multiple rings, or multiple fused rings, with one or more ring heteroatoms independently selected from nitrogen, oxygen, and sulfur. As used herein, heteroaryl includes 1 to 20 ring carbon atoms (i.e., C$_{1-20}$ heteroaryl), 3 to 12 ring carbon atoms (i.e., C$_{3-12}$ heteroaryl), or 3 to 8 carbon ring atoms (i.e., C$_{3-8}$ heteroaryl); and 1 to 5 heteroatoms, 1 to 4 heteroatoms, 1 to 3 ring heteroatoms, 1 to 2 ring heteroatoms, or 1 ring heteroatom independently selected from nitrogen, oxygen, and sulfur. Examples of heteroaryl groups include pyrimidinyl, purinyl, pyridyl, pyridazinyl, benzothiazolyl, and pyrazolyl. Examples of the fused-heteroaryl rings include, but are not limited to, benzo[d]thiazolyl, quinolinyl, isoquinolinyl, benzo[b]thiophenyl, indazolyl, benzo[d]imidazolyl, pyrazolo[1,5-a]pyridinyl, and imidazo[1,5-a]pyridinyl, where the heteroaryl can be bound via either ring of the fused system. Any aromatic ring, having a single or multiple fused rings, containing at least one heteroatom, is considered a heteroaryl regardless of the attachment to the remainder of the molecule (i.e., through any one of the fused rings). Heteroaryl does not encompass or overlap with aryl as defined above.

"Heterocyclyl" refers to a saturated or unsaturated cyclic alkyl group, with one or more ring heteroatoms independently selected from nitrogen, oxygen and sulfur. The term "heterocyclyl" includes heterocycloalkenyl groups (i.e. the heterocyclyl group having at least one double bond), bridged-heterocyclyl groups, fused-heterocyclyl groups, and spiro-heterocyclyl groups. A heterocyclyl may be a single ring or multiple rings wherein the multiple rings may be fused, bridged, or spiro. Any non-aromatic ring containing at least one heteroatom is considered a heterocyclyl, regardless of the attachment (i.e., can be bound through a carbon atom or a heteroatom). Further, the term heterocyclyl is intended to encompass any non-aromatic ring containing at least one heteroatom, which ring may be fused to an aryl or heteroaryl ring, regardless of the attachment to the remainder of the molecule. As used herein, heterocyclyl has 2 to 20 ring carbon atoms (i.e., C$_{2-20}$ heterocyclyl), 2 to 12 ring carbon atoms (i.e., C$_{2-12}$ heterocyclyl), 2 to 10 ring carbon atoms (i.e., C$_{2-10}$ heterocyclyl), 2 to 8 ring carbon atoms (i.e., C$_{2-8}$ heterocyclyl), 3 to 12 ring carbon atoms (i.e., C$_{3-12}$ heterocyclyl), 3 to 8 ring carbon atoms (i.e., C$_{3-8}$ heterocyclyl), or 3 to 6 ring carbon atoms (i.e., C$_{3-6}$ heterocyclyl); having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur or oxygen. Examples of heterocyclyl groups include pyrrolidinyl, piperidinyl, piperazinyl, oxetanyl, dioxolanyl, azetidinyl, and morpholinyl. Also used herein, the term "spiro-heterocyclyl" refers to a ring system in which a three- to ten-membered heterocyclyl has one or more additional ring, wherein the one or more additional ring is three- to ten-membered cycloalkyl or three- to ten-membered heterocyclyl, where a single atom of the one or more additional ring is also an atom of the three- to ten-membered heterocyclyl. Examples of the spiro-heterocyclyl rings include bicyclic and tricyclic ring systems, such as 2-oxa-7-azaspiro[3.5]nonanyl, 2-oxa-6-azaspiro[3.4]octanyl, and 6-oxa-1-azaspiro[3.3]heptanyl. Examples of the fused-heterocyclyl rings include, but are not limited to, 1,2,3,4-tetrahydroisoquinolinyl, 4,5,6,7-tetrahydrothieno[2,3-c]pyridinyl, indolinyl, and isoindolinyl, where the heterocyclyl can be bound via either ring of the fused system.

"Sulfonyl" refers to the group —S(O)$_2$R, where R is hydrogen, alkyl, alkenyl, alkynyl, cycloalkyl, heterocyclyl, aryl, heteroalkyl, or heteroaryl; each of which may be optionally substituted, as defined herein. Examples of sulfonyl are methylsulfonyl, ethylsulfonyl, phenylsulfonyl, and toluenesulfonyl.

"Sulfinyl" refers to the group —S(O)R, where R is hydrogen, alkyl, alkenyl, alkynyl, cycloalkyl, heterocyclyl, aryl, heteroalkyl, or heteroaryl; each of which may be optionally substituted, as defined herein. Examples of sulfinyl are methylsulfinyl, ethylsulfinyl, phenylsulfinyl, and toluenesulfinyl.

"Alkylsulfonyl" refers to the group —S(O)$_2$R, where R is alkyl.

"Alkylsulfinyl" refers to the group —S(O)R, where R is alkyl.

"Sulfinic acid" refers to the group —S(O)R, where R is alkyl.

Certain commonly used alternative chemical names may be used. For example, a divalent group such as a divalent "alkyl" group, a divalent "aryl" group, etc., may also be referred to as an "alkylene" group or an "alkylenyl" group, an "arylene" group or an "arylenyl" group, respectively. Also, unless indicated explicitly otherwise, where combinations of groups are referred to herein as one moiety, e.g. arylalkyl, the last mentioned group contains the atom by which the moiety is attached to the rest of the molecule.

The terms "optional" or "optionally" means that the subsequently described event or circumstance may or may not occur, and that the description includes instances where said event or circumstance occurs and instances in which it does not. Also, the term "optionally substituted" refers to any one or more hydrogen atoms on the designated atom or group may or may not be replaced by a moiety other than hydrogen.

The term "substituted" means that any one or more hydrogen atoms on the designated atom or group is replaced with one or more substituents other than hydrogen, provided that the designated atom's normal valence is not exceeded. The one or more substituents include, but are not limited to, alkyl, alkenyl, alkynyl, alkoxy, acyl, amino, amido, amidino, aryl, azido, carbamoyl, carboxyl, carboxyl ester, cyano, guanidino, halo, haloalkyl, haloalkoxy, heteroalkyl, heteroaryl, heterocyclyl, hydroxy, hydrazino, imino, oxo, nitro, alkylsulfinyl, sulfonic acid, alkylsulfonyl, thiocyanate, thiol, thione, or combinations thereof.

Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl) substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein. Unless specified otherwise, where a group is described as optionally substituted, any substituents of the group are themselves unsubstituted. For example, in some embodiments, the term "substituted alkyl" refers to an alkyl group having one or more substituents including hydroxyl, halo, alkoxy, acyl, oxo, amino, cycloalkyl, heterocyclyl, aryl, and heteroaryl. In other embodiments, the one or more substituents may be further substituted with halo, alkyl, haloalkyl, hydroxy, alkoxy, cycloalkyl, heterocyclyl, aryl, or heteroaryl, each of which is substituted. In other embodiments, the substituents may be further substituted with halo, alkyl, haloalkyl, alkoxy, hydroxy, cycloalkyl, heterocyclyl, aryl, or heteroaryl, each of which is unsubstituted.

Any formula or structure given herein, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl and $^{125}$I. Various isotopically labeled compounds of the present disclosure, for example those into which radioactive isotopes such as $^3$H, $^{13}$C and $^{14}$C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also includes "deuterated analogs" of compounds of Formula I in which from 1 to n hydrogens attached to a carbon atom is/are replaced by deuterium, in which n is the number of hydrogens in the molecule. Such compounds exhibit increased resistance to metabolism and are thus useful for increasing the half-life of any compound of Formula I when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}$F, $^3$H, $^{11}$C labeled compound may be useful for PET or SPECT or other imaging studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in the compound of Formula I.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

In many cases, the compounds of this disclosure are capable of forming acid and/or base salts by virtue of the presence of amino and/or carboxyl groups or groups similar thereto.

Provided are also pharmaceutically acceptable salts, hydrates, solvates, tautomeric forms, stereoisomers, and prodrugs of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use.

The term "pharmaceutically acceptable salt" of a given compound refers to salts that retain the biological effectiveness and properties of the given compound, and which are not biologically or otherwise undesirable. "Pharmaceutically acceptable salts" or "physiologically acceptable salts" include, for example, salts with inorganic acids and salts with an organic acid. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts. Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like. Likewise, pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines (i.e., $NH_2$(alkyl)), dialkyl amines (i.e., HN(alkyl)$_2$), trialkyl amines (i.e., N(alkyl)$_3$), substituted alkyl amines (i.e., $NH_2$(substituted alkyl)), di(substituted alkyl) amines (i.e., HN(substituted alkyl)$_2$), tri (substituted alkyl) amines (i.e., N(substituted alkyl)$_3$), alkenyl amines (i.e., $NH_2$(alkenyl)), dialkenyl amines (i.e., HN(alkenyl)$_2$), trialkenyl amines (i.e., N(alkenyl)$_3$), substituted alkenyl amines (i.e., $NH_2$(substituted alkenyl)), di(substituted alkenyl) amines (i.e., HN(substituted alkenyl)$_2$), tri(substituted alkenyl) amines (i.e., N(substituted alkenyl)$_3$, mono-, di- or tri-cycloalkyl amines (i.e., $NH_2$(cycloalkyl), HN(cycloalkyl)$_2$, N(cycloalkyl)$_3$), mono-, di- or tri-arylamines (i.e., $NH_2$(aryl), HN(aryl)$_2$, N(aryl)$_3$), or mixed amines, etc. Specific examples of suitable amines include, by way of example only, isopropylamine, trimethyl amine, diethyl amine, tri(iso-propyl) amine, tri(n-propyl) amine, ethanolamine, 2-dimethylaminoethanol, piperazine, piperidine, morpholine, N-ethylpiperidine, and the like.

The term "hydrate" refers to the complex formed by the combining of a compound of Formula I and water.

A "solvate" refers to an association or complex of one or more solvent molecules and a compound of the disclosure. Examples of solvents that form solvates include, but are not limited to, water, isopropanol, ethanol, methanol, dimethylsulfoxide, ethylacetate, acetic acid, and ethanolamine.

Some of the compounds exist as tautomers. Tautomers are in equilibrium with one another. For example, amide containing compounds may exist in equilibrium with imidic acid tautomers. Regardless of which tautomer is shown, and regardless of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

"Stereoisomers" are isomers that differ only in the way the atoms are arranged in space and include enantiomers and diastereomers.

"Enantiomers" are a pair of stereoisomers that are non-superimposable mirror images of each other. A 1:1 mixture of a pair of enantiomers is a "racemic" mixture.

"Diastereoisomers" are stereoisomers that have at least two asymmetric atoms, but which are not mirror-images of each other.

"Prodrugs" means any compound which releases an active parent drug according to Formula I in vivo when such prodrug is administered to a mammalian subject. Prodrugs of a compound of Formula I are prepared by modifying functional groups present in the compound of Formula I in such a way that the modifications may be cleaved in vivo to release the parent compound. Prodrugs may be prepared by modifying functional groups present in the compounds in such a way that the modifications are cleaved, either in routine manipulation or in vivo, to the parent compounds. Prodrugs include compounds of Formula I wherein a hydroxy, amino, carboxyl or sulfhydryl group in a compound of Formula I is bonded to any group that may be cleaved in vivo to regenerate the free hydroxyl, amino, or sulfhydryl group, respectively. Examples of prodrugs include, but are not limited to, esters (e.g., acetate, formate, and benzoate derivatives), amides, guanidines, carbamates (e.g., N,N-dimethylaminocarbonyl) of hydroxy functional groups in compounds of Formula I, and the like. Preparation, selection, and use of prodrugs is discussed in T. Higuchi and V. Stella, "Pro-drugs as Novel Delivery Systems," Vol. 14 of the A.C.S. Symposium Series; "Design of Prodrugs," ed. H. Bundgaard, Elsevier, 1985; and in Bioreversible Carriers in Drug Design, ed. Edward B. Roche, American Pharmaceutical Association and Pergamon Press, 1987, each of which are hereby incorporated by reference in their entirety.

As used herein, "pharmaceutically acceptable carrier" or "pharmaceutically acceptable excipient" or "excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

2. List of Abbreviations and Acronyms

| Abbreviation | Meaning |
|---|---|
| Ac | Acetyl |
| acid | Protic acid or Lewis acid |
| ACN | Acetonitrile |
| AIBN | Azobisisobutyronitrile |
| aq. | Aqueous |
| base | Organic base (e.g., amine base) or inorganic base |
| BINAP | (2,2'-bis(diphenylphosphino)-1,1'-binaphthyl) |
| $BH_3$—DMS | Borane dimethyl sulfide |
| BOC | Tert-butyloxycarbonyl- |
| BuLi | n-Butyllithium |
| BuOH | n-butanol |
| DCM | Dichloromethane |
| DDQ | 2,3-Dichloro-5,6-dicyano-1,4-benzoquinone |
| DEAD | Diethyl azodicarboxylate |
| DIPEA | N,N-Diisopropylethylamine |
| DMAP | 4-dimethylaminopyridine |
| DMF | Dimethylformamide |
| DME | Dimethyl ether |
| DMSO | Dimethylsulfoxide |
| dppf | 1,1'-Bis(diphenylphosphino)ferrocene |
| EDC•HCL | N'-ethylcarbodiimide hydrochloride |
| Et | Ethyl |
| EtOAc | Ethyl acetate |
| EtOH | Ethanol |
| HA | Protic acid |
| HATU | 1-[Bis(dimethylamino)methylene]-1H-1,2,3-triazolo[4,5-b]pyridinium 3-oxid hexafluorophosphate |
| HBTU | N,N,N',N'-Tetramethyl-O-(1H-benzotriazol-1-yl)uronium hexafluorophosphate |
| HOBt | 1-hydroxybenzotriazole |
| hrs or h | Hours |
| i-PrMgCl | Isopropylmagnesium chloride |
| LCMS | Liquid chromatography - mass spectrometry |
| MCPBA or m-CPBA | m-Chloroperoxybenzoic acid |
| Me | Methyl |

| Abbreviation | Meaning |
|---|---|
| MeCN(CH₃CN) | Acetonitrile |
| MeOH | Methanol |
| min | Minute(s) |
| MS | Mass spectrometry |
| N | Normal (Normality) |
| NaOAc | Sodium acetate |
| NBS | N-bromosuccinimide |
| OAc | Acetate |
| PCC | Pyridinium chlrochromate |
| Pd/C | Palladium on carbon |
| Pd(dba)₂ | Bis(dibenzylideneacetone)palladium(0) |
| Pd(dba)₃ | Tris(dibenzylideneacetone)dipalladium(0) |
| Ph | Phosphine |
| p-TsOH | p-toluenesulfonic acid |
| rt | Room temperature |
| s | Second(s) |
| TBAI | Tetrabutylammonium iodide |
| t-Bu (ᵗBu) | Tert-butyl |
| t-BuOK (ᵗBuOK) | Potassium tert-butoxide |
| TEA | Triethanolamine |
| Tf | Trifluoromethanesulfonyl |
| TFA | Trifluoroacetic acid |
| THF | Tetrahydrofuran |
| TLC | Thin layer chromatography |
| TMS—CN | Trimethylsilyl cyanide |
| TMSCF₃ | Trifluoromethyltrimethylsilane |
| TMS—NCO | Trimethylsilyl isocyanate |
| Tr | Trityl |
| Ts | p-Toluenesulphonyl |

3. Compounds

Provided herein are compounds that are useful for binding PCSK9. In one embodiment, provided is a compound of Formula (I):

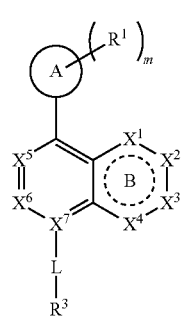

(I)

or a pharmaceutically acceptable salt, ester, prodrug, isomer, or mixture of isomers thereof;
wherein:
  m is 0, 1, or 2;
  $X^1$ is absent, $CR^2$, $CR^2R^2$, $C(O)$, N, $NR^2$, S, $SO_2$, or O;
  $X^2$, $X^3$, and $X^4$ are each independently $CR^2$, $CR^2R^2$, $C(O)$, N, $NR^2$, S, $SO_2$, or O;
  ring B is a five- or six-membered ring comprising one or more double bonds;
  $X^5$ and $X^6$ are either $CR^2$ or N;
  $X^7$ is C or N;

ring A is selected from:

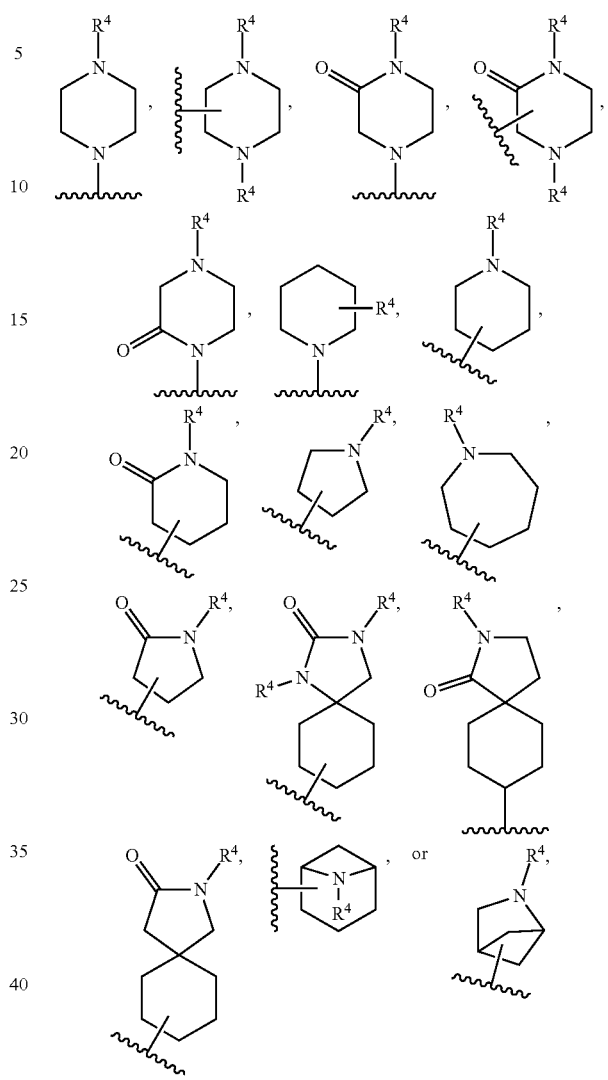

where the wavy line in ring A indicates the point of attachment to

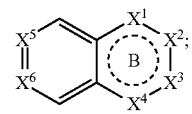

L is a bond, $C_{1-6}$-alkylene, —O—, —C(O)—, —SO₂—, —N($R^a$)—, —N($R^a$)SO₂—, or —SO₂N($R^a$)— where $R^a$ is hydrogen, $C_{1-6}$ alkyl, or $C_{1-6}$ heteroalkyl, wherein the $C_{1-6}$ alkyl or $C_{1-6}$ heteroalkyl are optionally substituted with 1 to 3 substituents independently selected from halo, oxo, hydroxy, $C_{1-6}$ alkyl, or $C_{1-6}$ heteroalkyl;

$R^1$ in each instance is independently halo, cyano, $C_{1-6}$ alkyl optionally substituted with halo or hydroxy, $C_{3-6}$ cycloalkyl, —NR$^b$C(O)NR$^b$R$^b$, or —NR$^b$S(O)₂R$^b$;
  wherein each $R^b$ is independently hydrogen, $C_{1-6}$ alkyl, $C_{3-6}$ cycloalkyl, or $C_{2-6}$ hydroxyalkyl;

$R^2$ in each instance is independently hydrogen, halo, $C_{1-6}$ alkyl optionally substituted with halo or hydroxy, $C_{3-6}$ cycloalkyl, $C_{2-6}$ hydroxyalkyl, cyano, —C(O)OR$^c$, or —C(O)NR$^c$R$^c$;
  wherein each R$^c$ is independently, hydrogen, $C_{1-6}$ alkyl, $C_{3-6}$ cycloalkyl, or $C_{2-6}$ hydroxyalkyl;
$R^3$ is hydrogen, halo, cyano, amino, $C_{1-12}$ alkyl, $C_{1-12}$ alkenyl, $C_{1-12}$ alkynyl, $C_{3-10}$ cycloalkyl, aryl, heteroalkyl, heterocyclyl, or heteroaryl;
  wherein each $C_{1-12}$ alkyl, $C_{1-12}$ alkenyl, $C_{1-12}$ alkynyl, $C_{3-10}$ cycloalkyl, aryl, heteroalkyl, heterocyclyl and heteroaryl of $R^3$ is optionally substituted with 1 to 3 substituents independently selected from halo, hydroxy, cyano, $C_{1-6}$ alkyl, $C_{1-6}$ alkenyl, $C_{1-6}$ alkynyl, $C_{1-6}$ alkoxy, acyl, $C_{3-10}$ cycloalkyl, heteroalkyl, heteroaryl, heterocyclyl, aryl, oxo, —N$_3$, —NO$_2$, —N(R$^f$)$_2$, —C(O)N(R$^f$)$_2$, —C(NR$^f$)(N(R$^f$)$_2$), —NR$^f$C(O)OR$^f$, —C(O)N(R$^f$)$_2$, —CO$_2$H, —CO$_2$R$^f$, —NR$^f$C(NR$^f$)(N(R$^f$)$_2$), haloalkyl, haloalkoxy, —N(R$^f$)N(R$^f$)$_2$, —C(NR$^f$)R$^f$, —S(O)R$^f$, —SO$_2$H, —S(O)$_2$R$^f$, —SCN, —SH, or (=S), and where each R$^f$ is independently H or $C_{1-6}$ alkyl; or when $X^7$ is N, then L-R$^3$ is absent;
$R^4$ in each instance is independently hydrogen, $C_{1-6}$ alkyl, —C(O)NR$^d$R$^d$, —C(NR$^d$)NR$^d$R$^d$, —C(O)R$^d$, or —S(O)$_2$NR$^d$R$^d$;
  wherein each R$^d$ is independently, hydrogen, $C_{1-6}$ alkyl, $C_{3-6}$ cycloalkyl, or $C_{2-6}$ hydroxyalkyl;
with the following provisos:
  1) when m is 0, then both $R^4$ and L-R$^3$ cannot be hydrogen;
  2) when m is 0, $R^4$ is hydrogen, $X^1$, $X^2$, $X^3$, $X^4$ are all CH, then L-R$^3$ is not CF$_3$;
  3) when $X^5$ and $X^6$ are both nitrogen, then L-R$^3$ is not hydrogen, —CH$_2$-aryl, or —CH$_2$-heteroaryl;
  4) when $X^1$, $X^2$, $X^3$, and $X^4$ are all CH or $X^1$ is nitrogen and $X^2$, $X^3$, and $X^4$ are all CH, then L-R$^3$ is not —SO$_2$-aryl, wherein the aryl is optionally substituted;
  5) when A is attached via a carbon atom to the remainder of the molecule and m is other than 0, then $R^1$ is not appended to the same carbon;
  6) the compound is not 3-bromo-8-(4-methylpiperidin-1-yl)quinoline or 4-methyl-1-(naphthalen-1-yl)piperidine; and
  7) when A is piperidinyl and L-R$^3$ is hydrogen, then $R^4$ is not C(O)NH$_2$.

In certain embodiments, provided is a compound of Formula (Ia):

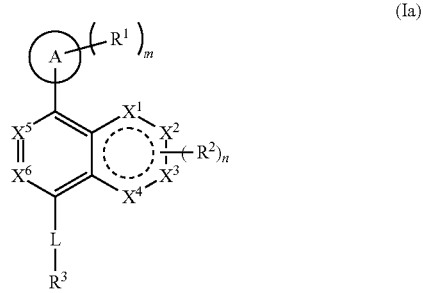

(Ia)

wherein:
  m is 0, 1, or 2;
  n is 0, 1, or 2;

$X^1$, $X^2$, $X^3$, and $X^4$ are each independently CH, C(O), N, NH, S, SO$_2$, or O; or
$X^1$ is absent and $X^2$, $X^3$, and $X^4$ are each independently CH, C(O), N, NH, S, SO$_2$, or O; and the dotted line can represent one or more double bonds;
$X^5$ and $X^6$ are either CH or N;
ring A is selected from:

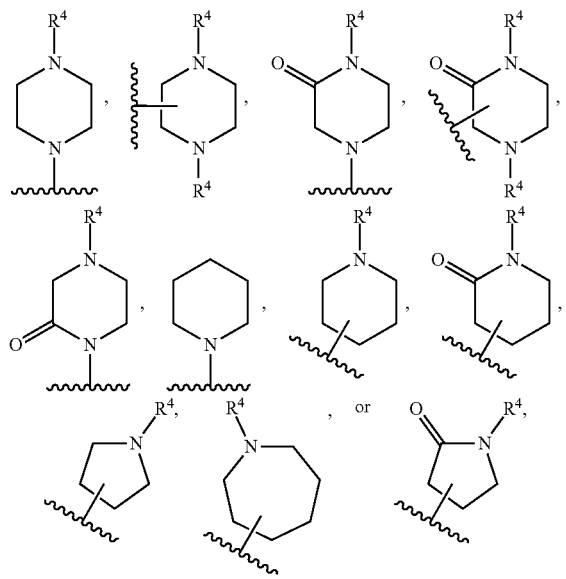

where the wavy line in ring A indicates the point of attachment to

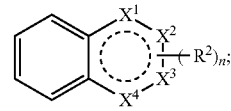

L is a bond, $C_{1-6}$-alkylene, —O—, —C(O)—, —SO$_2$—, or —N(R$^a$)—, where R$^a$ is hydrogen, $C_{1-6}$ alkyl, or $C_{1-6}$ heteroalkyl, wherein the $C_{1-6}$ alkyl or $C_{1-6}$ heteroalkyl are optionally substituted with 1 to 3 substituents independently selected from halo, oxo, hydroxy, $C_{1-6}$ alkyl, or $C_{1-6}$ heteroalkyl;
$R^1$ in each instance is independently, halo, cyano, $C_{1-6}$ alkyl optionally substituted with halo or hydroxy, $C_{3-6}$ cycloalkyl, —NR$^b$C(O)NR$^b$R$^b$, —NR$^b$S(O)$_2$R$^b$, —N(R$^b$)$_2$, or —NR$^b$C(O)R$^b$;
  where each R$^b$ is independently hydrogen, $C_{1-6}$ alkyl, $C_{3-6}$ cycloalkyl, or $C_{2-6}$ hydroxyalkyl;
$R^2$ in each instance is independently, halo, $C_{1-6}$ alkyl optionally substituted with halo or hydroxy, $C_{3-6}$ cycloalkyl, $C_{2-6}$ hydroxyalkyl, cyano, —C(O)OR$^c$, or —C(O)NR$^c$R$^c$;
  where each R$^c$ is independently, hydrogen, $C_{1-6}$ alkyl, $C_{3-6}$ cycloalkyl, or $C_{2-6}$ hydroxyalkyl;
$R^3$ is hydrogen, halo, cyano, $C_{1-12}$ alkyl, $C_{1-12}$ alkenyl, $C_{1-12}$ alkynyl, $C_{3-10}$ cycloalkyl, aryl, heteroalkyl, heterocyclyl, or heteroaryl,
  where each $C_{1-12}$ alkyl, $C_{1-12}$ alkenyl, $C_{1-12}$ alkynyl, $C_{3-10}$ cycloalkyl, aryl, heteroalkyl, heterocyclyl and heteroaryl is optionally substituted with 1 to 3 substituents independently selected from halo, hydroxy, cyano, $C_{1-6}$ alkyl, $C_{1-6}$ alkenyl, $C_{1-6}$ alkynyl, $C_{1-6}$ alkoxy, acyl, $C_{3-10}$ cycloalkyl, heteroalkyl, heteroaryl, heterocyclyl, aryl, oxo, —$N_3$, —$NO_2$, —$N(R^f)_2$, —$C(O)N(R^f)_2$, —$C(NR^f)(N(R^f)_2)$, —$NR^fC(O)OR^f$, —$C(O)N(R^f)_2$, —$CO_2H$, —$CO_2R^f$, —$NR^fC(NR^f)(N(R^f)_2)$, haloalkyl, haloalkoxy, —$N(R^f)N(R^f)_2$, —$C(NR^f)R^f$, —$S(O)R^f$, —$SO_2H$, —$S(O)_2R^f$, —SCN, —SH, or (=S), and where each $R^f$ is independently H or $C_{1-6}$ alkyl;

$R^4$ in each instance is independently, hydrogen, $C_{1-6}$ alkyl, —$C(O)NR^dR^d$, —$C(NR^d)NR^dR^d$, —$C(O)R^d$, or —$S(O)_2NR^dR^d$;

where each $R^d$ is independently, hydrogen, $C_{1-6}$ alkyl, $C_{3-6}$ cycloalkyl, or $C_{2-6}$ hydroxyalkyl;

or a pharmaceutically acceptable salt, ester, prodrug, isomer, or mixture of isomers thereof, with the following provisos:

1) when A is piperazin-4-yl, m is 0, $R^4$ is hydrogen, and L-$R^3$ is hydrogen, then

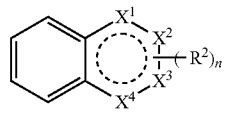

is not benzimidazole, benzoxazole, benzothiazole; and 2) when m is 0, $R^4$ is hydrogen, $X^1$, $X^2$, $X^3$, $X^4$ are all CH, then either L-$R^3$ is not $CF_3$ or n is not 0.

In certain embodiments, the compound is of Formula (Ia) with the further proviso that when m is 0, n is 0, $R^4$ is hydrogen, $X^1$, $X^2$, $X^3$, $X^4$ are all CH, then L-$R^3$ is not hydrogen.

In certain embodiments, the moiety

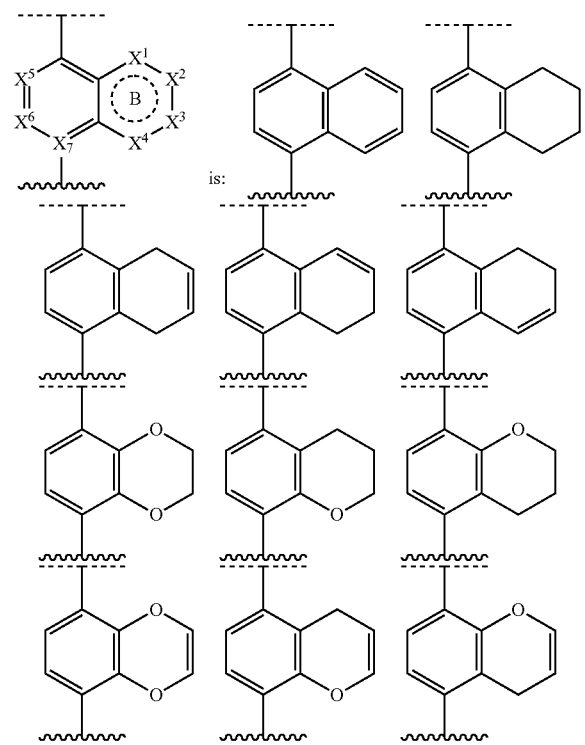

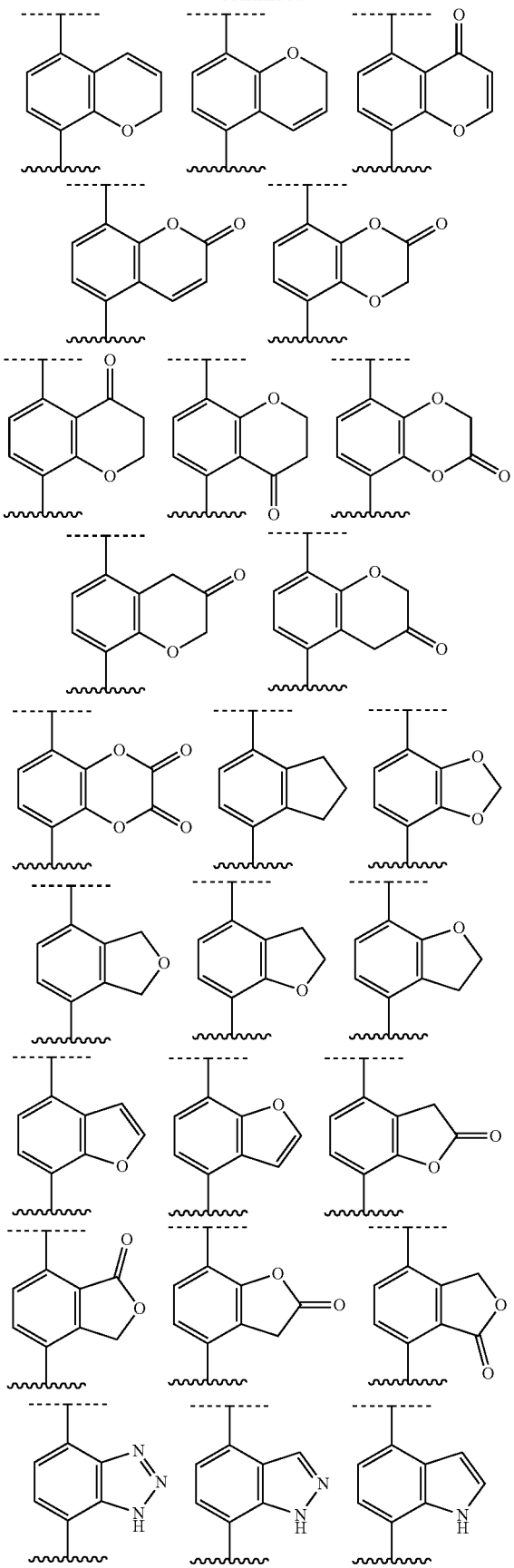

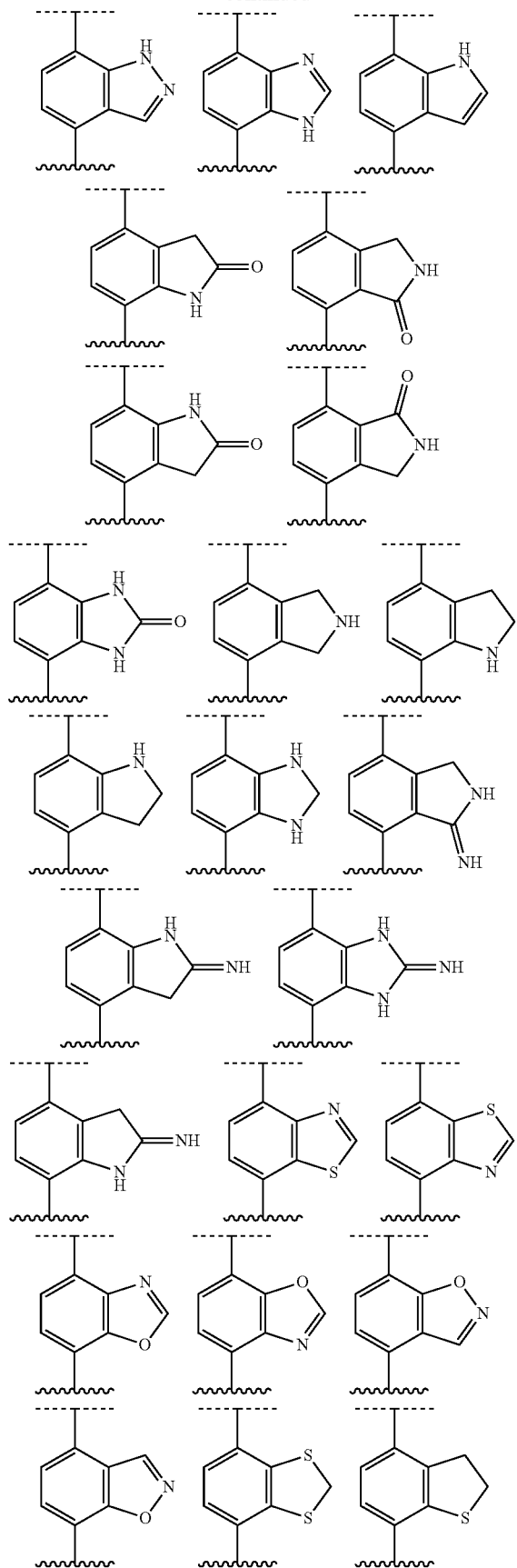
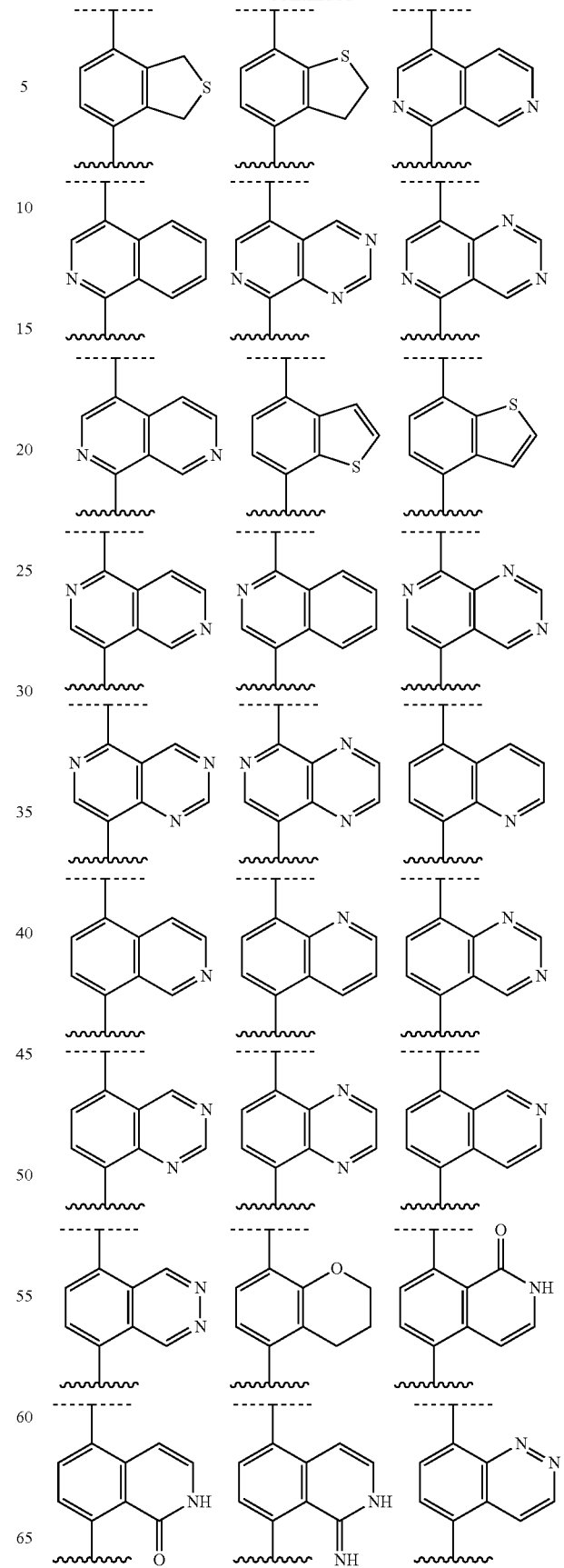

-continued

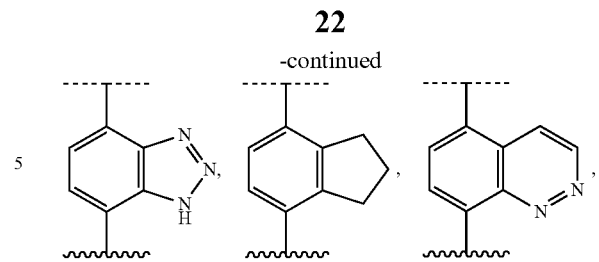

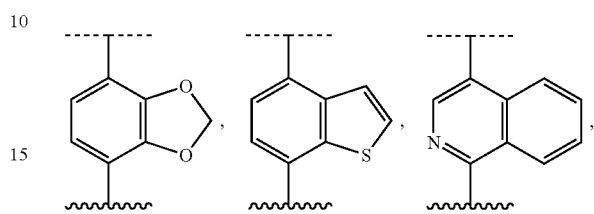

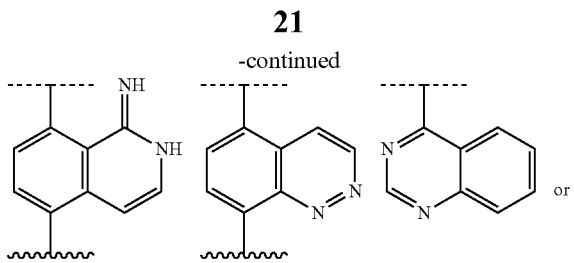

wherein the wavy line indicates the point of attachment to L and the dashed line represents the point of attachment to ring A.

In certain embodiments, the moiety

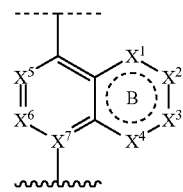

is:

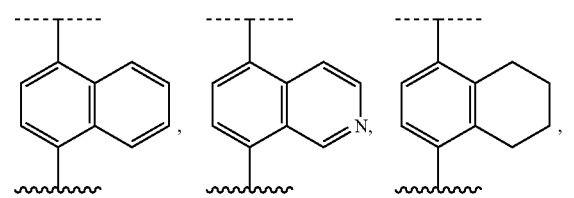

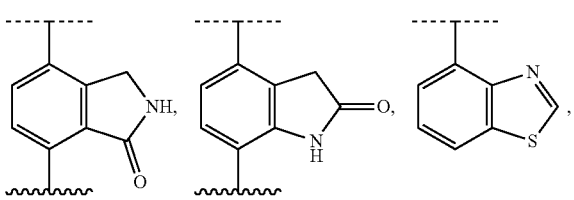

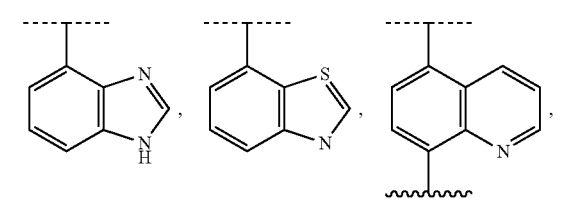

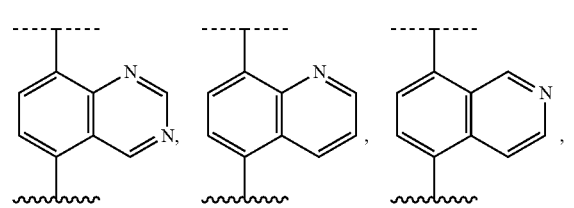

wherein the wavy line indicates the point of attachment to L and the dashed line represents the point of attachment to ring A, and further wherein the bicyclic ring may be optionally substituted with one or more $R^2$ selected from the group consisting of hydrogen, halo, $C_{1-6}$ alkyl optionally substituted with halo or hydroxy, $C_{3-6}$ cycloalkyl, $C_{2-6}$ hydroxyalkyl, cyano, —C(O)OR$^c$, and —C(O)NR$^c$R$^c$.

In certain embodiments, the moiety

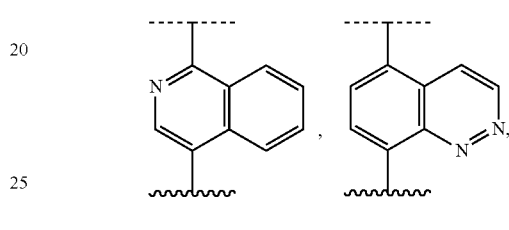

is:

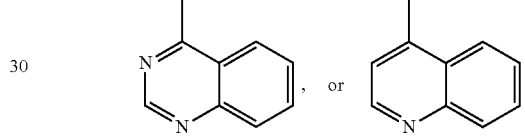

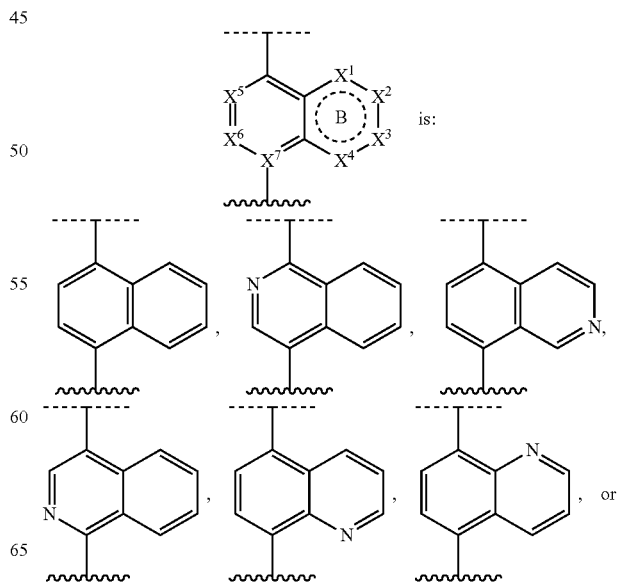

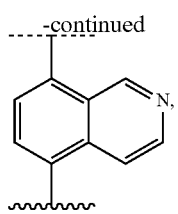

wherein the wavy line indicates the point of attachment to L and the dashed line represents the point of attachment to ring A, and further wherein the bicyclic ring may be optionally substituted with one or more $R^2$ selected from the group consisting of hydrogen, halo, $C_{1-6}$ alkyl optionally substituted with halo or hydroxy, $C_{3-6}$ cycloalkyl, $C_{2-6}$ hydroxyalkyl, cyano, —C(O)OR$^c$, and —C(O)NR$^c$R$^c$.

In certain embodiments, the moiety

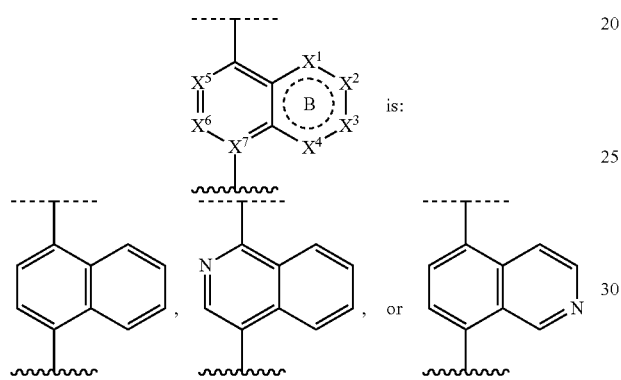

optionally substituted with 1, 2, or 3 $R^2$ as described herein.

In certain embodiments, the moiety

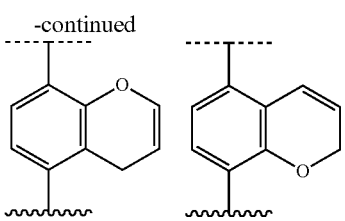

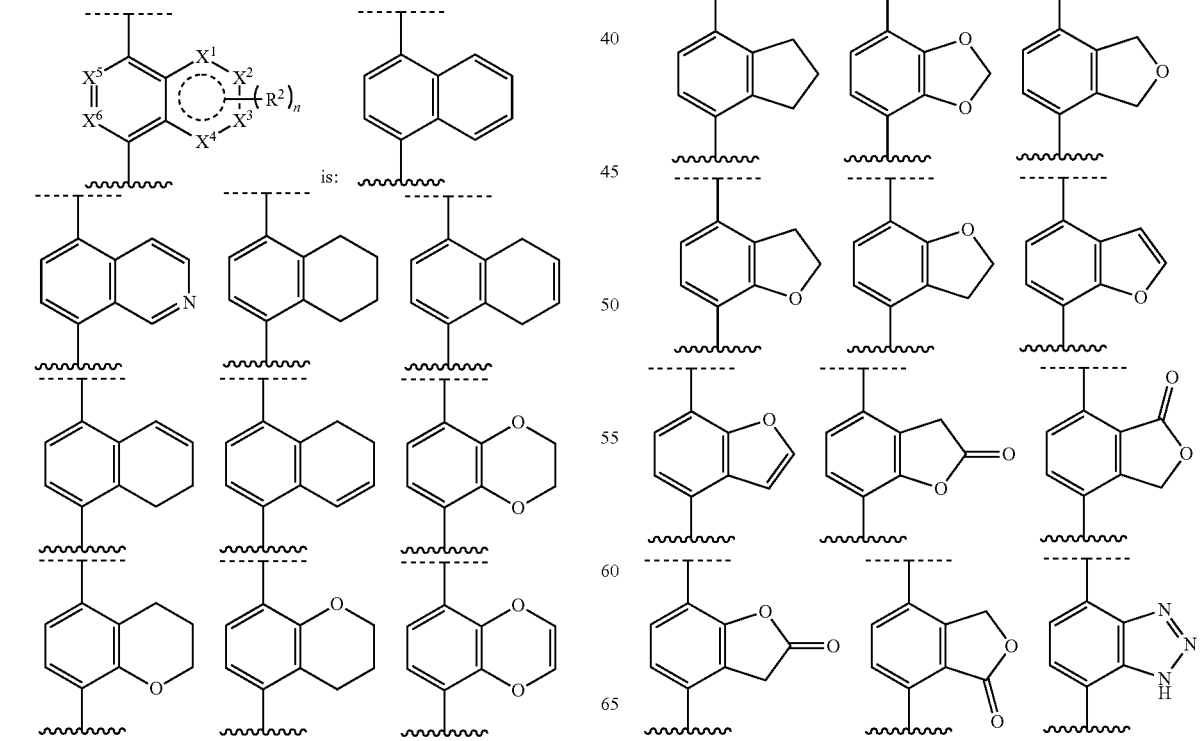

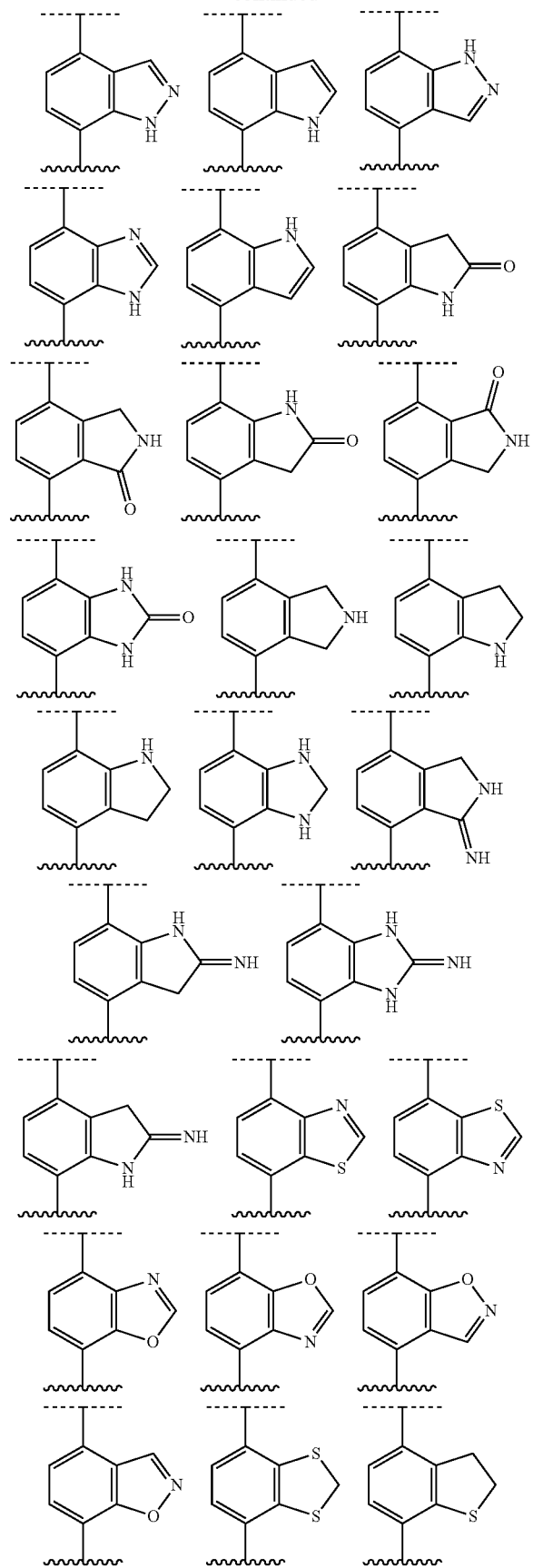
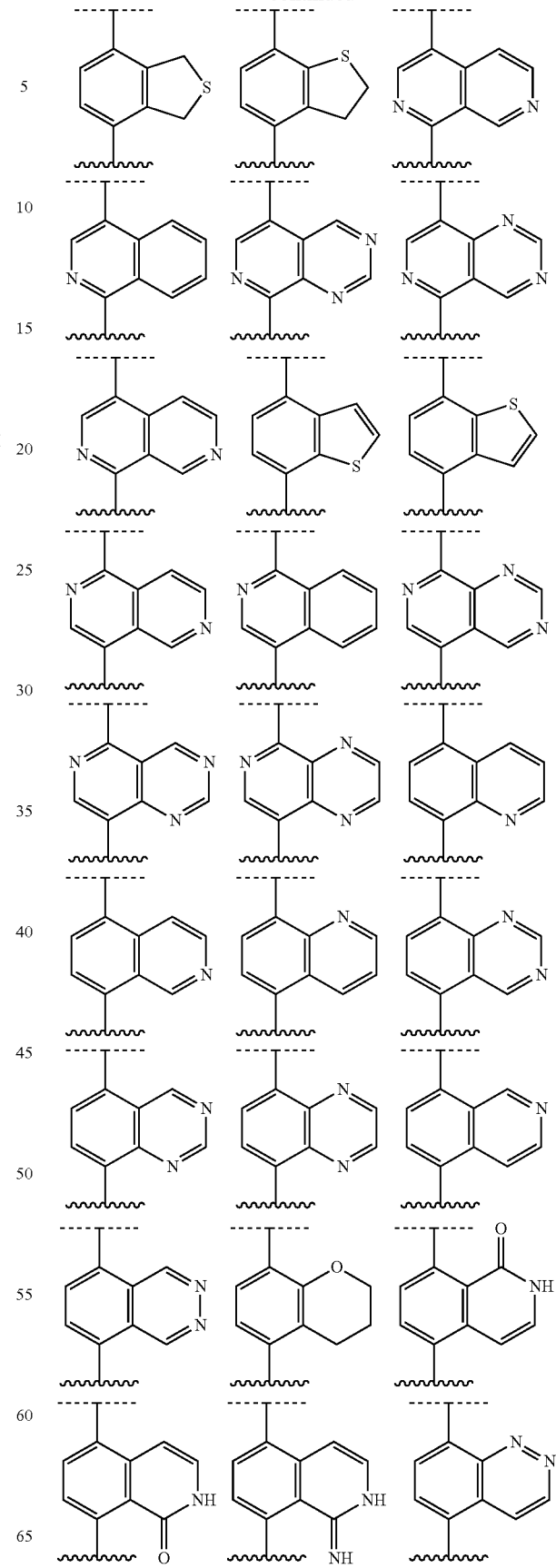

-continued

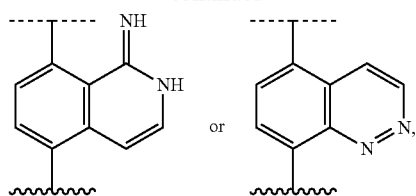

wherein the wavy line indicates the point of attachment to L and the dashed line represents the point of attachment to ring A.

In certain embodiments, the moiety

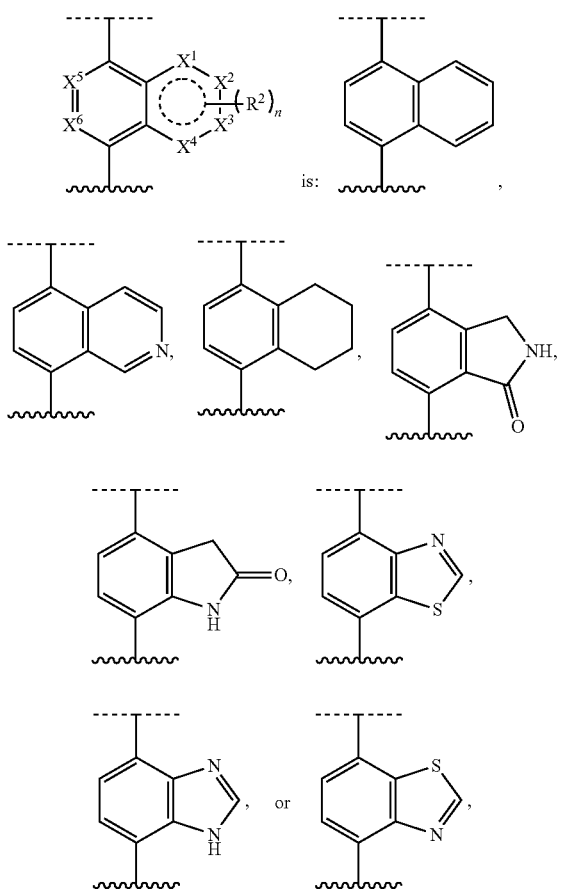

wherein the wavy line indicates the point of attachment to L and the dashed line represents the point of attachment to ring A.

In certain embodiments, ring A is:

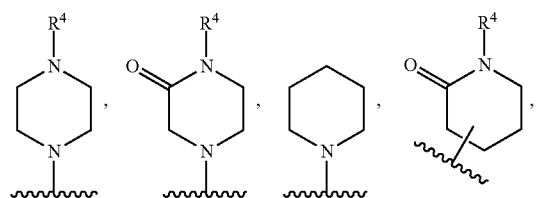

-continued

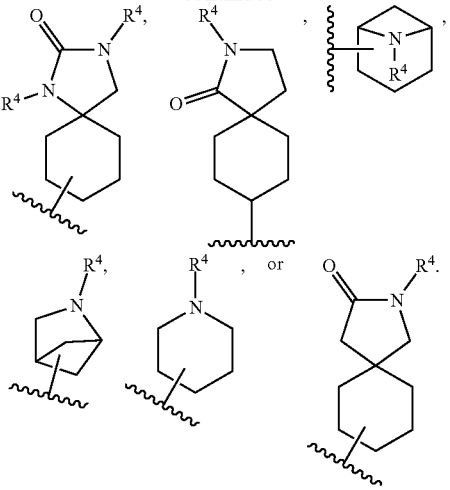

In certain embodiments, ring A is:

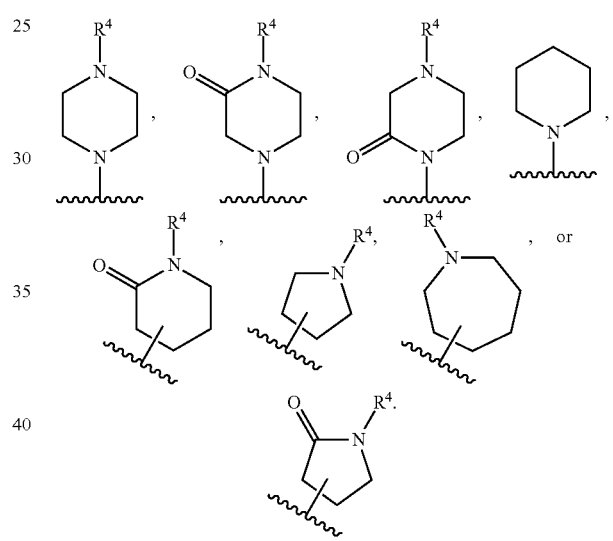

In certain embodiments, ring A is:

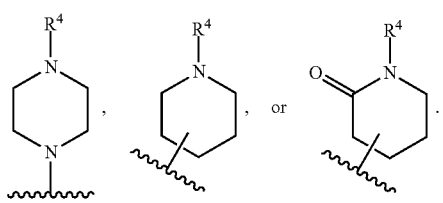

In certain embodiments, m is 0 or 1.

In certain embodiments, $R^4$ is hydrogen, —C(O)NH$_2$, or —C(NH)NH$_2$. In certain embodiments, $R^4$ is hydrogen.

In certain embodiments, $R^1$ is —NHC(O)NH$_2$, —NHS(O)$_2$CH$_3$, or —NHC(O)CH$_3$. In certain embodiments, $R^1$ is —NHS(O)$_2$CH$_3$, or —NHC(O)CH$_3$.

In certain embodiments, $R^2$ is hydrogen, C$_{1-6}$ alkyl, —CO$_2$H or —C(O)NH$_2$. In certain embodiments, $R^2$ is —CO$_2$H or —C(O)NH$_2$. In certain embodiments, R$^2$ is hydrogen. In certain embodiments, R$^2$ is hydrogen or methyl.

In certain embodiments, R$^4$ is hydrogen, —C(O)NH$_2$, or —C(NH)NH$_2$. In certain embodiments, R$^4$ is hydrogen.

In certain embodiments, L is a bond, —CH$_2$—, —O—, —C(O)—, —S(O)$_2$—, —S(O)$_2$NH—, or —NH—. In certain embodiments, L is —CH$_2$—, —O—, —C(O)—, —S(O)$_2$—, —S(O)$_2$NH—, or —NH—. In certain embodiments, L is —CH$_2$—, —O—, —C(O)—, —S(O)$_2$—, or —NH—. In certain embodiments, L is a bond.

In certain embodiments, R$^3$ is hydrogen, amino, halo, C$_{1-6}$ alkyl, aryl, or C$_{3-10}$ heterocyclyl, wherein C$_{1-6}$ alkyl, aryl, or C$_{3-10}$ heterocyclyl is optionally substituted with one or more halo. In certain embodiments, R$^3$ is hydrogen, C$_{1-6}$ alkyl, or C$_{3-10}$ heterocyclyl, wherein C$_{1-6}$alkyl or C$_{3-10}$ heterocyclyl is optionally substituted with one or more halo. In certain embodiments, R$^3$ is hydrogen. In certain embodiments, R$^3$ is CH$_3$. In certain embodiments, R$^3$ is CF$_3$. In certain embodiments, R$^3$ is F. In certain embodiments, R$^3$ is Cl. In certain embodiments, R$^3$ is NH$_2$. In certain embodiments, R$^3$ is cyclohexyl. In certain embodiments, R$^3$ is aryl. In one embodiment, R$^3$ is C$_{3-10}$ heterocyclyl.

In certain embodiments, L is a bond and R$^3$ is hydrogen, C$_{1-6}$ alkyl, haloalkyl, halo, C$_{3-10}$ cycloalkyl, heterocyclyl, or aryl. In certain embodiments, L is a bond and R$^3$ is hydrogen. In certain embodiments, L is a bond and R$^3$ is CH$_3$. In certain embodiments, L is a bond and R$^3$ is CF$_3$. In certain embodiments, L is a bond and R$^3$ is F. In certain embodiments, L is a bond and R$^3$ is Cl. In certain embodiments, L is a bond and R$^3$ is cyclohexyl. In certain embodiments, L is a bond, and R$^3$ is phenyl.

In certain embodiments, R$^3$ is:

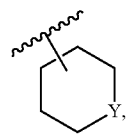

wherein:
Y is —O—, —N(R$^e$)—, —CH((CH$_2$)$_f$ OH), or —N((CH$_2$)$_f$OH);
each R$^e$ is independently hydrogen, C$_{1-6}$ alkyl, C$_{3-6}$ cycloalkyl, or C$_{2-6}$ alkyl where the C$_{2-6}$ alkyl is substituted with a hydroxy; and
f is 0, 1, 2, 3, or 4.

In certain embodiments, Y is —N(R$^e$)—.

In certain embodiments, provided is a compound of Formula (Ib):

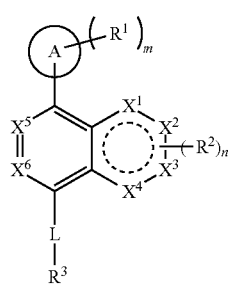

(Ib)

wherein:
m is 0, 1, or 2;
n is 0, 1, or 2;
X$^1$, X$^2$, X$^3$, and X$^4$ are each independently CH, C(O), N, NH, S, SO$_2$, or O; or X$^1$ is absent and X$^2$, X$^3$, and X$^4$ are each independently CH, C(O), N, NH, S, SO$_2$, or O; and the dotted line can represent one or more double bonds;

X$^5$ and X$^6$ are either CH or N;

ring A is selected from:

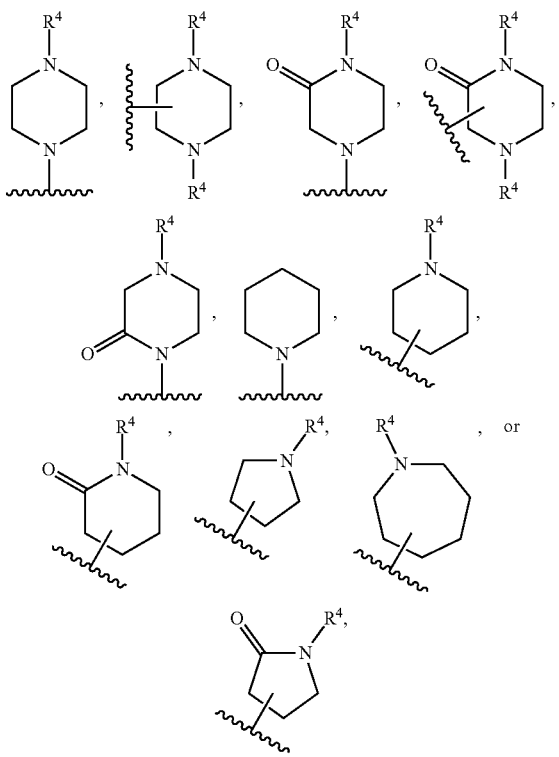

where the wavy line in ring A indicates the point of attachment to

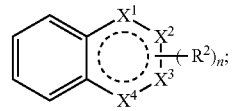

R$^1$ in each instance is independently, halo, cyano, C$_{1-6}$ alkyl optionally substituted with halo or hydroxy, C$_{3-6}$ cycloalkyl, —NR$^b$C(O)NR$^b$R$^b$, —NR$^b$S(O)$_2$R$^b$, —N(R$^b$)$_2$, or —NR$^b$C(O)R$^b$;

where each R$^b$ is independently hydrogen, C$_{1-6}$ alkyl, C$_{3-6}$ cycloalkyl, or C$_{2-6}$ hydroxyalkyl;

R$^2$ in each instance is independently, halo, C$_{1-6}$ alkyl optionally substituted with halo or hydroxy, C$_{3-6}$ cycloalkyl, C$_{2-6}$ hydroxyalkyl, cyano, —C(O)OR$^c$, or —C(O)NR$^c$R$^c$;

where each R$^c$ is independently, hydrogen, C$_{1-6}$ alkyl, C$_{3-6}$ cycloalkyl, or C$_{2-6}$ hydroxyalkyl;

R$^4$ in each instance is independently, hydrogen, C$_{1-6}$ alkyl, —C(O)NR$^d$R$^d$, —C(NR$^d$)NR$^d$R$^d$, —C(O)R$^d$, or —S(O)$_2$NR$^d$R$^d$;

where each R$^d$ is independently, hydrogen, C$_{1-6}$ alkyl, C$_{3-6}$ cycloalkyl, or C$_{2-6}$ hydroxyalkyl; and L-R³ is:

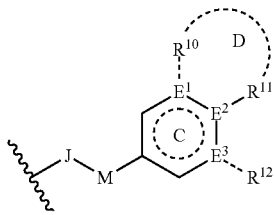

wherein:
  i) J is selected from the group consisting of —O—, —CO—, —CH₂—, —CF₂—, —SO₂—;
  ii) if J is —CH₂ or —CF₂ then M is nothing, if J is —O— then M is nothing or —CH₂, if J is —CO or SO₂ then M is —NH—;
  iii) Ring C is a 5 or 6 membered saturated or unsaturated aryl, heteroaryl, carbocyclic or heterocyclic ring. And ring C may be fused via $R^{11}$, $R^{12}$ to form a 5-6 membered aryl, heteroaryl, carbocyclic or heterocyclic ring;
  iv) $E^1$, $E^2$, and $E^3$ are independently selected from C or N;
  v) if M is nothing or —CH₂— then $R^{11}$ and $R^{12}$ are independently selected from the group consisting of lower alkyl, halo, hydroxy, amino, aminoalkyl, hydroxylalkyl, haloalkyl, carboxy, —C(O)NH₂, nitrile, —S-alkyl, —O-alkyl, acyl, and oxo; and
  vi) if M is —NH— then $R^{10}$, $R^{11}$, and $R^{12}$ are independently selected from the group consisting of lower alkyl, halo, hydroxy, amino, aminoalkyl, hydroxylalky, haloalkyl, carboxy, —C(O)NH₂, —C(O)N-alkyl, nitrile, —S-alkyl, —O-alkyl, acyl, oxo; and $R^{10}$ and $R^{11}$ may be joined to form a 5-6 membered fused saturated or unsaturated ring D containing 0-3 heteroatoms where Ring D may further be substituted at positions at least two atoms away from the juncture with Ring C, or a pharmaceutically acceptable salt, ester, prodrug, isomer, or mixture of isomers thereof.

In one embodiment, a compound may be selected from those compounds in Table 1 or a pharmaceutically acceptable salt, ester, prodrug, isomer, or mixture of isomers thereof.

TABLE 1

| No. | Name | Structure |
|---|---|---|
| 1 | 1-(4-(trifluoromethyl)naphthalen-1-yl)piperazine | |
| 2 | 4-(4-(trifluoromethyl)naphthalen-1-yl)piperidine | 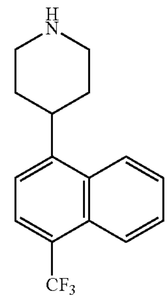 [SMILES: FC(F)(F)c1ccc(C2CCNCC2)c2ccccc12] |
| 3 | 1-(4-(trifluoromethyl)-5,6,7,8-tetrahydronaphthalen-1-yl)piperazine | 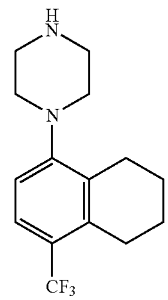 [SMILES: FC(F)(F)c1ccc(N2CCNCC2)c2c1CCCC2] |
| 4 | 1-(4-(piperidin-4-yloxy)naphthalen-1-yl)piperazine | 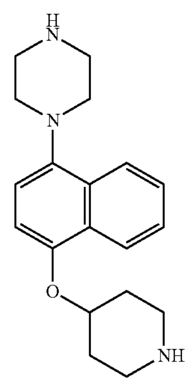 |
| 5 | N-(4-(piperazin-1-yl)naphthalen-1-yl)piperidin-4-amine | 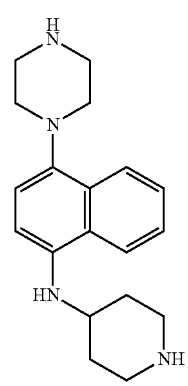 |

TABLE 1-continued

| No. | Name | Structure |
|---|---|---|
| 6 | 1-(4-(piperidin-4-ylmethyl)naphthalen-1-yl)piperazine | 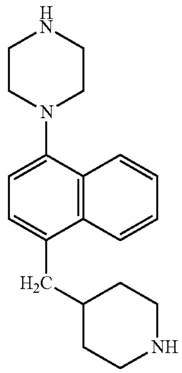 [SMILES: c1ccc2c(N3CCNCC3)ccc(CC3CCNCC3)c2c1] |
| 7 | 1-(4-(piperidin-4-ylsulfonyl)naphthalen-1-yl)piperazine | 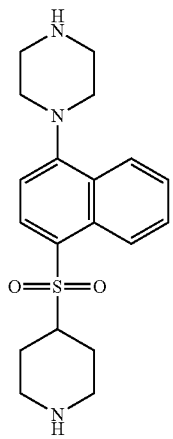 [SMILES: O=S(=O)(c1ccc(N2CCNCC2)c2ccccc12)C1CCNCC1] |
| 8 | piperazin-1-yl(4-(piperazin-1-yl)naphthalen-1-yl)methanone | 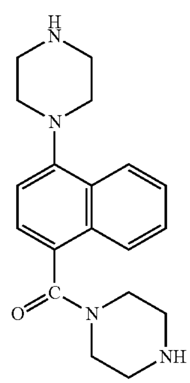 [SMILES: O=C(c1ccc(N2CCNCC2)c2ccccc12)N1CCNCC1] |
| 9 | 5-(piperazin-1-yl)-8-(piperidin-4-yloxy)isoquinoline | 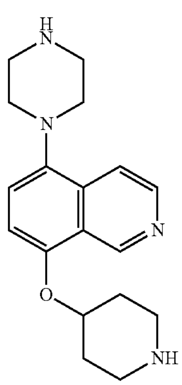 [SMILES: c1cc2c(N3CCNCC3)ccc(OC3CCNCC3)c2cn1] |
| 10 | 4-(naphthalen-1-yl)piperazine-1-carboximidamide | |
| 11 | 4-(naphthalen-1-yl)piperazine-1-carboxamide | |
| 12 | 4-(piperazin-1-yl)-7-(piperidin-4-yloxy)indolin-2-one | |
| 13 | 4-(piperazin-1-yl)-7-(piperidin-4-yloxy)isoindolin-1-one | |

TABLE 1-continued

| No. | Name | Structure |
|---|---|---|
| 14 | 5-(piperazin-1-yl)-8-(piperidin-4-yloxy)isoquinoline-3-carboxylic acid | |
| 15 | 5-(3-oxopiperazin-1-yl)-8-(piperidin-4-yloxy)isoquinoline-3-carboxamide | |
| 16 | 4-(8-(piperidin-4-yloxy)isoquinolin-5-yl)piperazin-2-one | |
| 17 | N-(1-(naphthalen-1-yl)piperidin-4-yl)methanesulfonamide | |
| 18 | N-(1-(naphthalen-1-yl)piperidin-4-yl)acetamide | 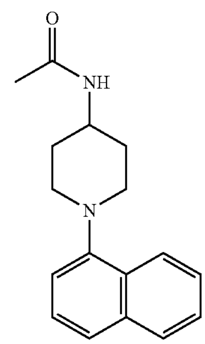 [SMILES: CC(=O)NC1CCN(c2cccc3ccccc23)CC1] |
| 19 | 1-(1-(naphthalen-1-yl)piperidin-4-yl)urea | 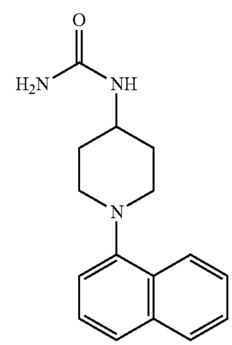 [SMILES: NC(=O)NC1CCN(c2cccc3ccccc23)CC1] |
| 20 | 4-(piperidin-4-yl)-1H-benzo[d]imidazole | 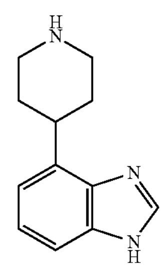 [SMILES: c1cc(C2CCNCC2)c2nc[nH]c2c1] |
| 21 | 4-(piperidin-4-yl)benzo[d]thiazole | 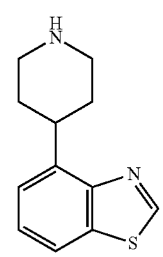 [SMILES: c1cc(C2CCNCC2)c2ncsc2c1] |
| 22 | 4-((4-(piperidin-4-yl)naphthalen-1-yl)methyl)piperidine | 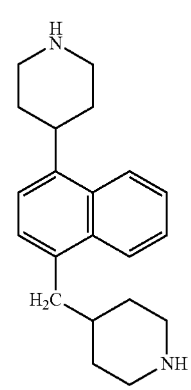 [SMILES: c1ccc2c(C3CCNCC3)ccc(CC3CCNCC3)c2c1] |

TABLE 1-continued

| No. | Name | Structure |
|---|---|---|
| 23 | 4-((4-(piperidin-4-yl)naphthalen-1-yl)sulfonyl)piperidine | 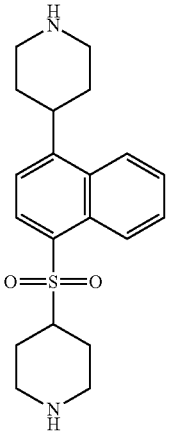 [SMILES: O=S(=O)(c1ccc(C2CCNCC2)c2ccccc12)C1CCNCC1] |
| 24 | 4-(piperidin-4-yl)-7-(piperidin-4-yloxy)indolin-2-one | 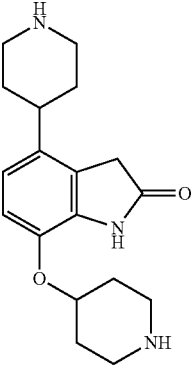 [SMILES: O=C1Cc2c(C3CCNCC3)ccc(OC3CCNCC3)c2N1] |
| 25 | 5-(piperidin-4-yl)-8-(piperidin-4-yloxy)isoquinoline-3-carboxylic acid | 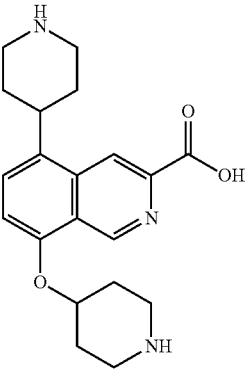 [SMILES: O=C(O)c1cc2c(C3CCNCC3)ccc(OC3CCNCC3)c2cn1] |
| 26 | 5-(2-oxopiperidin-4-yl)-8-(piperidin-4-yloxy)isoquinoline-3-carboxamide | 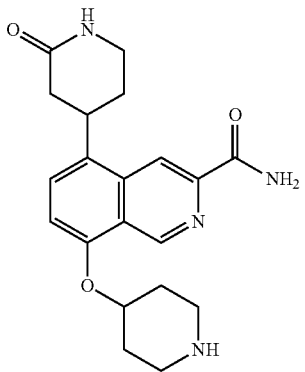 [SMILES: NC(=O)c1cc2c(C3CCNC(=O)C3)ccc(OC3CCNCC3)c2cn1] |
| 27 | 4-(8-(piperidin-4-yloxy)isoquinolin-5-yl)piperidin-2-one | 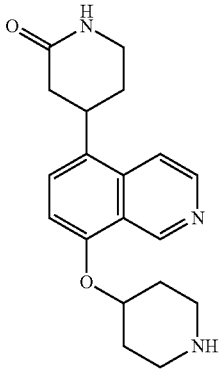 [SMILES: O=C1CC(c2ccc(OC3CCNCC3)c3cnccc23)CCN1] |
| 28 | 5-(piperazin-1-yl)-8-(piperidin-4-yloxy)quinoline-3-carboxylic acid | 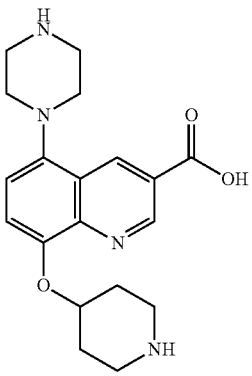 |
| 29 | 8-(piperazin-1-yl)-5-(piperidin-4-yloxy)quinazoline-2-carboxylic acid | 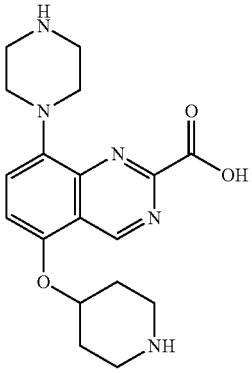 |
| 30 | 8-(piperazin-1-yl)-5-(piperidin-4-yloxy)quinoline-2-carboxylic acid | 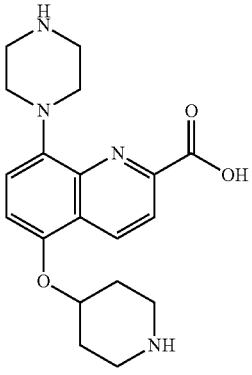 |

TABLE 1-continued

| No. | Name | Structure |
|---|---|---|
| 31 | 4-(piperazin-1-yl)-7-(piperidin-4-yloxy)benzo[d]thiazole | 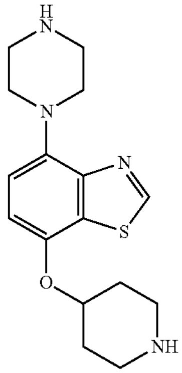 |
| 32 | 7-(piperazin-1-yl)-4-(piperidin-4-yloxy)benzo[d]thiazole | 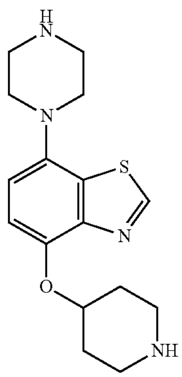 [SMILES: c1nc2c(OC3CCNCC3)ccc(N3CCNCC3)c2s1] |
| 33 | 8-(piperazin-1-yl)-5-(piperidin-4-yloxy)isoquinoline-3-carboxylic acid | 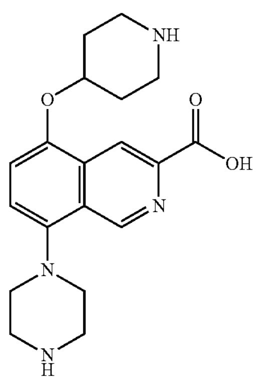 [SMILES: O=C(O)c1cc2c(OC3CCNCC3)ccc(N3CCNCC3)c2cn1] |
| 34 | 4-(piperazin-1-yl)-7-(piperidin-4-yloxy)-1H-benzo[d][1,2,3]triazole | 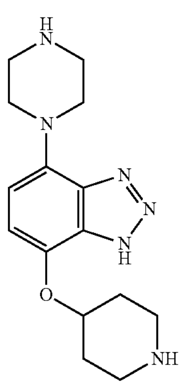 [SMILES: c1cc(OC2CCNCC2)c2[nH]nnc2c1N1CCNCC1] |
| 35 | 1-(7-(piperidin-4-yloxy)-2,3-dihydro-1H-inden-4-yl)piperazine | 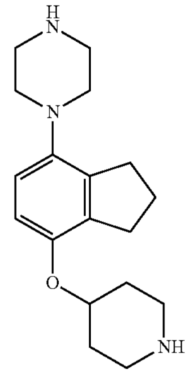 |
| 36 | 5-(piperazin-1-yl)-8-(piperidin-4-yloxy)quinoline | 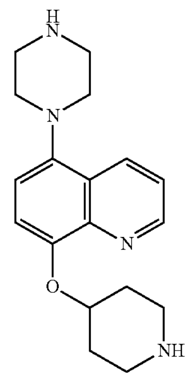 [SMILES: c1cnc2c(OC3CCNCC3)ccc(N3CCNCC3)c2c1] |
| 37 | 3-methyl-5-(piperidin-4-yl)-8-(piperidin-4-yloxy)cinnoline | 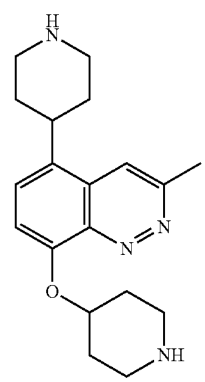 [SMILES: Cc1cc2c(C3CCNCC3)ccc(OC3CCNCC3)c2nn1] |
| 38 | 4-((7-(piperidin-4-yl)benzo[d][1,3]dioxol-4-yl)oxy)piperidine | 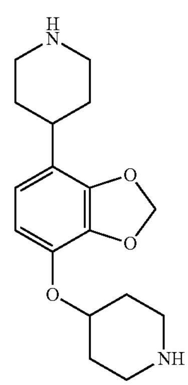 [SMILES: c1cc(C2CCNCC2)c2c(c1OC1CCNCC1)OCO2] |

TABLE 1-continued
| No. | Name | Structure |
|---|---|---|
| 39 | 1-(7-(piperidin-4-yloxy)benzo[b]thiophen-4-yl)piperazine | 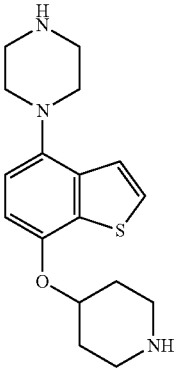 |
| 40 | 4-(piperazin-1-yl)-1H-benzo[d]imidazole | 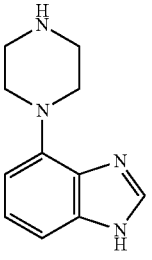 |
| 41 | 4-(piperazin-1-yl)benzo[d]thiazole | 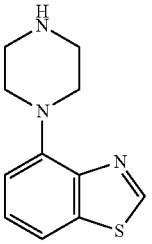 [SMILES: c1cc(N2CCNCC2)c2ncsc2c1] |
| 42 | 7-(piperazin-1-yl)benzo[d]thiazole | 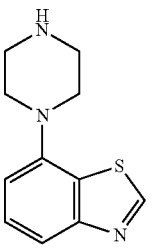 [SMILES: c1cc(N2CCNCC2)c2scnc2c1] |
| 43 | 4-(4-methylnaphthalen-1-yl)piperidine | 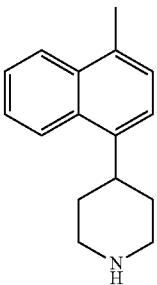 [SMILES: Cc1ccc(C2CCNCC2)c2ccccc12] |
| 44 | 4-(4-methoxynaphthalen-1-yl)piperidine | 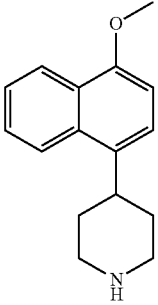 [SMILES: COc1ccc(C2CCNCC2)c2ccccc12] |
| 45 | 4-(piperidin-4-yl)isoquinoline | 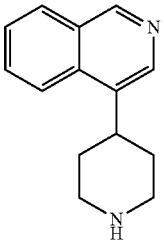 [SMILES: c1ccc2c(C3CCNCC3)cncc2c1] |
| 46 | 1-(piperidin-4-yl)isoquinoline | 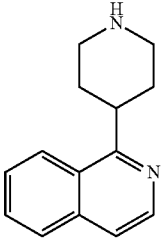 [SMILES: c1ccc2c(C3CCNCC3)nccc2c1] |
| 47 | 4-(piperidin-4-yl)naphthalen-1-ol | 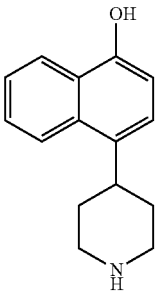 [SMILES: Oc1ccc(C2CCNCC2)c2ccccc12] |
| 48 | 4-(piperidin-4-yl)quinazoline | 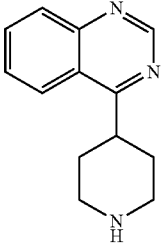 [SMILES: c1ccc2c(C3CCNCC3)ncnc2c1] |

TABLE 1-continued

| No. | Name | Structure |
|---|---|---|
| 49 | 4-(4-fluoronaphthalen-1-yl)piperidine | 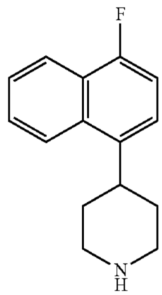 [SMILES: Fc1ccc(C2CCNCC2)c2ccccc12] |
| 50 | 4-(piperidin-4-yl)quinoline | 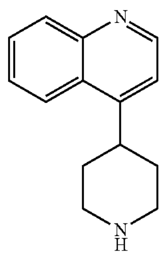 [SMILES: c1ccc2c(C3CCNCC3)ccnc2c1] |
| 51 | 8-fluoro-5-(piperidin-4-yl)quinoline | 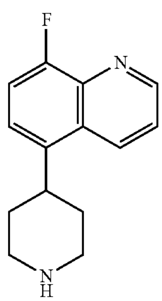 [SMILES: Fc1ccc(C2CCNCC2)c2cccnc12] |
| 52 | 8-fluoro-5-(piperidin-4-yl)isoquinoline | 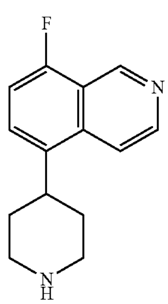 [SMILES: Fc1ccc(C2CCNCC2)c2ccncc12] |
| 53 | 4-(5-methylnaphthalen-1-yl)piperidine | 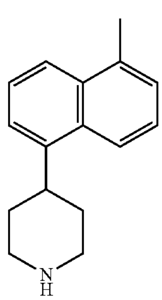 [SMILES: Cc1cccc2c(C3CCNCC3)cccc12] |
| 54 | (5-(piperidin-4-yl)naphthalen-1-yl)methanol | |
| 55 | 4-(6-methylnaphthalen-1-yl)piperidine | |
| 56 | 4-(piperidin-4-yl)naphthalen-1-amine | |
| 57 | 8-(piperidin-4-yl)quinoline | |
| 58 | 5-fluoro-8-(piperidin-4-yl)quinoline | |

TABLE 1-continued

| No. | Name | Structure |
|---|---|---|
| 59 | 4-(4-chloronaphthalen-1-yl)piperidine | 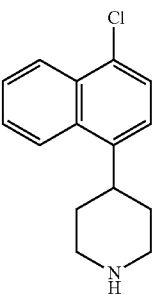 [SMILES: Clc1ccc(C2CCNCC2)c2ccccc12] |
| 60 | 4-(4-cyclohexylnaphthalen-1-yl)piperidine | 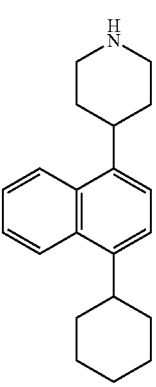 [SMILES: c1ccc2c(C3CCNCC3)ccc(C3CCCCC3)c2c1] |
| 61 | 4-(piperidin-4-yl)-N-(5,6,7,8-tetrahydronaphthalen-2-yl)naphthalene-1-sulfonamide | 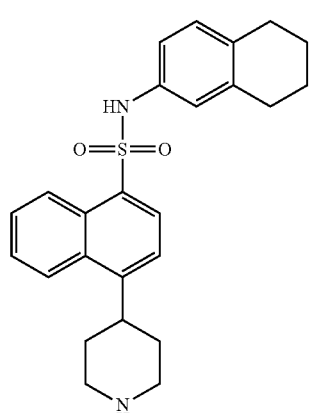 |
| 62 | N-phenyl-4-(piperidin-4-yl)naphthalene-1-sulfonamide | 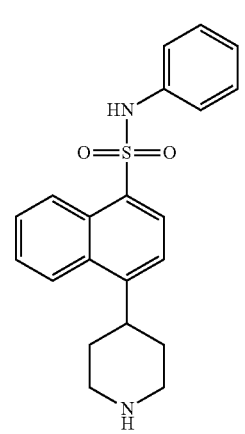 [SMILES: O=S(=O)(Nc1ccccc1)c1ccc(C2CCNCC2)c2ccccc12] |
| 63 | 4-(piperidin-4-yl)naphthalene-1-sulfonamide | 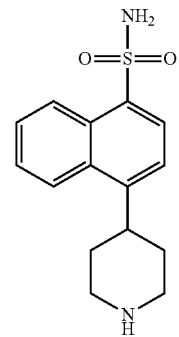 |
| 64 | 8-(piperidin-4-yl)-5-(trifluoromethyl)quinoline | 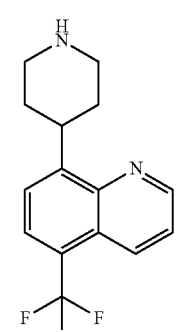 |
| 65 | 5-(piperidin-4-yl)-8-(trifluoromethyl)quinoline | 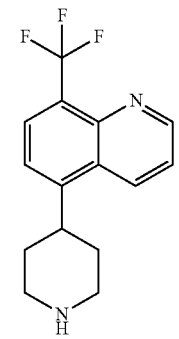 |
| 66 | 5-(piperidin-4-yl)-2-naphthamide | 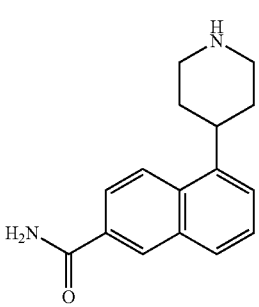 [SMILES: NC(=O)c1ccc2c(C3CCNCC3)cccc2c1] |

TABLE 1-continued

| No. | Name | Structure |
|---|---|---|
| 67 | 5-(piperidin-4-yl)-1-naphthamide | 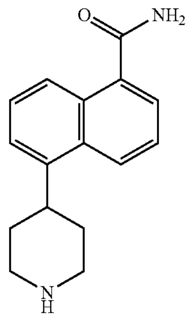 [SMILES: NC(=O)c1cccc2c(C3CCNCC3)cccc12] |
| 68 | 4-(piperidin-4-yl)-1-naphthamide | 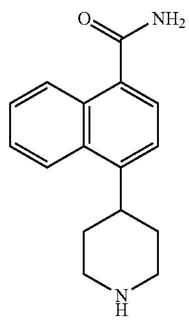 [SMILES: NC(=O)c1ccc(C2CCNCC2)c2ccccc12] |
| 69 | 8-(naphthalen-1-yl)-1,3-diazaspiro[4.5]decan-2-one | 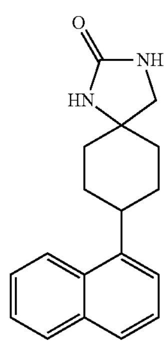 [SMILES: O=C1NCC2(CCC(c3cccc4ccccc34)CC2)N1] |
| 70 | N-(4-(piperidin-4-yl)naphthalen-1-yl)tetrahydro-2H-pyran-4-amine | 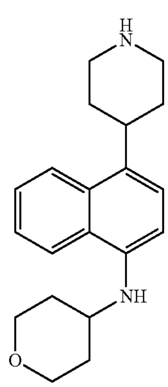 [SMILES: c1ccc2c(C3CCNCC3)ccc(NC3CCOCC3)c2c1] |
| 71 | 4-(4-((tetrahydro-2H-pyran-4-yl)oxy)naphthalen-1-yl)piperidine | |
| 72 | 4-(piperazin-1-yl)-N-(5,6,7,8-tetrahydronaphthalen-1-yl)naphthalene-1-sulfonamide | |
| 73 | N-phenyl-4-(piperazin-1-yl)naphthalene-1-sulfonamide | |
| 74 | 4-(piperazin-1-yl)naphthalene-1-sulfonamide | |

TABLE 1-continued

| No. | Name | Structure |
|---|---|---|
| 75 | 8-methoxy-5-(piperidin-4-yl)isoquinoline-3-carboxylic acid | 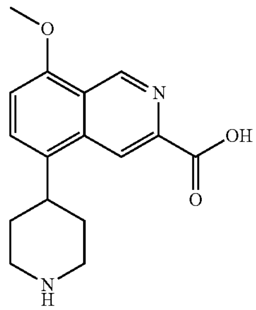 [SMILES: COc1ccc(C2CCNCC2)c2cc(C(=O)O)ncc12] |
| 76 | 8-methoxy-5-(piperidin-4-yl)isoquinoline-3-carboxamide | 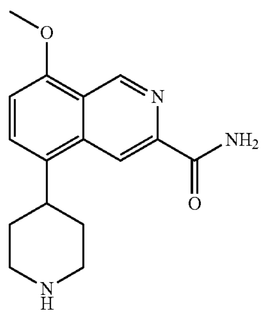 [SMILES: COc1ccc(C2CCNCC2)c2cc(C(N)=O)ncc12] |
| 77 | 8-(naphthalen-1-yl)-2-azaspiro[4.5]decan-3-one | 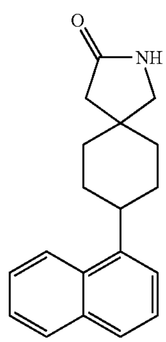 [SMILES: O=C1CC2(CCC(c3cccc4ccccc34)CC2)CN1] |
| 78 | 8-(naphthalen-1-yl)-2-azaspiro[4.5]decan-1-one | 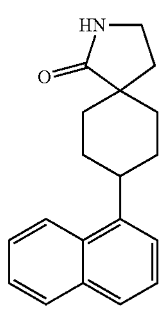 [SMILES: O=C1NCCC12CCC(c1cccc3ccccc13)CC2] |
| 79 | 5-fluoro-8-(piperidin-4-yl)isoquinoline | 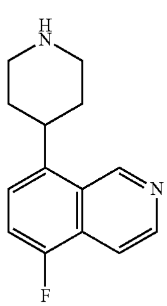 [SMILES: Fc1ccc(C2CCNCC2)c2cnccc12] |
| 80 | 4-fluoro-1-(piperidin-4-yl)isoquinoline | 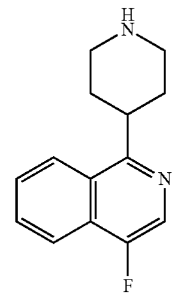 [SMILES: Fc1cnc(C2CCNCC2)c2ccccc12] |
| 81 | 4-(piperidin-4-yl)-1-(trifluoromethyl)isoquinoline | 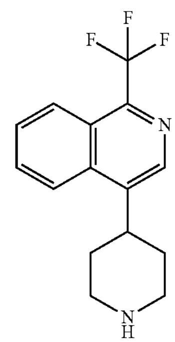 [SMILES: FC(F)(F)c1ncc(C2CCNCC2)c2ccccc12] |
| 82 | 1-(piperidin-4-yl)-4-(trifluoromethyl)isoquinoline | 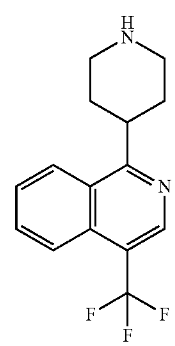 [SMILES: FC(F)(F)c1cnc(C2CCNCC2)c2ccccc12] |
| 83 | 8-(piperidin-4-yl)-5-(trifluoromethyl)isoquinoline | 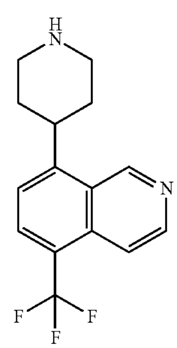 |

TABLE 1-continued

| No. | Name | Structure |
|---|---|---|
| 84 | 5-(piperidin-4-yl)-8-(trifluoromethyl)isoquinoline | 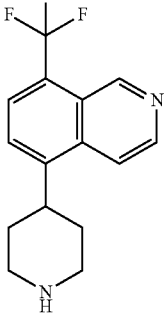 |
| 85 | 4-chloro-1-(piperidin-4-yl)isoquinoline | 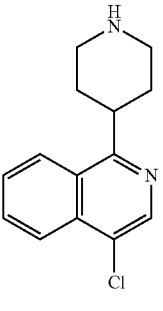 [SMILES: Clc1cnc(C2CCNCC2)c2ccccc12] |
| 86 | 5-chloro-8-(piperidin-4-yl)quinoline | 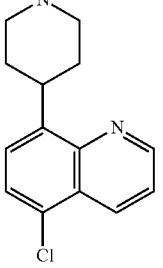 |
| 87 | 5-chloro-8-(piperidin-4-yl)isoquinoline | 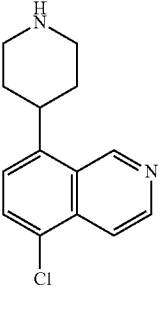 |
| 88 | 8-chloro-5-(piperidin-4-yl)isoquinoline | 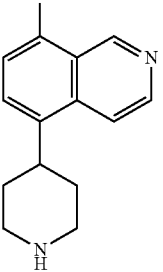 |
| 89 | 8-chloro-5-(piperidin-4-yl)quinoline | 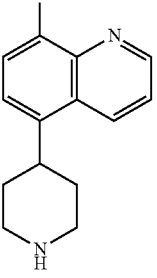 |
| 90 | 4-(4-phenoxynaphthalen-1-yl)piperidine | 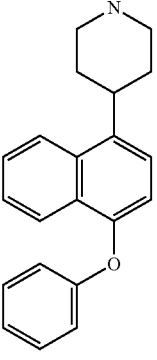 |
| 91 | 8-(piperidin-4-yl)-2-naphthamide | 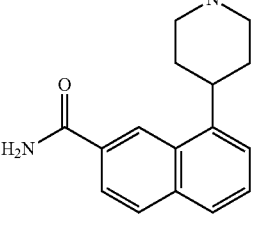 |
| 92 | 4-(piperidin-4-yl)-2-naphthamide | 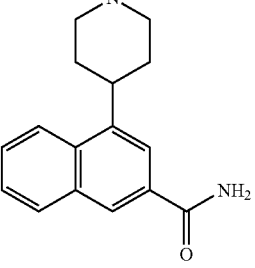 |
| 93 | 4-(5-(trifluoromethyl)naphthalen-1-yl)piperidine | 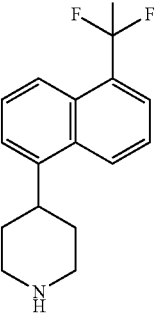 |

TABLE 1-continued

| No. | Name |
|---|---|
| 94 | 4-(6-(trifluoromethyl)naphthalen-1-yl)piperidine |
| 95 | 4-(4-phenylnaphthalen-1-yl)piperidine |
| 96 | 4-(4-(4-fluorobenzyl)naphthalen-1-yl)piperidine |
| 97 | 3-(naphthalen-1-yl)-6-azabicyclo[3.1.1]heptane |
| 98 | 3-(4-(trifluoromethyl)naphthalen-1-yl)-6-azabicyclo[3.1.1]heptane |
| 99 | 3-(4-chloronaphthalen-1-yl)-6-azabicyclo[3.1.1]heptane |
| 100 | 3-(4-methylnaphthalen-1-yl)-6-azabicyclo[3.1.1]heptane |
| 101 | 4-(piperidin-4-yl)-2-(trifluoromethyl)quinazoline |
| 102 | 5-(naphthalen-1-yl)-2-azabicyclo[2.1.1]hexane |
| 103 | 5-(4-(trifluoromethyl)naphthalen-1-yl)-2-azabicyclo[2.1.1]hexane |
| 104 | 5-(4-chloronaphthalen-1-yl)-2-azabicyclo[2.1.1]hexane |

TABLE 1-continued

| No. | Name | Structure |
|-----|------|-----------|
| 105 | 5-(2-oxopiperidin-4-yl)-8-(piperidin-4-yloxy)isoquinoline-3-carboxylic acid | 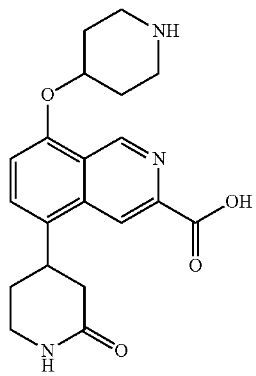 [SMILES: O=C1CC(c2ccc(OC3CCNCC3)c3cnc(C(=O)O)cc23)CCN1] |
| 106 | 5-(4-methylnaphthalen-1-yl)-2-azabicyclo[2.1.1]hexane | 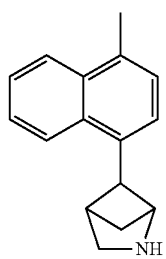 [SMILES: Cc1ccc(C2C3CNC2C3)c2ccccc12] |

In one embodiment, a compound may be selected from those compounds in Table 2 or a pharmaceutically acceptable salt, ester, prodrug, isomer, or mixture of isomers thereof.

TABLE 2

| No. | Name | Structure |
|-----|------|-----------|
| 107 | 1-(naphthalen-1-yl)piperazine | 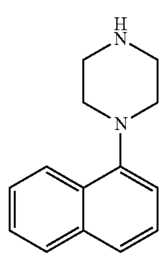 [SMILES: c1ccc2c(N3CCNCC3)cccc2c1] |
| 108 | 4-(naphthalen-1-yl)piperidine | 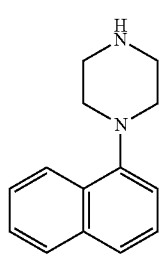 [SMILES: c1ccc2c(N3CCNCC3)cccc2c1] |

TABLE 2-continued

| No. | Name | Structure |
|-----|------|-----------|
| 109 | 5-(piperidin-4-yl)isoquinoline | 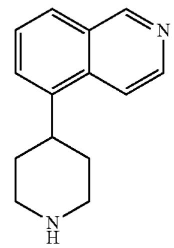 [SMILES: c1cc(C2CCNCC2)c2ccncc2c1] |
| 110 | 8-(piperidin-4-yl)isoquinoline | 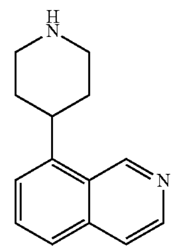 [SMILES: c1cc(C2CCNCC2)c2cnccc2c1] |
| 111 | 5-(piperidin-4-yl)quinoline | 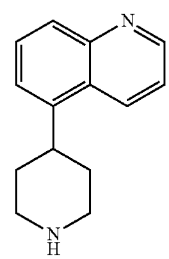 [SMILES: c1cc(C2CCNCC2)c2cccnc2c1] |

As discussed herein, the compounds provided herein, such as those provided in Table 1 and Table 2, are useful for binding to PCSK9 and modulating PCSK9 proprotein convertase enzyme activity.

4. Treatment Methods and Uses

"Treatment" or "treating" is an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival.

"Prevention" or "preventing" means any treatment of a disease or condition that causes the clinical symptoms of the disease or condition not to develop. Compounds may, in some embodiments, be administered to a subject (including a human) who is at risk or has a family history of the disease or condition.

"Subject" refers to an animal, such as a mammal (including a human), that has been or will be the object of treatment, observation or experiment. The methods described herein may be useful in human therapy and/or veterinary applications. In some embodiments, the subject is a mammal. In one embodiment, the subject is a human.

The term "therapeutically effective amount" or "effective amount" of a compound described herein or a pharmaceutically acceptable salt, tautomer, stereoisomer, mixture of stereoisomers, prodrug, or deuterated analog thereof means an amount sufficient to effect treatment when administered to a subject, to provide a therapeutic benefit such as amelioration of symptoms or slowing of disease progression. For example, a therapeutically effective amount may be an amount sufficient to decrease a symptom of a disease or condition of as described herein. The therapeutically effective amount may vary depending on the subject, and disease or condition being treated, the weight and age of the subject, the severity of the disease or condition, and the manner of administering, which can readily be determined by one or ordinary skill in the art.

The methods described herein may be applied to cell populations in vivo or ex vivo. "In vivo" means within a living individual, as within an animal or human. In this context, the methods described herein may be used therapeutically in an individual. "Ex vivo" means outside of a living individual. Examples of ex vivo cell populations include in vitro cell cultures and biological samples including fluid or tissue samples obtained from individuals. Such samples may be obtained by methods well known in the art. Exemplary biological fluid samples include blood, cerebrospinal fluid, urine, and saliva. In this context, the compounds and compositions described herein may be used for a variety of purposes, including therapeutic and experimental purposes. For example, the compounds and compositions described herein may be used ex vivo to determine the optimal schedule and/or dosing of administration of a compound of the present disclosure for a given indication, cell type, individual, and other parameters. Information gleaned from such use may be used for experimental purposes or in the clinic to set protocols for in vivo treatment. Other ex vivo uses for which the compounds and compositions described herein may be suited are described below or will become apparent to those skilled in the art. The selected compounds may be further characterized to examine the safety or tolerance dosage in human or non-human subjects. Such properties may be examined using commonly known methods to those skilled in the art.

Compounds of Formula (I), Formula (Ia), Formula (Ib), or additional Formulas or compounds described throughout, are contemplated to be useful in treating diseases or conditions mediated, at least in part by, PCSK9. Proprotein convertase subtilisin/kexin type 9, also known as PCSK9, is an enzyme that in humans is encoded by the PCSK9 gene. Seidah et al., "The secretory proprotein convertase neural apoptosis-regulated convertase 1 (NARC-1): liver regeneration and neuronal differentiation," *Proc. Natl. Acad. Sci. U.S.A.* 100 (3): 928-933 (2003). Similar genes (orthologs) are found across many species. Many enzymes, including PCSK9, are inactive when they are first synthesized, because they have a section of peptide chains that blocks their activity; proprotein convertases remove that section to activate the enzyme.

The PCSK9 gene encodes a proprotein convertase belonging to the proteinase K subfamily of the secretory subtilase family. The encoded protein is synthesized as a soluble zymogen that undergoes autocatalytic intramolecular processing in the endoplasmic reticulum. The protein may function as a proprotein convertase. For example, a human PCSK9 amino acid sequence is:

001 mgtvssrrsw wplplllll lllgpagara qededgdyee lvlalrseed glaeapehgt
061 tatfhrcakd pwrlpgtyvv vlkeethlsq sertarrlqa qaarrgyltk ilhvfhgllp
121 gflvkmsgdl lelalklphv dyieedssvf aqsipwnler itppryrade yqppdggslv
181 evylldtsiq sdhreiegry mvtdfenvpe edgtrfhrqa skcdshgthl agvvsgrdag
241 vakgasmrsl rvincqgkgt vsgtliglef irksqlvqpv gplvvllpla ggysrvinaa
301 cqrlaragvv lvtaagnfrd daclyspasa pevitvgatn aqdqpvtlgt lgtnfgrcvd
361 lfapgediig assdcstcfv sqsgtsqaaa hvagiaamml saepeltlae lrqrlihfsa
421 kdvineawfp edqrvltpnl vaalppsthg agwqlfcrtv wsahsgptrm atavarcapd
481 eellscssfs rsgkrrgerm eaqggklvcr ahnafggegv yaiarccllp qancsvhtap
541 paeasmgtry hchqqghvlt gcsshweved lgthkppvlr prgqpnqcvg hreasihasc
601 chapgleckv kehgipapqe qvtvaceegw tltgcsalpg tshvlgayav dntcvvrsrd
661 vsttgstseg avtavaiccr srhlaqasqe lq (Accession No. NP_777596) (SEQ ID NO:1).

PCSK9 is believed to play a regulatory role in cholesterol homeostasis. For example, PCSK9 can bind to the epidermal growth factor-like repeat A (EGF-A) domain of the low-density lipoprotein receptor (LDL-R) resulting in LDL-R internalization and degradation. Clearly, it would be expected that reduced LDL-R levels result in decreased metabolism of LDL-C, which could lead to hypercholesterolemia.

As it is estimated that approximately nine million Americans have a high or very high risk for heart-related problems that could benefit from PCSK9 inhibitors (especially when in combination with statins). PCSK9 inhibitors could result in such widespread usage having the potential to replace statins in certain conditions. PCSK9 has medical significance because it acts in cholesterol homeostasis. Drugs that block PCSK9 biological actions are believed to lower circulating low-density lipoprotein cholesterol (LDL-C) levels (e.g., by increasing the availability of LDL-Rs and, consequently, LDL-C clearance). Some such drugs, such as Evolocumab (trade name Repatha™ from Amgen, Inc.) and Alirocumab (tradename Praluent™ from Sanofi U.S., LLC and Regeneron Pharmaceuticals, Inc.) have been FDA approved, but are still in clinical trials to determine if they can improve outcomes in heart disease.

Variants of PCSK9 can reduce or increase circulating cholesterol. Abifadel et al., "Mutations in PCSK9 cause autosomal dominant hypercholesterolemia" Nat. Genet. 34 (2): 154-156 (2003). LDL-C is normally removed from the blood when it binds to an LDL-R on the surface of liver cells, and is internalized within the hepatocyte as a receptor-ligand complex. However, when PCSK9 binds to an LDL-R, the LDL-R is concomitantly degraded along with the complexed LDL particle. However, if a PCSK9 is not bound to an LDL-R, the LDL-R is recycled after internalization thereby returning to the surface of the cell for removal of more cholesterol.

Disclosed herein are compounds contemplated to have a modulation effect on PCSK9's ability to form an LDL-R/PCSK9 complex. In some embodiments, the compounds may bind to a PCSK9 protein and modulate the protein's biological activity. In some embodiments, compounds decrease LDL-R/PCSK9 complex formation and are thereby useful to treat various diseases involving lipid dysregulation. In some embodiments, compounds increase LDL-R/PCSK9 complex formation and are thereby useful in research and development of therapies relevant to LDL dysregulation.

Without being bound by any particular theory, it is believed that "gain-of-function" (GOF) PCSK9 mutants may result in conditions including, but not limited to, hypercholesterolemia. For example, compounds that bind to a PCSK9 and increase the affinity of PCSK9's low density lipoprotein receptor for a low density lipoprotein receptor on the surface of a cell (e.g., a hepatocyte) would be expected to increase the symptoms of hypercholesterolemia by increasing low density lipoprotein receptor internalization and degradation.

Further, and without being bound by any particular theory, it is believed that "loss-of-function" (LOF) PCSK9 mutants may result in conditions comprising reduced low density lipoproteins and would be expected to result in hypocholesterolemia thereby reducing the risk of cardiovascular diseases, including but not limited to, coronary heart disease. For example, compounds that bind to a PCSK9 that decrease the affinity of PCSK9's low density lipoprotein receptor binding site for a low density lipoprotein receptor on the surface of a cell (e.g., a hepatocyte) would be expected to reduce the symptoms of hypercholesterolemia by promoting low density lipoprotein internalization and clearance due to concomitant recycling of the low density lipoprotein receptor.

The compounds of the present disclosure are therefore useful for treating diseases and conditions mediated, at least in part by, PCSK9, including but not limited to cardiovascular diseases (e.g., a coronary disease) and metabolic diseases. For example, the compounds of the present disclosure are useful for treating diseases and conditions including, but not limited to hypercholesterolemia, atherosclerosis, and hypertension. Further, the compounds of the present disclosure are useful for reducing symptoms including, but not limited to elevated low density lipoprotein receptor density, reduced low density lipoprotein receptor density, symptoms of liver disease.

Without being bound by any particular theory, it is believed that the administration of a compound of the present disclosure, induces a conformational shift of the PCSK9 protein such that the affinity of the low density lipoprotein binding site for a low density lipoprotein receptor is decreased, wherein PCSK9/LDL-R complex formation is decreased. The decrease in PCSK9/LDL-R complex formation results in an increase in the bioavailability of LDL-R receptors for binding to circulating LDL, thereby increasing the internalization and clearance of LDL by LDL-R. It is further believed that administration of the compound may result in increased bioavailability of hepatocyte cell LDL-Rs.

Further, and also without being bound by any particular theory, it is believed that the administration of a compound of the present disclosure, induces a conformational shift of the PCSK9 protein such that the affinity of the low density lipoprotein binding site for a low density lipoprotein receptor is increased, wherein PCSK9/LDL-R complex formation is increased or stabilized. The increase or stabilization in PCSK9/LDL-R complex formation results in a decrease in the bioavailability of LDL-R receptors for binding to circulating LDL, thereby decreasing the internalization and clearance of LDL by LDL-R. It is further believed that a PCSK9 allosteric activator compound may result in decreased bioavailability of hepatocyte cell LDL-Rs.

In certain embodiments, provided herein is a method of treating a disease or condition mediated, at least in part, by PCSK9, the method comprising administering to a patient in need thereof a compound of Formula (I):

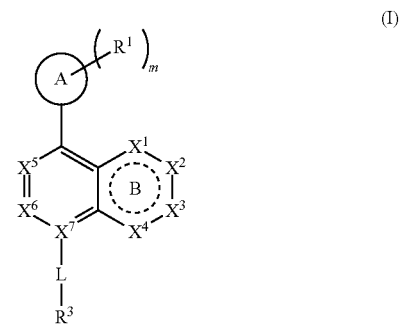

or a pharmaceutically acceptable salt, ester, prodrug, isomer, or mixture of isomers thereof;

wherein:

m is 0, 1, or 2;

$X^1$ is absent, $CR^2$, $CR^2R^2$, $C(O)$, N, $NR^2$, S, $SO_2$, or O;

$X^2$, $X^3$, and $X^4$ are each independently $CR^2$, $CR^2R^2$, $C(O)$, N, $NR^2$, S, $SO_2$, or O;

ring B is a five- or six-membered ring comprising one or more double bonds;

$X^5$ and $X^6$ are either $CR^2$ or N;

$X^7$ is C or N;

ring A is selected from:

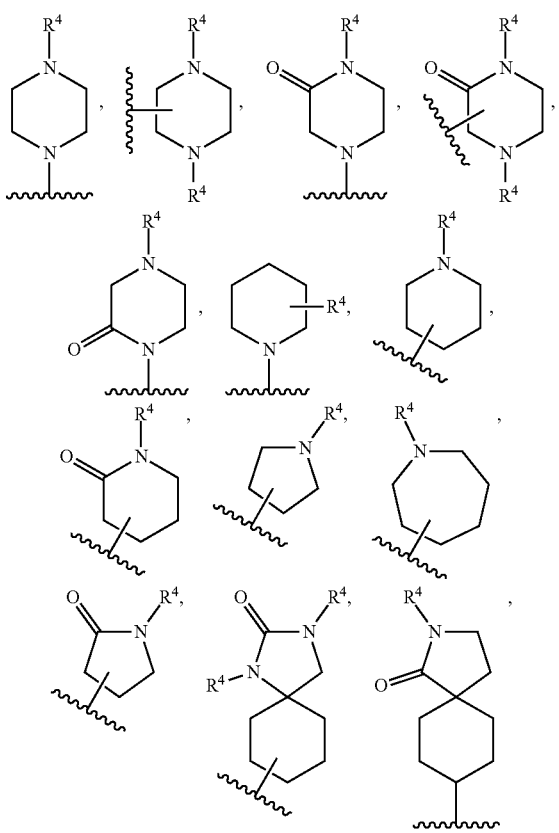

-continued

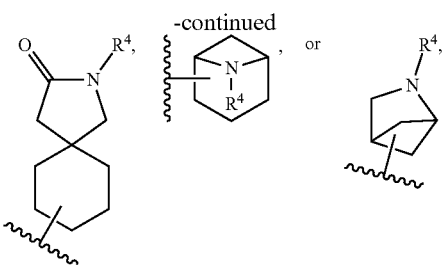

where the wavy line in ring A indicates the point of attachment to

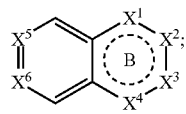

L is a bond, $C_{1-6}$-alkylene, —O—, —C(O)—, —SO$_2$—, —N(R$^a$)—, —N(R$^a$)SO$_2$—, or —SO$_2$N(R$^a$)— where R$^a$ is hydrogen, $C_{1-6}$ alkyl, or $C_{1-6}$ heteroalkyl, wherein the $C_{1-6}$ alkyl or $C_{1-6}$ heteroalkyl are optionally substituted with 1 to 3 substituents independently selected from halo, oxo, hydroxy, $C_{1-6}$ alkyl, or $C_{1-6}$ heteroalkyl;

R$^1$ in each instance is independently halo, cyano, $C_{1-6}$ alkyl optionally substituted with halo or hydroxy, $C_{3-6}$ cycloalkyl, —NR$^b$C(O)NR$^b$R$^b$, or —NR$^b$S(O)$_2$R$^b$; wherein each R$^b$ is independently hydrogen, $C_{1-6}$ alkyl, $C_{3-6}$ cycloalkyl, or $C_{2-6}$ hydroxyalkyl;

R$^2$ in each instance is independently hydrogen, halo, $C_{1-6}$ alkyl optionally substituted with halo or hydroxy, $C_{3-6}$ cycloalkyl, $C_{2-6}$ hydroxyalkyl, cyano, —C(O)OR$^c$, or —C(O)NR$^c$R$^c$;
wherein each R$^c$ is independently, hydrogen, $C_{1-6}$ alkyl, $C_{3-6}$ cycloalkyl, or $C_{2-6}$ hydroxyalkyl;

R$^3$ is hydrogen, halo, cyano, amino, $C_{1-12}$ alkyl, $C_{1-12}$ alkenyl, $C_{1-12}$ alkynyl, $C_{3-10}$ cycloalkyl, aryl, heteroalkyl, heterocyclyl, or heteroaryl;
wherein each $C_{1-12}$ alkyl, $C_{1-12}$ alkenyl, $C_{1-12}$ alkynyl, $C_{3-10}$ cycloalkyl, aryl, heteroalkyl, heterocyclyl and heteroaryl of R$^3$ is optionally substituted with 1 to 3 substituents independently selected from halo, hydroxy, cyano, $C_{1-6}$ alkyl, $C_{1-6}$ alkenyl, $C_{1-6}$ alkynyl, $C_{1-6}$ alkoxy, acyl, $C_{3-10}$ cycloalkyl, heteroalkyl, heteroaryl, heterocyclyl, aryl, oxo, —N$_3$, —NO$_2$, —N(R$^f$)$_2$, —C(O)N(R$^f$)$_2$, —C(NR$^f$)(N(R$^f$)$_2$), —NR$^f$C(O)OR$^f$, —C(O)N(R$^f$)$_2$, —CO$_2$H, —CO$_2$R$^f$, —NR$^f$C(NR$^f$)(N(R$^f$)$_2$), haloalkyl, haloalkoxy, —N(R$^f$)N(R$^f$)$_2$, —C(NR$^f$)R$^f$, —S(O)R$^f$, —SO$_2$H, —S(O)$_2$R$^f$, —SCN, —SH, or (═S), and where each R$^f$ is independently H or $C_{1-6}$ alkyl; or when X$^7$ is N, then L-R$^3$ is absent;

R$^4$ in each instance is independently hydrogen, $C_{1-6}$ alkyl, —C(O)NR$^d$R$^d$, —C(NR$^d$)NR$^d$R$^d$, —C(O)R$^d$, or —S(O)$_2$NR$^d$R$^d$;
wherein each R$^d$ is independently, hydrogen, $C_{1-6}$ alkyl, $C_{3-6}$ cycloalkyl, or $C_{2-6}$ hydroxyalkyl.

In certain embodiments, provided herein is a method of treating a disease or condition mediated, at least in part, by PCSK9, the method comprising administering to a patient in need thereof a compound of Formula (I), as defined herein, with the following provisos:
1) when m is zero then both R$^4$ and L-R$^3$ cannot be hydrogen;
2) when m is 0, R$^4$ is hydrogen, X$^1$, X$^2$, X$^3$, X$^4$ are all CH, then either L-R$^3$ is not CF$_3$ or n is not 0;
3) when X$^5$ and X$^6$ are both nitrogen, then L-R$^3$ is not hydrogen, —CH$_2$-aryl, or —CH$_2$-heteroaryl;
4) when X$^1$, X$^2$, X$^3$, and X$^4$ are all CH or X$^1$ is nitrogen and X$^2$, X$^3$, and X$^4$ are all CH, then L-R$^3$ is not —SO$_2$-aryl, wherein the aryl is optionally substituted;
5) when A is attached via a carbon atom to the remainder of the molecule, R$^1$ is not appended to the same carbon;
6) the compound is not 3-bromo-8-(4-methylpiperidin-1-yl)quinoline or 4-methyl-1-(naphthalen-1-yl)piperidine; and
7) when L-R$^3$ is hydrogen and A is piperidinyl, then R$^4$ is not C(O)NH$_2$.

In certain embodiments, provided herein is a method of treating a disease or condition mediated, at least in part, by PCSK9, the method comprising administering to a patient in need thereof a compound selected from Table 1 or a pharmaceutically acceptable salt, ester, prodrug, isomer, or mixture of isomers thereof. In certain embodiments, provided herein is a method of treating a disease or condition mediated, at least in part, by PCSK9, the method comprising administering to a patient in need thereof a compound selected from Table 2 or a pharmaceutically acceptable salt, ester, prodrug, isomer, or mixture of isomers thereof.

In certain embodiments, provided is a compound of Formula (I), as defined herein, for use in the treatment of a disease or condition mediated, at least in part, by PCSK9. In one embodiment, provided is a compound for use in the treatment of a disease or condition mediated, at least in part, by PCSK9, wherein the compound is of Formula (I), as defined herein, with the following provisos:
1) when m is zero then both R$^4$ and L-R$^3$ cannot be hydrogen;
2) when m is 0, R$^4$ is hydrogen, X$^1$, X$^2$, X$^3$, X$^4$ are all CH, then either L-R$^3$ is not CF$_3$ or n is not 0;
3) when X$^5$ and X$^6$ are both nitrogen, then L-R$^3$ is not hydrogen, —CH$_2$-aryl, or —CH$_2$-heteroaryl;
4) when X$^1$, X$^2$, X$^3$, and X$^4$ are all CH or X$^1$ is nitrogen and X$^2$, X$^3$, and X$^4$ are all CH, then L-R$^3$ is not —SO$_2$-aryl, wherein the aryl is optionally substituted;
5) when A is attached via a carbon atom to the remainder of the molecule, R$^1$ is not appended to the same carbon;
6) the compound is not 3-bromo-8-(4-methylpiperidin-1-yl)quinoline or 4-methyl-1-(naphthalen-1-yl)piperidine; and
7) when L-R$^3$ is hydrogen and A is piperidinyl, then R$^4$ is not C(O)NH$_2$.

In certain embodiments, provided is a compound of Formula (Ia), Formula (Ib), or any other Formula, as defined herein, for use in the treatment of a disease or condition mediated, at least in part, by PCSK9.

In certain embodiments, provided is use of a compound of Formula (I), as defined herein, for the treatment of a disease or condition mediated, at least in part, by PCSK9. In one embodiment, provided is a use of a compound for the treatment of a disease or condition mediated, at least in part, by PCSK9, wherein the compound is of Formula (I), as defined herein, with the following provisos:
1) when m is zero then both R$^4$ and L-R$^3$ cannot be hydrogen;
2) when m is 0, R$^4$ is hydrogen, X$^1$, X$^2$, X$^3$, X$^4$ are all CH, then either L-R$^3$ is not CF$_3$ or n is not 0;
3) when X$^5$ and X$^6$ are both nitrogen, then L-R$^3$ is not hydrogen, —CH$_2$-aryl, or —CH$_2$-heteroaryl;

4) when $X^1$, $X^2$, $X^3$, and $X^4$ are all CH or $X^1$ is nitrogen and $X^2$, $X^3$, and $X^4$ are all CH, then L-$R^3$ is not —SO$_2$-aryl, wherein the aryl is optionally substituted;

5) when A is attached via a carbon atom to the remainder of the molecule, $R^1$ is not appended to the same carbon;

6) the compound is not 3-bromo-8-(4-methylpiperidin-1-yl)quinoline or 4-methyl-1-(naphthalen-1-yl)piperidine; and 7) when L-$R^3$ is hydrogen and A is piperidinyl, then $R^4$ is not C(O)NH$_2$.

In certain embodiments, provided is use of a compound of Formula (Ia), (Ib) or any other Formula, as defined herein, for the treatment of a disease or condition mediated, at least in part, by PCSK9.

In certain embodiments, provided is use of a compound of Formula (I), as defined herein, for the manufacture of a medicament for treating a disease or condition mediated, at least in part, by PCSK9. In one embodiment, provided is a use of a compound for the manufacture of a medicament for treating a disease or condition mediated, at least in part, by PCSK9, wherein the compound is of Formula (I), as defined herein, with the following provisos:

1) when m is zero then both $R^4$ and L-$R^3$ cannot be hydrogen;

2) when m is 0, $R^4$ is hydrogen, $X^1$, $X^2$, $X^3$, $X^4$ are all CH, then either L-$R^3$ is not CF$_3$ or n is not 0;

3) when $X^5$ and $X^6$ are both nitrogen, then L-$R^3$ is not hydrogen, —CH$_2$-aryl, or —CH$_2$-heteroaryl;

4) when $X^1$, $X^2$, $X^3$, and $X^4$ are all CH or $X^1$ is nitrogen and $X^2$, $X^3$, and $X^4$ are all CH, then L-$R^3$ is not —SO$_2$-aryl, wherein the aryl is optionally substituted;

5) when A is attached via a carbon atom to the remainder of the molecule, $R^1$ is not appended to the same carbon;

6) the compound is not 3-bromo-8-(4-methylpiperidin-1-yl)quinoline or 4-methyl-1-(naphthalen-1-yl)piperidine; and 7) when L-$R^3$ is hydrogen and A is piperidinyl, then $R^4$ is not C(O)NH$_2$.

In certain embodiments, provided is use of a compound of Formula (Ia), (Ib) or any other Formula, as defined herein, for the manufacture of a medicament for treating a disease or condition mediated, at least in part, by PCSK9.

In certain embodiments, provided is a method of inhibiting the activity of PCSK9, where the method comprising binding a compound of Formula (I), as defined herein, to PCSK9, thereby inhibiting the activity of PCSK9. In certain embodiments, provided herein is a method of inhibiting the activity of PCSK9, where the method comprising binding a compound to PCSK9, thereby inhibiting the activity of PCSK9, where the compound is of Formula (I), as defined herein, with the following provisos:

1) when m is zero then both $R^4$ and L-$R^3$ cannot be hydrogen;

2) when m is 0, $R^4$ is hydrogen, $X^1$, $X^2$, $X^3$, $X^4$ are all CH, then either L-$R^3$ is not CF$_3$ or n is not 0;

3) when $X^5$ and $X^6$ are both nitrogen, then L-$R^3$ is not hydrogen, —CH$_2$-aryl, or —CH$_2$-heteroaryl;

4) when $X^1$, $X^2$, $X^3$, and $X^4$ are all CH or $X^1$ is nitrogen and $X^2$, $X^3$, and $X^4$ are all CH, then L-$R^3$ is not —SO$_2$-aryl, wherein the aryl is optionally substituted;

5) when A is attached via a carbon atom to the remainder of the molecule, $R^1$ is not appended to the same carbon;

6) the compound is not 3-bromo-8-(4-methylpiperidin-1-yl)quinoline or 4-methyl-1-(naphthalen-1-yl)piperidine; and 7) when L-$R^3$ is hydrogen and A is piperidinyl, then $R^4$ is not C(O)NH$_2$.

In certain embodiments, provided is a method of inhibiting the activity of PCSK9, where the method comprising binding a compound of Formula (Ia), (Ib) or any other Formula, as defined herein, to PCSK9, thereby inhibiting the activity of PCSK9.

In certain embodiments, provided is a method of inhibiting the activity of PCSK9, where the method comprising binding a compound, as described in Table 1 or Table 2, to PCSK9, thereby inhibiting the activity of PCSK9.

Hypercholesterolemia

Hypercholesterolemia (also spelled hypercholesterolaemia) is the presence of high levels of cholesterol in the blood. It is a form of "hyperlipidemia" (elevated levels of lipids in the blood) and "hyperlipoproteinemia" (elevated levels of lipoproteins in the blood). Durrington, P "Dyslipidaemia" The Lancet 2003; 362(9385):717-731. Hypercholesterolemia is typically due to a combination of environmental and genetic factors. Environmental factors include obesity and dietary choices. Genetic contributions are usually due to the additive effects of multiple genes, though occasionally may be due to a single gene defect such as in the case of familial hypercholesterolaemia. A number of secondary causes exist including: diabetes mellitus type 2, obesity, alcohol, monoclonal gammopathy, dialysis, nephrotic syndrome, obstructive jaundice, hypothyroidism, Cushing's syndrome, anorexia nervosa, medications (thiazide diuretics, ciclosporin, glucocorticoids, beta blockers, retinoic acid). Bhatnagar et al., (2008) "Hypercholesterolaemia and its management" BMJ 337: a993. Genetic abnormalities are in some cases completely responsible for hypercholesterolemia, such as in familial hypercholesterolemia where there is one or more genetic mutations in the autosomal dominant APOB gene, the autosomal recessive LDL-RAP1 gene, autosomal dominant familial hypercholesterolemia (HCHOLA3) variant of the PCSK9 gene, or the LDL receptor gene. "Hypercholesterolemia" Genetics Home Reference U.S. National Institutes of Health, ghr.nlm.nih.gov/condition=hypercholesterolemia. Even when there is no single mutation responsible for hypercholesterolemia, genetic predisposition still plays a major role in combination with sedentary lifestyle, obesity, or an atherogenic diet. Citkowitz et al., (2010) "Polygenic Hypercholesterolemia". eMedicine Medscape, emedicine.medscape.com/article/121424-overview.

Cholesterol is a sterol. It is one of three major classes of lipids which all animal cells utilize to construct their membranes and is thus manufactured by all animal cells. Plant cells do not manufacture cholesterol. It is also the precursor of the steroid hormones, bile acids and vitamin D. Since cholesterol is insoluble in water, it is transported in the blood plasma within protein particles (lipoproteins). Lipoproteins are classified by their density: very low density lipoprotein (VLDL), intermediate density lipoprotein (IDL), low density lipoprotein (LDL) and high density lipoprotein (HDL). Biggerstaff et al., (2004). "Understanding lipoproteins as transporters of cholesterol and other lipids" Adv Physiol Educ 28 (1-4): 105-6. All the lipoproteins carry cholesterol, but elevated levels of the lipoproteins other than HDL (termed non-HDL cholesterol), particularly LDL-cholesterol are associated with an increased risk of atherosclerosis and coronary heart disease. Carmena et al., (2004) "Atherogenic lipoprotein particles in atherosclerosis" Circulation 109(23 Suppl 1): III 2-7. In contrast, higher levels of HDL cholesterol are protective. Kontush et al., (2006) "Antiatherogenic small, dense HDL—guardian angel of the arterial wall?" Nat Clin Pract Cardiovasc Med 3(3):144-153. Elevated levels of non-HDL cholesterol and LDL in the blood may be a consequence of diet, obesity, inherited (genetic) diseases (such as LDL receptor mutations in familial hypercholesterolemia), or the presence of other diseases such as diabetes and an underactive thyroid. Total cholesterol is the amount of all of the fats in your blood. These fats are called lipids.

There are different types of lipid that make up your total cholesterol. The two most important types are: low density lipoprotein (LDL)—"bad" cholesterol and high density lipoprotein (HDL)—"good" cholesterol. High cholesterol, especially "bad" cholesterol (LDL), can clog your arteries. This may reduce blood flow to your heart. It can lead to heart disease, stroke, or heart attack. Cholesterol is measured in milligrams per deciliter (mg/dL). In conditions such as heart disease or diabetes, LDL cholesterol should stay below 100 mg/dL. If there is a risk for heart disease, LDL cholesterol should be lower than 130 mg/dL. In general, LDL cholesterol should be lower than 160-190 mg/dL. Alternative, HDL "good" cholesterol should be high. For example, HDL levels in men should be above 40 mg/dL, while HDL levels should be above 50 mg/dL for women.

One symptom of hypercholesterolemia comprises a long-standing elevation of serum cholesterol that can lead to atherosclerosis. Bhatnagar et al., (2008) "Hypercholesterolaemia and its management" *BMJ* 337: a993. Over a period of decades, chronically elevated serum cholesterol contributes to formation of atheromatous plaques in the arteries. This can lead to progressive stenosis (narrowing) or even complete occlusion (blockage) of the involved arteries. Alternatively smaller plaques may rupture and cause a clot to form and obstruct blood flow. Finn A V, Nakano M, Narula J, Kolodgie F D, Virmani R (July 2010). "Concept of vulnerable/unstable plaque" *Arterioscler. Thromb. Vasc. Biol.* 30(7): 1282-1292. A sudden occlusion of a coronary artery results in a myocardial infarction or heart attack. An occlusion of an artery supplying the brain can cause a stroke. If the development of the stenosis or occlusion is gradual blood supply to the tissues and organs slowly diminishes until organ function becomes impaired. At this point that tissue ischemia (restriction in blood supply) may manifest as specific symptoms including, but not limited to, temporary ischemia of the brain (commonly referred to as a transient ischemic attack) may manifest as temporary loss of vision, dizziness and impairment of balance, aphasia (difficulty speaking), paresis (weakness) and paresthesia (numbness or tingling), usually on one side of the body. Insufficient blood supply to the heart may manifest as chest pain, and ischemia of the eye may manifest as transient visual loss in one eye. Insufficient blood supply to the legs may manifest as calf pain when walking, while in the intestines it may present as abdominal pain after eating a meal. Grundy et al., (1998) "Primary prevention of coronary heart disease: guidance from Framingham: a statement for healthcare professionals from the AHA Task Force on Risk Reduction. American Heart Association" *Circulation* 97(18):1876-1887.

Hypocholesterolemia

Hypocholesterolemia is the presence of abnormally low (hypo-) levels of cholesterol in the blood (-emia). Although the presence of high total cholesterol (hyper-cholesterolemia) correlates with cardiovascular disease, a defect in the body's production of cholesterol can lead to adverse consequences as well. Cholesterol is an essential component of mammalian cell membranes and is required to establish proper membrane permeability and fluidity. It is not clear if a lower than average cholesterol level is directly harmful; it is often encountered in particular illnesses.

Possible causes of low cholesterol include, but are not limited to, statins, hyperthyroidism, or an overactive thyroid gland, adrenal insufficiency, liver disease, malabsorption (inadequate absorption of nutrients from the intestines), such as in celiac disease, malnutrition, abetalipoproteinemia (a genetic disease that causes cholesterol readings below 50 mg/dl), hypobetalipoproteinemia (a genetic disease that causes cholesterol readings below 50 mg/dl, manganese deficiency, Smith-Lemli-Opitz syndrome, Marfan syndrome, leukemias and other hematological diseases.

Demographic studies suggest that low cholesterol is associated with increased mortality, mainly due to depression, cancer, hemorrhagic stroke, aortic dissection and respiratory diseases. Jacobs et al., (1992). "Report of the Conference on Low Blood Cholesterol: Mortality Associations" *Circulation* 86 (3): 1046-1060; and Suarez E. C., (1999) "Relations of trait depression and anxiety to low lipid and lipoprotein concentrations in healthy young adult women". *Psychosom Med* 61(3): 273-279. It is also possible that whatever causes the low cholesterol level also causes mortality, and that the low cholesterol is simply a marker of poor health.

Diabetes

Diabetes affects more than 20 million Americans. Over 40 million Americans have pre-diabetes (which often develops before type 2 diabetes). Diabetes is usually a lifelong (chronic) disease in which there is a high level of sugar in the blood. Insulin is a hormone produced by the pancreas to control blood sugar. Diabetes can be caused by too little insulin, resistance to insulin, or both. To understand diabetes, it is important to first understand the normal process by which food is broken down and used by the body for energy.

Several things happen when food is digested. A sugar called glucose enters the bloodstream. Glucose is a source of fuel for the body. An organ called the pancreas makes insulin. The role of insulin is to move glucose from the bloodstream into muscle, fat, and liver cells, where it can be used as fuel.

People with diabetes have high blood sugar because their body cannot move sugar into fat, liver, and muscle cells to be stored for energy. This is because either their pancreas does not make enough insulin or their cells do not respond to insulin normally.

There are two major types of diabetes. The causes and risk factors are different for each type. Type 1 diabetes can occur at any age, but it is most often diagnosed in children, teens, or young adults. In this disease, the body makes little or no insulin. Daily injections of insulin are needed. The exact cause is unknown. Type 2 diabetes makes up most diabetes cases. It most often occurs in adulthood. But because of high obesity rates, teens and young adults are now being diagnosed with it. Many people with type 2 diabetes do not know they have it.

Gestational diabetes is high blood sugar that develops at any time during pregnancy in a woman who does not have diabetes.

Diabetes symptoms may result from high blood sugar level and include, but are not limited to, blurry vision, excess thirst, fatigue, hunger, urinating often and weight loss.

Combination Therapy

Patients being treated by administration of the compounds of the disclosure often exhibit diseases or conditions that benefit from treatment with other therapeutic agents. These diseases or conditions can be of cardiovascular nature or can be related to pulmonary disorders, metabolic disorders, gastrointestinal disorders and the like.

Cardiovascular Agent Combination Therapy

Cardiovascular related diseases or conditions that can benefit from a combination treatment of the compounds of the disclosure with other therapeutic agents include, without limitation, angina including stable angina, unstable angina (UA), exercised-induced angina, variant angina, arrhythmias, intermittent claudication, myocardial infarction including non-STE myocardial infarction (NSTEMI), pulmonary hypertension including pulmonary arterial hypertension, heart failure including congestive (or chronic) heart failure and diastolic heart failure and heart failure with preserved ejection fraction (diastolic dysfunction), acute heart failure, or recurrent ischemia.

Therapeutic agents suitable for treating cardiovascular related diseases or conditions include anti-anginals, heart failure agents, antithrombotic agents, antiarrhythmic agents, antihypertensive agents, and lipid lowering agents.

The co-administration of the compounds of the disclosure with therapeutic agents suitable for treating cardiovascular related conditions allows enhancement in the standard of care therapy the patient is currently receiving. In some embodiments, the compounds of the disclosure are co-administered with ranolazine (RANEXA®).

Anti-Anginals

Anti-anginals include beta-blockers, calcium channel blockers, and nitrates. Beta blockers reduce the heart's need for oxygen by reducing its workload resulting in a decreased heart rate and less vigorous heart contraction. Examples of beta-blockers include acebutolol (Sectral®), atenolol (Tenormin®), betaxolol (Kerlone®), bisoprolol/hydrochlorothiazide (Ziac®), bisoprolol (Zebeta®), carteolol (Cartrol®), esmolol (Brevibloc®), labetalol (Normodyne®, Trandate®), metoprolol (Lopressor®, Toprol® XL), nadolol (Corgard®), propranolol (Inderal®), sotalol (Betapace®), and timolol (Blocadren®).

Nitrates dilate the arteries and veins thereby increasing coronary blood flow and decreasing blood pressure. Examples of nitrates include nitroglycerin, nitrate patches, isosorbide dinitrate, and isosorbide-5-mononitrate.

Calcium channel blockers prevent the normal flow of calcium into the cells of the heart and blood vessels causing the blood vessels to relax thereby increasing the supply of blood and oxygen to the heart. Examples of calcium channel blockers include amlodipine (Norvasc®, Lotrel®), bepridil (Vascor®), diltiazem (Cardizem®, Tiazac®), felodipine (Plendil®), nifedipine (Adalat®, Procardia®), nimodipine (Nimotop®), nisoldipine (Sular®), verapamil (Calan®, Isoptin®, Verelan®), and nicardipine.

Heart Failure Agents

Agents used to treat heart failure include diuretics, ACE inhibitors, vasodilators, and cardiac glycosides. Diuretics eliminate excess fluids in the tissues and circulation thereby relieving many of the symptoms of heart failure. Examples of diuretics include hydrochlorothiazide, metolazone (Zaroxolyn®), furosemide (Lasix®), bumetanide (Bumex®), spironolactone (Aldactone®), and eplerenone (Inspra®).

Angiotensin converting enzyme (ACE) inhibitors reduce the workload on the heart by expanding the blood vessels and decreasing resistance to blood flow. Examples of ACE inhibitors include benazepril (Lotensin®), captopril (Capoten®), enalapril (Vasotec®), fosinopril (Monopril®), lisinopril (Prinivil®, Zestril®), moexipril (Univasc®), perindopril (Aceon®), quinapril (Accupril®), ramipril (Altace®), and trandolapril (Mavik®).

Vasodilators reduce pressure on the blood vessels by making them relax and expand. Examples of vasodilators include hydralazine, diazoxide, prazosin, clonidine, and methyldopa. ACE inhibitors, nitrates, potassium channel activators, and calcium channel blockers also act as vasodilators.

Cardiac glycosides are compounds that increase the force of the heart's contractions. These compounds strengthen the pumping capacity of the heart and improve irregular heartbeat activity. Examples of cardiac glycosides include digitalis, digoxin, and digitoxin.

Antithrombotic Agents

Antithrombotics inhibit the clotting ability of the blood. There are three main types of antithrombotics—platelet inhibitors, anticoagulants, and thrombolytic agents.

Platelet inhibitors inhibit the clotting activity of platelets, thereby reducing clotting in the arteries. Examples of platelet inhibitors include acetylsalicylic acid (aspirin), ticlopidine, clopidogrel (Plavix®), prasugrel (Effient®), dipyridamole, cilostazol, persantine sulfinpyrazone, dipyridamole, indomethacin, and glycoprotein IIb/IIIa inhibitors, such as abciximab, tirofiban, and eptifibatide (Integrelin®). Beta blockers and calcium channel blockers also have a platelet-inhibiting effect.

Anticoagulants prevent blood clots from growing larger and prevent the formation of new clots. Examples of anticoagulants include bivalirudin (Angiomax®), warfarin (Coumadin®), unfractionated heparin, low molecular weight heparin, danaparoid, lepirudin, and argatroban.

Thrombolytic agents act to break down an existing blood clot. Examples of thrombolytic agents include streptokinase, urokinase, and tenecteplase (TNK), and tissue plasminogen activator (t-PA).

Antiarrhythmic Agents

Antiarrhythmic agents are used to treat disorders of the heart rate and rhythm. Examples of antiarrhythmic agents include amiodarone, dronedarone, quinidine, procainamide, lidocaine, and propafenone. Cardiac glycosides and beta blockers are also used as antiarrhythmic agents.

Combinations with amiodarone and dronedarone are of particular interest (see U.S. Patent Application Publication No. 2010/0056536 and U.S. Patent Application Publication No. 2011/0183990, the entirety of which are incorporated herein).

Antihypertensive Agents

Antihypertensive agents are used to treat hypertension, a condition in which the blood pressure is consistently higher than normal. Hypertension is associated with many aspects of cardiovascular disease, including congestive heart failure, atherosclerosis, and clot formation. Examples of antihypertensive agents include alpha-1-adrenergic antagonists, such as prazosin (Minipress®), doxazosin mesylate (Cardura®), prazosin hydrochloride (Minipress®), prazosin, polythiazide (Minizide®), and terazosin hydrochloride (Hytrin®); beta-adrenergic antagonists, such as propranolol (Inderal®), nadolol (Corgard®), timolol (Blocadren®), metoprolol (Lopressor®), and pindolol (Visken®); central alpha-adrenoceptor agonists, such as clonidine hydrochloride (Catapres®), clonidine hydrochloride and chlorthalidone (Clorpres®, Combipres®), guanabenz Acetate (Wytensin®), guanfacine hydrochloride (Tenex®), methyldopa (Aldomet®), methyldopa and chlorothiazide (Aldoclor®), methyldopa and hydrochlorothiazide (Aldoril®); combined alpha/beta-adrenergic antagonists, such as labetalol (Normodyne®, Trandate®), carvedilol (Coreg®); adrenergic neuron blocking agents, such as guanethidine (Ismelin®), reserpine (Serpasil®); central nervous system-acting antihypertensives, such as clonidine (Catapres®), methyldopa (Aldomet®), guanabenz (Wytensin®); anti-angiotensin II agents; ACE inhibitors, such as perindopril (Aceon®) captopril (Capoten®), enalapril (Vasotec®), lisinopril (Prinivil®, Zestril®); angiotensin-II receptor antagonists, such as candesartan (Atacand®), eprosartan (Teveten®), irbesartan (Avapro®), losartan (Cozaar®), telmisartan (Micardis®), valsartan (Diovan®); calcium channel blockers, such as verapamil (Calan®, Isoptin®), diltiazem (Cardizem®), nifedipine (Adalat®, Procardia®); diuretics; direct vasodilators, such as nitroprusside (Nipride®), diazoxide (Hyperstat® IV), hydralazine (Apresoline®), minoxidil (Loniten®), verapamil; and potassium channel activators, such as aprikalim, bimakalim, cromakalim, emakalim, nicorandil, and pinacidil.

Lipid Lowering Agents

Lipid lowering agents are used to lower the amounts of cholesterol or fatty sugars present in the blood. Examples of lipid lowering agents include bezafibrate (Bezalip®), ciprofibrate (Modalim®), and statins, such as atorvastatin (Lipitor®), fluvastatin (Lescol®), lovastatin (Mevacor®, Altocor®), mevastatin, pitavastatin (Livalo®, Pitava®) pravastatin (Lipostat®), rosuvastatin (Crestor®), and simvastatin (Zocor®).

PCSK9 Inhibitors

Drugs that block PCSK9 biological actions are believed to lower circulating low-density lipoprotein cholesterol (LDL-C) levels (e.g., by increasing the availability of LDL-Rs and, consequently, LDL-C clearance). Examples include FDA approved Evolocumab (trade name Repatha™ from Amgen, Inc.) and FDA approved Alirocumab (tradename Praluent™ from Sanofi U.S., LLC and Regeneron Pharmaceuticals, Inc.).

Additional Combination Therapies

A patient presenting with an acute coronary disease event often suffers from secondary medical conditions such as one or more of a metabolic disorder, a pulmonary disorder, or a peripheral vascular disorder. Such patients can benefit from treatment of a combination therapy comprising administering to the patient a compound of the disclosure in combination with at least one therapeutic agent.

Pulmonary Disorders Combination Therapy

Pulmonary disorder refers to any disease or condition related to the lungs. Examples of pulmonary disorders include, without limitation, asthma, chronic obstructive pulmonary disease (COPD), bronchitis, and emphysema.

Examples of therapeutics agents used to treat pulmonary disorders include bronchodilators including beta2 agonists and anticholinergics, corticosteroids, and electrolyte supplements. Specific examples of therapeutic agents used to treat pulmonary disorders include epinephrine, terbutaline (Brethaire®, Bricanyl®), albuterol (Proventil®), salmeterol (Serevent®, Serevent Diskus®), theophylline, ipratropium bromide (Atrovent®), tiotropium (Spiriva®), methylprednisolone (Solu-Medrol®, Medrol®), magnesium, and potassium.

Metabolic Disorders Combination Therapy

Examples of metabolic disorders include, without limitation, diabetes, including type I and type II diabetes, metabolic syndrome, dyslipidemia, obesity, glucose intolerance, hypertension, elevated serum cholesterol, and elevated triglycerides.

Examples of therapeutic agents used to treat metabolic disorders include antihypertensive agents and lipid lowering agents, as described in the section "Cardiovascular Agent Combination Therapy" above. Additional therapeutic agents used to treat metabolic disorders include insulin, sulfonylureas, biguanides, alpha-glucosidase inhibitors, and incretin mimetics.

Peripheral Vascular Disorders Combination Therapy

Peripheral vascular disorders are disorders related to the blood vessels (arteries and veins) located outside the heart and brain, including, for example peripheral arterial disease (PAD), a condition that develops when the arteries that supply blood to the internal organs, arms, and legs become completely or partially blocked as a result of atherosclerosis.

Accordingly, one aspect of the disclosure provides for a composition comprising the compounds of the disclosure and at least one therapeutic agent. In an alternative embodiment, the composition comprises the compounds of the disclosure and at least two therapeutic agents. In further alternative embodiments, the composition comprises the compounds of the disclosure and at least three therapeutic agents, the compounds of the disclosure and at least four therapeutic agents, or the compounds of the disclosure and at least five therapeutic agents.

The methods of combination therapy include co-administration of a single formulation containing the compounds of the disclosure and therapeutic agent or agents, essentially contemporaneous administration of more than one formulation comprising the compounds of the disclosure and therapeutic agent or agents, and consecutive administration of a compound of the disclosure and therapeutic agent or agents, in any order, wherein preferably there is a time period where the compounds of the disclosure and therapeutic agent or agents simultaneously exert their therapeutic effect.

These and other embodiments of the present disclosure will readily occur to those of ordinary skill in the art in view of the disclosure herein and are specifically contemplated.

5. Kits

Provided herein are also kits that include a compound of the disclosure, or a pharmaceutically acceptable salt, tautomer, stereoisomer, mixture of stereoisomers, prodrug, or deuterated analog thereof, and suitable packaging. In one embodiment, a kit further includes instructions for use. In one aspect, a kit includes a compound of the disclosure, or a pharmaceutically acceptable salt, tautomer, stereoisomer, mixture of stereoisomers, prodrug, or deuterated analog thereof, and a label and/or instructions for use of the compounds in the treatment of the indications, including the diseases or conditions, described herein.

Provided herein are also articles of manufacture that include a compound described herein or a pharmaceutically acceptable salt, tautomer, stereoisomer, mixture of stereoisomers, prodrug, or deuterated analog thereof in a suitable container. The container may be a vial, jar, ampoule, preloaded syringe, and intravenous bag.

6. Pharmaceutical Compositions and Modes of Administration

Compounds provided herein are usually administered in the form of pharmaceutical compositions. Thus, provided herein are also pharmaceutical compositions that contain one or more of the compounds described herein or a pharmaceutically acceptable salt, tautomer, stereoisomer, mixture of stereoisomers, prodrug, or deuterated analog thereof and one or more pharmaceutically acceptable vehicles selected from carriers, adjuvants and excipients. Suitable pharmaceutically acceptable vehicles may include, for example, inert solid diluents and fillers, diluents, including sterile aqueous solution and various organic solvents, permeation enhancers, solubilizers and adjuvants. Such compositions are prepared in a manner well known in the pharmaceutical art. See, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.).

The pharmaceutical compositions may be administered in either single or multiple doses. The pharmaceutical composition may be administered by various methods including, for example, rectal, buccal, intranasal and transdermal routes. In certain embodiments, the pharmaceutical composition may be administered by intra-arterial injection, intravenously, intraperitoneally, parenterally, intramuscularly, subcutaneously, orally, topically, or as an inhalant.

One mode for administration is parenteral, for example, by injection. The forms in which the pharmaceutical compositions described herein may be incorporated for administration by injection include, for example, aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Oral administration may be another route for administration of the compounds described herein. Administration may be via, for example, capsule or enteric coated tablets. In making the pharmaceutical compositions that include at least one compound described herein or a pharmaceutically acceptable salt, tautomer, stereoisomer, mixture of stereoisomers, prodrug, or deuterated analog thereof, the active ingredient is usually diluted by an excipient and/or enclosed within such a carrier that can be in the form of a capsule, sachet, paper or other container. When the excipient serves as a diluent, it can be in the form of a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include lubricating agents such as talc, magnesium stearate, and mineral oil; wetting agents; emulsifying and suspending agents; preserving agents such as methyl and propylhydroxy-benzoates; sweetening agents; and flavoring agents.

The compositions that include at least one compound described herein or a pharmaceutically acceptable salt, tautomer, stereoisomer, mixture of stereoisomers, prodrug, or deuterated analog thereof can be formulated so as to provide quick, sustained or delayed release of the active ingredient after administration to the subject by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods disclosed herein employ transdermal delivery devices ("patches"). Such transdermal patches may be used to provide continuous or discontinuous infusion of the compounds described herein in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

For preparing solid compositions such as tablets, the principal active ingredient may be mixed with a pharmaceutical excipient to form a solid preformulation composition containing a homogeneous mixture of a compound described herein or a pharmaceutically acceptable salt, tautomer, stereoisomer, mixture of stereoisomers, prodrug, or deuterated analog thereof. When referring to these preformulation compositions as homogeneous, the active ingredient may be dispersed evenly throughout the composition so that the composition may be readily subdivided into equally effective unit dosage forms such as tablets, pills and capsules.

The tablets or pills of the compounds described herein may be coated or otherwise compounded to provide a dosage form affording the advantage of prolonged action, or to protect from the acid conditions of the stomach. For example, the tablet or pill can include an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation may include solutions and suspensions in pharmaceutically acceptable, aqueous or organic solvents, or mixtures thereof, and powders. The liquid or solid compositions may contain suitable pharmaceutically acceptable excipients as described herein. In some embodiments, the compositions are administered by the oral or nasal respiratory route for local or systemic effect. In other embodiments, compositions in pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

7. Dosing

The specific dose level of a compound of the present application for any particular subject will depend upon a variety of factors including the activity of the specific compound employed, the age, body weight, general health, sex, diet, time of administration, route of administration, and rate of excretion, drug combination and the severity of the particular disease in the subject undergoing therapy. For example, a dosage may be expressed as a number of milligrams of a compound described herein per kilogram of the subject's body weight (mg/kg). Dosages of between about 0.1 and 150 mg/kg may be appropriate. In some embodiments, about 0.1 and 100 mg/kg may be appropriate. In other embodiments a dosage of between 0.5 and 60 mg/kg may be appropriate. Normalizing according to the subject's body weight is particularly useful when adjusting dosages between subjects of widely disparate size, such as occurs when using the drug in both children and adult humans or when converting an effective dosage in a non-human subject such as dog to a dosage suitable for a human subject.

The daily dosage may also be described as a total amount of a compound described herein administered per dose or per day. Daily dosage of a compound of Formula I may be between about 1 mg and 4,000 mg, between about 2,000 to 4,000 mg/day, between about 1 to 2,000 mg/day, between about 1 to 1,000 mg/day, between about 10 to 500 mg/day, between about 20 to 500 mg/day, between about 50 to 300 mg/day, between about 75 to 200 mg/day, or between about 15 to 150 mg/day.

When administered orally, the total daily dosage for a human subject may be between 1 mg and 1,000 mg, between about 1,000-2,000 mg/day, between about 10-500 mg/day, between about 50-300 mg/day, between about 75-200 mg/day, or between about 100-150 mg/day.

The compounds of the present application or the compositions thereof may be administered once, twice, three, or four times daily, using any suitable mode described above. Also, administration or treatment with the compounds may be continued for a number of days; for example, commonly treatment would continue for at least 7 days, 14 days, or 28 days, for one cycle of treatment. Treatment cycles are well known in cancer chemotherapy, and are frequently alternated with resting periods of about 1 to 28 days, commonly about 7 days or about 14 days, between cycles. The treatment cycles, in other embodiments, may also be continuous.

In a particular embodiment, the method comprises administering to the subject an initial daily dose of about 1 to 800 mg of a compound described herein and increasing the dose by increments until clinical efficacy is achieved. Increments of about 5, 10, 25, 50, or 100 mg can be used to increase the dose. The dosage can be increased daily, every other day, twice per week, or once per week.

8. Synthesis of the Compounds

The compounds may be prepared using the methods disclosed herein and routine modifications thereof, which will be apparent given the disclosure herein and methods well known in the art. Conventional and well-known synthetic methods may be used in addition to the teachings herein. The synthesis of typical compounds described herein may be accomplished as described in the following examples. If available, reagents may be purchased commercially, e.g., from Sigma Aldrich or other chemical suppliers.

The compounds of this disclosure can be prepared from readily available starting materials using, for example, the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in Wuts, P. G. M., Greene, T. W., & Greene, T. W. (2006). *Greene's protective groups in organic synthesis.* Hoboken, N.J., Wiley-Interscience, and references cited therein.

Furthermore, the compounds of this disclosure may contain one or more chiral centers. Accordingly, if desired, such compounds can be prepared or isolated as pure stereoisomers, i.e., as individual enantiomers or diastereomers or as stereoisomer-enriched mixtures. All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wisconsin, USA), Bachem (Torrance, California, USA), Emka-Chemce or Sigma (St. Louis, Missouri, USA). Others may be prepared by procedures or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989) organic Reactions, Volumes 1-40 (John Wiley, and Sons, 1991), March's Advanced Organic Chemistry, (John Wiley, and Sons, $5^{th}$ Edition, 2001), Larock's Comprehensive Organic Transformations (VCH Publishers Inc., 1989), Heterocyclic Chemistry (Blackwell Publishing, $4^{th}$ Edition, 2002), Vogel's Textbook of Practical Organic Chemistry (Prentice Hall, $5^{th}$ Edition, 1996).

The terms "solvent," "inert organic solvent" or "inert solvent" refer to a solvent inert under the conditions of the reaction being described in conjunction therewith (including, for example, benzene, toluene, acetonitrile, tetrahydrofuran ("THF"), dimethylformamide ("DMF"), chloroform, methylene chloride (or dichloromethane), diethyl ether, methanol, pyridine and the like).

Scheme 1 shows exemplary synthetic routes (Route A and Route B) for preparing compounds of Formula I, wherein ring A, $X^1$, $X^2$, $X^3$, $X^4$, $X^5$, $X^6$, $R^1$, $R^2$, $R^3$, m, n, and L are as defined herein and $Z^1$, $Z^2$, $Z^3$, and $Z^4$ are functional groups suitable for coupling reactions (e.g., halogen, hydroxyl, etc.).

Scheme 1

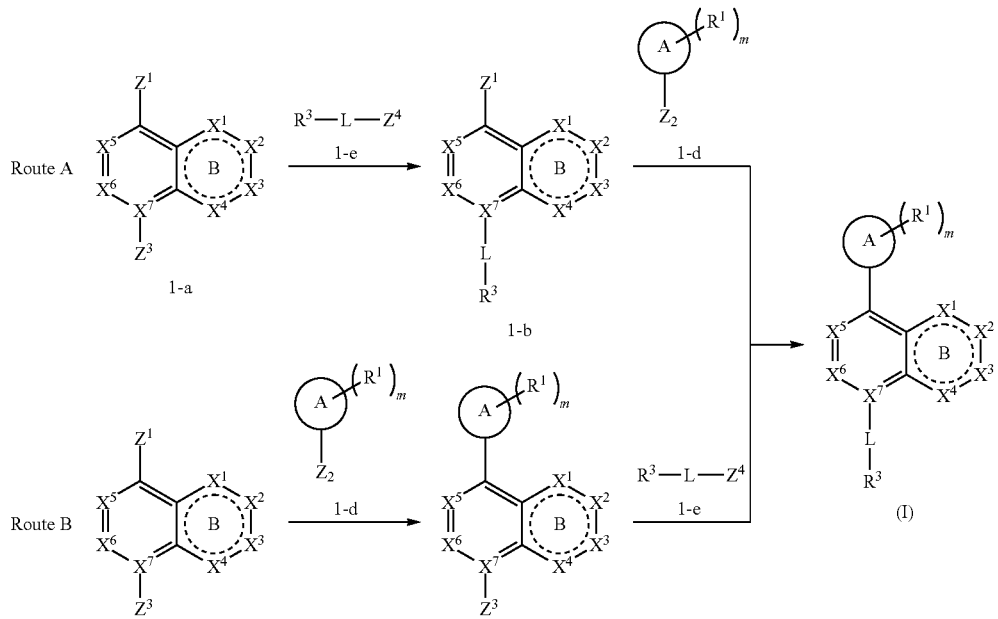

In Scheme 1, Route A, compound 1-b can be provided by contacting compound 1-a with compound 1-e under reaction conditions suitable for coupling, where $Z^3$ and $Z^4$ are functional groups that are complementary with respect to a particular coupling reaction. Compounds of formula I can then be provided from compound 1-b by contacting compound 1-b with compound 1-d under reaction conditions suitable for coupling, where $Z^1$ and $Z^2$ are functional groups that are complementary with respect to a particular coupling reaction. For example, the coupling can be a cross coupling reaction, such as a Heck reaction, Negishi coupling, Stille coupling, Suzuki reaction, Kumada coupling, and the like.

In Scheme 1, Route B, compound 1-c can be provided by contacting compound 1-a with compound 1-d under reaction conditions suitable for coupling, where $Z^1$ and $Z^2$ are functional groups that are complementary with respect to a particular coupling reaction. For example, the coupling can be a cross coupling reaction, such as a Heck reaction, Negishi coupling, Stille coupling, Suzuki reaction, Kumada coupling, and the like. Compounds of formula I can then be provided from compound 1-c by contacting compound 1-e with compound 1-e under reaction conditions suitable for coupling, where $Z^3$ and $Z^4$ are functional groups that are complementary with respect to a particular coupling reaction.

Alternatively, compounds of formula I where L is a bond and $R^3$ is a heterocyclic ring bound to the core via nitrogen can be prepared according to Scheme 2, where the aminated core is reacted with compound 1-f under alkylation reaction conditions. In Scheme 2, $X^1$, $X^2$, $X^3$, $X^4$, $X^5$, $X^6$, $R^2$, and n are as defined herein, each $Z^5$ is a leaving group (e.g., chloro, bromo, iodo, or any other suitable leaving group) and $R^{13}$ is an alkylene or heteroalkylene.

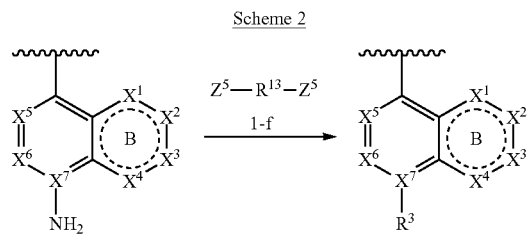

Scheme 2

It will be appreciated that any one of compounds 1-a, 1-b, 1-c, 1-d, 1-e, or 1-f may be purchased from commercial sources or prepared according to literature methods available to the skilled artisan, and may be optionally further functionalized (e.g., with one or more $R^2$ moieties) for use in Scheme 1 or Scheme 2.

EXAMPLES

The following examples are included to demonstrate specific embodiments of the disclosure. It should be appreciated by those of skill in the art that the techniques disclosed in the examples which follow represent techniques to function well in the practice of the disclosure, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the disclosure.

Unless otherwise stated all temperatures are in degrees Celsius (° C.).

As indicated in certain example below, certain synthetic processes were monitored by at least one of the following LCMS methods.

Method 1 employed an Acquity BEH C-18 (2.1×100 mm, 1.7 um) column eluting with 5 mM ammonium acetate in water (solvent A) and acetonitrile (solvent B) using the following elution gradient: 0-1.0 min 10% B, 1.0-2.0 min 15% B, 2.0-4.5 min 55% B, 4.5-6.0 min 90% B, 6.0-8.0 min 90B, 8.0-9.0 min 10% B, 9.0-10.0 min 10% B at a flow rate of 0.3 ml/min and a column temperature of 30° C.

Method 2 employed an Acquity BEH C-18 (2.1×100 mm, 1.7 um) column eluting with 5 mM ammonium acetate in water (solvent A) and acetonitrile (solvent B) using the following elution gradient: 0-2.0 min 2% B, 2.0-6.0 min 50% B, 6.0-7.0 min 80% B, 7.0-8.5 min 2% B, 8.5-10.0 min 2% B at a flow rate of 0.3 ml/min and a column temperature of 30° C.

Method 3 employed a Kinetex C-18 (2.1×100 mm, 1.7 um) column eluting with 0.01% TFA in water (solvent A) and acetonitrile (solvent B) using the following elution gradient: 0-10 min 5% B-90% B, 10.0-15.0 min 90% B, at a flow rate of 0.5 ml/min and a column temperature of 30° C.

Example 1

1-(4-(Trifluoromethyl)naphthalen-1-yl)piperazine (1)

a) 1-bromo-4-(trifluoromethyl)naphthalene

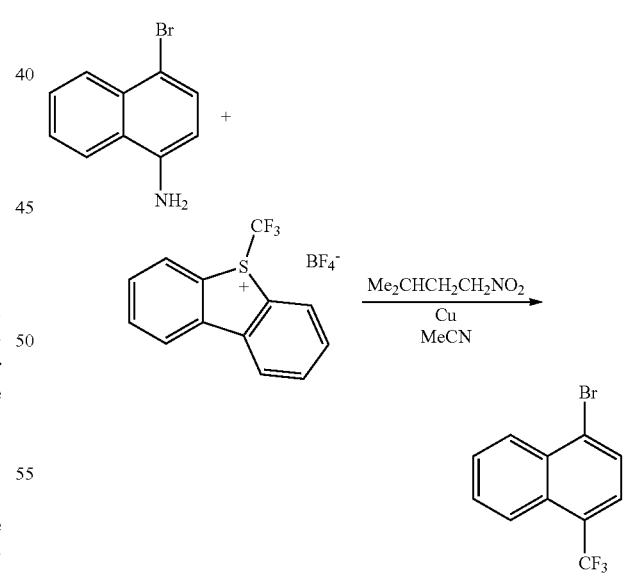

Place 4-bromonaphthalen-1-amine (1 mmol), 5-(trifluoromethyl)dibenzothiophenium tetrafluoroborate (1.5 mmol), and copper powder (3.0 mmol) in a Schlenk tube. Evacuate and backfill the Schlenk tube with argon three times and then cool to 0° C. Add acetonitrile and isoamyl nitrite (3.0 mmol) to the resulting mixture and stir for 8 h. Purify the mixture by flash chromatography to prepare the title compound.

b) Tert-butyl 4-(4-(trifluoromethyl)naphthalen-1-yl)piperazine-1-carboxylate

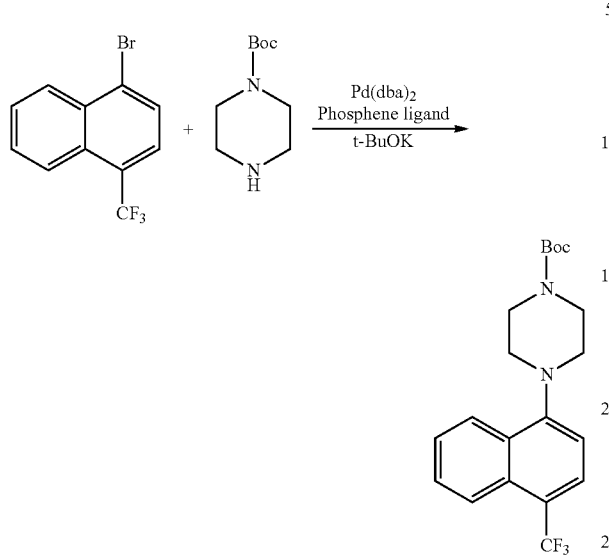

Dissolve 1-bromo-4-(trifluoromethyl)naphthalene (1.00 mmol), tert-butyl piperazine-1-carboxylate (1.20 mmol), Pd$_2$(dba)$_3$ (0.05 mmol), BINAP (0.15 mmol), and NaO$^t$Bu (1.40 mmol) in toluene and degas the resulting solution under a stream of argon. Heat the reaction mixture to 80° C. for 8 h and subsequently cool to room temperature. Dilute the solution with ethyl acetate and wash with brine. Separate the organic phase, dry over sodium sulfate, filter, and concentrate the filtrate under vacuum. Purify the resulting by flash chromatography to prepare the title compound.

c) 1-(4-(trifluoromethyl)naphthalen-1-yl)piperazine

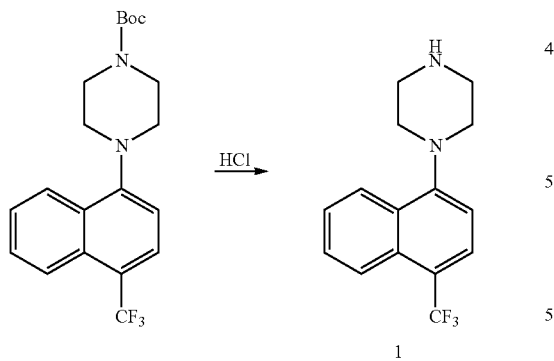

Dissolve tert-butyl 4-(4-(trifluoromethyl)naphthalen-1-yl)piperazine-1-carboxylate (1.00 mmol) in HCl/dioxane (4 N) and stir the resulting solution at room temperature for 2 h. Concentrate the mixture under vacuum and purify the residue by reverse phase chromatography to prepare the title compound.

1-(4-(Trifluoromethyl)naphthalen-1-yl)piperazine (1) can also be prepared via the following alternative synthesis.

a) 1-bromo-4-(trifluoromethyl)naphthalene

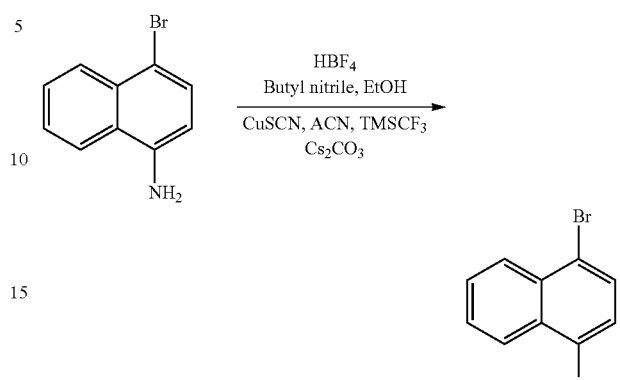

To a stirred solution of 4-bromonaphthalen-1-amine (500 mg, 2.252 mmol) dissolved in a mixture of EtOH (1 ml) and 50% aq. HBF$_4$ (0.28 mL, 4.504 mmol) was added tert-butyl nitrite (0.53 mL, 4.5 mmol) drop wise at 0° C. The resulting reaction mixture was stirred at RT for 1 h. After completion of the reaction the reaction mixture was diluted and triturated with diethyl ether (15 mL) to give a precipitate. The precipitate was filtered to give the diazonium tetra fluoro borate intermediate, which was used in the next step.

To a stirred solution of CuSCN (164 mg, 3.37 mmol) and Cs$_2$CO$_3$ (1.1 gr, 3.78 mmol) in acetonitrile (5 mL) was added drop wise TMSCF$_3$ (0.5 mL, 3.37 mmol) under an inert atmosphere. The resulting reaction mixture was stirred at RT for 10 min. A solution of the diazonium tetra fluoro borate intermediate (610 mg, 2.24 mmol) in acetonitrile (5 mL) was added drop wise to the reaction mixture at 0° C. The resulting reaction mixture was cooled to 0-15° C. and stirred for 5 h. The reaction was monitored by TLC and LCMS. The reaction mixture was filtered through a celite pad and washed with ethyl acetate. The filtrate was concentrated under reduced pressure and the residue was purified by silica-gel column chromatography using 2% EtOAc in hexane to furnish 1-bromo-4-(trifluoromethyl)naphthalene. $^1$H-NMR (400 MHz, DMSO-d$_6$): δ 8.41 (d, 1H), 8.30 (d, 1H), 7.85-7.65 (m, 4H).

b) 1-(4-(trifluoromethyl)naphthalen-1-yl)piperazine

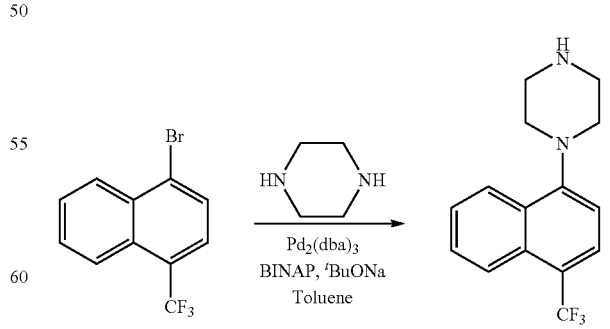

An oven dried Schlenk flask was evacuated and back filled with inert gas. The flask was charged with BINAP (181 mg, 0.2909 mmol) and Pd$_2$(dba)$_3$ (133 mg, 0.1454 mmol) in toluene (5 mL) at room temperature under an inert atmosphere. The resultant reaction mixture was evacuated on stirring for 5 min and then reaction mixture was heated to 115° C. for 1-2 min to give a catalyst, to which 1-bromo-4-(trifluoromethyl)naphthalene (400 mg, 1.4545 mmol)), piperazine (1.25 g, 14.54 mmol), ʹBuONa (280 mg, 2.909 mmol) and 15 mL of toluene were added. The resulting reaction mixture was heated to 120° C. for 4 h. The reaction was monitored by TLC and LCMS. The reaction mixture was filtered through a celite pad and washed with ethyl acetate. The filtrate was concentrated under reduced pressure and the residue was purified by preparative HPLC to furnish 1-(4-(trifluoromethyl)naphthalen-1-yl)piperazine product. LCMS purity: 97.892%, RT=5.279 min, m/z=281.2 [M+H]$^+$, (Method 3). $^1$H-NMR (400 MHz, DMSO-d$_6$): δ 9.05 (brs, 1H), 8.30 (d, 1H), 8.11 (d, 1H), 7.95 (d, 1H), 7.80-7.65 (m, 2H), 7.25 (d, 1H), 3.51-3.41 (m, 4H), 3.31-3.20 (m, 4H).

Example 2

4-(4-(Trifluoromethyl)naphthalen-1-yl)piperidine (2)

a) Tert-butyl 4-(4,4,5,5-tetramethyl-1,3,2-dioxaborolan-2-yl)-5,6-dihydropyridine-1(2H)-carboxylate

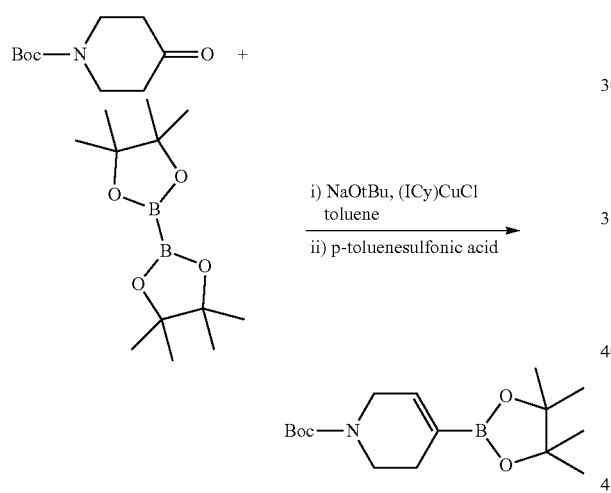

Dissolve tert-butyl 4-oxopiperidine-1-carboxylate (1.00 mmol), bis(pinacolato)diboron (1.10 mmol), NaO$^t$Bu (0.05 mmol), and (ICy)CuCl (0.03 mmol) in toluene and heat the resulting solution to 50° C. After 24 h, cool the reaction mixture to room temperature and filter through celite. Add p-toluenesulfonic acid (2.00 mmol) and methylene chloride to the crude product and heat the resulting mixture to 50° C. After 24 h, concentrate the reaction under vacuum and purify the residue by flash chromatography to prepare the title compound.

b) Tert-butyl 4-(4-(trifluoromethyl)naphthalen-1-yl)-5,6-dihydropyridine-1(2H)-carboxylate

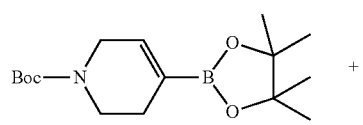

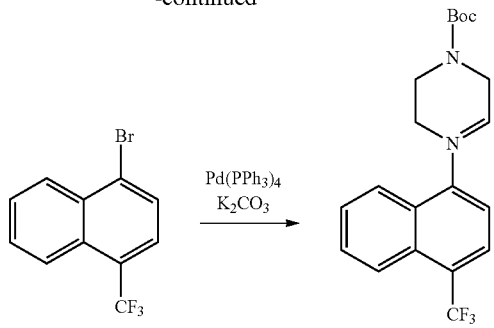

Prepare a suspension of tert-butyl 4-(4,4,5,5-tetramethyl-1,3,2-dioxaborolan-2-yl)-5,6-dihydropyridine-1(2H)-carboxylate (1.00 mmol), 1-bromo-4-(trifluoromethyl)naphthalene (1.00 mmol), Pd(PPh$_3$)$_4$ (0.1 mmol), and K$_2$CO$_3$ (2.00 mmol) dioxane/water (2/1, v/v) and degas the resulting solution under a stream of argon. Heat the reaction mixture to 90° C. for 8 h, and subsequently cool to room temperature. Dilute the solution with ethyl acetate and wash with brine. Separate the organic phase, dry over sodium sulfate, filter, and concentrate the filtrate under vacuum. Purify the residue by flash chromatography to prepare the title compound.

c) 4-(4-(trifluoromethyl)naphthalen-1-yl)piperidine

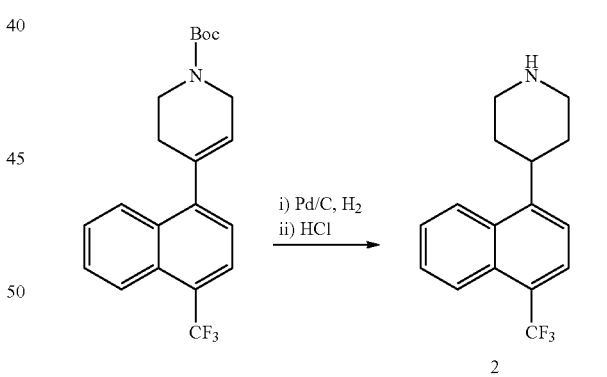

Prepare a suspension of tert-butyl 4-(4-(trifluoromethyl)naphthalen-1-yl)-5,6-dihydropyridine-1(2H)-carboxylate (1.00 mmol) and Pd/C (10%) in ethyl acetate and stir the resulting solution under an atmosphere of hydrogen (1 atm) for 8 h. Filter the resulting suspension was filtered through celite and concentrate the filtrate under vacuum. Dissolve the residue in HCl/dioxane (4 N) and stir the resulting solution at room temperature for 2 h. Concentrate the mixture under vacuum and purify the residue by reverse phase chromatography to prepare the title compound.

Example 3

1-(4-(Trifluoromethyl)-5,6,7,8-tetrahydronaphthalen-1-yl)piperazine (3)

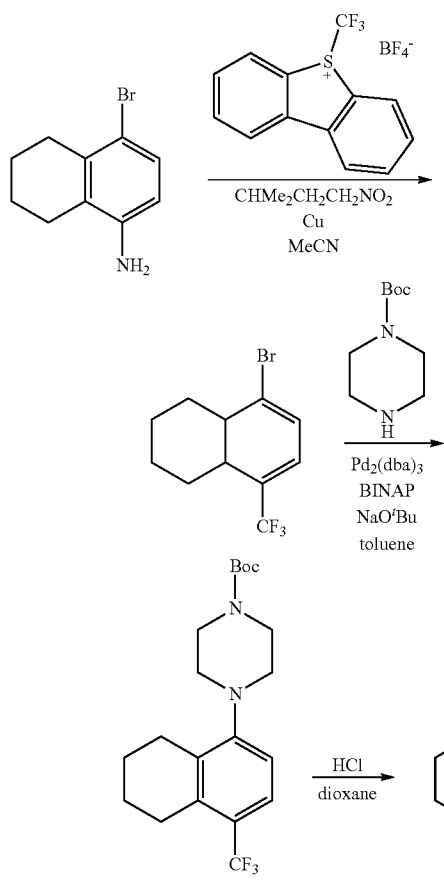

The title compound may be synthesized using methods similar to Example 1 using 4-bromo-5,6,7,8-tetrahydronaphthalen-1-amine as the starting material.

Example 4

1-(4-(Piperidin-4-yloxy)naphthalen-1-yl)piperazine (4)

a) Tert-butyl 4-(4-bromonaphthalen-1-yl)piperazine-1-carboxylate

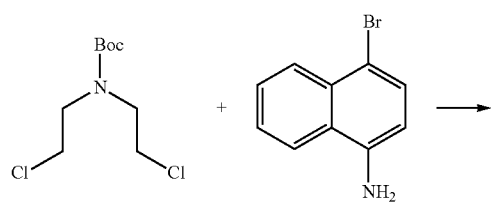

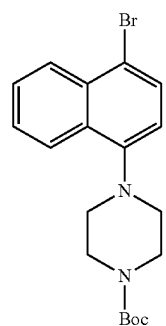

Dissolve tert-butyl bis(2-chloroethyl)carbamate (1.00 mmol), 4-bromonaphthalen-1-amine (1.00 mmol), and potassium carbonate in DMF and stir the resulting suspension at 90° C. for 18 h. Dilute the solution with ethyl acetate and wash with brine. Separate the organic phase, dry over sodium sulfate, filter and concentrate the filtrate under vacuum. Purify the residue by flash chromatography to prepare the title compound.

b) Tert-butyl 4-(4-((1-(tert-butoxycarbonyl)piperidin-4-yl)oxy)naphthalen-1-yl)piperazine-1-carboxylate

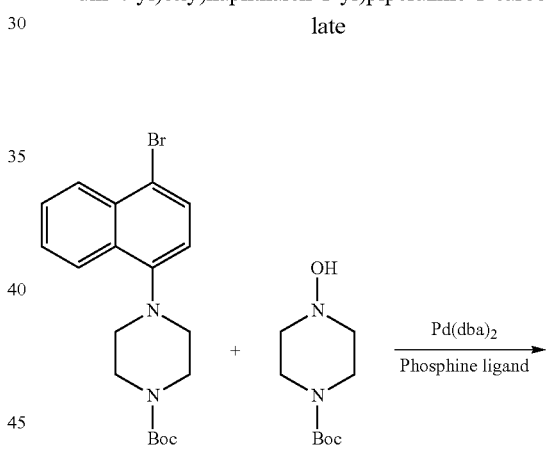

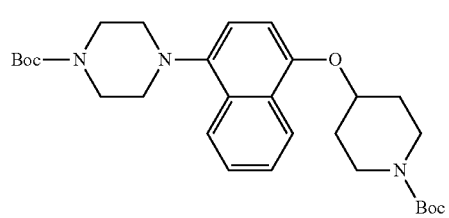

Prepare a suspension of tert-butyl 4-(4-bromonaphthalen-1-yl)piperazine-1-carboxylate (1.00 mmol), tert-butyl 4-hydroxypiperidine-1-carboxylate (1.50 mmol), Pd(OAc)$_2$ (0.10 mmol), [1,1'-binaphthalen]-2-yldi-tert-butylphosphine (0.15 mmol), and Cs$_2$CO$_3$ (2.50 mmol) in toluene and degas under a stream of argon. Heat the reaction mixture to 80° C. for 24 h. Dilute the solution with ethyl acetate and wash with brine. Separate the organic phase, dry over sodium sulfate, filter, and concentrate the filtrate was under vacuum. Purify the residue was purified by flash chromatography to prepare the title compound.

c) 1-(4-(piperidin-4-yloxy)naphthalen-1-yl)piperazine

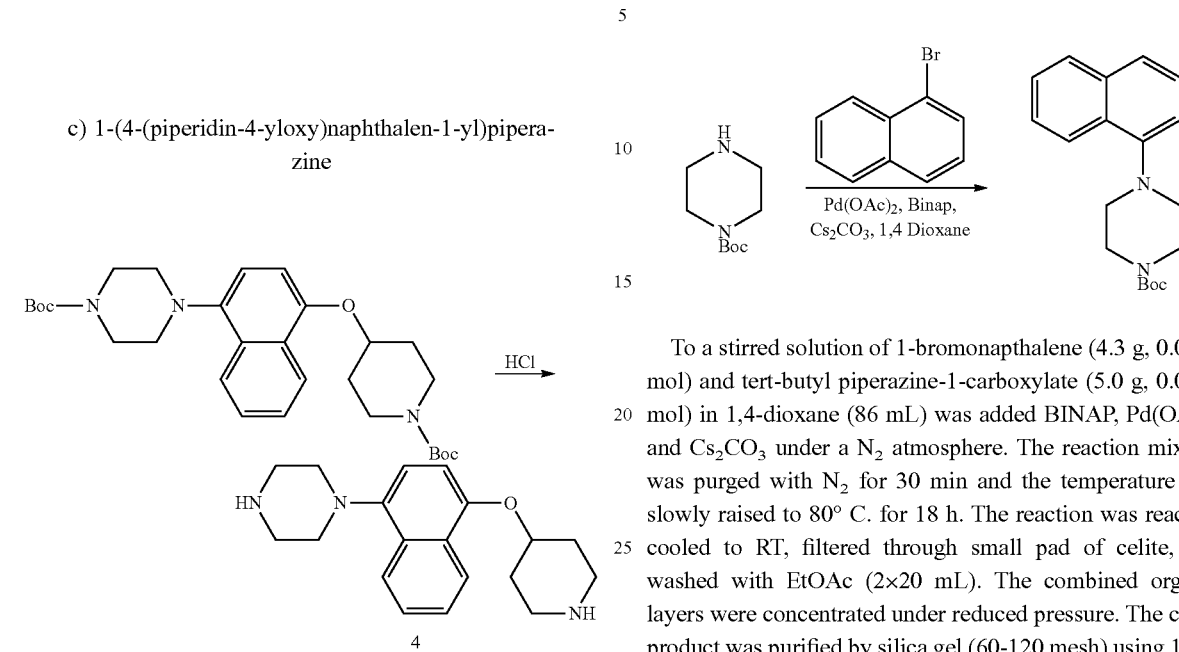

Dissolve tert-butyl 4-(4-((1-(tert-butoxycarbonyl)piperidin-4-yl)oxy)naphthalen-1-yl)piperazine-1-carboxylate in HCl/dioxane (4 N) and stir the resulting solution at room temperature for 2 h. Concentrate the mixture under vacuum and purify the residue by reverse phase chromatography to prepare the title compound.

1-(4-(piperidin-4-yloxy)naphthalen-1-yl)piperazine (4) can also be prepared by the following alternative synthesis.

a) Tert-butyl Piperazine-1-carboxylate

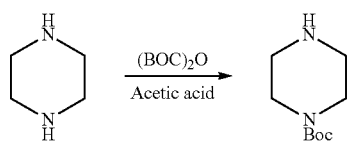

To a stirred solution of piperazine (5.0 g, 0.0580 mol) was added slowly acetic acid (50 mL) at 0° C. under a $N_2$ atmosphere for 20 min and the resulting solution was stirred at RT for a further 20 min. (Boc)$_2$O (13.3 mL dissolved in 40 mL acetic acid) was added drop wise to the reaction mixture at 0° C. for 30 min and stirring was continued for 2 h at RT. The reaction mixture was poured onto ice cold water and basified with saturated aqueous KOH. The material that was formed was separated by filtration and dried under vacuum to give tert-butyl piperazine-1-carboxylate.

b) Tert-butyl 4-(naphthalen-1-yl)piperazine-1-carboxylate

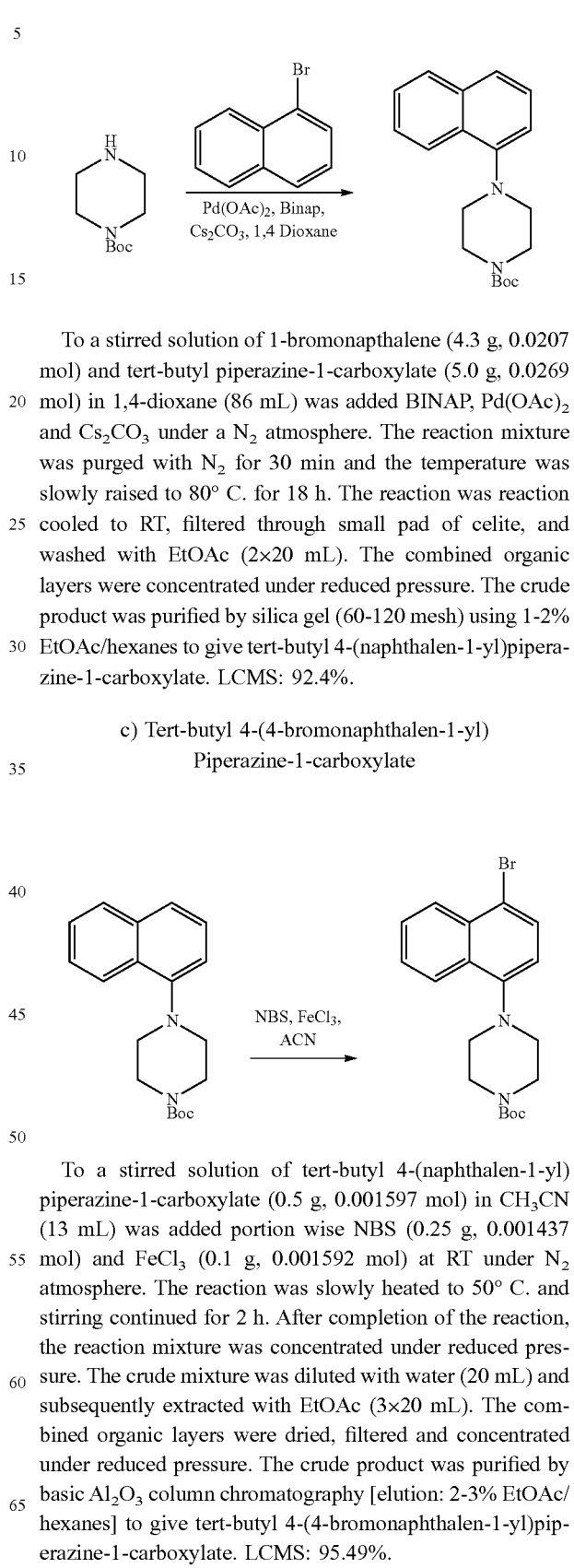

To a stirred solution of 1-bromonapthalene (4.3 g, 0.0207 mol) and tert-butyl piperazine-1-carboxylate (5.0 g, 0.0269 mol) in 1,4-dioxane (86 mL) was added BINAP, Pd(OAc)$_2$ and Cs$_2$CO$_3$ under a N$_2$ atmosphere. The reaction mixture was purged with N$_2$ for 30 min and the temperature was slowly raised to 80° C. for 18 h. The reaction was reaction cooled to RT, filtered through small pad of celite, and washed with EtOAc (2×20 mL). The combined organic layers were concentrated under reduced pressure. The crude product was purified by silica gel (60-120 mesh) using 1-2% EtOAc/hexanes to give tert-butyl 4-(naphthalen-1-yl)piperazine-1-carboxylate. LCMS: 92.4%.

c) Tert-butyl 4-(4-bromonaphthalen-1-yl) Piperazine-1-carboxylate

To a stirred solution of tert-butyl 4-(naphthalen-1-yl) piperazine-1-carboxylate (0.5 g, 0.001597 mol) in CH$_3$CN (13 mL) was added portion wise NBS (0.25 g, 0.001437 mol) and FeCl$_3$ (0.1 g, 0.001592 mol) at RT under N$_2$ atmosphere. The reaction was slowly heated to 50° C. and stirring continued for 2 h. After completion of the reaction, the reaction mixture was concentrated under reduced pressure. The crude mixture was diluted with water (20 mL) and subsequently extracted with EtOAc (3×20 mL). The combined organic layers were dried, filtered and concentrated under reduced pressure. The crude product was purified by basic Al$_2$O$_3$ column chromatography [elution: 2-3% EtOAc/ hexanes] to give tert-butyl 4-(4-bromonaphthalen-1-yl)piperazine-1-carboxylate. LCMS: 95.49%.

d) Tert-butyl 4-(4-(1-(tert-butoxycarbonyl)piperidin-4-yloxy)naphthalen-1-yl)piperazine-1-carboxylate

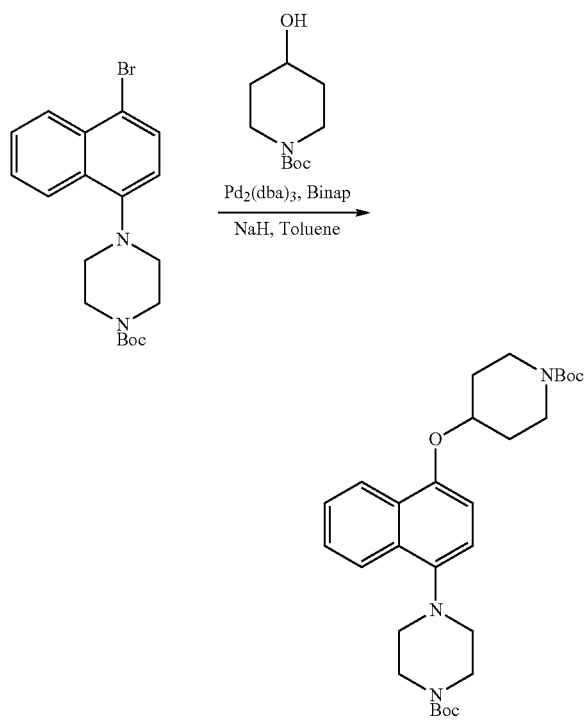

To a stirred solution of tert-butyl 4-hydroxypiperidine-1-carboxylate (0.23 g, 0.001147 mol) in dry toluene (6 mL) was added NaH (0.07 g, 0.00153 mol) at 0° C. under $N_2$ atmosphere. The reaction mixture was slowly raised to 70° C. and stirred for 1 h. tert-Butyl 4-(4-bromonaphthalen-1-yl)piperazine-1-carboxylate (0.3 g, 0.000765 mol), $Pd_2(dba)_3$ and BINAP were added to the reaction at rt under $N_2$ atmosphere and the resulting solution was slowly raised to 80° C. and stirred for 18 h. Ice cold water was added and the mixture was extracted with EtOAc (3×20 mL). The combined organic layers were dried filtered and concentrated under reduced pressure. The crude product was purified by basic $Al_2O_3$ column chromatography using 10% EtOAc/hexanes to give tert-butyl 4-(4-((1-(tert-butoxycarbonyl)piperidin-4-yl)oxy)naphthalen-1-yl)piperazine-1-carboxylate. LCMS: 91.9%.

e) 1-(4-(piperidin-4-yloxy)naphthalen-1-yl)piperazine

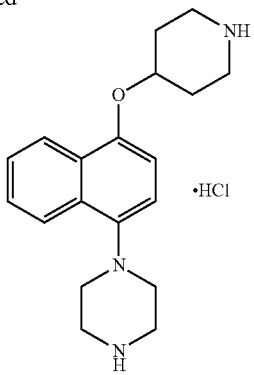

To stirred solution of tert-butyl 4-(4-((1-(tert-butoxycarbonyl)piperidin-4-yl)oxy)naphthalen-1-yl)piperazine-1-carboxylate (0.120 g, 0.234 mol) in dry DCM (2.4 mL) was added HCl in diethyl ether (2.4 mL) at RT under a $N_2$ atmosphere. The reaction was stirred at RT for 3 h and monitored by TLC. After completion of the reaction, solvents were decanted and the resulting material was washed with diethyl ether (3×5 mL). The resulting material was dried under high vacuum to give 1-(4-(piperidin-4-yloxy)naphthalen-1-yl)piperazine. LCMS: 92.58%. RT=2.806 min, m/z=312.3 [M+H]$^+$, (method 3). $^1$H-NMR (300 MHz, DMSO-d6): δ 9.34 (1H, s), 9.12 (1H, d), 8.23-8.20 (1H, m), 8.17-8.14 (1H, m), 7.60-7.52 (2H, m), 7.11 (1H, d), 7.03 (1H, d), 4.84 (1H, m), 4.38-4.21 (8H, m), 3.39-3.16 (6H, m), 2.18 (2H, brs), 2.06-1.92 (2H, m).

Example 5

N-(4-(Piperazin-1-yl)naphthalen-1-yl)piperidin-4-amine (5)

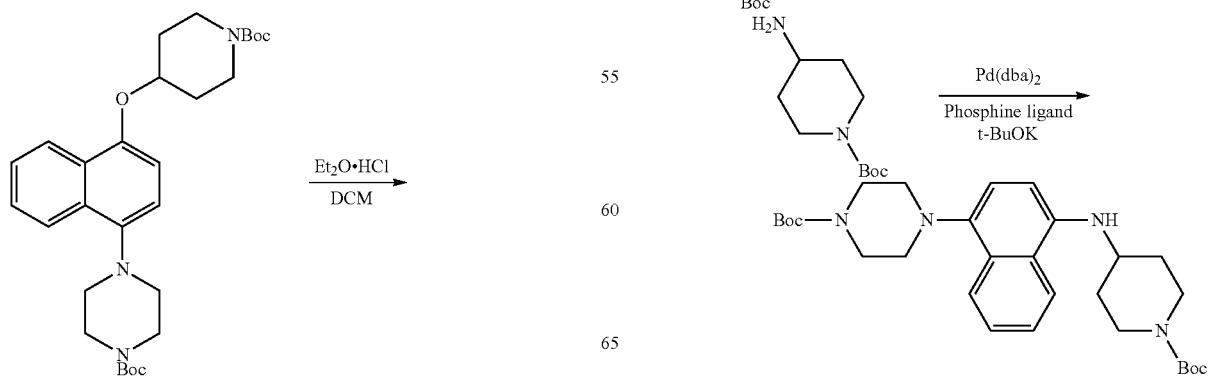

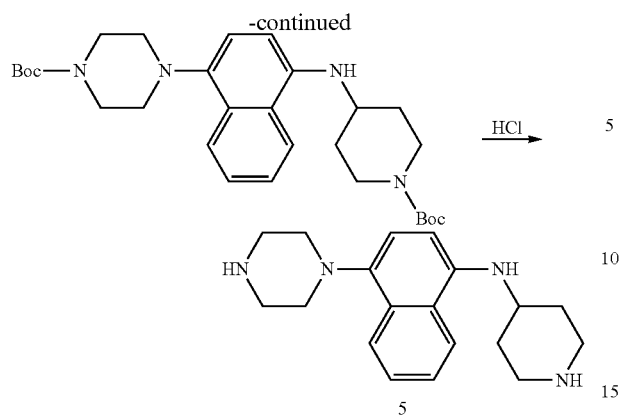

The title compound may be synthesized using methods similar to Example 1, except using tert-butyl 4-(4-bromonaphthalen-1-yl)piperazine-1-carboxylate and tert-butyl 4-aminopiperidine-1-carboxylate as the starting materials.

N-(4-(Piperazin-1-yl)naphthalen-1-yl)piperidin-4-amine (5) can also be prepared using the following alternative synthesis.

a) Tert-butyl 4-(4-(1-(tert-butoxycarbonyl)piperidin-4-ylamino)naphthalen-1-yl)piperazine-1-carboxylate

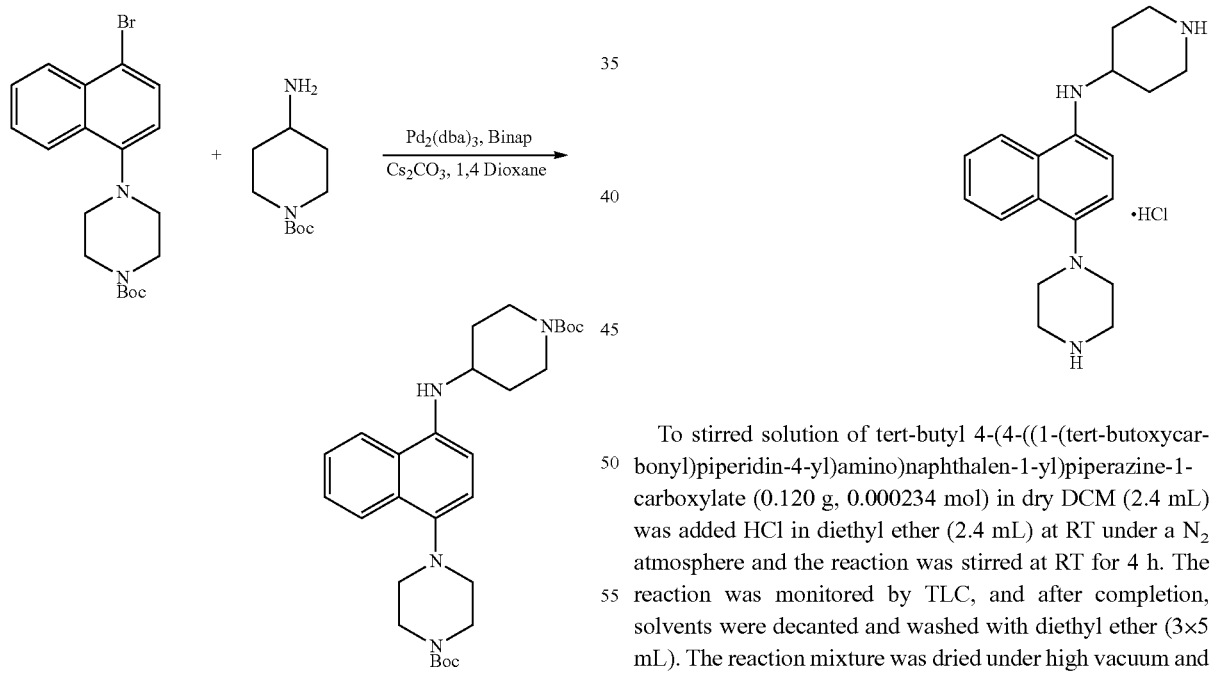

To stirred solution of tert-butyl 4-(4-bromonaphthalen-1-yl)piperazine-1-carboxylate (0.3 g, 0.000765 mol) and tert-butyl 4-aminopiperidine-1-carboxylate (0.306 g, 0.00153 mol) in 1,4 dioxane (12 mL) were added BINAP and $Cs_2CO_3$ at RT under $N_2$ atmosphere. The reaction mixture was purged with $N_2$ for 30 min and Pd(OAc)$_2$ (34 mg, 0.000153 mol) was added. The temperature was slowly raised to 70° C. and the resulting solution stirred for 18 h. The reaction was monitored by TLC, and after completion, filtered through a small pad of celite and washed with EtOAc (3×5 mL). The combined filtrate was concentrated under reduced pressure. The crude was purified by silica gel (60-120 mesh) column chromatography using 10% EtOAc/Hexanes to give tert-butyl 4-(4-((1-(tert-butoxycarbonyl)piperidin-4-yl)amino)naphthalen-1-yl)piperazine-1-carboxylate. LCMS: 93.7%.

b) N-(4-(piperazin-1-yl)naphthalen-1-yl)piperidin-4-amine

To stirred solution of tert-butyl 4-(4-((1-(tert-butoxycarbonyl)piperidin-4-yl)amino)naphthalen-1-yl)piperazine-1-carboxylate (0.120 g, 0.000234 mol) in dry DCM (2.4 mL) was added HCl in diethyl ether (2.4 mL) at RT under a $N_2$ atmosphere and the reaction was stirred at RT for 4 h. The reaction was monitored by TLC, and after completion, solvents were decanted and washed with diethyl ether (3×5 mL). The reaction mixture was dried under high vacuum and the resulting material was washed with hexanes (3×10 mL) to give N-(4-(piperazin-1-yl)naphthalen-1-yl)piperidin-4-amine. LCMS: 97.65%. RT=2.405 min, m/z=311.3 [M+H]$^+$, (method 3) $^1$H-NMR (300 MHz, DMSO-d6): δ 8.29-8.26 (1H, m), δ 7.81 (1H, d), δ 7.52-7.46 (2H, m), δ 6.99 (1H, d), δ 6.60-6.58 (1H, m), δ 4.08-4.06 (4H, m), δ 3.64-3.53 (1H, m), δ 3.01 (4H, t), δ 2.13 (2H, d), δ 1.62-1.55 (4H, m), δ 1.54 (1H, bs), δ 1.48-1.45 (4H, m).

Example 6

1-(4-(Piperidin-4-ylmethyl)naphthalen-1-yl)piperazine (6)

a) 4-(4-(tert-butoxycarbonyl)piperazin-1-yl)-1-naphthoic Acid

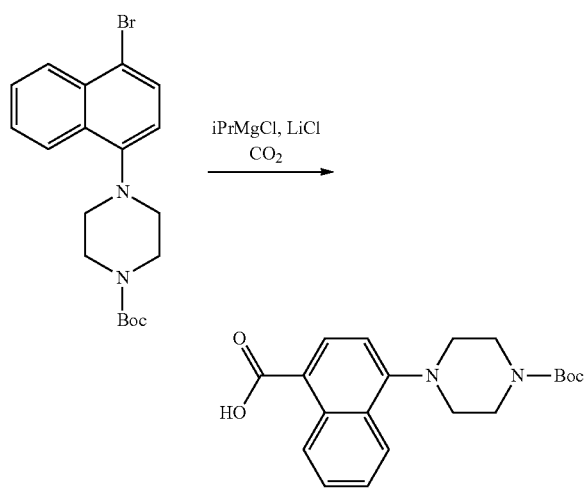

To a solution of tert-butyl 4-(4-bromonaphthalen-1-yl)piperazine-1-carboxylate (1.00 mmol) in THF at 0° C., add a solution of $^i$PrMgCl:LiCl in THF (1.50 mmol). Stir the resulting at 0° C. for 0.5 h, then warm to room temperature and stir the resulting mixture for 3 h. Cool the mixture to −10° C. and bubble $CO_2$ gas through the solution for 1 h. Add 1 N aqueous HCl and extract the resulting solution with ethyl acetate to prepare the title compound.

b) Tert-Butyl 4-(4-(hydroxymethyl)naphthalen-1-yl)piperazine-1-carboxylate

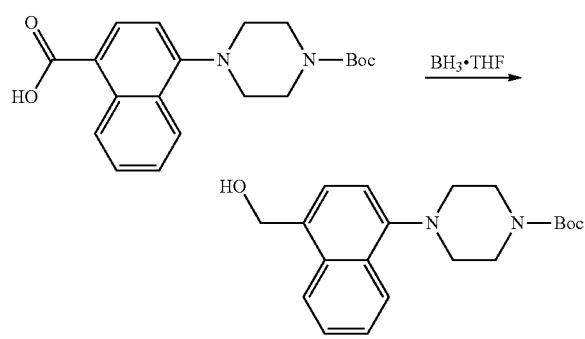

Dissolve 4-(4-(tert-Butoxycarbonyl)piperazin-1-yl)-1-naphthoic acid (1.00 mmol) in THF and add a solution of borane in THF (2.00 mmol). Stir the resulting solution at room temperature for 24 h. Add aqueous HCl and stir the resulting solution for 1 h. Dilute the solution with ethyl acetate and wash with brine. Separate the organic phase, dry over sodium sulfate, filter, and concentrate the filtrate under vacuum. Purify the residue by flash chromatography to prepare the title compound.

c) Tert-butyl 4-(4-formylnaphthalen-1-yl)piperazine-1-carboxylate

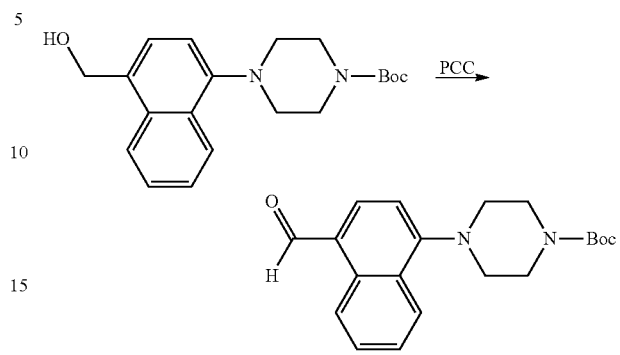

Dissolve tert-Butyl 4-(4-(hydroxymethyl)naphthalen-1-yl)piperazine-1-carboxylate (1.00 mmol) in methylene chloride and add PCC (2.00 mmol) and $SiO_2$. Stir the resulting suspension at room temperature for 2 h and subsequently filter through celite to give tert-butyl 4-(4-formylnaphthalen-1-yl)piperazine-1-carboxylate to prepare the title compound.

d) (1-(tert-butoxycarbonyl)piperidin-4-yl)triphenylphosphonium Bromide

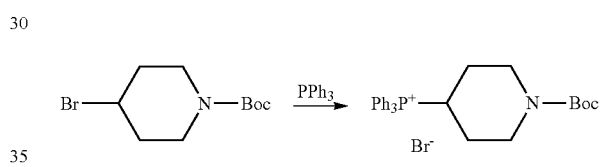

Dissolve tert-Butyl 4-bromopiperidine-1-carboxylate (1.00 mmol) and triphenylphosphine (1.50 mmol) in toluene and stir the resulting solution at 80° C. for 12 h. Cool the solution to room temperature and filter to remove the precipitate. Concentrate the filtrate to prepare the title compound.

e) Tert-butyl 4-(4-((1-(tert-butoxycarbonyl)piperidin-4-ylidene)methyl)naphthalen-1-yl)piperazine-1-carboxylate

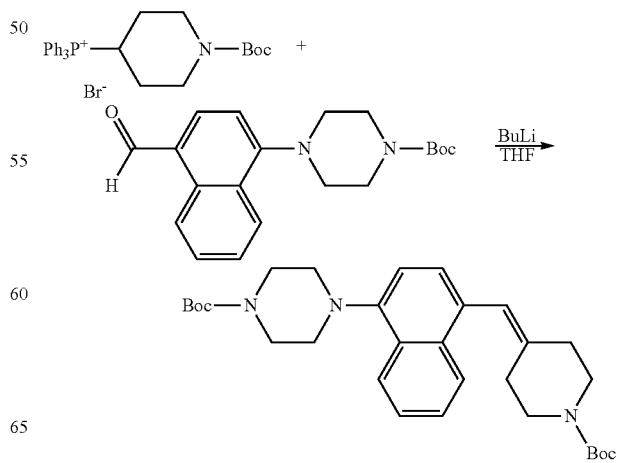

Slowly add n-BuLi (1.20 mmol) to a solution of (1-(tert-butoxycarbonyl)piperidin-4-yl)triphenylphosphonium bromide (1.00 mmol) in THF at −20° C. Stir the resulting suspension was stirred at room temperature for 2 h. To the suspension, add a solution of tert-butyl 4-(4-formylnaphthalen-1-yl)piperazine-1-carboxylate (1.00 mmol) in THF and stir the resulting solution at room temperature for 4 h. Filter the suspension through celite and concentrate the filtrate under vacuum. Purify the residue was purified by flash chromatography to prepare the title compound.

f) 1-(4-(piperidin-4-ylmethyl)naphthalen-1-yl)piperazine

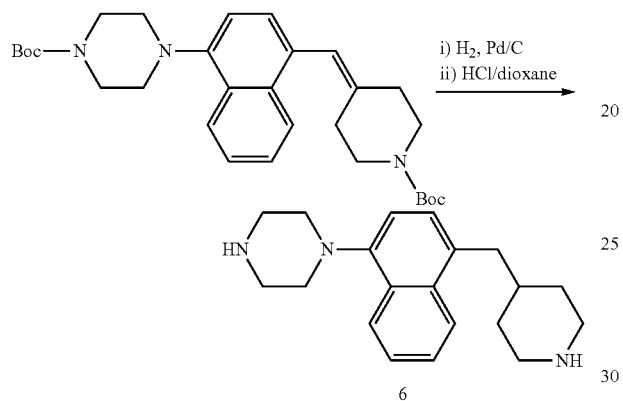

Prepare a suspension of tert-Butyl 4-(4-((1-(tert-butoxycarbonyl)piperidin-4-ylidene)methyl)naphthalen-1-yl)piperazine-1-carboxylate (1.00 mmol) and Pd/C (10%) in ethyl acetate and stir the resulting solution under an atmosphere of hydrogen (1 atm) for 8 h. Filter the resulting suspension through celite and concentrate the filtrate under vacuum. Dissolve the residue in HCl/dioxane (4 N) and stir the resulting solution at room temperature for 2 h. Concentrate the mixture under vacuum and purify the residue by reverse phase chromatography to prepare the title compound.

Example 7

1-(4-(Piperidin-4-ylsulfonyl)naphthalen-1-yl)piperazine (7)

a) Tert-butyl 4-(4-((1-(tert-butoxycarbonyl)piperidin-4-yl)sulfonyl)naphthalen-1-yl)piperazine-1-carboxylate

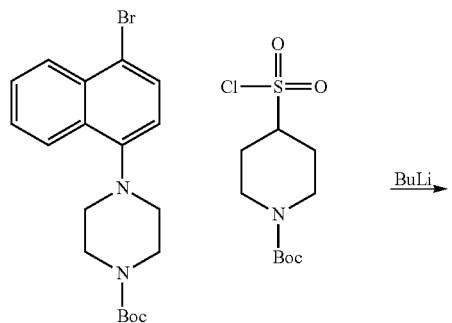

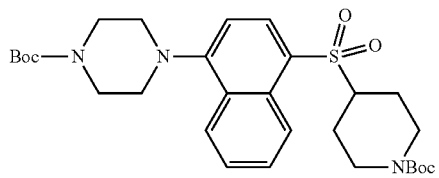

Add n-BuLi (1.10 mmol) to a solution of tert-butyl 4-(4-bromonaphthalen-1-yl)piperazine-1-carboxylate (1.00 mmol) in THF at −78° C. and stir the resulting solution at −78° C. for 1 h. To the reaction mixture, add a solution of tert-butyl 4-(chlorosulfonyl)piperidine-1-carboxylate (1.00 mmol) in THF and allow the resulting solution to warm to room temperature. Add aqueous HCl followed by ethyl acetate. Separate the organic phase was separated, dry over sodium sulfate, filter, and concentrate the filtrate under vacuum. Purify the residue by flash chromatography to prepare the title compound.

1p;2p b) 1-(4-(piperidin-4-ylsulfonyl)naphthalen-1-yl)piperazine

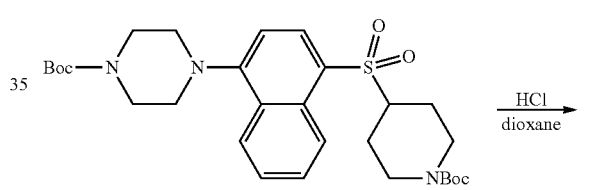

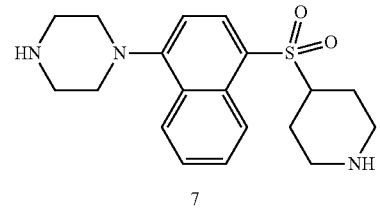

Dissolve tert-Butyl 4-(4-((1-(tert-butoxycarbonyl)piperidin-4-yl)sulfonyl)naphthalen-1-yl)piperazine-1-carboxylate in HCl/dioxane (4 N) and stir the resulting solution at room temperature for 2 h. Concentrate the mixture under vacuum and purify the residue by reverse phase chromatography to prepare the title compound.

1-(4-(Piperidin-4-ylsulfonyl)naphthalen-1-yl)piperazine (7) can also be prepared by the following alternative synthesis.

a) Synthesis of Tert-butyl 4-(4-(1-(tert-butoxycarbonyl)piperidin-4-ylthio)naphthalen-1-yl)piperazine-1-carboxylate

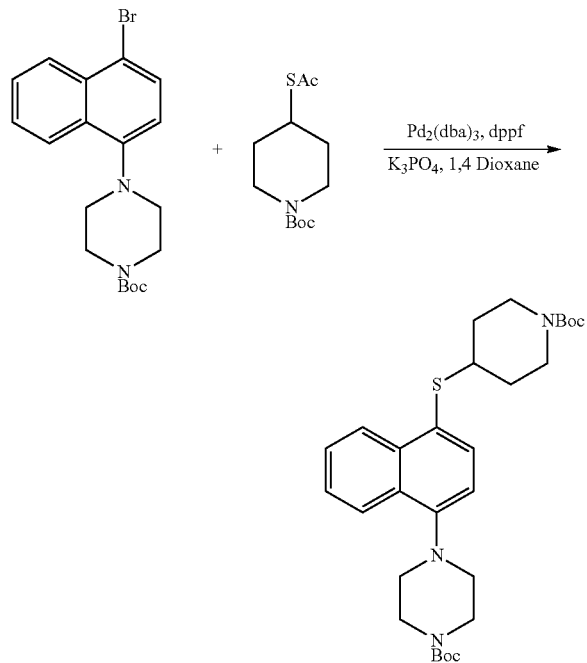

To a stirred solution of tert-butyl 4-(4-bromonaphthalen-1-yl)piperazine-1-carboxylate (1.36 g, 0.00347 mol) and tert-butyl 4-(acetylthio)piperidine-1-carboxylate (0.9 g, 0.00344 mol) in 1,4-dioxane (30 mL) was added Pd(dba)$_2$ (0.099 g, 0.008175 mol), dppf (0.135 g, 0.000243 mol) and K$_3$PO$_4$ (0.879 g, 0.004169 mol) at RT under N$_2$ atmosphere. The reaction mixture was purged with N$_2$ for 30 min and slowly raised to 120° C. for 2 days. After completion of the reaction the solution was cooled to RT, and the solvents were evaporated under reduced pressure. The crude product was purified by silica gel (60-120 mesh) column chromatography using 2-8% EtOAc/Hexanes to give tert-butyl 4-(4-((1-(tert-butoxycarbonyl)piperidin-4-yl)thio)naphthalen-1-yl)piperazine-1-carboxylate. LCMS: 52.1%.

b) Tert-butyl 4-(4-(1-(tert-butoxycarbonyl)piperidin-4-ylsulfonyl)naphthalen-1-yl)piperazine-1-carboxylate

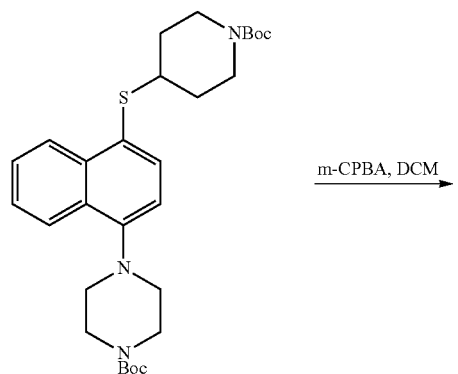

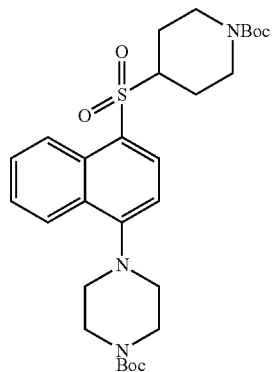

To a stirred solution of tert-butyl 4-(4-((1-(tert-butoxycarbonyl)piperidin-4-yl)thio)naphthalen-1-yl)piperazine-1-carboxylate (0.34 g, 0.0006584 mol) in dry DCM (7 mL) was added m-CPBA (0.332 g, 0.3393 mol) at 0° C. under N$_2$ atmosphere. The reaction was stirred at RT overnight. After completion of the reaction, the mixture was quenched with sat. NaHCO$_3$ solution (10 mL) and extracted with DCM (3×20 mL). The combined organic layers were dried and concentrated under reduced pressure. The crude material was purified by neutral Al$_2$O$_3$ using 10-30% EtOAc/Hexanes to give tert-butyl 4-(4-((1-(tert-butoxycarbonyl)piperidin-4-yl)sulfonyl)naphthalen-1-yl)piperazine-1-carboxylate. LCMS: 81.76%.

c) 1-(4-(piperidin-4-ylsulfonyl)naphthalen-1-yl)piperazine

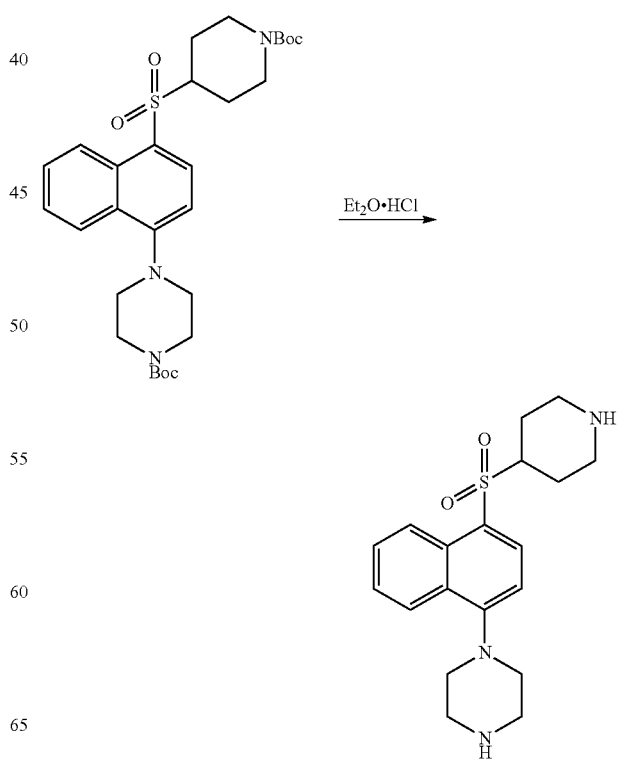

To stirred solution of compound tert-butyl 4-(4-((1-(tert-butoxycarbonyl)piperidin-4-yl)sulfonyl)naphthalen-1-yl)piperazine-1-carboxylate (0.2 g, 0.0003577 mol) in dry DCM (3.3 mL) was added HCl in diethyl ether (3.3 mL). The reaction was stirred at RT for 4 h under an atmosphere of nitrogen. The reaction was monitored by TLC, and after completion, solvents were decanted and washed with diethyl ether (3×5 mL). The reaction mixture was dried under high vacuum and the resulting material was washed with hexanes (3×10 mL) to give 1-(4-(piperidin-4-ylsulfonyl)naphthalen-1-yl)piperazine. LCMS: 94.36%. RT=2.670 min, m/z=360.3 [M+H]$^+$, (method 3). $^1$H-NMR (300 MHz, DMSO-d$_6$): δ 9.66 (2H, s), δ 9.39 (1H, d), δ 8.93 (1H, d), δ 8.63 (1H, d), δ 8.27 (1H, d), δ 8.11 (1H, d), δ 7.79-7.67 (2H, m), δ 7.34 (1H, d), δ 3.72 (1H, bs), δ 3.37 (8H, m), δ 3.26 (2H, d), δ 2.83 (2H, d), δ 1.89 (4H, s).

Example 8

Piperazin-1-yl(4-(piperazin-1-yl)naphthalen-1-yl)methanone (8)

a) Tert-butyl 4-(4-(4-(tert-butoxycarbonyl)piperazin-1-yl)-1-naphthoyl)piperazine-1-carboxylate

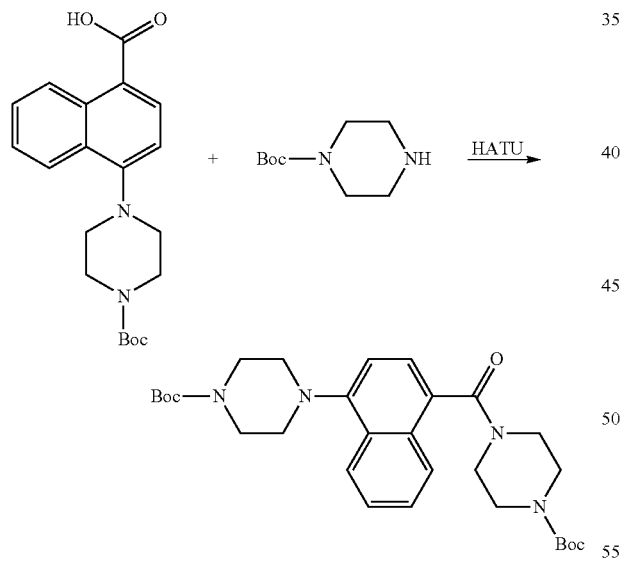

Dissolve 4-(4-(tert-butoxycarbonyl)piperazin-1-yl)-1-naphthoic acid (1.00 mmol), tert-butyl piperazine-1-carboxylate (1.00 mmol), HATU (1.20 mmol) and DIPEA (2.00 mmol) in DMF and stir the resulting solution at room temperature for 4 h. Dilute the solution with ethyl acetate and wash with brine. Separate the organic phase, dry over sodium sulfate, filter, and concentrate the filtrate under vacuum. Purify the residue by flash chromatography to prepare the title compound.

b) Piperazin-1-yl(4-(piperazin-1-yl)naphthalen-1-yl)methanone

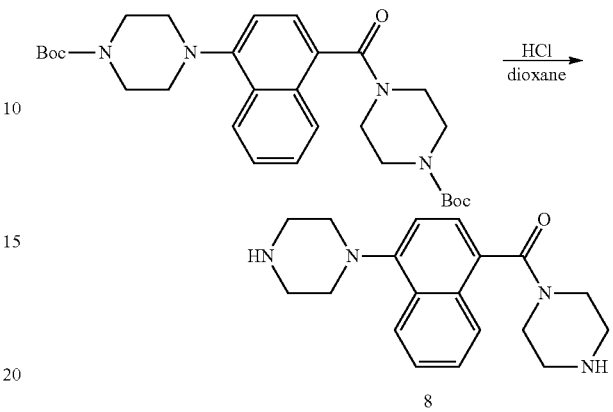

Dissolve tert-Butyl 4-(4-(4-(tert-butoxycarbonyl)piperazin-1-yl)-1-naphthoyl)piperazine-1-carboxylate in HCl/dioxane (4 N) and stir the resulting solution at room temperature for 2 h. Concentrate the mixture under vacuum and purify the residue by reverse phase chromatography to prepare the title compound.

Piperazin-1-yl(4-(piperazin-1-yl)naphthalen-1-yl)methanone (8) can also be prepared by the following alternative synthesis.

a) Tert-butyl 4-(4-(ethoxycarbonyl)naphthalen-1-yl)piperazine-1-carboxylate

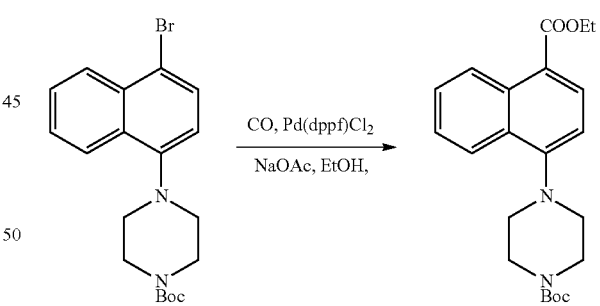

tert-Butyl 4-(4-bromonaphthalen-1-yl)piperazine-1-carboxylate (0.3 g, 0.000765 mol) was dissolved in EtOH (30 mL) in a pressure vessel and NaOAc (0.125 g, 0.00153 mol) and Pd(dppf)Cl$_2$ (0.0279 g, 0.000038 mol) were added. The reaction was degassed with N$_2$ and the vessel was pressurized with CO gas (2 BAR). The temperature was slowly raised to 110° C. and the resulting solution was stirred overnight. After completion of the reaction the solution was filtered through a small pad of celite and washed with EtOH (3×50 mL). The solvents were evaporated under reduced pressure and the crude tert-butyl 4-(4-(ethoxycarbonyl)

naphthalen-1-yl)piperazine-1-carboxylate (0.180 g, 61.4%) was used without further purification. LCMS: 98.65%.

b) 4-(4-(tert-butoxycarbonyl)piperazin-1-yl)-1-naphthoic Acid

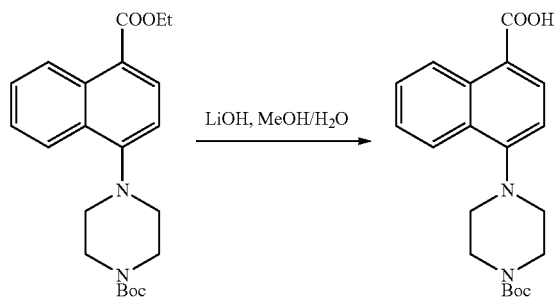 [SMILES: CCOC(=O)c1ccc(N2CCN(C(=O)OC(C)(C)C)CC2)c2ccccc12 ; CC(C)(C)OC(=O)N1CCN(c2ccc(C(=O)O)c3ccccc23)CC1]

To a stirred solution of tert-butyl 4-(4-(ethoxycarbonyl)naphthalen-1-yl)piperazine-1-carboxylate (0.5 g, 0.00130 mol) in MeOH/H$_2$O (2:1, 15 mL) was added LiOH·H$_2$O (0.059 g, 0.001432 mol) at RT. After stirring overnight the solvent was evaporated under reduced pressure. The residue was acidified with saturated citric acid solution and extracted with DCM (3×5 mL). The combined organic layers were dried, filtered and concentrated under reduced pressure to give 4-(4-(tert-butoxycarbonyl)piperazin-1-yl)-1-naphthoic. LCMS: 91.95%.

c) Tert-butyl 4-(4-(4-(tert-butoxycarbonyl)piperazin-1-yl)-1-naphthoyl)piperazine-1-carboxylate

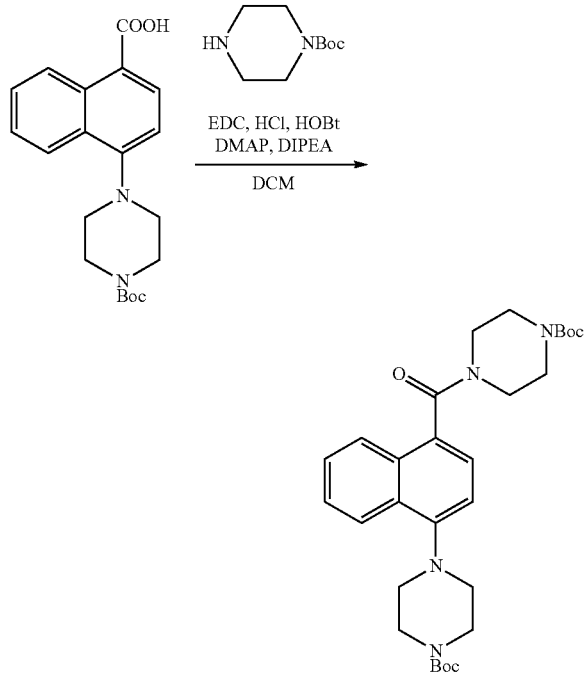

To a stirred solution of 4-(4-(tert-butoxycarbonyl)piperazin-1-yl)-1-naphthoic acid (0.15 g, 0.4216 mmol) in dry DCM (4 mL) at 0° C. was added EDC.HCl (0.097 g, 0.5056 mmol), HOBt (11.3 mg, 0.064 mmol), DMAP (10.2 mg, 0.064 mmol), DIPEA (0.5 mL, 0.82 mmol) and tert-butyl piperazine-1-carboxylate (0.086 g, 0.463 mmol). The resulting solution was stirred at RT overnight. After completion of the reaction ice cold water was added and the resulting solution was extracted with DCM (3×10 mL). The combined organic layers were dried concentrated under reduced pressure. The crude material was purified by silica gel (60-120 mesh) column chromatography using 10-30% EtOAc/hexanes to give tert-butyl 4-(4-(4-(tert-butoxycarbonyl)piperazin-1-yl)-1-naphthoyl)piperazine-1-carboxylate. LCMS: 98.72%.

d) Piperazin-1-yl(4-(piperazin-1-yl)naphthalen-1-yl)methanone

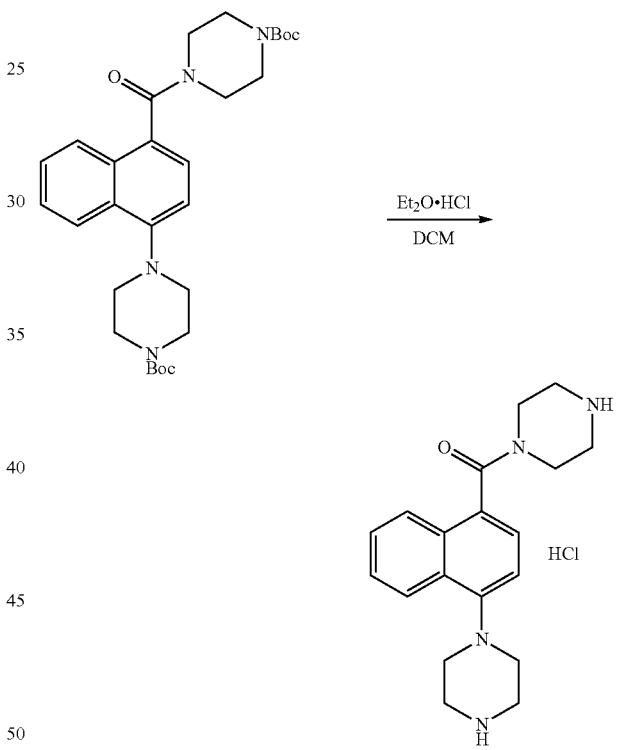

To stirred solution of tert-butyl 4-(4-(4-(tert-butoxycarbonyl)piperazin-1-yl)-1-naphthoyl)piperazine-1-carboxylate (0.07 g, 0.000133 mol) in dry DCM (1.4 mL) was added HCl in diethyl ether (1.4 mL). The reaction was stirred at RT for 4 h under an atmosphere of nitrogen. The reaction was monitored by TLC, and after completion, solvents were decanted and washed with diethyl ether (3×5 mL). The reaction mixture was dried under high vacuum and the resulting material was washed with hexanes (3×10 mL) to give piperazin-1-yl(4-(piperazin-1-yl)naphthalen-1-yl)methanone. LCMS: 98.8%. RT=1.945 min, m/z=325.3 [M+H]$^+$, (method 3). $^1$H-NMR (300 MHz, DMSO-d$_6$): δ 9.69 (2H, d), δ 8.22-8.19 (1H, m), δ 7.82-7.79 (1H, m), δ

7.61-7.57 (2H, m), δ 7.49 (1H, d), δ 7.19 (1H, d), δ 5.22-5.00 (8H, m), δ 3.99 (2H, s), δ 3.43-3.33 (6H, m), δ 2.92 (2H, d).

Example 9

5-(Piperazin-1-yl)-8-(piperidin-4-yloxy)isoquinoline (9)

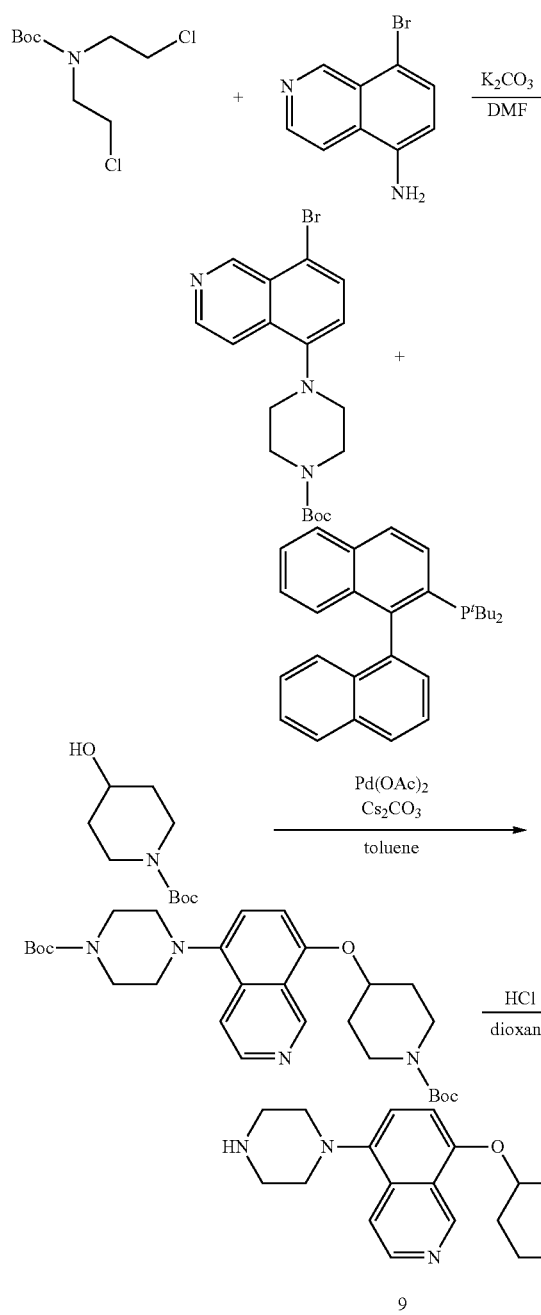

The title compound may be synthesized using the same methods similar to of Example 11, except using 8-bromoisoquinolin-5-amine as the starting material.

5-(Piperazin-1-yl)-8-(piperidin-4-yloxy)isoquinoline (9) can also be prepared using the following alternative synthesis.

a) Tert-butyl 4-(methylsulfonyloxy)piperidine-1-carboxylate

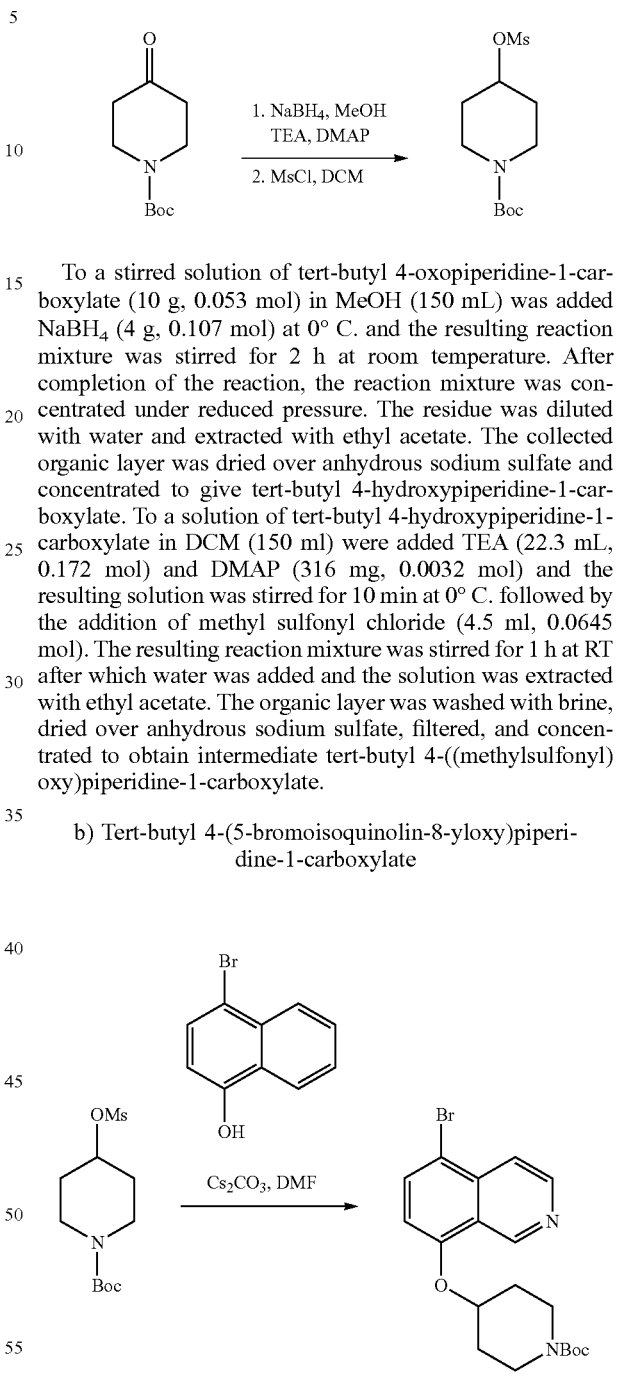

To a stirred solution of tert-butyl 4-oxopiperidine-1-carboxylate (10 g, 0.053 mol) in MeOH (150 mL) was added NaBH$_4$ (4 g, 0.107 mol) at 0° C. and the resulting reaction mixture was stirred for 2 h at room temperature. After completion of the reaction, the reaction mixture was concentrated under reduced pressure. The residue was diluted with water and extracted with ethyl acetate. The collected organic layer was dried over anhydrous sodium sulfate and concentrated to give tert-butyl 4-hydroxypiperidine-1-carboxylate. To a solution of tert-butyl 4-hydroxypiperidine-1-carboxylate in DCM (150 ml) were added TEA (22.3 mL, 0.172 mol) and DMAP (316 mg, 0.0032 mol) and the resulting solution was stirred for 10 min at 0° C. followed by the addition of methyl sulfonyl chloride (4.5 ml, 0.0645 mol). The resulting reaction mixture was stirred for 1 h at RT after which water was added and the solution was extracted with ethyl acetate. The organic layer was washed with brine, dried over anhydrous sodium sulfate, filtered, and concentrated to obtain intermediate tert-butyl 4-((methylsulfonyl)oxy)piperidine-1-carboxylate.

b) Tert-butyl 4-(5-bromoisoquinolin-8-yloxy)piperidine-1-carboxylate

To a solution of 4-bromonaphthalen-1-ol (500 mg, 2.232 mmol) in DMF (6 mL) was added tert-butyl 4-(methylsulfonyloxy)piperidine-1-carboxylate (809 mg, 2.901 mmol) and Cs$_2$CO$_3$ (2.18 g, 6.696 mmol) and the resulting mixture was heated to 80° C. for 4 h. The reaction mixture was poured into ice water and extracted with ethyl acetate (3×15 mL). The combined organic layers were dried over anhydrous sodium sulfate, filtered, and concentrated. The obtained crude product was purified by basic alumina column chromatography using 30% ethyl acetate in hexane to yield compound tert-butyl 4-((5-bromoisoquinolin-8-yl)oxy)piperidine-1-carboxylate. LCMS Purity: 93.416%.

c) Tert-butyl 4-(5-(piperazin-1-yl)isoquinolin-8-yloxy)piperidine-1-carboxylate

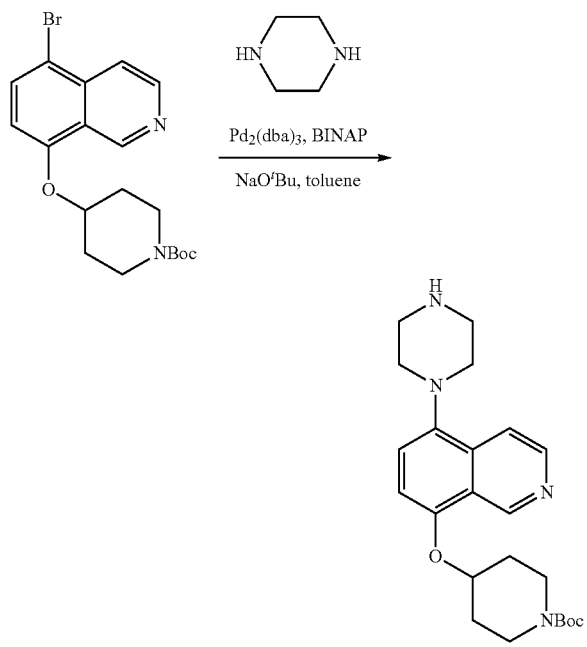

To a stirred solution of compound tert-butyl 4-((5-bromoisoquinolin-8-yl)oxy)piperidine-1-carboxylate (500 mg, 0.0012 mol) and in toluene (12 mL) was added piperazine (530 mg, 0.0061 mol), Pd$_2$(dba)$_3$ (113 mg, 0.00012 mol), BINAP (15.3 mg, 0.000246 mol) and NaO$^t$Bu (355 mg, 0.0037 mol). The resulting reaction mixture was degassed and then heated to 110° C. for 5 h. The reaction was cooled to room temperature and filtered through a celite pad. The collected filtrate was concentrated under reduced pressure and purified by basic alumina column chromatography using 10% methanol in DCM give tert-butyl 4-((5-(piperazin-1-yl)isoquinolin-8-yl)oxy)piperidine-1-carboxylate. LCMS Purity: 81.262%.

d) 5-(piperazin-1-yl)-8-(piperidin-4-yloxy)isoquinoline

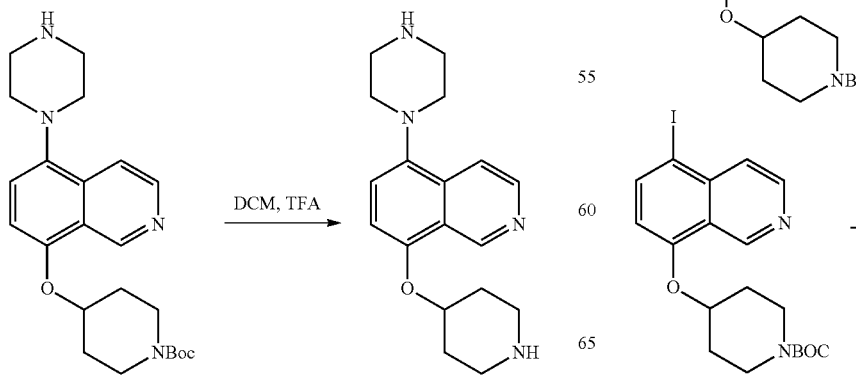

To a stirred solution of tert-butyl 4-(5-(piperazin-1-yl)isoquinolin-8-yloxy)piperidine-1-carboxylate (300 mg, 0.72 mmol) in DCM (10 mL) was added TFA (2 ml) and the resulting reaction mixture was stirred for 1 h at room temperature. The reaction mixture was concentrated under vacuum and the crude product was purified by preparative HPLC to yield 5-(piperazin-1-yl)-8-(piperidin-4-yloxy)isoquinoline. LCMS Purity: 97.340%, RT=0.879 min, m/z=313.3 (M+H)$^+$ (Method 3). $^1$H-NMR (400 MHz, DMSO-d$_6$): δ 9.72 (1H, s), 9.08 (1H, brs), 8.78 (1H, brs), 8.62 (1H, d), 8.18 (1H, d), 7.50 (1H, d), 7.26 (1H, d), 4.98 (1H, brs), 3.58-3.02 (12H, m), 2.25-1.92 (1H, m).

Example 10

4-(8-(Piperidin-4-yloxy)isoquinolin-5-yl)piperazin-2-one (16)

4-(8-(Piperidin-4-yloxy)isoquinolin-5-yl)piperidin-2-one (27)

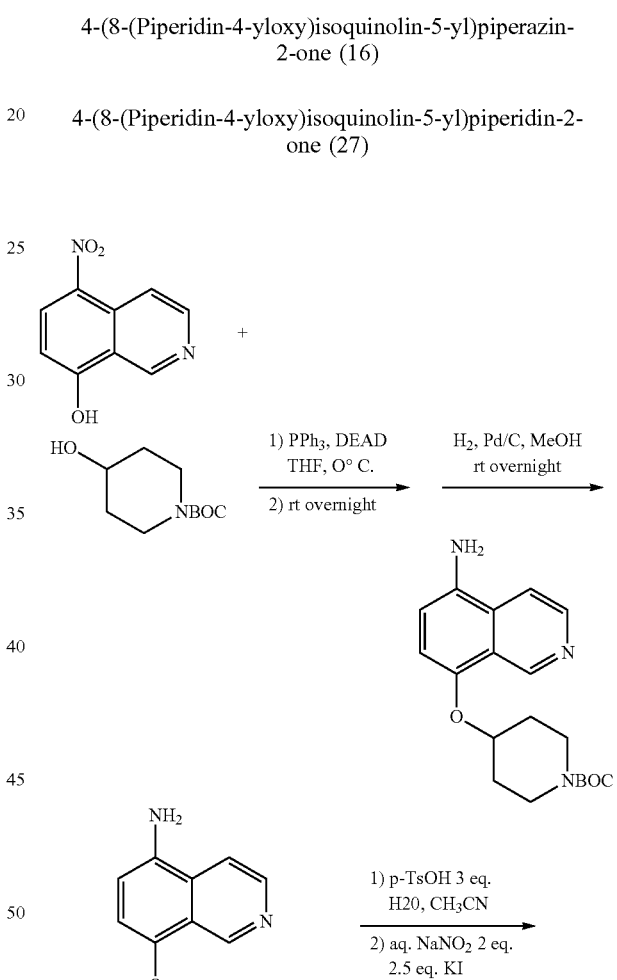

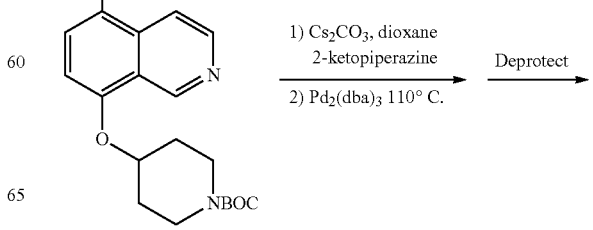

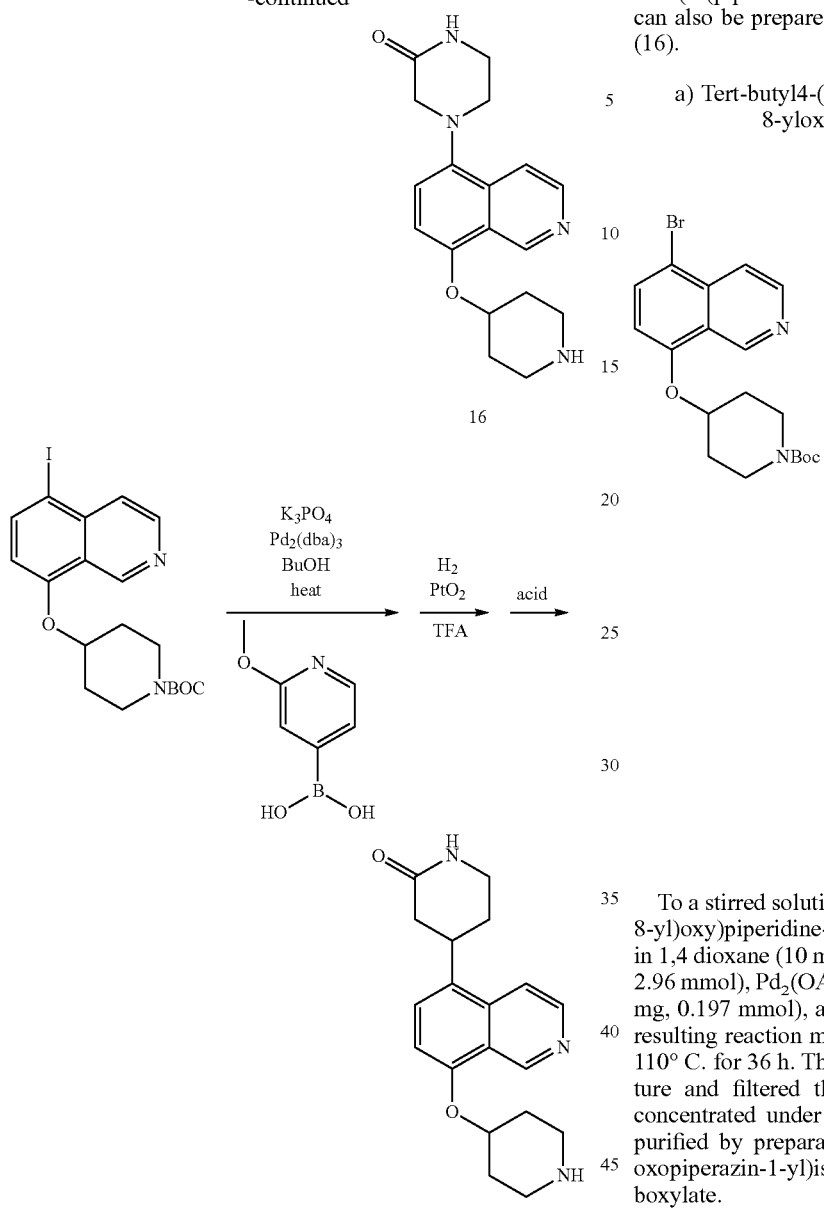
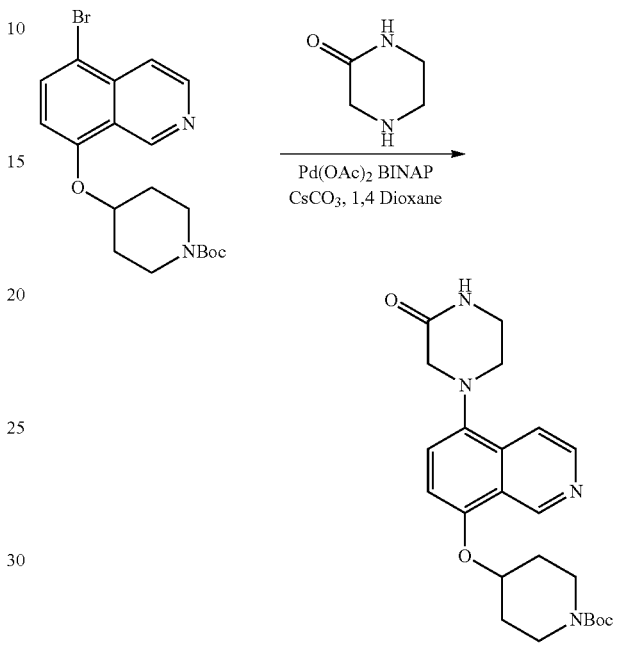

4-(8-(piperidin-4-yloxy)isoquinolin-5-yl)piperazin-2-one can also be prepared by the following alternative synthesis (16).

a) Tert-butyl 4-(5-(3-oxopiperazin-1-yl)isoquinolin-8-yloxy)piperidine-1-carboxylate To a stirred solution of tert-butyl 4-((5-bromoisoquinolin-8-yl)oxy)piperidine-1-carboxylate (400 mg, 0.98 mmol) and in 1,4 dioxane (10 mL) was added piperazin-2-one (296 mg, 2.96 mmol), $Pd_2(OAc)_2$ (22 mg, 0.0987 mmol), BINAP (122 mg, 0.197 mmol), and $Cs_2CO_3$ (965 mg, 2.962 mmol). The resulting reaction mixture was degassed and then heated to 110° C. for 36 h. The reaction was cooled to room temperature and filtered through a celite pad. The filtrate was concentrated under reduced pressure and the residue was purified by preparative HPLC to give tert-butyl 4-((5-(3-oxopiperazin-1-yl)isoquinolin-8-yl)oxy)piperidine-1-carboxylate.

b) 4-(8-(piperidin-4-yloxy)isoquinolin-5-yl)piperazin-2-one

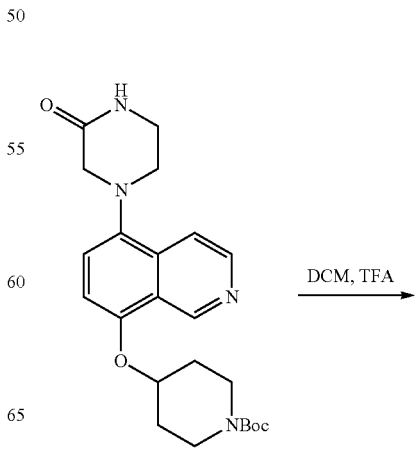

The known 5-nitroisoquinolin-8-ol is reacted with triphenylphosphine/DEAD/THF (Johansson, G. et al WO 2004000828) and combined with 1-BOC-4-hydroxypiperidine, giving N—BOC-5-nitro-8-(piperidin-4-yloxy)isoquinoline.

The nitro group is reduced to the amine; the amine is converted the diazonium salt using sodium nitrite and, subsequently, to the iodide (Knochel, P. et al *Synthesis*, 2007, 81-84).

The iodide may be coupled using palladium catalysts with either 2-ketopiperazine (Ford, D. et al WO 2013096051) or (2-methoxypyridin-4-yl)boronic acid (Marsilje, T. H. et al *J. Med. Chem.* 2013, 56, 5675-90) to afford, after deprotection, either 4-(8-(piperidin-4-yloxy)isoquinolin-5-yl)piperazin-2-one (16) or 4-(8-(piperidin-4-yloxy)isoquinolin-5-yl)piperidin-2-one (27).

105

-continued

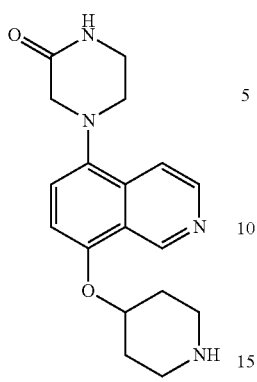

To a stirred solution of tert-butyl 4-((5-(3-oxopiperazin-1-yl)isoquinolin-8-yl)oxy)piperidine-1-carboxylate (35 mg, 0.0825 mmol) in DCM (10 mL) was added TFA (2 ml) and the resulting reaction mixture was stirred for 1 h at room temperature. The solvents were removed under reduced pressure and the crude product was recrystallized by using diethyl ether to yield 4-(8-(piperidin-4-yloxy)isoquinolin-5-yl)piperazin-2-one. LCMS Purity: 97.42%, RT=2.242 min, m/z=327.3 (M+H)$^+$, (Method 3). $^1$H-NMR (400 MHz, DMSO-d$_6$): δ 8.8-8.5 (3H, m), 8.05 (1H, s), 7.45 (1H, d), 7.23 (1H, d), 4.96 (1H, s), 3.52-3.26 (6H, m), 3.25-3.08 (4H, m), 2.23-1.94 (4H, m).

Example 11

4-Bromonaphthalene-1-thiolen-1-yl)sulfonyl)piperidine (23)

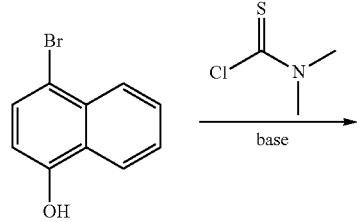

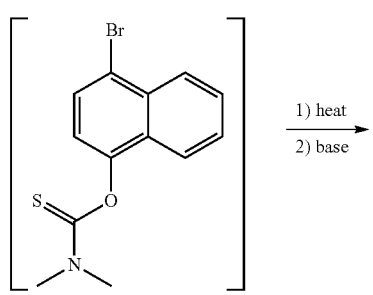

106

-continued

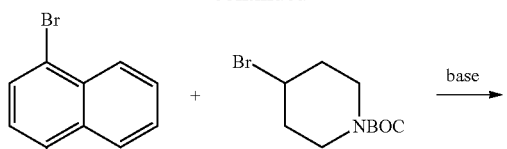

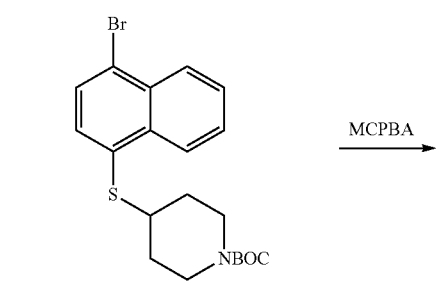

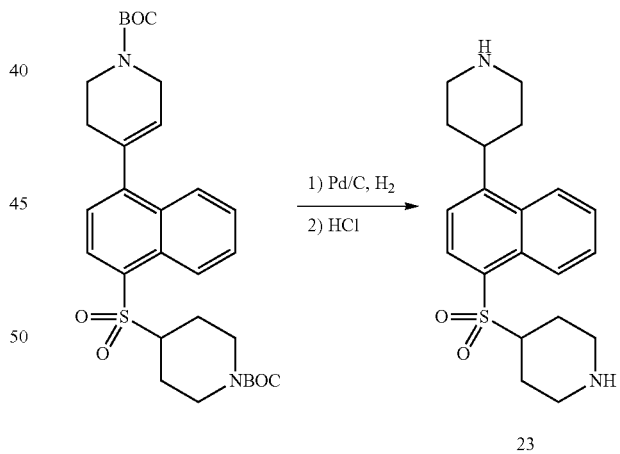

Using the Newman-Kwart reaction, 4-bromonaphthalen-1-ol, is converted to a dimethyaminoisothiourea intermediate, which rearranges on vigorous heating to give, on hydrolysis, 4-bromonaphthalene-1-thiol. The thiol is reacted with N—BOC-piperidine-4-Br and the sulfur oxidized to the corresponding sulfone. The aryl bromide is coupled to a second piperidine subunit. Reduction/deprotection leads to the desired 4-bromonaphthalene-1-thiolen-1-yl)sulfonyl)piperidine (23).

Example 12
5-(Piperazin-1-yl)-8-(piperidin-4-yloxy)isoquinoline-3-carboxylic Acid (14)
5-(3-Oxopiperazin-1-yl)-8-(piperidin-4-yloxy)isoquinoline-3-carboxamide (15)
5-(2-Oxopiperidin-4-yl)-8-(piperidin-4-yloxy)isoquinoline-3-carboxamide (26)
5-(Piperidin-4-yl)-8-(piperidin-4-yloxy)isoquinoline-3-carboxylic Acid (25)
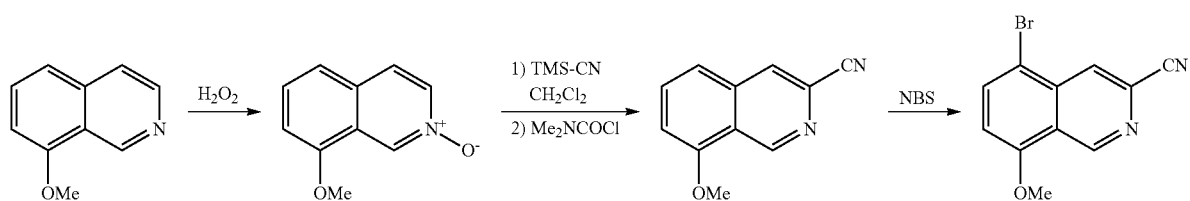
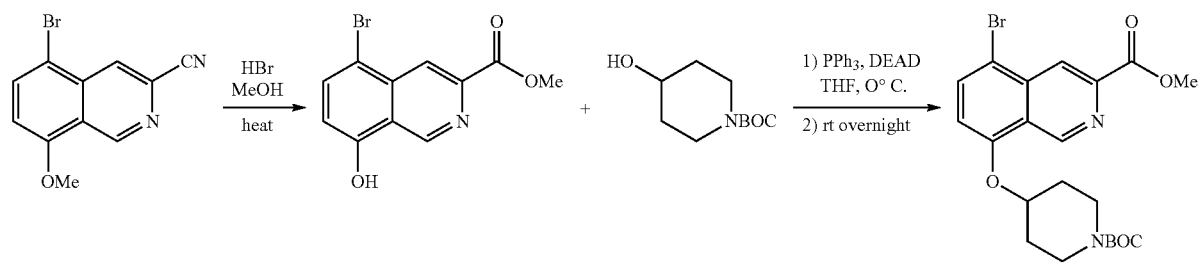
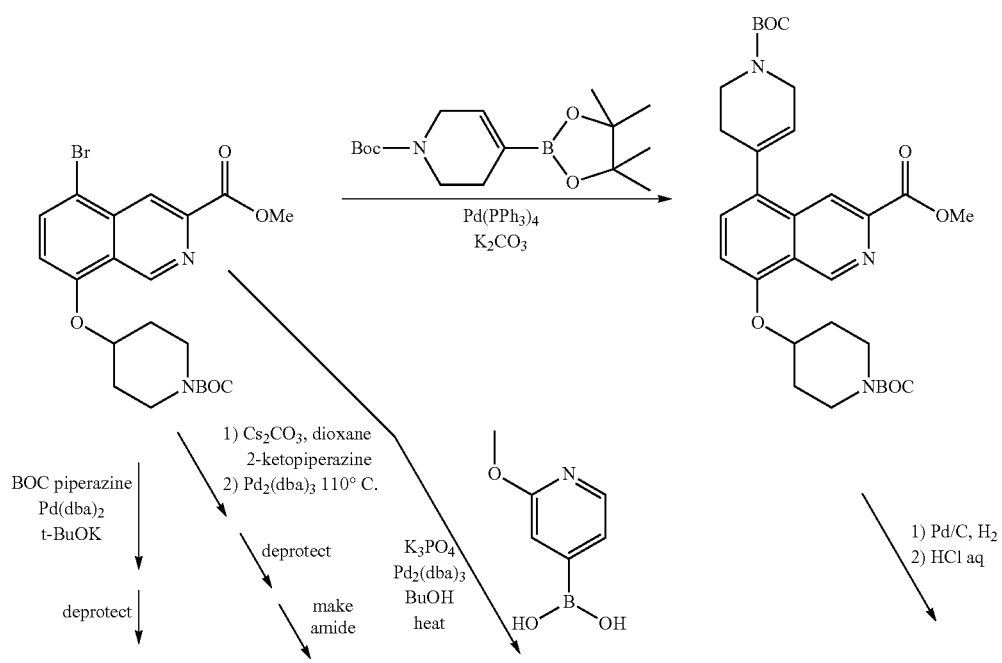

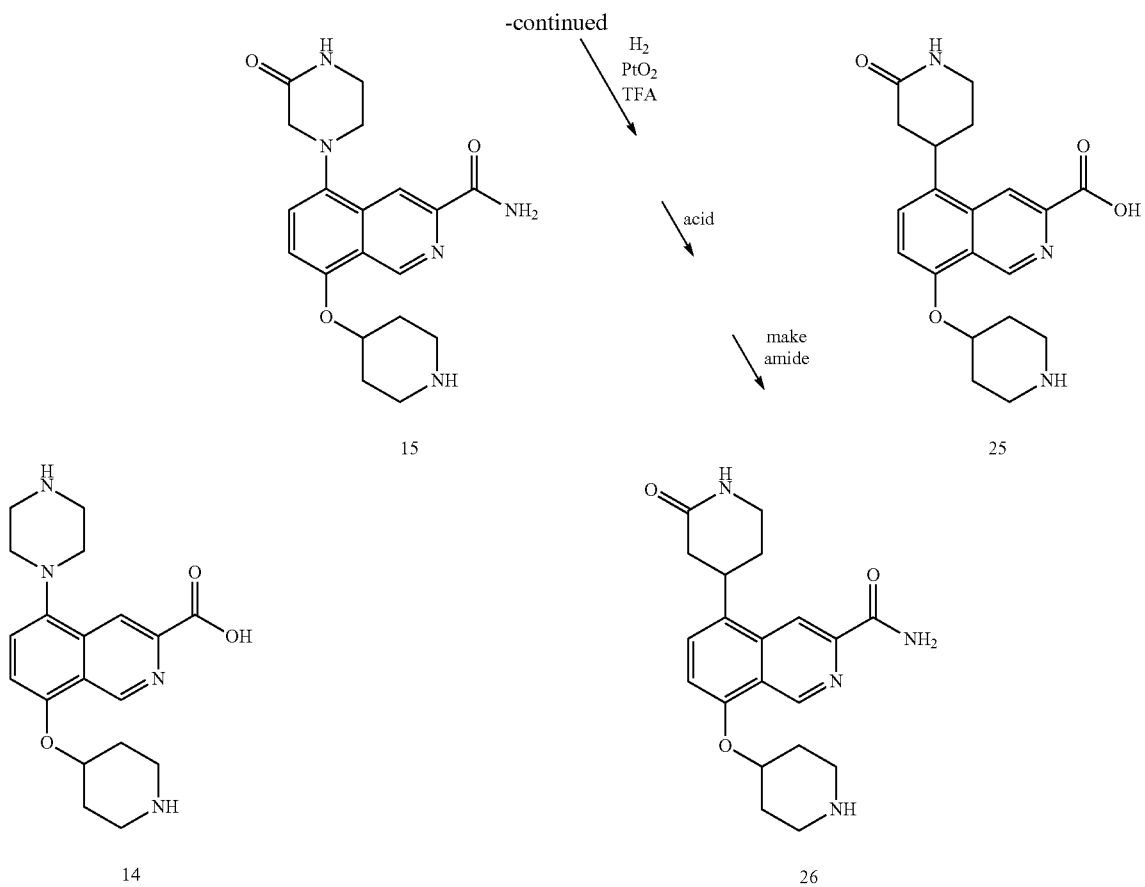

The commercial 8-methoxyisoquinoline is N-oxidized (Dirnberger, D. et al *Archiv der Pharmazie* 1990, 323, 323) and treated with TMS-CN (Norrby, T. et al *Acta Chemica Scand.* 1998, 52, 77), affording 8-methoxyisoquinoline-3-carbonitrile.

The carbonitrile is brominated. The key bromide, 5-bromo-8-methoxyisoquinoline-3-carbonitrile, may be coupled using palladium reagents and subsequently modified and deprotected to give piperazine (5-(piperazin-1-yl)-8-(piperidin-4-yloxy)isoquinoline-3-carboxylic acid (22)), piperazone (5-(3-oxopiperazin-1-yl)-8-(piperidin-4-yloxy)isoquinoline-3-carboxamide (15)), piperidone (5-(2-oxopiperidin-4-yl)-8-(piperidin-4-yloxy)isoquinoline-3-carboxylic acid (110)), and piperidine (5-(piperidin-4-yl)-8-(piperidin-4-yloxy)isoquinoline-3-carboxylic acid (25)) analogs.

Example 13

1-(4-(Piperidin-4-ylmethyl)naphthalen-1-yl)piperazine (22)

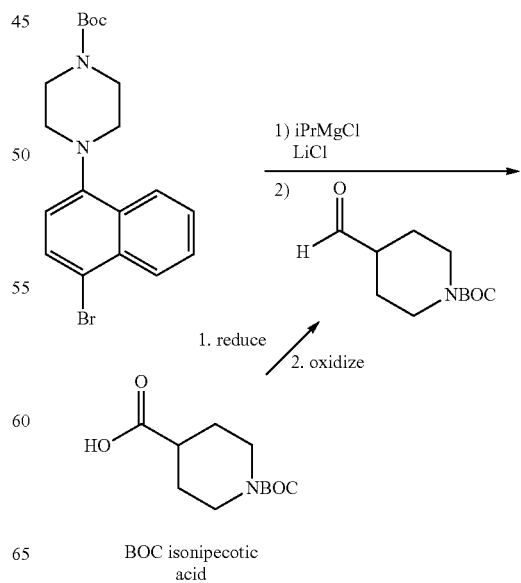

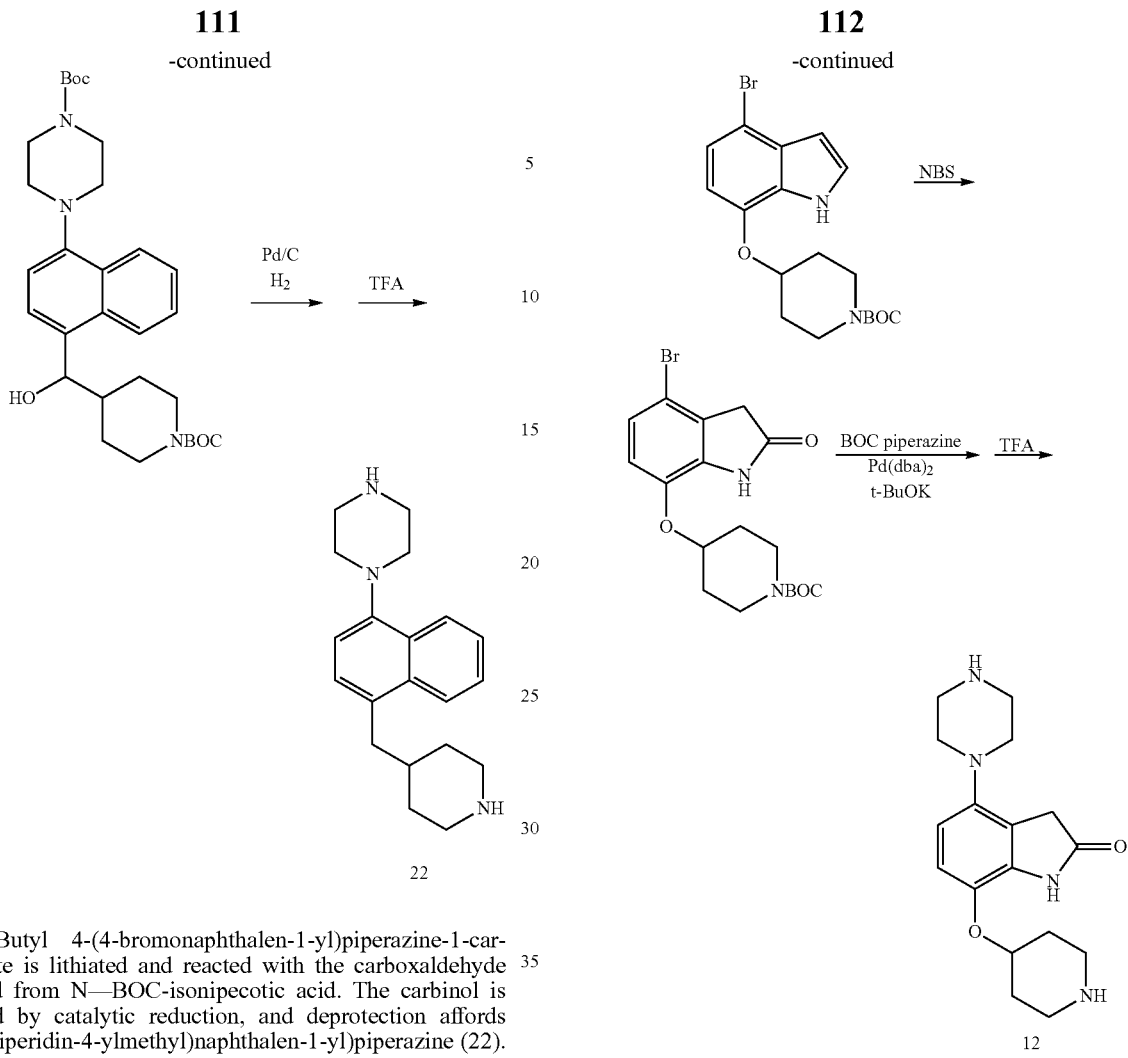
tert-Butyl 4-(4-bromonaphthalen-1-yl)piperazine-1-carboxylate is lithiated and reacted with the carboxaldehyde derived from N—BOC-isonipecotic acid. The carbinol is cleaved by catalytic reduction, and deprotection affords 1-(4-(piperidin-4-ylmethyl)naphthalen-1-yl)piperazine (22).
Example 14
4-(Piperazin-1-yl)-7-(piperidin-4-yloxy)indolin-2-one (12)
4-(Piperidin-4-yl)-7-(piperidin-4-yloxy)indolin-2-one (24)
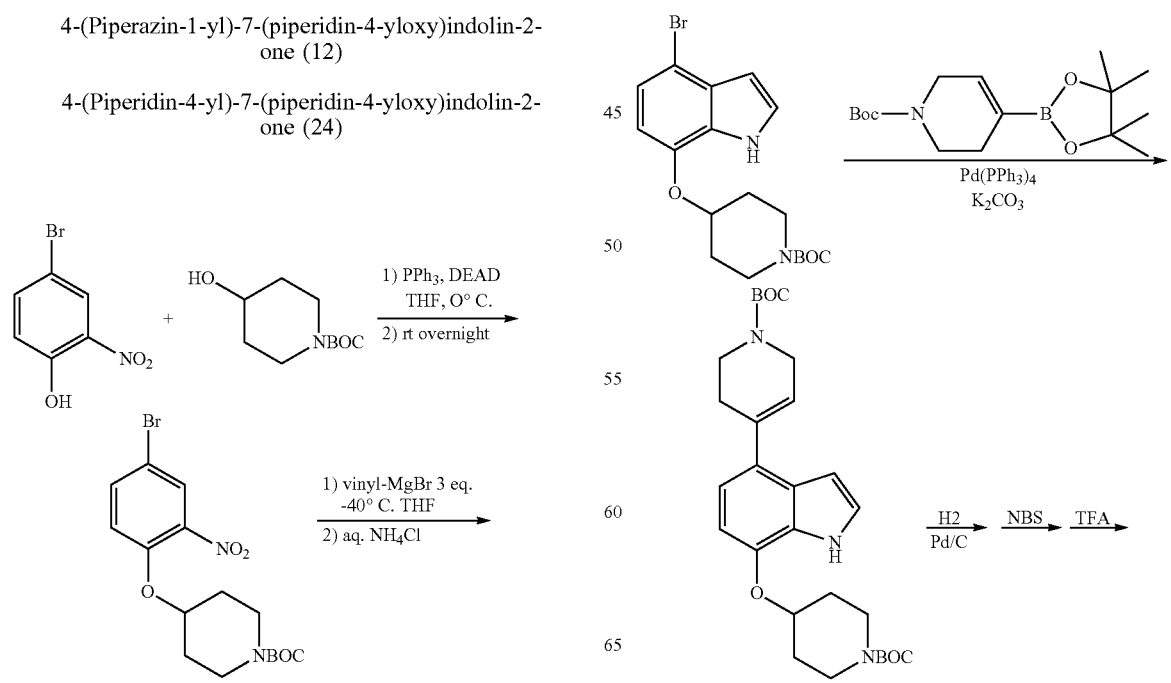

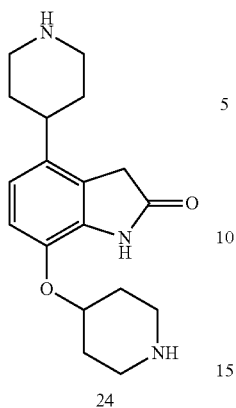

24

4-Bromo-2-nitrophenol is combined with N—BOC-4-hydroxypiperidine, employing Mitsonubo conditions. Vinyl magnesium bromide at low temperature installs an indole ring via the Bartoli reaction.

The ultimate indolines, 4-(piperidin-4-yl)-7-(piperidin-4-yloxy)indolin-2-one (24) or 4-(piperazin-1-yl)-7-(piperidin-4-yloxy)indolin-2-one (12), can be targeted by oxidizing the indole rings to indolines using, for example, NBS, and performing the appropriate palladium couplings and deprotections according to the scheme.

Example 15

4-(Piperazin-1-yl)-7-(piperidin-4-yloxy)isoindolin-1-one (13)

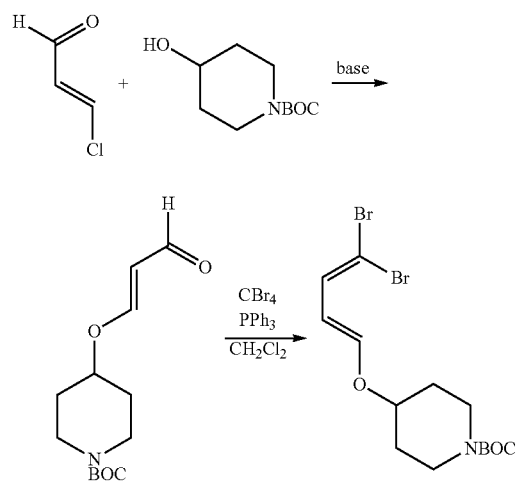

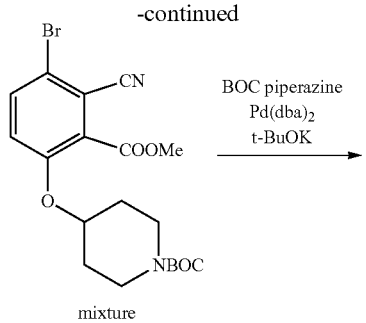

mixture

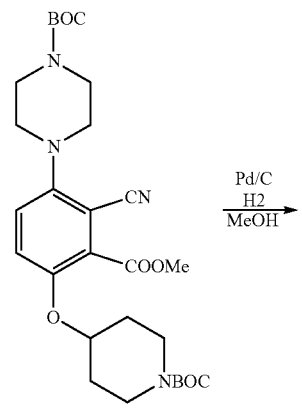

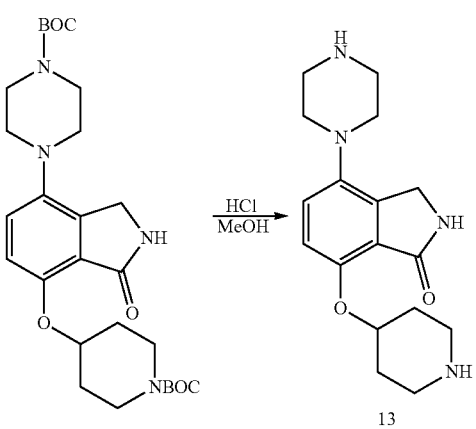

13

3-Chloroacrolein is condensed with 1-BOC-piperidin-ol by means of a Michael reaction, giving N—BOC-(E)-3-(piperidin-4-yloxy)acrylaldehyde. The aldehyde can dibromoolefinated using CBr₄/PPh₃, giving a diene which can undergo a thermal or Lewis acid catalyzed Diels-Alder cyclization, followed by aromatization with loss of HBr.

The aryl bromide may be coupled to BOC-piperazine. Reduction of the nitrile induces cyclization to the indicated lactam affording, on deprotection, the isoindolone, 4-(piperazin-1-yl)-7-(piperidin-4-yloxy)isoindolin-1-one (13).

Example 16

4-(Naphthalen-1-yl)piperazine-1-carboximidamide (10)

a) 1-(naphthalen-1-yl)piperazine

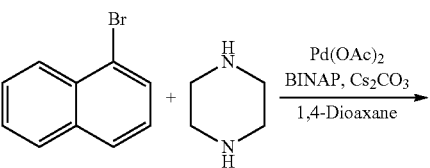

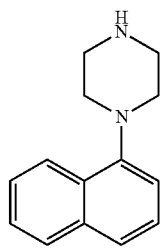

An oven dried Schlenk flask was evacuated and back filled with inert gas. Then to the flask was charged with BINAP (1.2 g, 1.93 mmol) and palladium (II)-acetate (216 mg, 0.96 mmol) in dioxane (5 mL) at room temperature under an inert atmosphere. The resultant reaction mixture was evacuated on stirring for 5 min and then the reaction mixture was heated to 115° C. for 1-2 min to give a catalyst, to which 1-bromo naphthalene (2 g, 9.65 mmol), piperazine (4.1 g, 48.2 mmol), $Cs_2CO_3$ (6.2 g, 19.31 mmol) and also 20 mL of dioxane were added. The resulting reaction mixture was heated to 110° C. for 4 h. The reaction was monitored by TLC and LCMS. The reaction mixture was filtered through a celite pad and was washed with ethyl acetate. The filtrate was concentrated under reduced pressure and the residue was purified on basic alumina with a gradient elution of 3% MeOH in DCM to furnish 1-(naphthalen-1-yl)piperazine. LCMS purity: 93.356%, m/z=213.3 [M+H]⁺.

b) 4-(naphthalen-1-yl)piperazine-1-carboximidamide

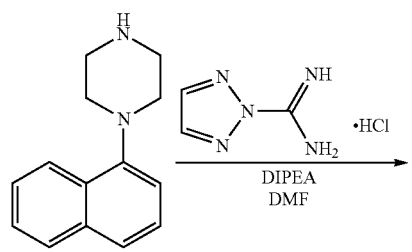

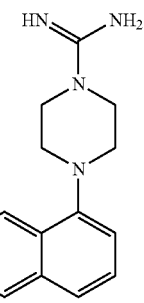

To a stirred solution of 1-(naphthalen-1-yl)piperazine (300 mg, 1.41 mmol) and 2H-1,2,3-triazole-2-carboximidamide hydrochloride (207 mg, 1.41 mmol) in DMF (2.5 mL) was added DIPEA (0.26 mL, 0.00141 mol) and the resulting mixture was heated to 80° C. for 10 h. The reaction mixture was monitored by TLC. After completion of the reaction the mixture was concentrated under reduced pressure the crude product was purified by column chromatography on basic alumina with a gradient elution of 20% MeOH in DCM to furnish 4-(naphthalen-1-yl)piperazine-1-carboximidamide. LCMS purity: 97.938%, RT=5.067 min, m/z=255.3 (M+H)⁺ (Method 3). ¹H-NMR (400 MHz, DMSO-$d_6$): δ 8.20 (d, 1H), 7.91 (d, 1H), 7.75-7.60 (m, 4H), 7.55-7.41 (brs, 2H), 7.20 (d, 1H), 3.79-3.60 (m, 4H), 3.09-2.91 (m, 4H).

Example 17

4-(Naphthalen-1-yl)piperazine-1-carboxamide (11)

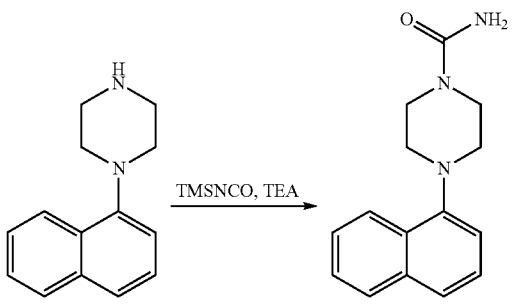 [SMILES: c1ccc2c(N3CCNCC3)cccc2c1 ; NC(=O)N1CCN(c2cccc3ccccc23)CC1]

To a stirred solution of 1-(naphthalen-1-yl)piperazine (200 mg, 0.942 mmol) and TEA (0.16 mL, 1.88 mmol) in DCM (8 mL) was added TMSNCO (0.16 mL, 1.22 mmol) and the resulting solution was stirred at room temperature for 2 h. The reaction mixture was monitored by TLC. After completion of the reaction the mixture was concentrated under reduced pressure and the residue was purified by column chromatography on basic alumina with a gradient elution of 2% MeOH in DCM to furnish 4-(naphthalen-1-yl)piperazine-1-carboxamide. LCMS purity: 90.785%, RT=5.712 min, m/z=256.3 (M+H)⁺ (Method 3). ¹H-NMR (400 MHz, DMSO-$d_6$): δ 8.20 (d, 1H), 7.91 (d, 1H), 7.70-7.39 (m, 4H), 7.1 (d, 1H), 6.1 (brs, 2H), 3.80-3.61 (m, 4H), 3.11-2.90 (m, 4H).

Example 18

4-(4-Methylnaphthalen-1-yl)piperidine (43)

a) Tert-butyl 4-(4-methylnaphthalen-1-yl)-3,6-dihydropyridine-1(2H)-carboxylate

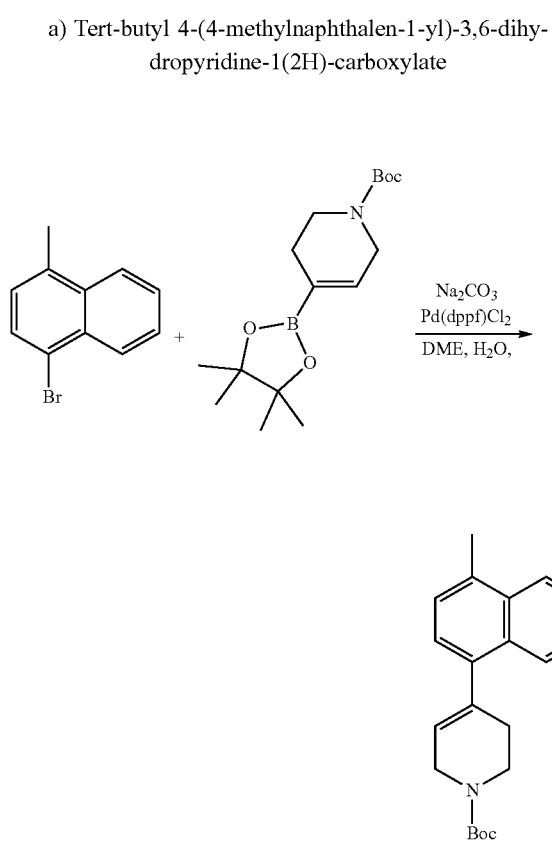

A mixture of 1-bromo-4-methylnaphthalene (1.0 g, 4.52 mmol, 1.0 eq), tert-butyl 4-(4,4,5,5-tetramethyl-1,3,2-dioxaborolan-2-yl)-3,6-dihydropyridine-1(2H)-carboxylate (2.1 g, 6.78 mmol, 1.5 eq) and Na₂CO₃ (1.43 g, 13.56 mmol, 3.0 eq) in a mixture of 1,2-DME (15 mL) and water (5 mL) was purged with nitrogen for 15 min. Pd(dppf)Cl₂·DCM (0.36 g, 0.45 mmol, 0.1 eq) was added to the reaction mixture and was stirred under nitrogen atmosphere, at 80° C. for 2 h. After complete consumption of starting material, the mixture was cooled to ambient temperature and partitioned between water and ethyl acetate. The organic extract was separated and the aqueous extract was again extracted with ethyl acetate. The combined organic extract was washed with brine, dried over anhydrous Na₂SO₄, filtered and solvents evaporated from the filtrate under reduced pressure to obtain a crude product, which was purified by flash chromatography on silica gel, 230-400 mesh, using gradient of ethyl acetate in hexanes as eluent to obtain tert-butyl 4-(4-methylnaphthalen-1-yl)-3,6-dihydropyridine-1(2H)-carboxylate. LCMS: Purity 82.42%. MS calculated for [M]323.44 and found [M+H]⁺ 324.20.

b) Tert-butyl 4-(4-methylnaphthalen-1-yl)piperidine-1-carboxylate

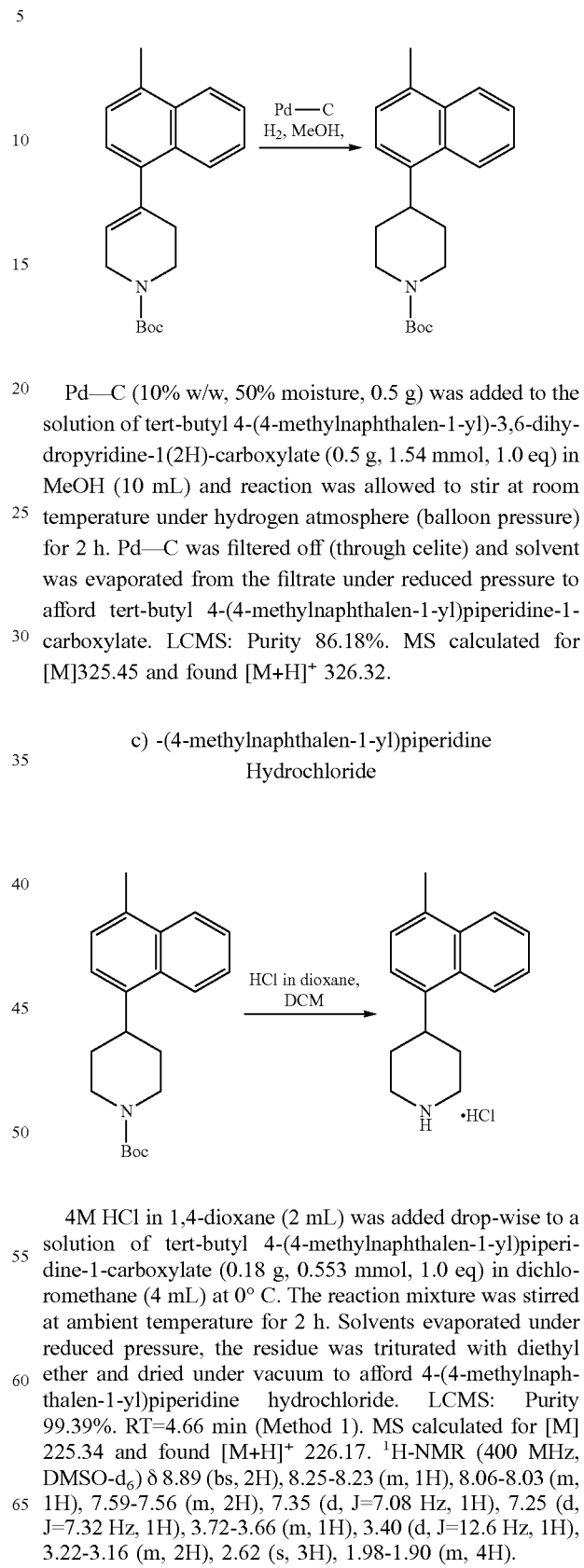

Pd—C (10% w/w, 50% moisture, 0.5 g) was added to the solution of tert-butyl 4-(4-methylnaphthalen-1-yl)-3,6-dihydropyridine-1(2H)-carboxylate (0.5 g, 1.54 mmol, 1.0 eq) in MeOH (10 mL) and reaction was allowed to stir at room temperature under hydrogen atmosphere (balloon pressure) for 2 h. Pd—C was filtered off (through celite) and solvent was evaporated from the filtrate under reduced pressure to afford tert-butyl 4-(4-methylnaphthalen-1-yl)piperidine-1-carboxylate. LCMS: Purity 86.18%. MS calculated for [M]325.45 and found [M+H]⁺ 326.32.

c) -(4-methylnaphthalen-1-yl)piperidine Hydrochloride

4M HCl in 1,4-dioxane (2 mL) was added drop-wise to a solution of tert-butyl 4-(4-methylnaphthalen-1-yl)piperidine-1-carboxylate (0.18 g, 0.553 mmol, 1.0 eq) in dichloromethane (4 mL) at 0° C. The reaction mixture was stirred at ambient temperature for 2 h. Solvents evaporated under reduced pressure, the residue was triturated with diethyl ether and dried under vacuum to afford 4-(4-methylnaphthalen-1-yl)piperidine hydrochloride. LCMS: Purity 99.39%. RT=4.66 min (Method 1). MS calculated for [M] 225.34 and found [M+H]⁺ 226.17. ¹H-NMR (400 MHz, DMSO-d₆) δ 8.89 (bs, 2H), 8.25-8.23 (m, 1H), 8.06-8.03 (m, 1H), 7.59-7.56 (m, 2H), 7.35 (d, J=7.08 Hz, 1H), 7.25 (d, J=7.32 Hz, 1H), 3.72-3.66 (m, 1H), 3.40 (d, J=12.6 Hz, 1H), 3.22-3.16 (m, 2H), 2.62 (s, 3H), 1.98-1.90 (m, 4H).

Example 19

4-(Piperidin-4-yl)-1H-benzo[d]imidazole (20)

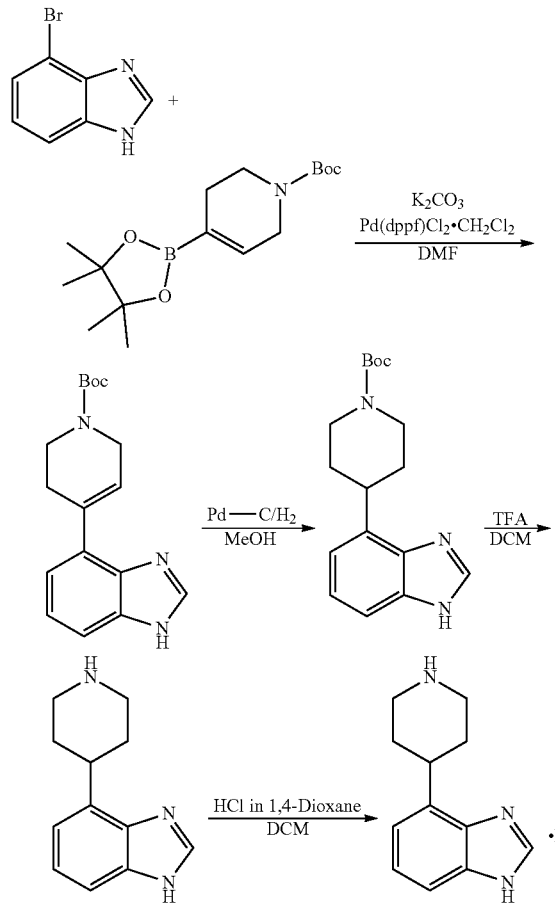

4-(piperidin-4-yl)-1H-benzo[d]imidazole (20) may be prepared by methods similar to those described in Example 18, using 4-bromo-1H-benzo[d]imidazole as the aryl halide starting material. LCMS RT=4.97 min, m/z=202.34 [M+H]$^+$ (Method 1).

Example 20

4-(Piperidin-4-yl)benzo[d]thiazole (21)

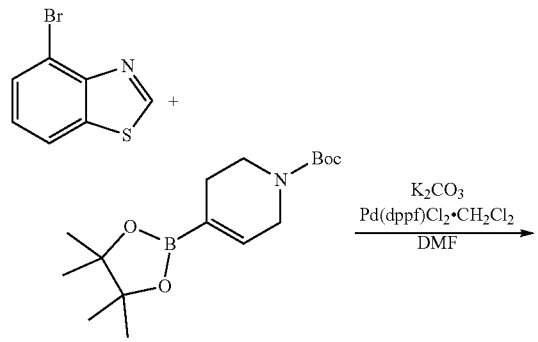

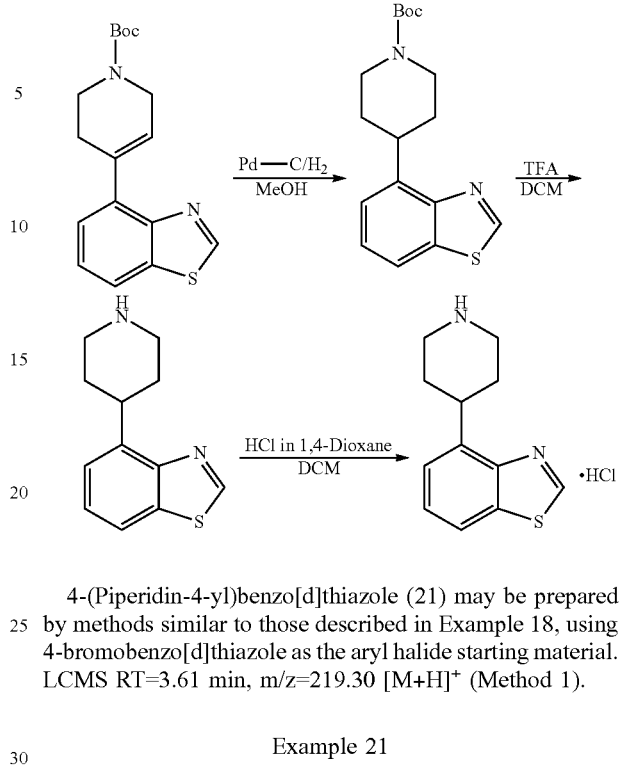

4-(Piperidin-4-yl)benzo[d]thiazole (21) may be prepared by methods similar to those described in Example 18, using 4-bromobenzo[d]thiazole as the aryl halide starting material. LCMS RT=3.61 min, m/z=219.30 [M+H]$^+$ (Method 1).

Example 21

5-(Piperidin-4-yl)isoquinoline (109)

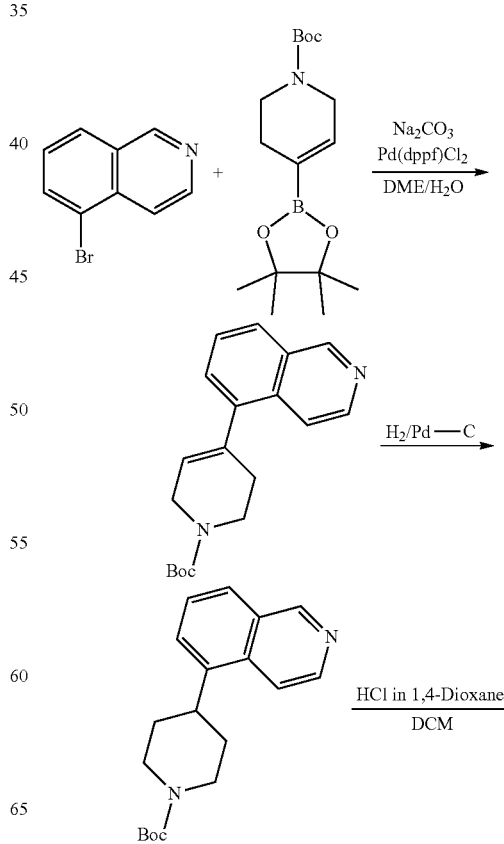

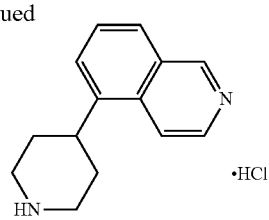

5-(piperidin-4-yl)isoquinoline (109) may be prepared by methods similar to those described in Example 18, using 5-bromoisoquinoline as the aryl halide starting material. LCMS RT=5.21 min, m/z=213.12 [M+H]$^+$ (Method 1).

Example 22

4-(4-Methoxynaphthalen-1-yl)piperidine (44)

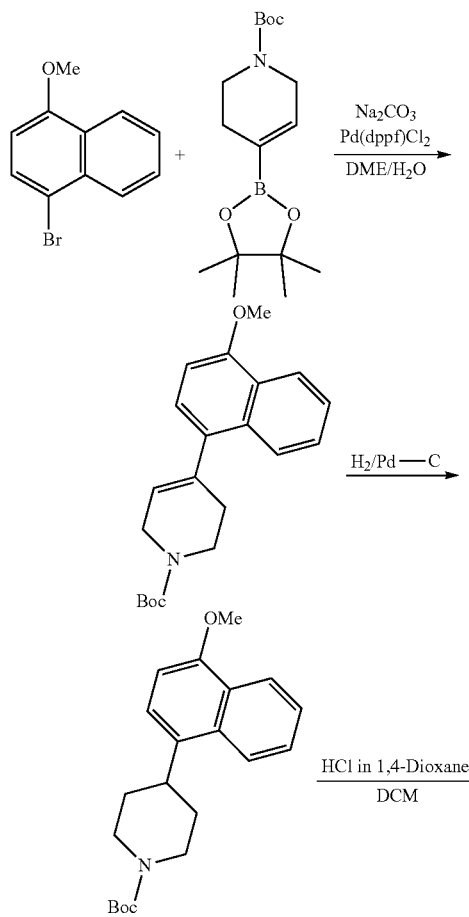

4-(4-methoxynaphthalen-1-yl)piperidine (47) may be prepared using similar methods as described in Example 18, except using 1-bromo-4-methoxynaphthalene as the aryl halide starting material. LCMS RT=5.21 min, m/z=213.12 [M+H]$^+$ (Method 1).

Example 23

8-(Piperidin-4-yl)isoquinoline (110)

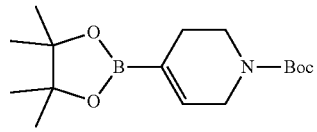
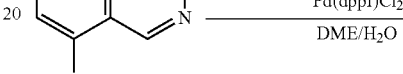
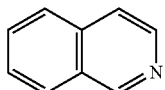
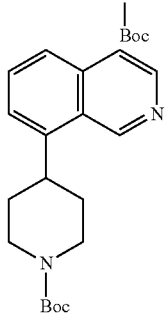
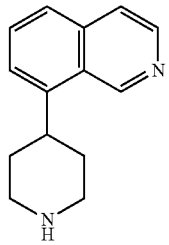

8-(Piperidin-4-yl)isoquinoline (110) may be prepared by methods similar to those described in Example 18, using 8-bromoisoquinoline as the aryl halide starting material. LCMS RT=3.42 min, m/z=213.12 [M+H]$^+$ (Method 1).

Example 24

4-(Piperidin-4-yl)isoquinoline (45)

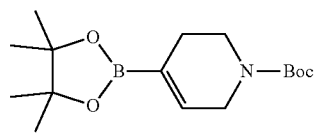
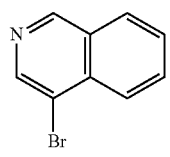

-continued

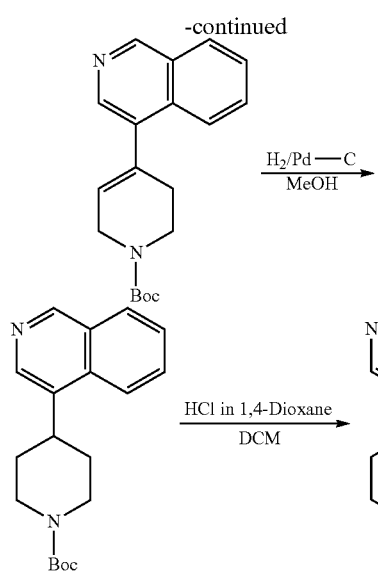

4-(piperidin-4-yl)isoquinoline (45) may be prepared by methods similar to those described in Example 18, using 4-bromoisoquinoline as the aryl halide starting material. LCMS RT=3.33 min, m/z=213.14 [M+H]$^+$ (Method 1).

Example 25

1-(Piperidin-4-yl)isoquinoline (46)

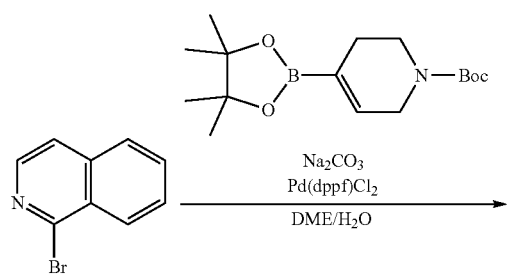

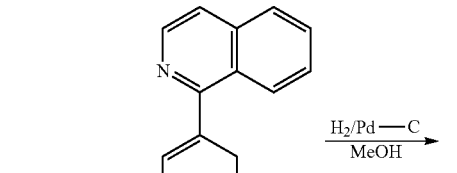

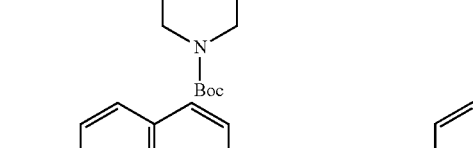

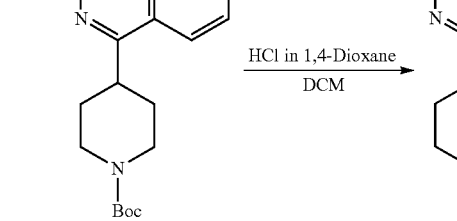

1-(piperidin-4-yl)isoquinoline (46) may be prepared by methods similar to those described in Example 18, using 1-bromoisoquinoline as the aryl halide starting material. LCMS RT=3.82 min, m/z=213.12 [M+H]$^+$ (Method 1).

Example 26

4-(Piperidin-4-yl)naphthalen-1-ol (47)

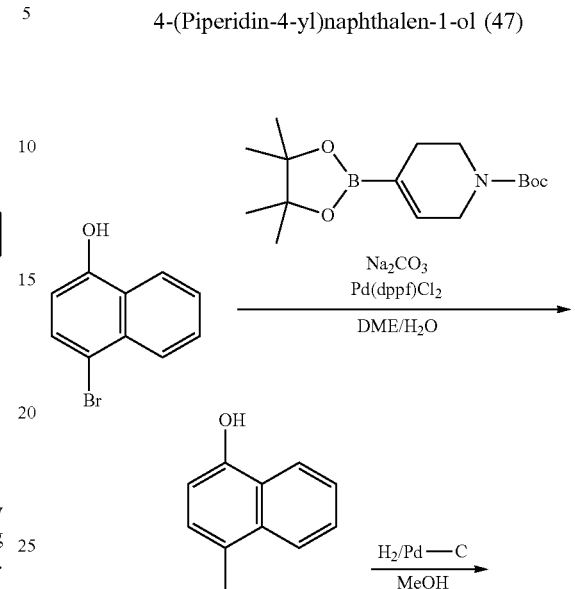

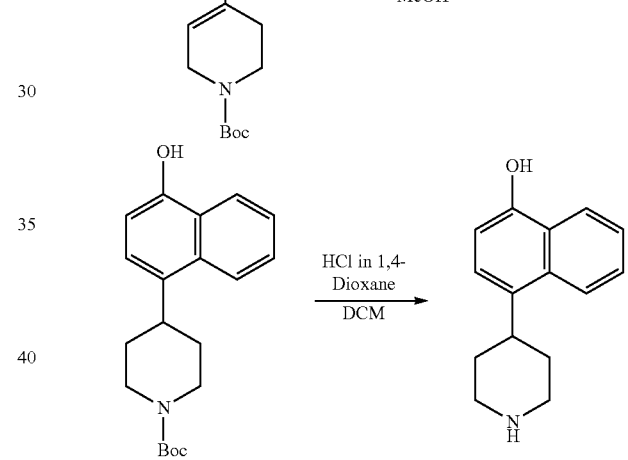

4-(piperidin-4-yl)naphthalen-1-ol (47) may be prepared by methods similar to those described in Example 18, using 4-bromonaphthalen-1-ol as the aryl halide starting material. LCMS RT=3.82 min, m/z=228.12 [M+H]$^+$ (Method 1).

Example 27

4-(Piperidin-4-yl)quinazoline (48)

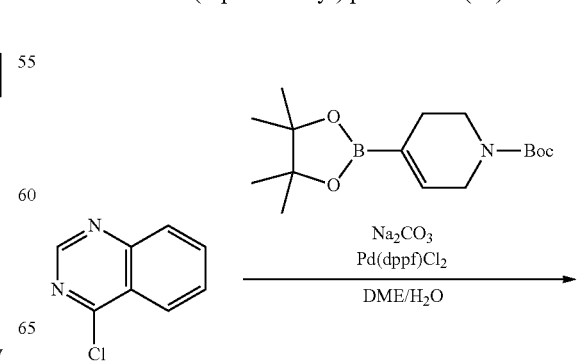

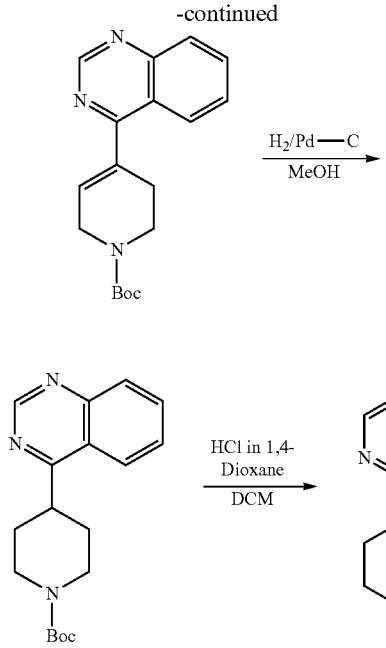
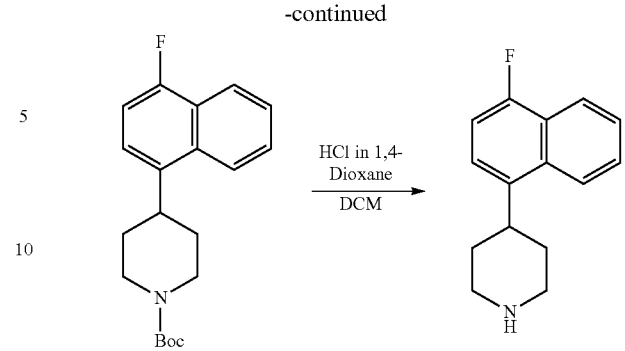

4-(piperidin-4-yl)quinazoline (48) may be prepared by methods similar to those described in Example 18, using 4-chloroquinazoline as the aryl halide starting material. LCMS m/z=214.2 [M+H]$^+$ (Method 1).

Example 28

4-(4-Fluoronaphthalen-1-yl)piperidine (49)

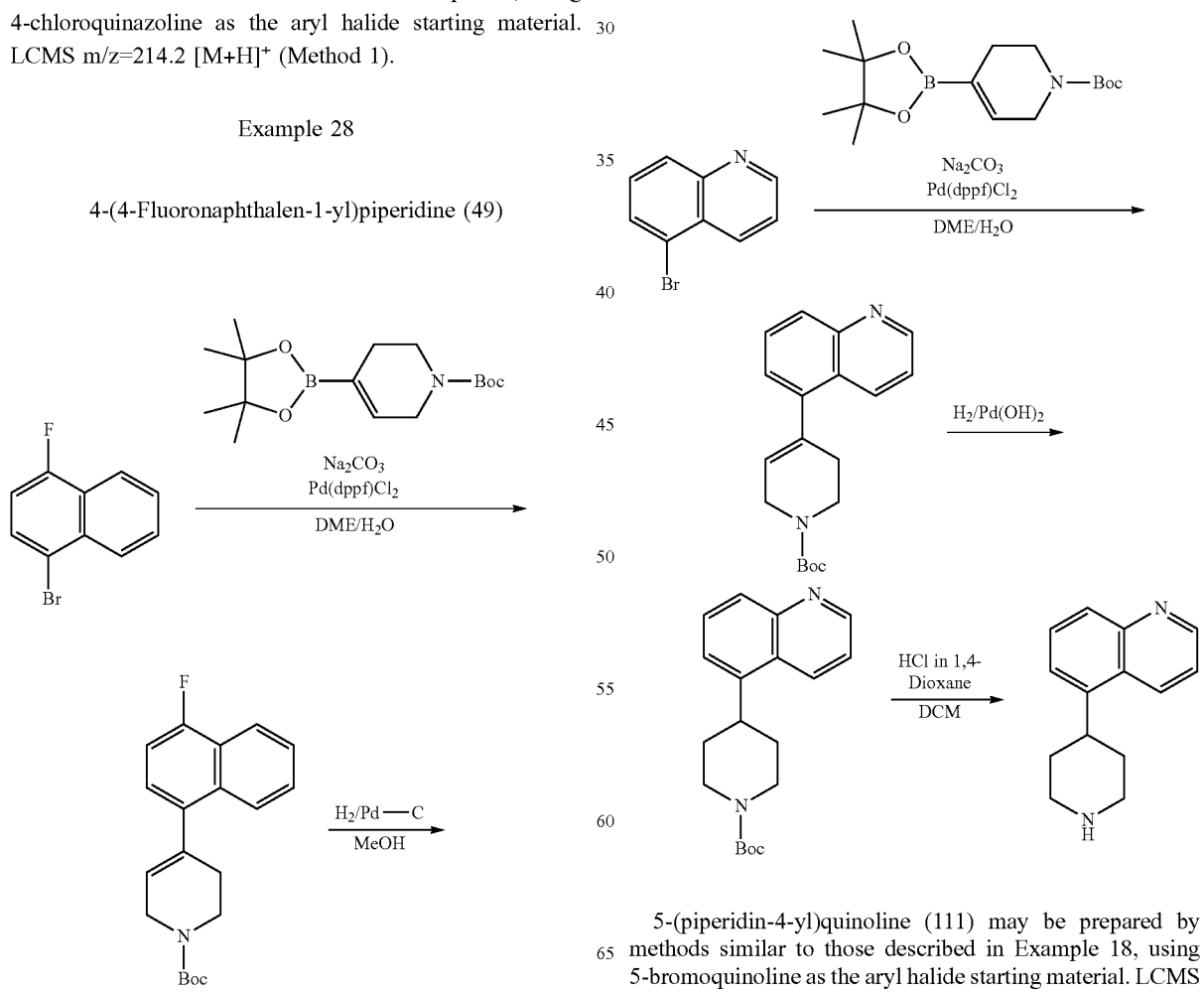

4-(4-fluoronaphthalen-1-yl)piperidine (49) may be prepared by methods similar to those described in Example 18, using 1-bromo-4-fluoronaphthalene as aryl halide starting material. LCMS RT=4.56 min, m/z=230.28 [M+H]$^+$ (Method 1).

Example 29

5-(Piperidin-4-yl)quinoline (111)

5-(piperidin-4-yl)quinoline (111) may be prepared by methods similar to those described in Example 18, using 5-bromoquinoline as the aryl halide starting material. LCMS RT=4.48 min, m/z=213.15 [M+H]$^+$ (Method 2).

Example 30

4-(Piperidin-4-yl)quinoline (50)

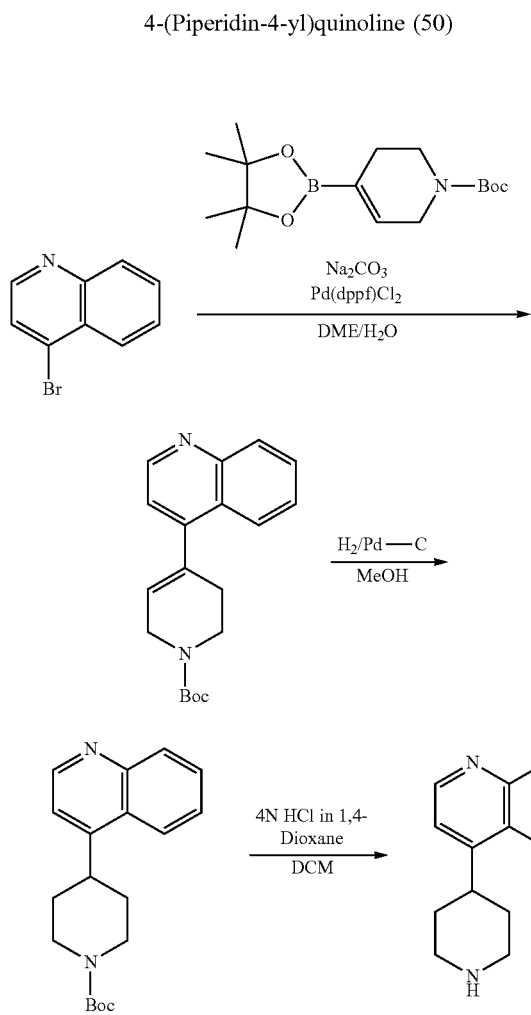

4-(piperidin-4-yl)quinoline (50) may be prepared by methods similar to those described in Example 18, using 4-bromoquinoline as the aryl halide starting material. LCMS RT=4.28 min, m/z=212.97 [M+H]$^+$ (Method 2).

Example 31

8-Fluoro-5-(piperidin-4-yl)quinoline (51)

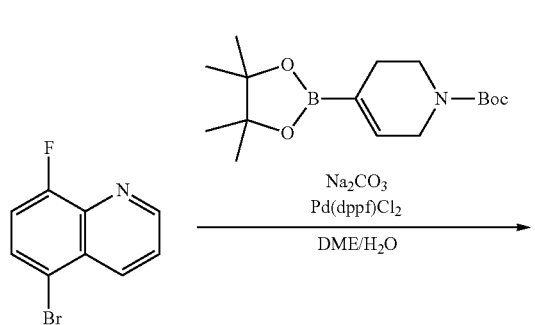

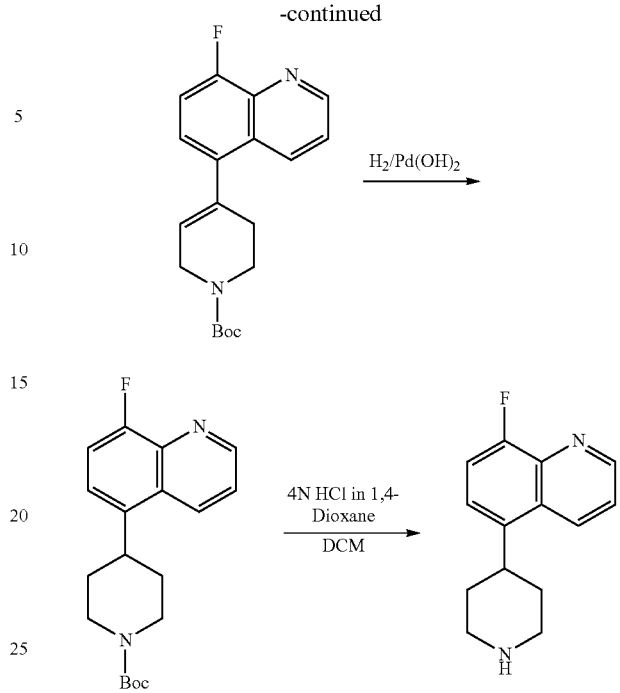

8-fluoro-5-(piperidin-4-yl)quinoline (51) may be prepared by methods similar to those described in Example 18, using 5-bromo-8-fluoroquinoline as the aryl halide starting material. LCMS RT=4.22 min, m/z=231.12 [M+H]$^+$ (Method 2).

Example 32

8-Fluoro-5-(piperidin-4-yl)isoquinoline (52)

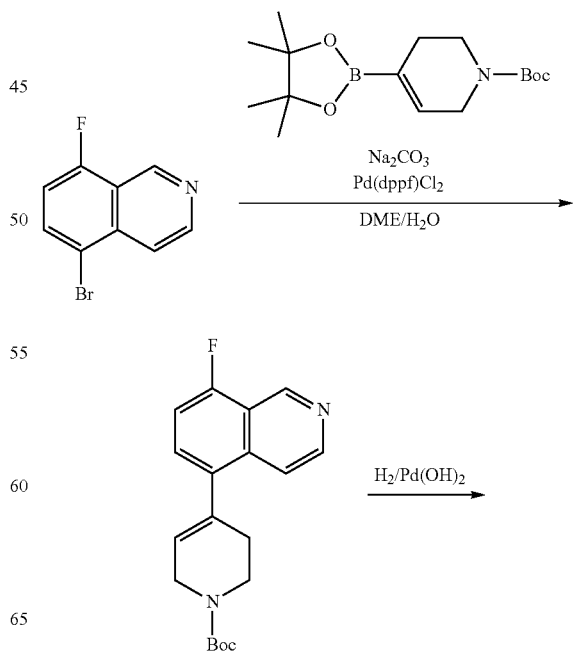

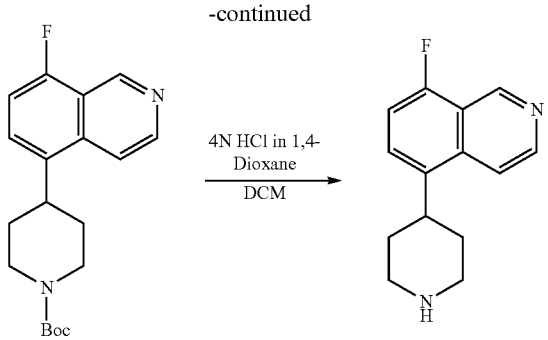

8-fluoro-5-(piperidin-4-yl)isoquinoline (52) may be prepared by methods similar to those described in Example 18, using 5-bromo-8-fluoroisoquinoline as the aryl halide starting material. LCMS RT=3.30 min, m/z=231.04 [M+H]$^+$ (Method 1).

Example 33

4-(5-Methylnaphthalen-1-yl)piperidine (53)

a) (5-bromonaphthalen-1-yl)methanol

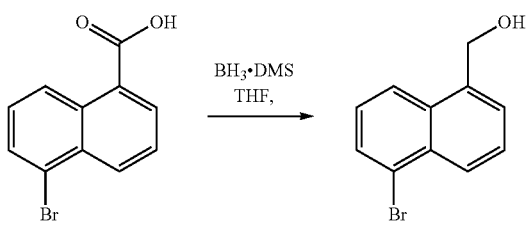 [SMILES: O=C(O)c1cccc2c(Br)cccc12 ; OCc1cccc2c(Br)cccc12]

Borane dimethylsulfide (1.51 g, 19.9 mmol, 2.5 eq) was added to the solution of 5-bromo-1-naphthoic acid (2.0 g, 7.96 mmol, 1.0 eq) in THF (50 mL) under nitrogen atmosphere at 0° C. and the solution was stirred at ambient temperature for 16 h. After complete consumption of starting material, the reaction mixture was quenched with dropwise addition of MeOH at 0° C., diluted with water and extracted with ethyl acetate. The combined organic extract was washed with brine, dried over anhydrous Na$_2$SO$_4$, filtered and solvents evaporated from the filtrate under reduced pressure to afford (5-bromonaphthalen-1-yl)methanol.

b) 1-bromo-5-(bromomethyl)naphthalene

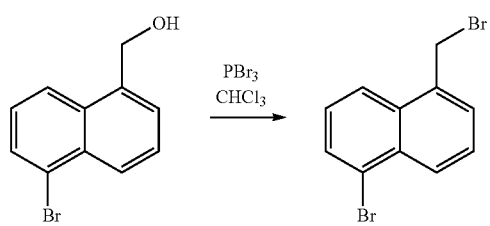 [SMILES: OCc1cccc2c(Br)cccc12 ; BrCc1cccc2c(Br)cccc12]

Phosphorus tribromide (0.89 g, 3.3 mmol, 1.2 eq) was added to the solution of (5-bromonaphthalen-1-yl) methanol (0.65 g, 2.75 mmol, 1.0 eq) in CHCl$_3$ (20 mL) under nitrogen atmosphere at 0° C. and the solution was stirred at ambient temperature for 2 h. After complete consumption of starting material, the reaction mixture was diluted with dichloromethane and washed with water, saturated aqueous sodium bicarbonate and brine. The organic extract was then dried over anhydrous sodium sulfate, filtered, and solvent evaporated from the filtrate under reduced pressure to afford 1-bromo-5-(bromomethyl)naphthalene.

c) 1-bromo-5-methylnaphthalene

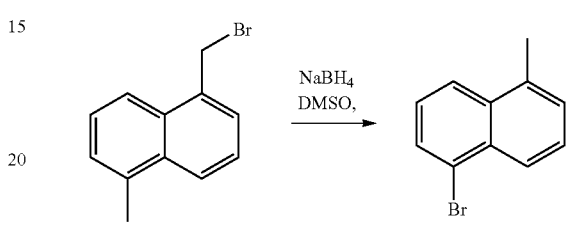

Sodium borohydride (0.56 g, 14.8 mmol, 8.0 eq) was added to the solution of 1-bromo-5-(bromomethyl)naphthalene (0.55 g, 1.85 mmol, 1.0 eq) in DMSO (5 mL) under nitrogen atmosphere at 0° C. and the solution was stirred at ambient temperature for 2 h. After complete consumption of starting material, the reaction mixture was poured into chilled water. The precipitate was filtered and dried under vacuum to afford 1-bromo-5-methylnaphthalene.

d) Tert-butyl 4-(5-methylnaphthalen-1-yl)-3,6-dihydropyridine-1(2H)-carboxylate

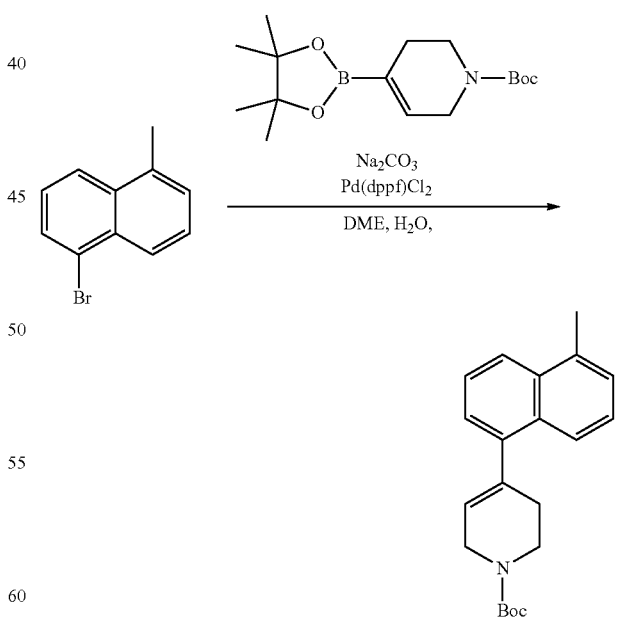

A mixture of 1-bromo-5-methylnaphthalene (0.28 g, 1.24 mmol, 1.0 eq), tert-butyl 4-(4,4,5,5-tetramethyl-1,3,2-dioxaborolan-2-yl)-3,6-dihydropyridine-1(2H)-carboxylate (0.422 g, 1.36 mmol, 1.1 eq) and Na$_2$CO$_3$ (0.395 g, 3.73 mmol, 3.0 eq) in a mixture of 1,2-DME (8 mL) and water (2 mL) was purged with nitrogen for 15 min. Pd(dppf)Cl$_2$·DCM (0.101 g, 0.124 mmol, 0.1 eq) was added to the reaction mixture and was stirred under nitrogen atmosphere, at 80° C. for 2 h. After complete consumption of starting material, the mixture was cooled to ambient temperature and partitioned between water and ethyl acetate. The organic extract was separated and the aqueous extract was again extracted with ethyl acetate. The combined organic extract was washed with brine, dried over anhydrous Na$_2$SO$_4$, filtered and solvents evaporated from the filtrate under reduced pressure to obtain a crude product, which was purified by flash chromatography on silica gel, 230-400 mesh, using gradient of ethyl acetate in hexanes as eluent to obtain tert-butyl 4-(5-methylnaphthalen-1-yl)-3,6-dihydropyridine-1(2H)-carboxylate.

e) Tert-butyl 4-(5-methylnaphthalen-1-yl)piperidine-1-carboxylate

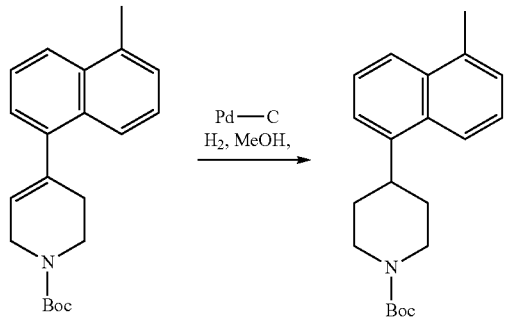

Pd—C (10% w/w, 50% moisture, 0.08 g) was added to the solution of tert-butyl 4-(5-methylnaphthalen-1-yl)-3,6-dihydropyridine-1(2H)-carboxylate (0.28 g, 0.866 mmol, 1.0 eq) in MeOH (5 mL) and reaction was allowed to stir at room temperature under hydrogen atmosphere (balloon pressure) for 1 h. Pd—C was filtered off (through celite) and solvent was evaporated from the filtrate under reduced pressure to obtain a crude product, which was purified by flash chromatography on silica gel, 230-400 mesh, using gradient of ethyl acetate in hexanes as eluent to obtain tert-butyl 4-(5-methylnaphthalen-1-yl)piperidine-1-carboxylate. LCMS: Purity 97.77%. MS calculated for [M] 325.45 and found [M+H]$^+$ 326.42.

f) 4-(5-methylnaphthalen-1-yl)piperidine Hydrochloride

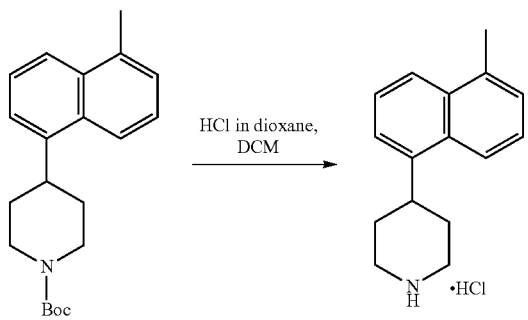 [SMILES: Cc1cccc2c(C3CCN(C(=O)OC(C)(C)C)CC3)cccc12 ; Cc1cccc2c(C3CCNCC3)cccc12 ; Cl]

4M HCl in 1,4-dioxane (1 mL) was added dropwise to a solution of tert-butyl 4-(5-methylnaphthalen-1-yl)piperidine-1-carboxylate (0.12 g, 0.36 mmol, 1.0 eq) in dichloromethane (2 mL) at 0° C. The reaction mixture was stirred at ambient temperature for 2 h. Solvents evaporated under reduced pressure, the residue was triturated with diethyl ether and dried under vacuum to afford 4-(5-methylnaphthalen-1-yl)piperidine hydrochloride. LCMS: Purity 99.25%. RT=5.02 min (Method 1). MS calculated for [M] 225.34 and found [M+H]$^+$ 226.09. $^1$H-NMR (400 MHz, DMSO-d$_6$) δ 8.88 (bs, 2H), 8.10 (d, J=8.56 Hz, 1H), 7.93 (d, J=8.36 Hz, 1H), 7.54 (t, J=7.48 Hz, 1H), 7.46 (t, J=7.04 Hz, 1H), 7.39 (d, J=6.88 Hz, 2H), 3.76-3.70 (m, 1H), 3.42-3.39 (m, 2H), 3.22-3.16 (m, 2H), 2.65 (s, 3H), 2.00-1.92 (m, 4H).

Example 34

(5-(Piperidin-4-yl)naphthalen-1-yl)methanol (54)

a) Methyl 5-bromo-1-naphthoate

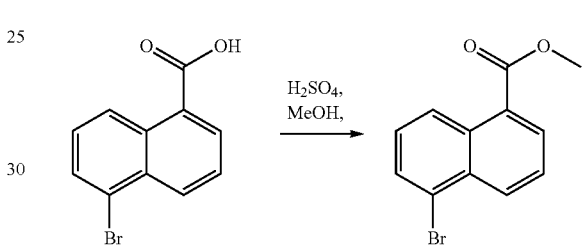

Sulfuric acid (0.3 mL) was added to the solution of 5-bromo-1-naphthoic acid (1.5 g, 5.97 mmol, 1.0 eq) in MeOH (50 mL) at room temperature and the solution was stirred under nitrogen atmosphere, at 80° C. for 16 h. After complete consumption of starting material, the reaction mixture was evaporated under reduced pressure, dissolved in ethyl acetate and washed with saturated aqueous sodium bicarbonate. The aqueous extract was again extracted with ethyl acetate. The combined organic extract was washed with brine, dried over anhydrous Na$_2$SO$_4$, filtered and solvents evaporated from the filtrate under reduced pressure to afford methyl 5-bromo-1-naphthoate. LCMS: Purity 93.15%. MS calculated for [M] 263.98 and found [M+H]$^+$ 265.05.

b) Tert-butyl 4-(5-(methoxycarbonyl)naphthalen-1-yl)-3,6-dihydropyridine-1(2H)-carboxylate

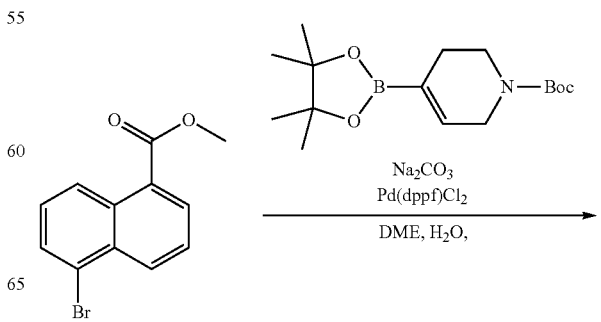

-continued

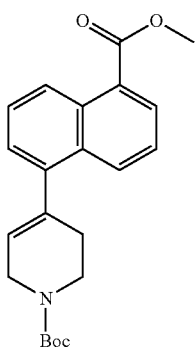

A mixture of methyl 5-bromo-1-naphthoate (1.3 g, 4.92 mmol, 1.0 eq), tert-butyl 4-(4,4,5,5-tetramethyl-1,3,2-dioxaborolan-2-yl)-3,6-dihydropyridine-1(2H)-carboxylate (1.67 g, 5.41 mmol, 1.1 eq) and Na$_2$CO$_3$ (1.56 g, 14.77 mmol, 3.0 eq) in a mixture of 1,2-DME (16 mL) and water (4 mL) was purged with nitrogen for 15 min. Pd(dppf)Cl$_2$·DCM (0.4 g, 0.49 mmol, 0.1 eq) was added to the reaction mixture and was stirred under nitrogen atmosphere, at 80° C. for 2 h. After complete consumption of starting material, the mixture was cooled to ambient temperature and partitioned between water and ethyl acetate. The organic extract was separated and the aqueous extract was again extracted with ethyl acetate. The combined organic extract was washed with brine, dried over anhydrous Na$_2$SO$_4$, filtered and solvents evaporated from the filtrate under reduced pressure to obtain a crude product, which was purified by flash chromatography on silica gel, 230-400 mesh, using gradient of ethyl acetate in hexanes as eluent to obtain tert-butyl 4-(5-(methoxycarbonyl)naphthalen-1-yl)-3,6-dihydropyridine-1(2H)-carboxylate. LCMS: Purity 99.35%. MS calculated for [M] 367.45 and found [M+H]$^+$ 368.26.

c) Tert-butyl 4-(5-(methoxycarbonyl)naphthalen-1-yl)piperidine-1-carboxylate

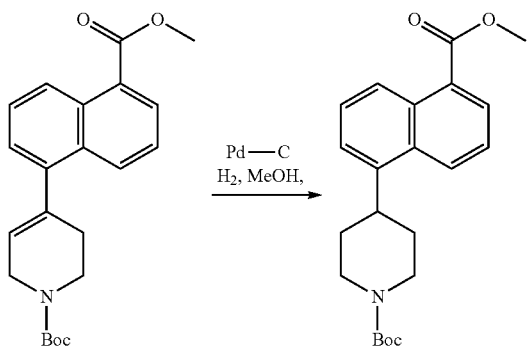

Pd—C (10% w/w, 50% moisture, 0.8 g) was added to the solution of tert-butyl 4-(5-(methoxycarbonyl)naphthalen-1-yl)-3,6-dihydropyridine-1(2H)-carboxylate (1.3 g, 3.54 mmol, 1.0 eq) in MeOH (50 mL) and reaction was allowed to stir at room temperature under hydrogen atmosphere (balloon pressure) for 4 h. Pd—C was filtered off (through celite) and solvent was evaporated from the filtrate under reduced pressure to obtain tert-butyl 4-(5-(methoxycarbonyl)naphthalen-1-yl)piperidine-1-carboxylate. LCMS: Purity 97.77%.

d) Tert-butyl 4-(5-(hydroxymethyl)naphthalen-1-yl)piperidine-1-carboxylate

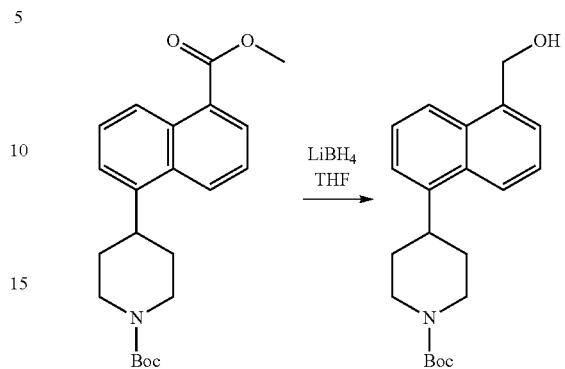

Lithium borohydride (0.89 g, 4.12 mmol, 5.0 eq) was added to the solution of tert-butyl 4-(5-(methoxycarbonyl)naphthalen-1-yl)piperidine-1-carboxylate (0.3 g, 0.82 mmol, 1.0 eq) in THF (10 mL) under nitrogen atmosphere at 0° C. and the reaction mixture was stirred under nitrogen atmosphere, at 60° C. for 4 h. After complete consumption of starting material, saturated aqueous ammonium chloride was added drop-wise at 0° C., the mixture was diluted with water and extracted with ethyl acetate. The combined organic extract was washed with brine, dried over anhydrous Na$_2$SO$_4$, filtered and solvents evaporated from the filtrate under reduced pressure to afford tert-butyl 4-(5-(hydroxymethyl)naphthalen-1-yl)piperidine-1-carboxylate. LCMS: Purity 99.54%. MS calculated for [M] 341.20 and found [M+H]$^+$ 342.17.

e) (5-(piperidin-4-yl)naphthalen-1-yl)methanol Hydrochloride

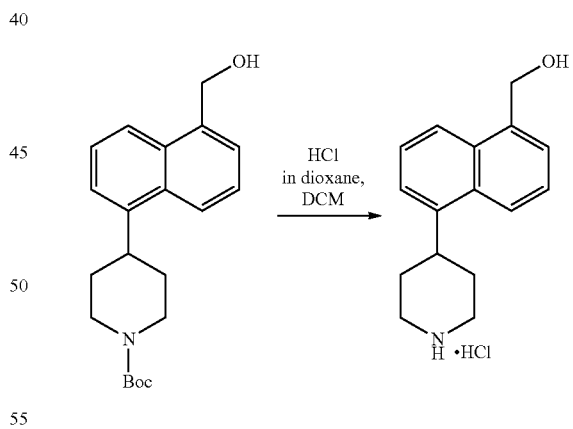

4M HCl in 1,4-dioxane (2 mL) was added dropwise to a solution of tert-butyl 4-(5-(hydroxymethyl)naphthalen-1-yl)piperidine-1-carboxylate (0.1 g, 0.29 mmol, 1.0 eq) in dichloromethane (2 mL) at 0° C. The reaction mixture was stirred at ambient temperature for 16 h. Solvents evaporated under reduced pressure, the residue was triturated with diethyl ether and dried under vacuum to afford (5-(piperidin-4-yl)naphthalen-1-yl)methanol hydrochloride. LCMS: Purity 97.08%. RT=3.94 min (Method 1). MS calculated for [M] 241.33 and found [M+H]$^+$ 242.13. $^1$H-NMR (400 MHz, DMSO-d$_6$) δ 8.90 (bs, 1H), 8.75 (bs, 1H), 8.16 (d, J=8.2 Hz, 1H), 7.98 (d, J=8.48 Hz, 1H), 7.59-7.51 (m, 3H), 7.38 (d, J=7.12 Hz, 1H), 5.32 (bs, 1H), 4.96 (s, 2H), 3.77-3.71 (m, 1H), 3.42-3.39 (m, 2H), 3.24-3.16 (m, 2H), 2.03-1.91 (m, 4H).

Example 35

4-(6-Methylnaphthalen-1-yl)piperidine (55)

a) (5-bromonaphthalen-2-yl)methanol

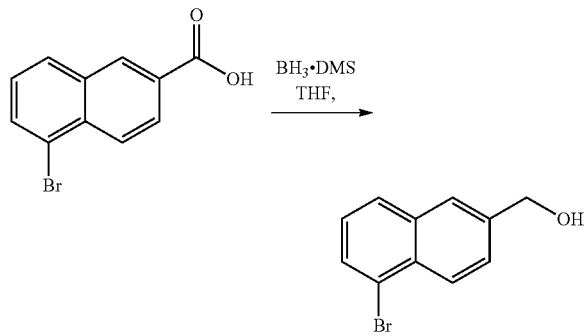

Borane dimethylsulfide (1.51 g, 19.9 mmol, 2.5 eq) was added to the solution of 5-bromo-2-naphthoic acid (2.0 g, 7.96 mmol, 1.0 eq) in THF (20 mL) under nitrogen atmosphere at 0° C. and the solution was stirred at ambient temperature for 16 h. After complete consumption of starting material, the reaction mixture was quenched by dropwise addition of MeOH at 0° C., diluted with water and extracted with ethyl acetate. The combined organic extract was washed with brine, dried over anhydrous Na₂SO₄, filtered and solvents evaporated from the filtrate under reduced pressure to afford (5-bromonaphthalen-2-yl)methanol.

b) 1-bromo-6-(bromomethyl)naphthalene

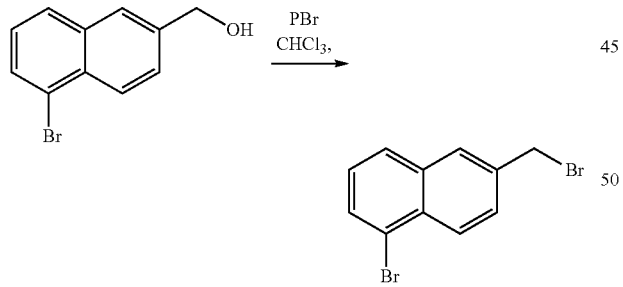

Phosphorus tribromide (2.4 g, 8.89 mmol, 1.2 eq) was added to the solution of (5-bromonaphthalen-2-yl)methanol (1.75 g, 7.4 mmol, 1.0 eq) in CHCl₃ (20 mL) under nitrogen atmosphere at 0° C. and the solution was stirred at ambient temperature for 2 h. After complete consumption of starting material, the reaction mixture was diluted with dichloromethane and washed with water followed by saturated aqueous sodium bicarbonate and brine. The organic extract was then dried over anhydrous sodium sulfate, filtered, and solvent evaporated from the filtrated under reduced pressure to afford 1-bromo-6-(bromomethyl)naphthalene. MS calculated for [M] 299.99.

c) 1-bromo-6-methylnaphthalene

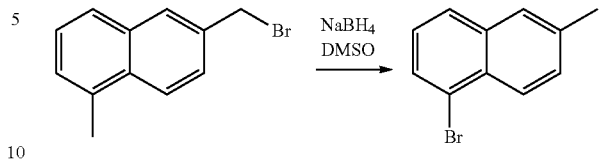

سodium borohydride (1.2 g, 31.8 mmol, 8.0 eq) was added to the solution of 1-bromo-6-(bromomethyl)naphthalene (1.89 g, 6.36 mmol, 1.0 eq) in DMSO (15 mL) under nitrogen atmosphere at 0° C. and the solution was stirred at ambient temperature for 2 h. After complete consumption of starting material, the reaction mixture was partitioned between water and ethyl acetate. The organic extract was separated and the aqueous extract was again extracted with ethyl acetate. The combined organic extract was washed with brine, dried over anhydrous Na₂SO₄, filtered and solvents evaporated from the filtrate under reduced pressure to afford 1-bromo-6-methylnaphthalene.

d) Tert-butyl 4-(6-methylnaphthalen-1-yl)-3,6-dihydropyridine-1(2H)-carboxylate

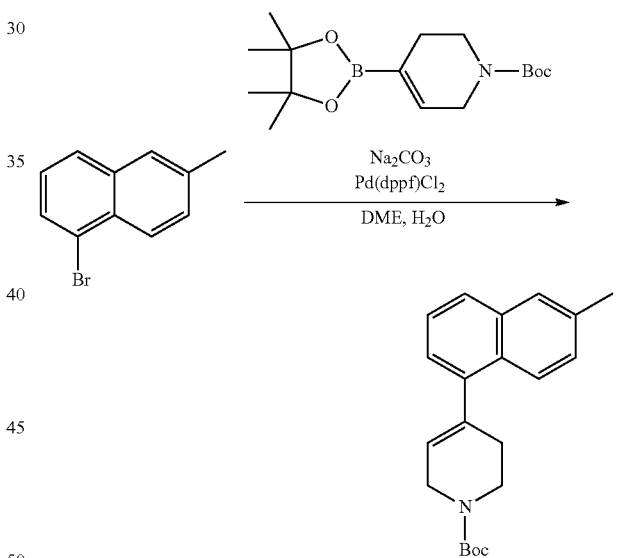

A mixture of 1-bromo-6-methylnaphthalene (0.9 g, 4.09 mmol, 1.0 eq), tert-butyl 4-(4,4,5,5-tetramethyl-1,3,2-dioxaborolan-2-yl)-3,6-dihydropyridine-1(2H)-carboxylate (1.39 g, 4.49 mmol, 1.1 eq) and Na₂CO₃ (1.3 g, 12.27 mmol, 3.0 eq) in a mixture of 1,2-DME (16 mL) and water (4 mL) was purged with nitrogen for 15 min. Pd(dppf)Cl₂·DCM (0.33 g, 0.409 mmol, 0.1 eq) was added to the reaction mixture and was stirred under nitrogen atmosphere, at 80° C. for 2 h. After complete consumption of starting material, the mixture was cooled to ambient temperature and partitioned between water and ethyl acetate. The organic extract was separated and the aqueous extract was again extracted with ethyl acetate. The combined organic extract was washed with brine, dried over anhydrous Na₂SO₄, filtered and solvents evaporated from the filtrate under reduced pressure to obtain a crude product, which was purified by flash chromatography on silica gel, 230-400 mesh, using gradient of ethyl acetate in hexanes as eluent to obtain tert-butyl 4-(6-methylnaphthalen-1-yl)-3,6-dihydropyridine-1(2H)-carboxylate. LCMS: Purity 91.97%. MS calculated for [M]323.44 and found [M+H]$^+$ 324.28.

e) Tert-butyl 4-(6-methylnaphthalen-1-yl)piperidine-1-carboxylate

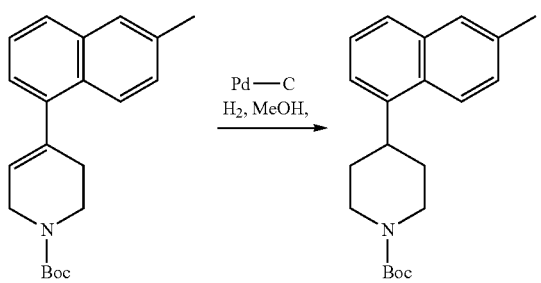

Pd—C (10% w/w, 50% moisture, 0.9 g) was added to the solution of tert-butyl 4-(6-methylnaphthalen-1-yl)-3,6-dihydropyridine-1(2H)-carboxylate (0.81 g, 2.5 mmol, 1.0 eq) in MeOH (100 mL) and reaction was allowed to stir at room temperature under hydrogen atmosphere (balloon pressure) for 24 h. Pd—C was filtered off (through celite) and solvent was evaporated from the filtrate under reduced pressure to obtain a crude product, which was purified by flash chromatography on silica gel, 230-400 mesh, using gradient of ethyl acetate in hexanes as eluent to obtain tert-butyl 4-(6-methylnaphthalen-1-yl)piperidine-1-carboxylate. LCMS: Purity 99.81%. MS calculated for [M] 325.45 and found [M-56]$^+$ 270.25.

f) 4-(6-methylnaphthalen-1-yl)piperidine Hydrochloride

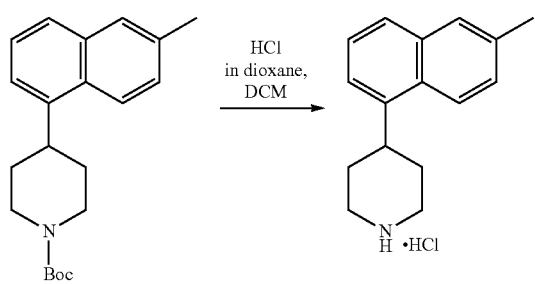 [SMILES: Cc1ccc2c(C3CCN(C(=O)OC(C)(C)C)CC3)cccc2c1 ; Cc1ccc2c(C3CCNCC3)cccc2c1 ; Cl]

4M HCl in 1,4-dioxane (2 mL) was added dropwise to a solution of tert-butyl 4-(6-methylnaphthalen-1-yl)piperidine-1-carboxylate (0.08 g, 0.24 mmol, 1.0 eq) in dichloromethane (2 mL) at 0° C. The reaction mixture was stirred at ambient temperature for 16 h. Solvents evaporated under reduced pressure, the residue was triturated with diethyl ether and dried under vacuum to afford 4-(6-methylnaphthalen-1-yl)piperidine hydrochloride. LCMS: Purity 99.43%. RT=5.05 min (Method 1) MS calculated for [M] 225.34 and found [M+H]$^+$ 226.14. $^1$H-NMR (400 MHz, DMSO-$d_6$) δ 8.98 (bs, 1H), 8.84 (bs, 1H), 8.13 (d, J=8.76 Hz, 1H), 7.72-7.20 (m, 2H), 7.47-7.40 (m, 2H), 7.29 (d, J=7.04 Hz, 1H), 3.71-3.66 (m, 1H), 3.41-3.38 (m, 2H), 3.20-3.18 (m, 2H), 1.98-1.91 (m, 4H).

Example 36

4-(Piperidin-4-yl)naphthalen-1-amine (56)

a) Di-boc Protected 4-bromonaphthalen-1-amine

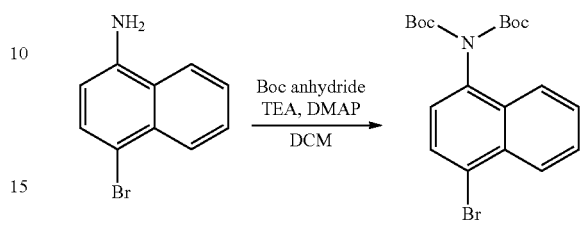

Boc anhydride (1.5 g, 6.75 mmol, 1.0 eq) was added to the solution of 4-bromonaphthalen-1-amine (1.0 g, 4.5 mmol, 1.1 eq), Et$_3$N (0.68 g, 6.75 mmol, 1.5 eq), DMAP (0.1 g) in dichloromethane (20 mL) under nitrogen atmosphere at 0° C. and the solution was stirred at ambient temperature for 12 h. After complete consumption of starting material, the reaction mixture was diluted with dichloromethane and washed with water followed by brine. The organic extract was then dried over anhydrous sodium sulfate, filtered, and solvent evaporated from the filtrated under reduced pressure to afford diboc protected 4-bromonaphthalen-1-amine. LCMS: Purity 48.07%.

b) Diboc Protected Tert-butyl 4-(4-aminonaphthalen-1-yl)-3,6-dihydropyridine-1(2H)-carboxylate

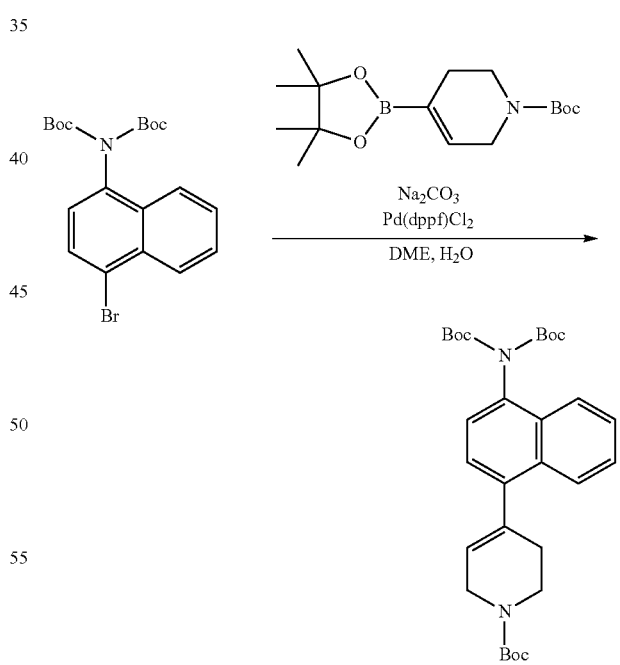

A mixture of diboc protected 4-bromonaphthalen-1-amine (0.5 g, 1.18 mmol, 1.0 eq), tert-butyl 4-(4,4,5,5-tetramethyl-1,3,2-dioxaborolan-2-yl)-3,6-dihydropyridine-1(2H)-carboxylate (0.4 g, 1.3 mmol, 1.1 eq) and Na$_2$CO$_3$ (0.376 g, 3.55 mmol, 3.0 eq) in a mixture of 1,2-DME (15 mL) and water (5 mL) was purged with nitrogen for 15 min. Pd(dppf)Cl$_2$·DCM (0.96 g, 0.118 mmol, 0.1 eq) was added to the reaction mixture and was stirred under nitrogen atmosphere, at 80° C. for 2 h. After complete consumption of starting material, the mixture was cooled to ambient temperature and partitioned between water and ethyl acetate. The organic extract was separated and the aqueous extract was again extracted with ethyl acetate. The combined organic extract was washed with brine, dried over anhydrous $Na_2SO_4$, filtered and solvents evaporated from the filtrate under reduced pressure to obtain a crude product, which was purified by flash chromatography on silica gel, 230-400 mesh, using gradient of ethyl acetate in hexanes as eluent to obtain diboc protected tert-butyl 4-(4-aminonaphthalen-1-yl)-3,6-dihydropyridine-1(2H)-carboxylate. LCMS: Purity 72.43%. MS calculated for [M] 524.66 and found [M+H]$^+$ 525.38.

c) Diboc Protected Tert-butyl 4-(4-aminonaphthalen-1-yl)piperidine-1-carboxylate

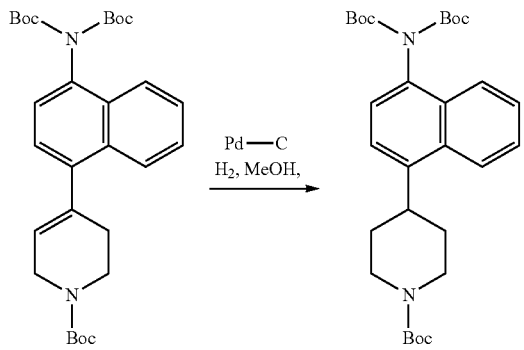

Pd—C (10% w/w, 50% moisture, 0.3 g) was added to the solution of diboc protected tert-butyl 4-(4-aminonaphthalen-1-yl)-3,6-dihydropyridine-1(2H)-carboxylate (0.3 g, 0.572 mmol, 1.0 eq) in MeOH (10 mL) and reaction was allowed to stir at room temperature under hydrogen atmosphere (balloon pressure) for 2 h. Pd—C was filtered off (through celite) and solvent was evaporated from the filtrate under reduced pressure to afford diboc protected tert-butyl 4-(4-aminonaphthalen-1-yl)piperidine-1-carboxylate. LCMS: Purity 88.43%. MS calculated for [M] 526.56 and found [M-200]$^+$ 326.29.

d) 4-(piperidin-4-yl)naphthalen-1-amine Dihydrochloride

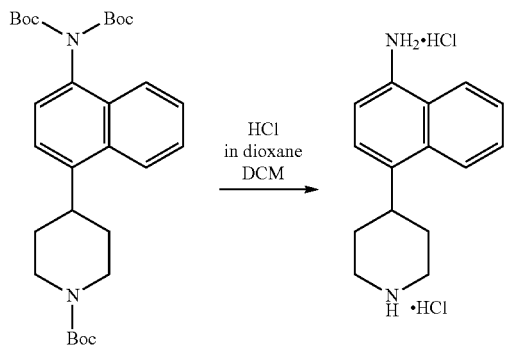

4M HCl in 1,4-dioxane (2 mL) was added dropwise to a solution of diboc protected tert-butyl 4-(4-aminonaphthalen-1-yl)piperidine-1-carboxylate (0.2 g, 0.38 mmol, 1.0 eq) in dichloromethane (4 mL) at 0° C. The reaction mixture was stirred at ambient temperature for 1 h. Solvents evaporated under reduced pressure, the residue was triturated with diethyl ether and dried under vacuum to afford 4-(piperidin-4-yl)naphthalen-1-amine dihydrochloride. LCMS: Purity 98.72%. RT=5.17 min (Method 2). MS calculated for [M] 226.32 and found [M+H]$^+$ 227.15. $^1$H-NMR (400 MHz, DMSO-$d_6$) δ 9.02 (bs, 1H), 8.91-8.89 (m, 2H), 8.30-8.28 (m, 1H), 8.10-8.08 (m, 1H), 7.66-7.64 (m, 2H), 7.44 (m, 1H), 7.35 (d, J=7.68 Hz, 1H), 3.77-3.67 (bs, 1H), 3.40 (d, J=12 Hz, 2H), 3.20-3.17 (m, 2H), 1.97-1.91 (m, 4H).

Example 37

8-(Piperidin-4-yl)quinoline (57)

a) Tert-butyl 4-(quinolin-8-yl)-3,6-dihydropyridine-1(2H)-carboxylate

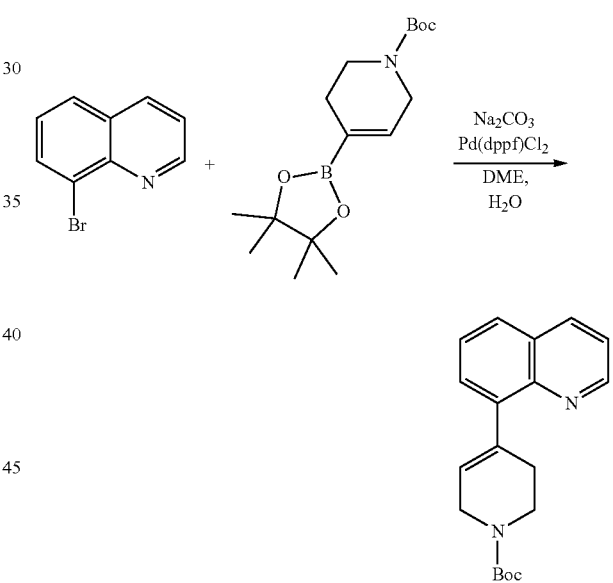

A mixture of 8-bromoquinoline (0.5 g, 2.4 mmol, 1.0 eq), tert-butyl 4-(4,4,5,5-tetramethyl-1,3,2-dioxaborolan-2-yl)-3,6-dihydropyridine-1(2H)-carboxylate (0.96 g, 3.12 mmol, 1.3 eq) and $Na_2CO_3$ (0.76 g, 7.2 mmol, 3.0 eq) in a mixture of 1,2-DME (5 mL) and water (2 mL) was purged with nitrogen for 20 min. Pd(dppf)$Cl_2$·DCM (0.19 g, 0.24 mmol, 0.1 eq) was added to the reaction mixture and nitrogen was bubbled into it for an additional 5 min. The reaction mixture was stirred under nitrogen atmosphere, at 80° C. for 2 h. After complete consumption of starting material, the mixture was cooled to ambient temperature and partitioned between water and ethyl acetate. The organic extract was separated and the aqueous extract was again extracted with ethyl acetate. The combined organic extract was washed with brine, dried over anhydrous $Na_2SO_4$, filtered and solvents evaporated from the filtrate under reduced pressure to obtain a crude product, which was purified by flash chromatography on silica gel, 230-400 mesh, using gradient of ethyl acetate in hexanes as eluent to obtain tert-butyl 4-(quinolin-8-yl)-3,6-dihydropyridine-1(2H)-carboxylate. LCMS: Purity 91.94%. MS calculated for [M] 310.40 and found [M+H]$^+$ 311.21.

b) Tert-butyl 4-(1,2,3,4-tetrahydroquinolin-8-yl)piperidine-1-carboxylate

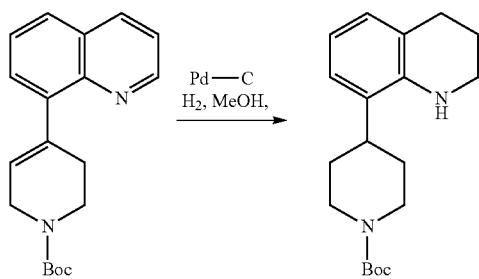

Pd—C (10% w/w, 50% moisture, 0.5 g) was added to the solution of tert-butyl 4-(quinolin-8-yl)-3,6-dihydropyridine-1(2H)-carboxylate (0.5 g, 1.61 mmol, 1.0 eq) in MeOH (5 mL) and reaction was allowed to stir at room temperature under hydrogen atmosphere (balloon pressure) for 2 h. Pd—C was filtered off (through celite) and solvent was evaporated from the filtrate under reduced pressure to afford tert-butyl 4-(1,2,3,4-tetrahydroquinolin-8-yl)piperidine-1-carboxylate. LCMS: Purity 80.48%. MS calculated for [M] 316.45 and found [M+H]$^+$ 317.30.

c) Tert-butyl 4-(quinolin-8-yl)piperidine-1-carboxylate

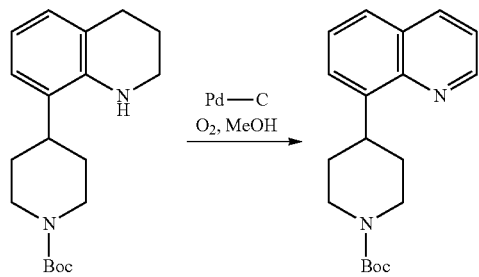

Pd—C (10% w/w, 50% moisture, 0.2 g) was added to the solution of tert-butyl 4-(1,2,3,4-tetrahydroquinolin-8-yl)piperidine-1-carboxylate (0.2 g, 0.63 mmol, 1.0 eq) in MeOH (10 mL) and reaction was allowed to stir at room temperature under oxygen atmosphere (balloon pressure) for 16 h. Pd—C was filtered off (through celite) and solvent was evaporated from the filtrate under reduced pressure to afford tert-butyl 4-(quinolin-8-yl)piperidine-1-carboxylate. MS calculated for [M] 312.41 and found [M+H]$^+$ 313.27.

d) 8-(piperidin-4-yl)quinoline dihydrochloride

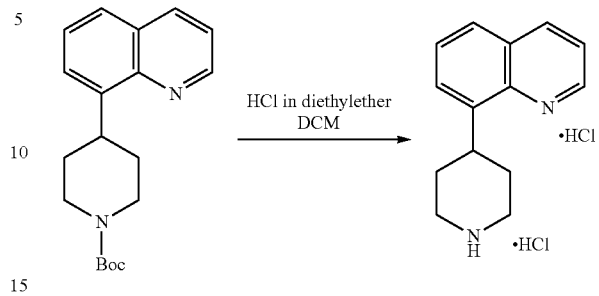

2M HCl in diethyl ether (2 mL) was added dropwise to a solution of tert-butyl 4-(quinolin-8-yl)piperidine-1-carboxylate (0.1 g, 0.32 mmol, 1.0 eq) in dichloromethane (3 mL) at 0° C. The reaction mixture was stirred at ambient temperature for 4 h. Solvents evaporated under reduced pressure, the residue was triturated with pentane and dried under vacuum to afford 8-(piperidin-4-yl)quinoline dihydrochloride. LCMS: Purity 98.92%. RT=3.74 min (Method 1). MS calculated for [M] 212.30 and found [M+H]$^+$ 213.12. $^1$H-NMR (400 MHz, DMSO-d$_6$) δ 9.08-8.98 (m, 3H), 8.59 (d, J=7.28 Hz, 1H), 7.99-7.96 (m, 1H), 7.72-7.69 (m, 3H), 4.35-4.15 (m, 1H), 3.43-3.40 (m, 2H), 3.20-3.14 (m, 2H), 2.05-1.99 (m, 4H).

Example 38

5-Fluoro-8-(piperidin-4-yl)quinoline (58)

a) Tert-butyl 4-(5-fluoroquinolin-8-yl)-3,6-dihydropyridine-1(2H)-carboxylate

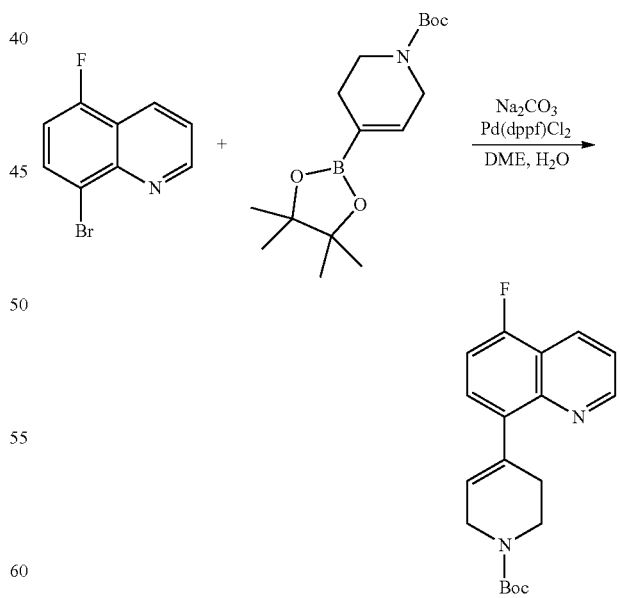

A mixture of 8-bromo-5-fluoroquinoline (0.7 g, 3.09 mmol, 1.0 eq), tert-butyl 4-(4,4,5,5-tetramethyl-1,3,2-dioxaborolan-2-yl)-3,6-dihydropyridine-1(2H)-carboxylate (1.4 g, 4.64 mmol, 1.5 eq) and $Na_2CO_3$ (0.98 g, 9.29 mmol, 3.0 eq) in a mixture of 1,2-DME (7 mL) and water (3 mL) was purged with nitrogen for 15 min. Pd(dppf)Cl$_2$·DCM (0.25 g, 0.309 mmol, 0.1 eq) was added to the reaction mixture and was stirred under nitrogen atmosphere, at 85° C. for 4 h. After complete consumption of starting material, the mixture was cooled to ambient temperature and partitioned between water and ethyl acetate. The organic extract was separated and the aqueous extract was again extracted with ethyl acetate. The combined organic extract was washed with brine, dried over anhydrous Na$_2$SO$_4$, filtered and solvents evaporated from the filtrate under reduced pressure to obtain a crude product, which was purified by flash chromatography on silica gel, 230-400 mesh, using gradient of ethyl acetate in hexanes as eluent to obtain tert-butyl 4-(5-fluoroquinolin-8-yl)-3,6-dihydropyridine-1(2H)-carboxylate. LCMS: Purity 96.19%. MS calculated for [M] 328.39 and found [M+H]$^+$ 329.26.

b) Tert-butyl 4-(5-fluoro-1,2,3,4-tetrahydroquinolin-8-yl)piperidine-1-carboxylate

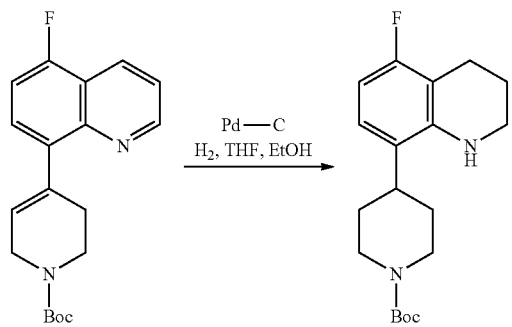

Pd—C (10% w/w, 50% moisture, 0.5 g) was added to the solution of tert-butyl 4-(5-fluoroquinolin-8-yl)-3,6-dihydropyridine-1(2H)-carboxylate (0.85 g, 2.59 mmol, 1.0 eq) in mixture of EtOH (1 mL) and THF (3 mL). The reaction was allowed to stir at room temperature under hydrogen atmosphere (balloon pressure) for 12 h. Pd—C was filtered off (through celite) and solvent was evaporated from the filtrate under reduced pressure to afford tert-butyl 4-(5-fluoro-1,2,3,4-tetrahydroquinolin-8-yl)piperidine-1-carboxylate. LCMS: Purity 78.70%. MS calculated for [M] 334.44 and found [M+H]$^+$ 335.25.

c) Tert-butyl 4-(5-fluoroquinolin-8-yl)piperidine-1-carboxylate

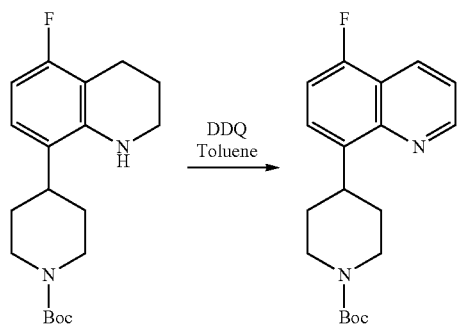 [SMILES: CC(C)(C)OC(=O)N1CCC(c2ccc(F)c3c2NCCC3)CC1 ; CC(C)(C)OC(=O)N1CCC(c2ccc(F)c3cccnc23)CC1]

DDQ (1.63 g, 7.18 mmol, 3.0 eq) was added to the solution of tert-butyl 4-(5-fluoro-1,2,3,4-tetrahydroquinolin-8-yl)piperidine-1-carboxylate (0.8 g, 2.39 mmol, 1.0 eq) in toluene (10 mL). The reaction mixture was heated at 110° C. for 12 h. After complete consumption of starting material, the mixture was cooled to ambient temperature and partitioned between water and ethyl acetate. The organic extract was separated and the aqueous extract was again extracted with ethyl acetate. The combined organic extract was washed with brine, dried over anhydrous Na$_2$SO$_4$, filtered and solvents evaporated from the filtrate under reduced pressure to obtain a crude product, which was purified by flash chromatography on silica gel, 230-400 mesh, using gradient of ethyl acetate in hexanes as eluent to obtain tert-butyl 4-(5-fluoroquinolin-8-yl) piperidine-1-carboxylate. LCMS: Purity 99.09%. MS calculated for [M]330.40 and found [M+H]$^+$ 331.16.

d) 5-fluoro-8-(piperidin-4-yl)quinoline Hydrochloride

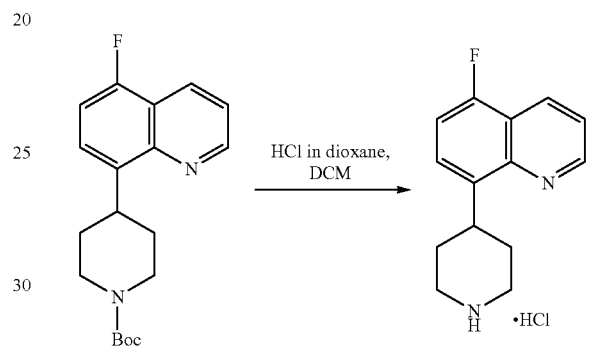

4M HCl in 1,4-dioxane (2.5 mL) was added dropwise to a solution of tert-butyl 4-(5-fluoroquinolin-8-yl)piperidine-1-carboxylate (0.05 g, 0.156 mmol, 1.0 eq) in dichloromethane (5 mL) at 0° C. The reaction mixture was stirred at ambient temperature for 2 h. Solvents evaporated under reduced pressure, the residue was triturated with diethyl ether followed by pentane and dried under vacuum to afford 5-fluoro-8-(piperidin-4-yl)quinoline hydrochloride. LCMS: Purity 97.11%. RT=3.91 (Method 1). MS calculated for [M] 230.29 and found [M+H]$^+$ 231.12. $^1$H-NMR (400 MHz, DMSO-d$_6$) δ 9.04-9.03 (m, 3H), 8.52 (d, J=8.36 Hz, 1H), 7.71-7.67 (m, 1H), 7.59 (t, J=8.0 Hz, 1H), 7.46 (t, J=9.72 Hz, 1H), 4.15-4.09 (m, 1H), 3.41-3.38 (m, 2H), 3.18-3.08 (m, 2H), 2.03-2.01 (m, 4H).

Example 39

4-(4-Chloronaphthalen-1-yl)piperidine (59)

a) Tert-butyl 4-(2-tosylhydrazono)piperidine-1-carboxylate

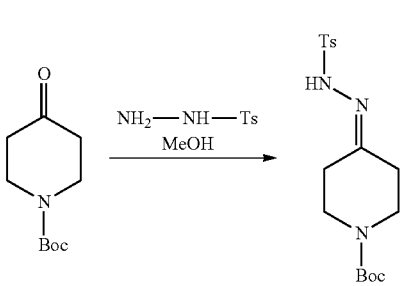 [SMILES: "MeOH" ; CC(C)(C)OC(=O)N1CCC(=O)CC1 ; Cc1ccc(S(=O)(=O)NN)cc1 ; Cc1ccc(S(=O)(=O)NN=C2CCN(C(=O)OC(C)(C)C)CC2)cc1]

To a solution of tosylhydrazine (0.93 g, 5.01 mmol, 1.0 eq) in MeOH (5 mL), a solution of tert-butyl 4-oxopiperidine-1-carboxylate (1.0 g, 5.01 mmol, 1.0 eq) in MeOH (5 mL) was added drop-wise under nitrogen atmosphere and the solution was stirred at ambient temperature for 3 h. After complete consumption of starting material, the reaction mixture was evaporated under reduced pressure to afford tert-butyl 4-(2-tosylhydrazono)piperidine-1-carboxylate. LCMS: Purity 96.84%. MS calculated for [M]367.46 and found [M+H]$^+$ 368.30.

b) 4-chloronaphthalen-1-yl Trifluoromethanesulfonate

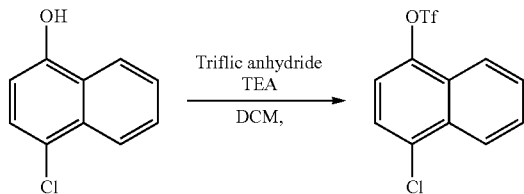 [SMILES: Oc1ccc(Cl)c2ccccc12 ; O=S(=O)(Oc1ccc(Cl)c2ccccc12)C(F)(F)F]

Triflic anhydride (6.63 g, 23.59 mmol, 1.4 eq) was added dropwise to the solution of 4-chloronaphthalen-1-ol (3.0 g, 16.85 mmol, 1.0 eq) and Et$_3$N (6.8 g, 64.41 mmol, 4.0 eq) in dichloromethane (30 mL) under nitrogen atmosphere at 0° C. and the solution was stirred at ambient temperature for 2 h. After complete consumption of starting material, the reaction mixture was diluted with dichloromethane and washed with water and brine. The organic extract was then dried over anhydrous sodium sulfate, filtered, and solvent evaporated under reduced pressure to afford 4-chloronaphthalen-1-yl trifluoromethanesulfonate. LCMS: Purity 80.81%.

c) 2-(4-chloronaphthalen-1-yl)-4,4,5,5-tetramethyl-1,3,2-dioxaborolane

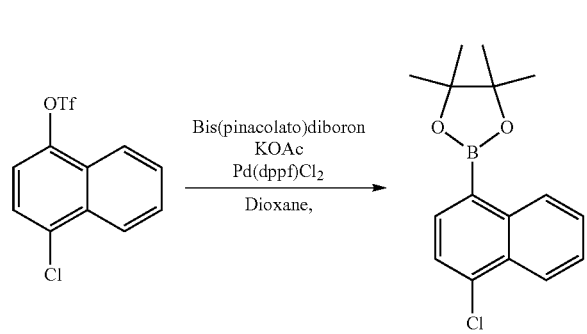 [SMILES: O=S(=O)(Oc1ccc(Cl)c2ccccc12)C(F)(F)F ; CC1(C)OB(c2ccc(Cl)c3ccccc23)OC1(C)C]

A mixture of 4-chloronaphthalen-1-yl trifluoromethanesulfonate (3.3 g, 10.61 mmol, 1.0 eq), bis(pinacolato)diboron (5.3 g, 21.29 mmol, 2.0 eq) and KOAc (1.45 g, 14.86 mmol, 1.4 eq) in 1,4-dioxane (30 mL) was purged with nitrogen for 15 min. Pd(dppf)Cl$_2$·DCM (0.86 g, 1.06 mmol, 0.1 eq) was added to the reaction mixture and was stirred under nitrogen atmosphere, at 100° C. for 12 h. After complete consumption of starting material, the mixture was cooled to ambient temperature and partitioned between water and ethyl acetate. The organic extract was separated and the aqueous extract was again extracted with ethyl acetate. The combined organic extract was washed with brine, dried over anhydrous Na$_2$SO$_4$, filtered and solvents evaporated from the filtrate under reduced pressure to obtain a crude product, which was purified by flash chromatography on silica gel, 230-400 mesh, using gradient of ethyl acetate in hexanes as eluent to obtain 2-(4-chloronaphthalen-1-yl)-4,4,5,5-tetramethyl-1,3,2-dioxaborolane. LCMS: Purity 98.76%. MS calculated for [M]288.11 and found [M+H]$^+$ 288.99.

d) Tert-butyl 4-(4-chloronaphthalen-1-yl)piperidine-1-carboxylate

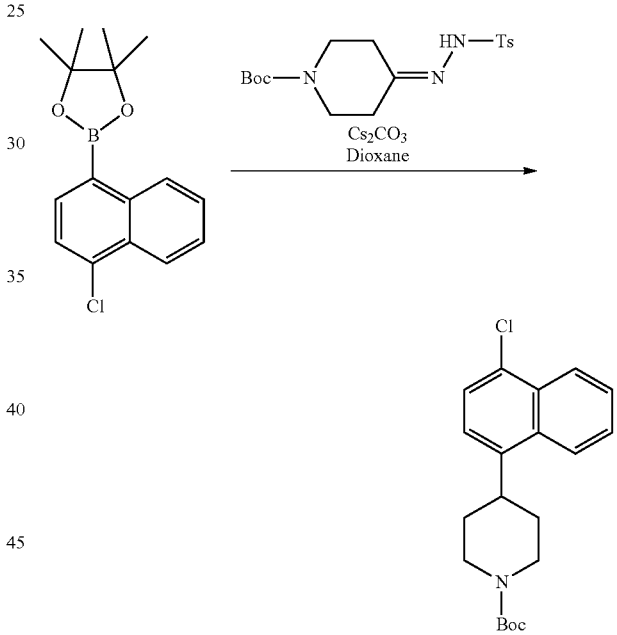

Cesium carbonate (1.69 g, 5.2 mmol, 1.5 eq) was added to a mixture of 2-(4-chloronaphthalen-1-yl)-4,4,5,5-tetramethyl-1,3,2-dioxaborolane (1.0 g, 3.47 mmol, 1.0 eq) and tert-butyl 4-(2-tosylhydrazono)piperidine-1-carboxylate (1.5 g, 4.16 mmol, 1.2 eq) in 1,4-dioxane (10 mL). The reaction mixture was heated at 110° C. for 12 h. After complete consumption of starting material, the mixture was cooled to ambient temperature and partitioned between water and ethyl acetate. The organic extract was separated and the aqueous extract was again extracted with ethyl acetate. The combined organic extract was washed with brine, dried over anhydrous Na$_2$SO$_4$, filtered and solvents evaporated from the filtrate under reduced pressure to obtain tert-butyl 4-(4-chloronaphthalen-1-yl)piperidine-1-carboxylate. LCMS: Purity 97.73%. MS calculated for [M]345.87 and found [M+H]$^+$ 346.17.

e) 4-(4-chloronaphthalen-1-yl)piperidine Hydrochloride

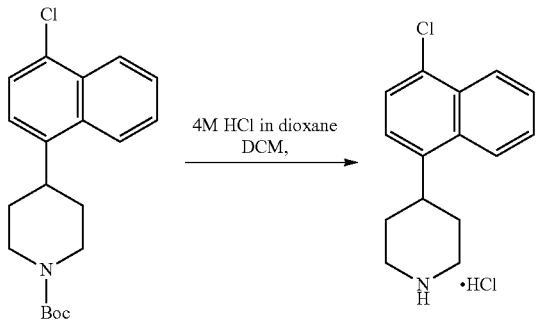 [SMILES: CC(C)(C)OC(=O)N1CCC(c2ccc(Cl)c3ccccc23)CC1 ; Clc1ccc(C2CCNCC2)c2ccccc12 ; Cl]

4M HCl in 1,4-dioxane (4 mL) was added dropwise to a solution of tert-butyl 4-(4-chloronaphthalen-1-yl)piperidine-1-carboxylate (0.25 g, 0.724 mmol, 1.0 eq) in dichloromethane (5 mL) at 0° C. The reaction mixture was stirred at ambient temperature for 2 h. Solvents evaporated under reduced pressure, the residue was triturated with diethyl ether and pentane, dried under vacuum to afford 4-(4-chloronaphthalen-1-yl)piperidine hydrochloride. LCMS: Purity 98.99%. RT=4.98 min (Method 1). MS calculated for [M]245.75 and found [M+H]$^+$ 246.08. $^1$H-NMR (400 MHz, DMSO-d$_6$) δ 8.92 (bs, 2H), 8.35 (d, J=8.64 Hz, 1H), 8.25 (d, J=9.16 Hz, 1H), 7.74-7.69 (m, 3H), 7.36 (d, J=7.8 Hz, 1H), 3.77-3.72 (m, 1H), 3.42-3.39 (m, 2H), 3.22-3.16 (m, 2H), 2.00-1.91 (m, 4H).

Example 40

4-(4-Cyclohexylnaphthalen-1-yl)piperidine (60)

a) 4-(cyclohex-1-en-1-yl) naphthalen-1-ol

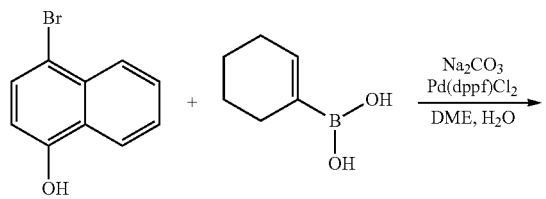

A mixture of 4-bromonaphthalen-1-ol (2.0 g, 8.96 mmol, 1.0 eq), cyclohex-1-en-1-ylboronic acid (2.42 g, 11.65 mmol, 1.3 eq) and Na$_2$CO$_3$ (2.85 g, 26.9 mmol, 3.0 eq) in a mixture of 1,2-DME (36 mL) and water (4 mL) was purged with nitrogen for 15 min. Pd(dppf)Cl$_2$·DCM (2.92 g, 3.58 mmol, 0.4 eq) was added to the reaction mixture and was stirred under nitrogen atmosphere, at 100° C. for 16 h. After complete consumption of starting material, the mixture was cooled to ambient temperature and partitioned between water and ethyl acetate. The organic extract was separated and the aqueous extract was again extracted with ethyl acetate. The combined organic extract was washed with brine, dried over anhydrous Na$_2$SO$_4$, filtered and solvents evaporated from the filtrate under reduced pressure to obtain a crude product, which was purified by flash chromatography on silica gel, 230-400 mesh, using gradient of ethyl acetate in hexanes as eluent to obtain 4-(cyclohex-1-en-1-yl)naphthalen-1-ol. LCMS: Purity 92.23%. MS calculated for [M] 224.30 and found [M–H]$^+$ 223.09.

b) 4-(cyclohex-1-en-1-yl)naphthalen-1-yl trifluoromethanesulfonate

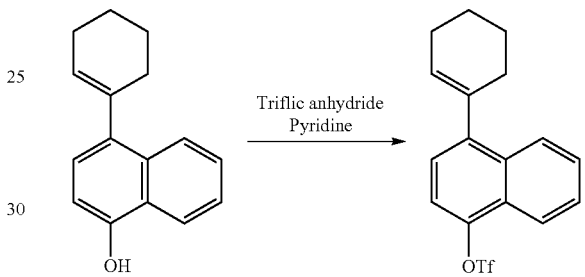

Triflic anhydride (1.76 g, 6.25 mmol, 2.0 eq) was added dropwise to the solution of 4-(cyclohex-1-en-1-yl)naphthalen-1-ol (0.7 g, 3.12 mmol, 1.0 eq) in pyridine (5 mL) at 0° C. The reaction mixture was stirred under nitrogen atmosphere, at room temperature for 2 h. After complete consumption of starting material, 1N HCl was added to the reaction mixture, diluted with water and extracted with ethyl acetate. The combined organic extract was washed with brine, dried over anhydrous Na$_2$SO$_4$, filtered and solvents evaporated from the filtrate under reduced pressure to afford 4-(cyclohex-1-en-1-yl)naphthalen-1-yl trifluoromethanesulfonate. LCMS: Purity 88.36%. MS calculated for [M] 356.36 and found [M+H]$^+$ 357.07.

c) Tert-butyl 4-(4-(cyclohex-1-en-1-yl)naphthalen-1-yl)-3,6-dihydropyridine-1(2H)-carboxylate

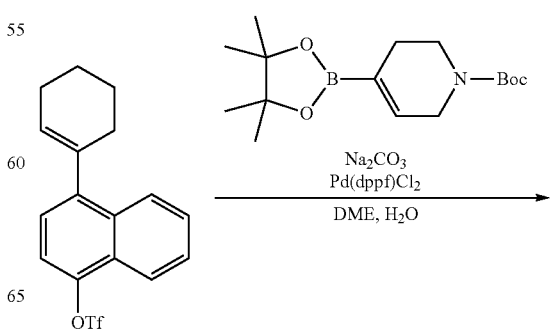

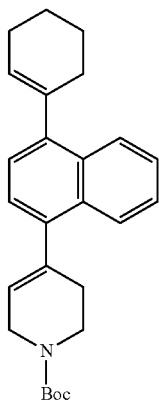

A mixture of 4-(cyclohex-1-en-1-yl)naphthalen-1-yl trifluoromethanesulfonate (0.61 g, 1.7 mmol, 1.0 eq), tert-butyl 4-(4,4,5,5-tetramethyl-1,3,2-dioxaborolan-2-yl)-3,6-dihydropyridine-1(2H)-carboxylate (0.63 g, 2.05 mmol, 1.2 eq) and Na$_2$CO$_3$ (0.54 g, 5.12 mmol, 3.0 eq) in a mixture of 1,2-DME (16 mL) and water (4 mL) was purged with nitrogen for 15 min. Pd(dppf)Cl$_2$·DCM (0.278 g, 0.34 mmol, 0.2 eq) was added to the reaction mixture and was stirred under nitrogen atmosphere, at 80° C. for 2 h. After complete consumption of starting material, the mixture was cooled to ambient temperature and partitioned between water and ethyl acetate. The organic extract was separated and the aqueous extract was again extracted with ethyl acetate. The combined organic extract was washed with brine, dried over anhydrous Na$_2$SO$_4$, filtered and solvents evaporated from the filtrate under reduced pressure to obtain a crude product, which was purified by flash chromatography on silica gel, 230-400 mesh, using gradient of ethyl acetate in hexanes as eluent to obtain tert-butyl 4-(4-(cyclohex-1-en-1-yl)naphthalen-1-yl)-3,6-dihydropyridine-1(2H)-carboxylate. LCMS: Purity 91.18%. MS calculated for [M] 389.54 and found [M+H]$^+$ 390.23.

d) Tert-butyl 4-(4-cyclohexylnaphthalen-1-yl)piperidine-1-carboxylate

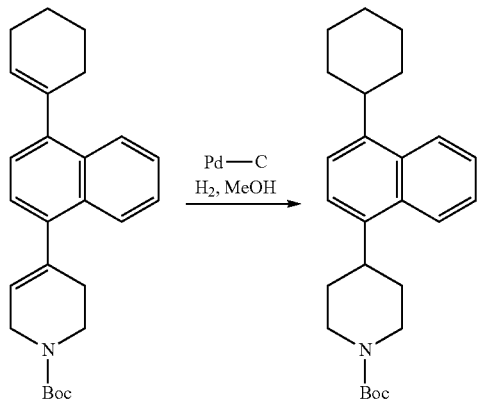

Pd—C (10% w/w, 50% moisture, 0.6 g) was added to the solution of tert-butyl 4-(4-(cyclohex-1-en-1-yl)naphthalen-1-yl)-3,6-dihydropyridine-1(2H)-carboxylate (0.6 g, 1.54 mmol, 1.0 eq) in MeOH (50 mL) and reaction was allowed to stir at room temperature under hydrogen atmosphere (balloon pressure) for 4 h. Pd—C was filtered off (through celite) and solvent was evaporated from the filtrate under reduced pressure to obtain a crude product, which was purified by flash chromatography on silica gel, 230-400 mesh, using gradient of ethyl acetate in hexanes as eluent to obtain tert-butyl 4-(4-cyclohexylnaphthalen-1-yl)piperidine-1-carboxylate. LCMS: Purity 98.99%. MS calculated for [M] 393.57 and found [M-56]$^+$ 338.24.

e) 4-(4-cyclohexylnaphthalen-1-yl)piperidine Hydrochloride

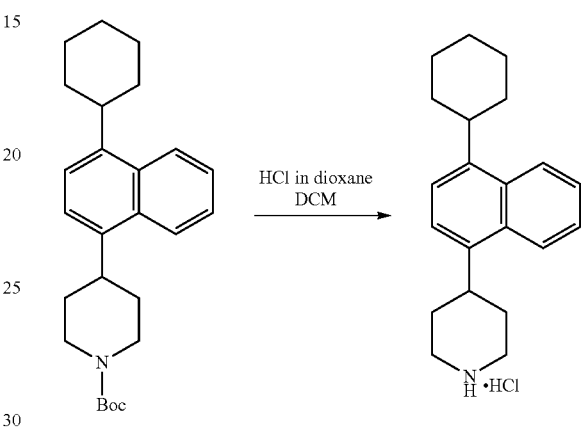

4M HCl in 1,4-dioxane (2 mL) was added drop-wise to a solution of tert-butyl 4-(4-cyclohexylnaphthalen-1-yl)piperidine-1-carboxylate (0.15 g, 0.38 mmol, 1.0 eq) in dichloromethane (2 mL) at 0° C. The reaction mixture was stirred at ambient temperature for 4 h. Solvents evaporated under reduced pressure, the residue was triturated with diethyl ether and dried under vacuum to afford 4-(4-cyclohexylnaphthalen-1-yl)piperidine hydrochloride. LCMS: Purity 98.38%. RT=6.17 min (Method 1). MS calculated for [M] 293.45 and found [M+H]$^+$ 294.21. $^1$H-NMR (400 MHz, DMSO-d$_6$) δ 8.77 (bs, 2H), 8.26-8.23 (m, 1H), 8.20-8.18 (m, 1H), 7.58-7.55 (m, 2H), 7.40 (d, J=7.6 Hz, 1H), 7.32 (d, J=7.6 Hz, 1H), 3.68-3.66 (m, 1H), 3.42-4.39 (m, 1H), 3.22-3.16 (m, 1H), 2.02-1.77 (m, 10H), 1.61-1.28 (m, 5H).

Example 41

4-(Piperazin-1-yl)-1H-benzo[d]imidazole (40)

a) 4-bromo-1-trityl-1H-benzo[d]imidazole

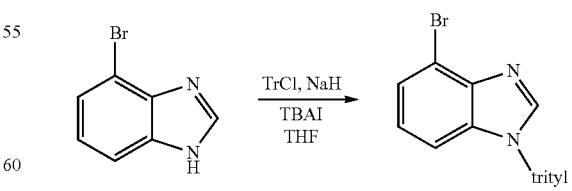

To a stirred solution of 4-bromo-1H-benzo[d]imidazole (150 mg, 0.761 mmol) in THF (5 mL) was added NaH (36 mg, 0.91 mmol) at 0° C. and the resulting mixture was stirred at rt for 30 min. Trityl chloride (275 mg, 0.98 mmol) and a catalytic amount of TBAI were added and the resulting reaction mixture was heated to reflux for 5 h. The reaction mixture was cooled and quenched with ice water and subsequently extracted with ethyl acetate (3×10 mL). The combined organic layers were dried over anhydrous sodium sulfate and concentrated to obtain 4-bromo-1-trityl-1H-benzo[d]imidazole. LCMS Purity: 92.612%, m/z=441.2 [M+H]$^+$.

b) 4-(piperazin-1-yl)-1-trityl-1H-benzo[d]imidazole

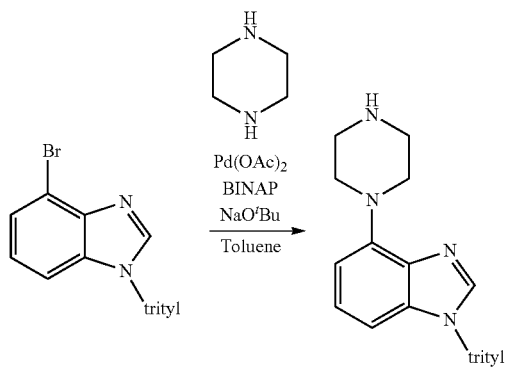

To a stirred solution of 4-bromo-1-trityl-1H-benzo[d]imidazole (200 mg, 0.4552 mmol) in toluene (5 mL) was added piperazine (195 mg, 2.27 mmol), Pd$_2$(dba)$_3$ (41 mg, 0.04 mmol), BINAP (56 mg, 0.09 mmol), and NaO$^t$Bu (131 mg, 1.365 mmol). The resulting reaction mixture was degassed and heated to 110° C. for 12 h. After completion, the reaction was cooled to room temperature and filtered through a celite pad. The filtrate was concentrated under reduced pressure and the residue was purified by basic alumina column chromatography using 10% methanol in DCM to furnish 4-(piperazin-1-yl)-1-trityl-1H-benzo[d]imidazole. LCMS Purity: 91.821%, m/z=445.4 (M+H)$^+$.

c) 4-(piperazin-1-yl)-1H-benzo[d]imidazole

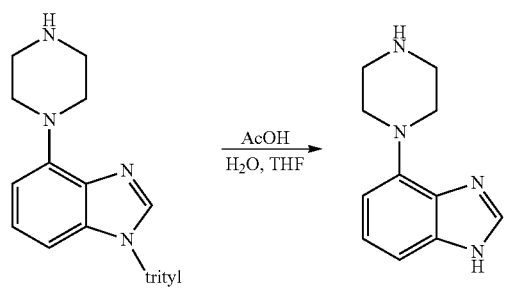

To a stirred solution of compound 4-(piperazin-1-yl)-1-trityl-1H-benzo[d]imidazole (40 mg) in THF (0.5 mL) were added AcOH (0.5 mL) and water (0.5 mL) at room temperature and the reaction mixture was heated to 60° C. for 4 h. The reaction was concentrated under reduced pressure and then basified with sat. aq. Na$_2$CO$_3$ and extracted with DCM (2×5 mL). The organic phase was dried over anhydrous sodium sulfate and concentrated. The residue was purified by preparative HPLC to give 4-(piperazin-1-yl)-1H-benzo[d]imidazole. LCMS Purity: 91.821%, RT=1.126, m/z=203.3 [M+H]$^+$ (Method 3). $^1$H-NMR (400 MHz, DMSO-d$_6$): δ 9.15 (1H, s), 9.01 (2H, s), 7.42-7.37 (2H, m), 6.97 (1H, d), 3.55-3.21 (8H, m).

Example 42

4-(Piperazin-1-yl)benzo[d]thiazole (41)

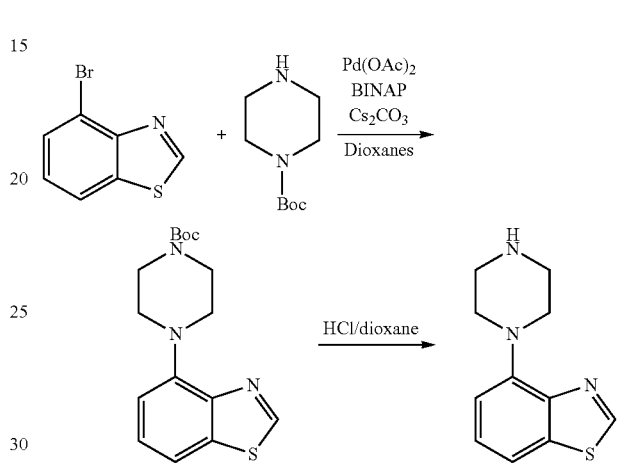

4-(piperazin-1-yl)benzo[d]thiazole (41) may be prepared by methods similar to those described in Example 41, using 4-bromobenzo[d]thiazole as the aryl halide starting material. LCMS RT=3.508 min, m/z=220.2 [M+H]$^+$ (Method 3).

Example 43

7-(Piperazin-1-yl)benzo[d]thiazole (42)

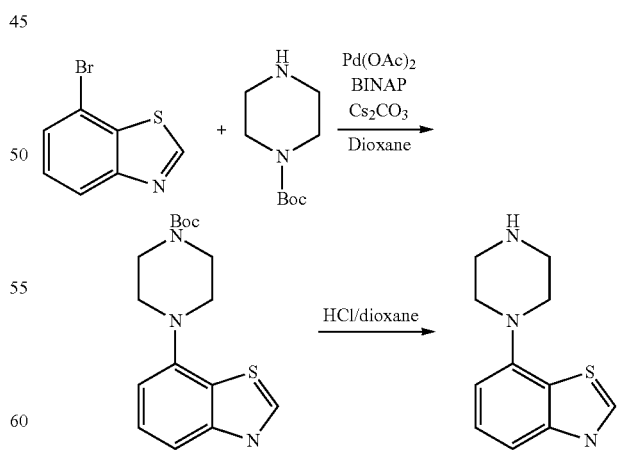

7-(piperazin-1-yl)benzo[d]thiazole (42) may be prepared methods similar to those described in Example 41, using 7-bromobenzo[d]thiazole as the aryl halide starting material. LCMS RT=3.072 min, m/z=220.2 [M+H]$^+$ (Method 3).

Example 44

4-(Piperidin-4-yl)-N-(5,6,7,8-tetrahydronaphthalen-2-yl)naphthalene-1-sulfonamide (61)

a) 4-bromonaphthalene-1-sulfonyl Chloride

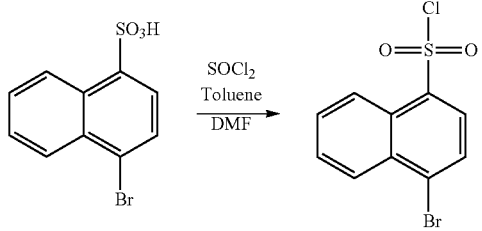

Thionyl chloride (1.56 g, 13.11 mmol, 1.5 eq) was added drop-wise to the solution of 4-bromonaphthalene-1-sulfonic acid (2.5 g, 8.74 mmol, 1.0 eq) in a mixture of toluene (20 mL) and DMF (2 mL) under nitrogen atmosphere, at room temperature and the solution was at heated at 110° C. for 4 h. After complete consumption of starting material, the mixture was cooled to ambient temperature and evaporated under reduced pressure to afford 4-bromonaphthalene-1-sulfonyl chloride, which was used in the next step without purification.

b) 4-bromo-N-(5,6,7,8-tetrahydronaphthalen-2-yl)naphthalene-1-sulfonamide

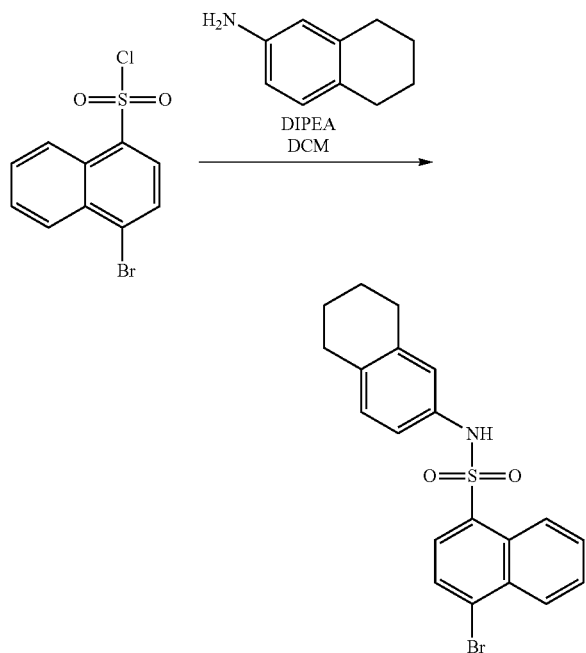

A solution of 5,6,7,8-tetrahydronaphthalen-2-amine (1.24 g, 4.07 mmol, 1.2 eq) in dichloromethane (5 mL) was added drop-wise to solution of 4-bromonaphthalene-1-sulfonyl chloride (0.5 g, 3.39 mmol, 1.0 eq) and DIPEA (1.31 g, 10.2 mmol, 3.0 eq) in dichloromethane (15 mL) under nitrogen atmosphere at 0° C. and the solution was stirred at ambient temperature for 2 h. After complete consumption of starting material, the reaction mixture was diluted with dichloromethane and washed with water and brine. The organic extract was then dried over anhydrous sodium sulfate, filtered, and solvent evaporated from the filtrated under reduced pressure to afford 4-bromo-N-(5,6,7,8-tetrahydronaphthalen-2-yl)naphthalene-1-sulfonamide. LCMS: Purity 92.04%. MS calculated for [M] 415.02 and found [M−H]⁺ 414.13.

c) Tert-butyl 4-(4-(N-(5,6,7,8-tetrahydronaphthalen-2-yl)sulfamoyl)naphthalen-1-yl)-3,6-dihydropyridine-1(2H)-carboxylate

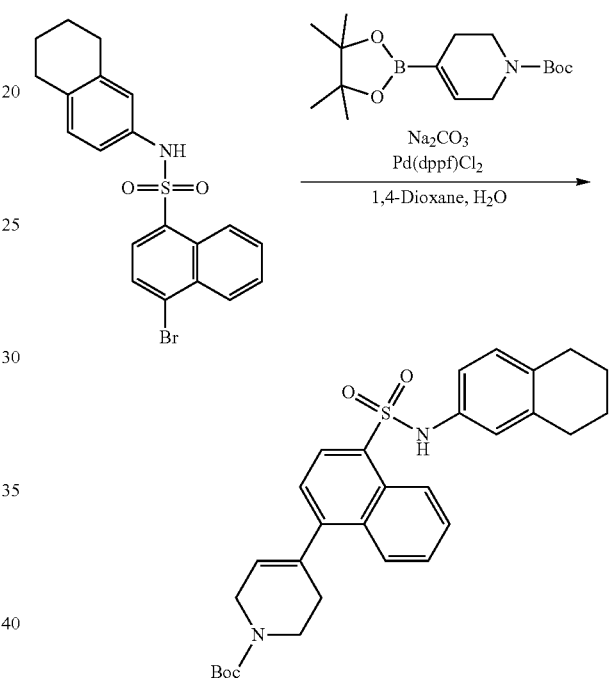

A mixture of 4-bromo-N-(5,6,7,8-tetrahydronaphthalen-2-yl)naphthalene-1-sulfonamide (0.2 g, 0.48 mmol, 1.0 eq), tert-butyl 4-(4,4,5,5-tetramethyl-1,3,2-dioxaborolan-2-yl)-3,6-dihydropyridine-1(2H)-carboxylate (0.222 g, 0.72 mmol, 1.5 eq) and Na$_2$CO$_3$ (0.152 g, 1.44 mmol, 3.0 eq) in a mixture of 1,4-Dioxane (3.2 mL) and H$_2$O (0.8 mL) was purged with nitrogen for 15 min. Pd(dppf)Cl$_2$·DCM (0.039 g, 0.048 mmol, 0.1 eq) was added to the reaction mixture and was stirred under nitrogen atmosphere, at 90° C. for 1 h. After complete consumption of starting material, the mixture was cooled to ambient temperature and partitioned between water and ethyl acetate. The organic extract was separated and the aqueous extract was again extracted with ethyl acetate. The combined organic extract was washed with brine, dried over anhydrous Na$_2$SO$_4$, filtered and solvents evaporated from the filtrate under reduced pressure to obtain a crude product, which was purified by flash chromatography on silica gel, 230-400 mesh, using gradient of ethyl acetate in hexanes as eluent to obtain tert-butyl 4-(4-(((tetrahydro-2H-pyran-4-yl)amino)naphthalen-1-yl)-3,6-dihydropyridine-1 (2H)-carboxylate. LCMS: Purity 95.72%. MS calculated for [M] 518.67 and found [M−H]⁺ 517.36.

d) Tert-butyl 4-(4-(N-(5,6,7,8-tetrahydronaphthalen-2-yl)sulfamoyl)naphthalen-1-yl)piperidine-1-carboxylate

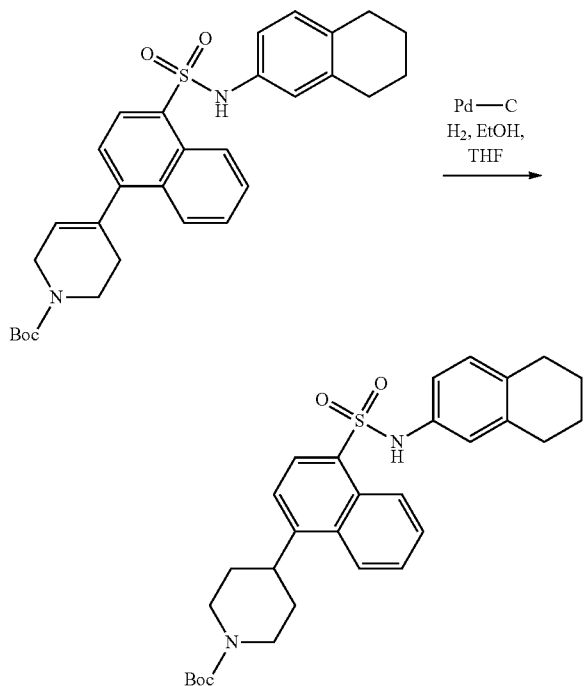

Pd—C (10% w/w, 50% moisture, 0.1 g) was added to the solution of tert-butyl 4-(4-(N-(5,6,7,8-tetrahydronaphthalen-2-yl)sulfamoyl)naphthalen-1-yl)-3,6-dihydropyridine-1(2H)-carboxylate (0.2 g, 0.386 mmol, 1.0 eq) in a mixture of EtOH (5 mL) and THF (10 mL). The reaction was allowed to stir at room temperature under hydrogen atmosphere (balloon pressure) for 16 h. Pd—C was filtered off (through celite) and solvent was evaporated from the filtrate under reduced pressure to afford tert-butyl 4-(4-(N-(5,6,7,8-tetrahydronaphthalen-2-yl)sulfamoyl)naphthalen-1-yl)piperidine-1-carboxylate. LCMS: Purity 90.20%. MS calculated for [M] 520.69 and found [M−H]+ 519.33.

e) 4-(piperidin-4-yl)-N-(5,6,7,8-tetrahydronaphthalen-2-yl)naphthalene-1-sulfonamide Hydrochloride

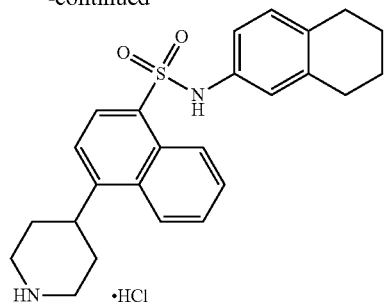

4M HCl in 1,4-dioxane (2 mL) was added to a solution of tert-butyl 4-(4-(N-(5,6,7,8-tetrahydronaphthalen-2-yl)sulfamoyl)naphthalen-1-yl)piperidine-1-carboxylate (0.2 g, 0.384 mmol, 1.0 eq) in dichloromethane (2 mL) at 0° C. and the mixture was stirred for 2 h at room temperature. Solvents evaporated under reduced pressure, the residue was triturated with diethyl ether, followed by pentane, and dried under vacuum to afford 4-(piperidin-4-yl)-N-(5,6,7,8-tetrahydronaphthalen-2-yl)naphthalene-1-sulfonamide hydrochloride. LCMS: Purity 93.27%. RT=5.24 min (Method 1). MS calculated for [M] 420.57 and found [M+H]+ 421.03. 1H-NMR (400 MHz, DMSO-d6) δ 10.50 (s, 1H), 8.85 (bs, 1H), 8.78 (d, J=8.6 Hz, 1H), 8.68-8.65 (m, 1H), 8.38 (d, J=8.44 Hz, 1H), 8.19 (d, J=7.84 Hz, 1H), 7.76-7.70 (m, 2H), 7.49 (d, J=7.88 Hz, 1H), 6.80 (d, J=8.24 Hz, 1H), 6.75 (d, J=8.48 Hz, 1H), 6.69 (s, 1H), 3.79-3.76 (m, 1H), 3.42-3.39 (m, 2H), 3.23-3.17 (m, 2H), 2.02-1.88 (m, 4H), 4.18 (s, 4H).

Example 45

N-phenyl-4-(piperidin-4-yl)naphthalene-1-sulfonamide (62)

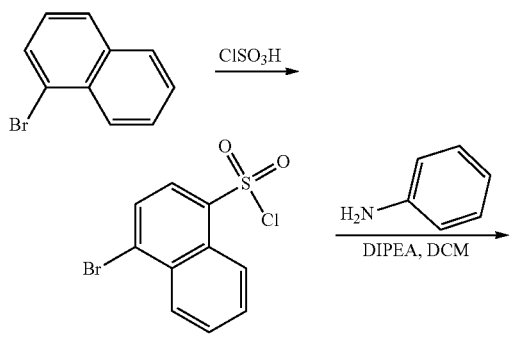

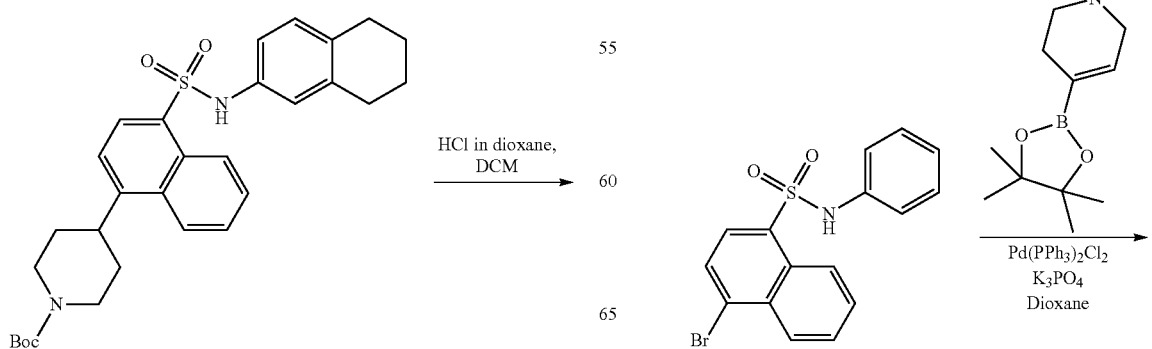

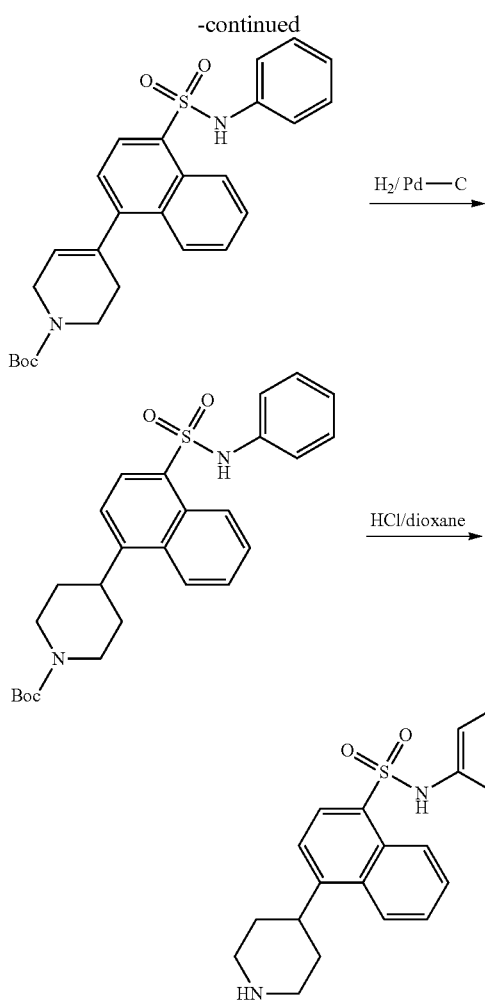

N-phenyl-4-(piperidin-4-yl)naphthalene-1-sulfonamide may be prepared by methods similar to those described in Example 44, using aniline as the arylamine in step 2. LCMS RT=4.76 min, m/z=367.17 [M+H]+ (Method 1).

Example 46

4-(Piperidin-4-yl)naphthalene-1-sulfonamide (63)

a) 4-bromonaphthalene-1-sulfonyl Chloride

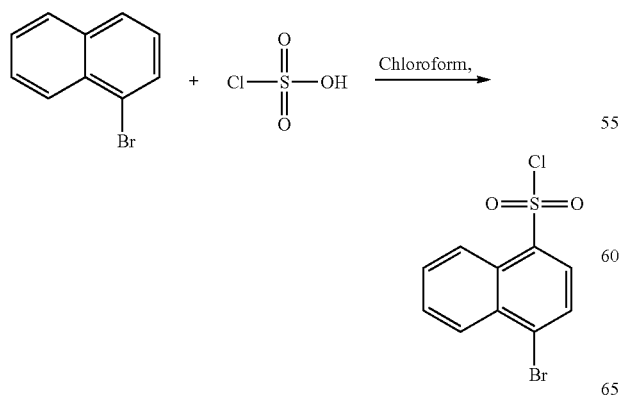

Chlorosulphonic acid (5.63 g, 48.3 mmol, 2.0 eq) was added drop-wise to the solution of 1-bromonaphthalene (5.0 g, 24.1 mmol, 1.0 eq) in chloroform (50 mL) under nitrogen atmosphere at 0° C. and the solution was stirred at ambient temperature for 1 h. After complete consumption of starting material, the reaction mixture was poured into chilled water and extracted with dichloromethane. The organic extract was separated and the aqueous extract was again extracted with dichloromethane. The combined organic extract was washed with brine, dried over anhydrous Na$_2$SO$_4$, filtered and solvents evaporated from the filtrate under reduced pressure to obtain 4-bromonaphthalene-1-sulfonyl chloride, which was used in the next step without purification.

b) 4-bromonaphthalene-1-sulfonamide

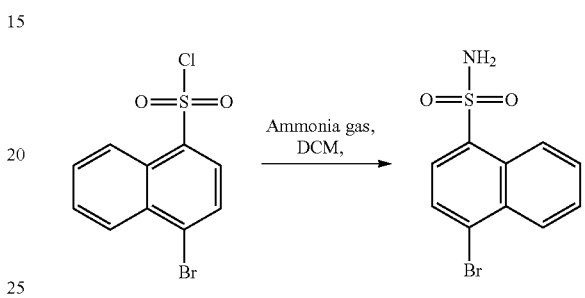

Ammonia gas was purged to a solution of 4-bromonaphthalene-1-sulfonyl chloride (1.0 g, 3.29 mmol, 1.0 eq) in dichloromethane (10 mL) and the solution was stirred at ambient temperature for 2 h. After complete consumption of starting material, the reaction mixture was evaporated under reduced pressure to obtain a crude product, which was purified by flash chromatography on silica gel, 234-400 mesh, using gradient of ethyl acetate in hexanes as eluent to obtain 4-bromonaphthalene-1-sulfonamide. LCMS: Purity 85.83%. MS calculated for [M] 286.14 and found [M−H]+ 285.97.

c) Tert-butyl 4-(4-sulfamoylnaphthalen-1-yl)-3,6-dihydropyridine-1(2H)-carboxylate

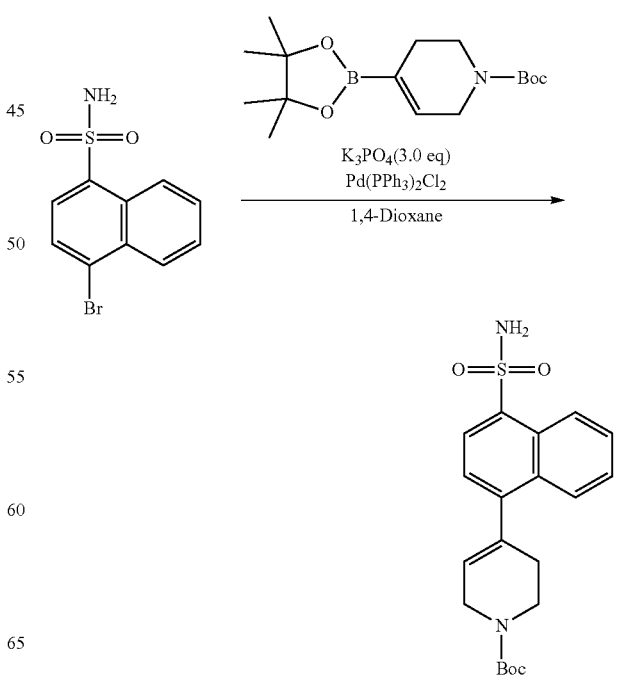

A mixture of 4-bromonaphthalene-1-sulfonamide (0.825 g, 2.89 mmol, 1.0 eq), tert-butyl 4-(4,4,5,5-tetramethyl-1,3,2-dioxaborolan-2-yl)-3,6-dihydropyridine-1(2H)-carboxylate (2.25 g, 7.23 mmol, 2.5 eq) and $K_3PO_4$ (1.84 g, 8.68 mmol, 3.0 eq) in 1,4-Dioxane (10 mL) was purged with nitrogen for 15 min. $Pd(PPh_3)_2Cl_2$ (0.203 g, 0.289 mmol, 0.1 eq) was added to the reaction mixture and was stirred under nitrogen atmosphere, at 100° C. for 16 h. After complete consumption of starting material, the mixture was cooled to ambient temperature and partitioned between water and ethyl acetate. The organic extract was separated and the aqueous extract was again extracted with ethyl acetate. The combined organic extract was washed with brine, dried over anhydrous $Na_2SO_4$, filtered and solvents evaporated from the filtrate under reduced pressure to obtain a crude product, which was purified by flash chromatography on silica gel, 100-200 mesh, using gradient of ethyl acetate in hexanes as eluent to obtain tert-butyl 4-(4-sulfamoylnaphthalen-1-yl)-3,6-dihydropyridine-1(2H)-carboxylate. LCMS: Purity 96.79%. MS calculated for [M] 388.48 and found [M−H]$^+$ 387.25.

d) Tert-butyl 4-(4-sulfamoylnaphthalen-1-yl)piperidine-1-carboxylate

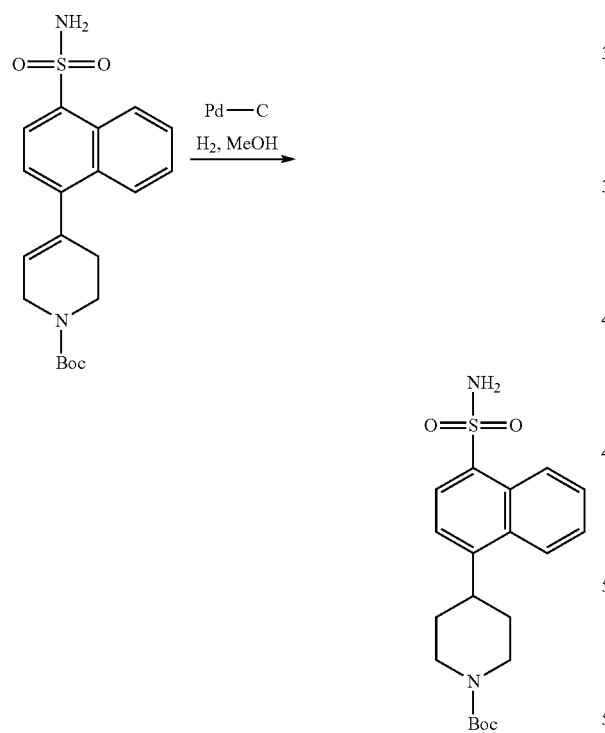

Pd—C (10% w/w, 50% moisture, 0.25 g) was added to the solution of tert-butyl 4-(4-sulfamoylnaphthalen-1-yl)-3,6-dihydropyridine-1(2H)-carboxylate (0.25 g, 0.644 mmol, 1.0 eq) in MeOH (5 mL). The reaction was allowed to stir at room temperature under hydrogen atmosphere (balloon pressure) for 2 h. Pd—C was filtered off (through celite) and solvent was evaporated from the filtrate under reduced pressure to afford tert-butyl 4-(4-sulfamoylnaphthalen-1-yl)piperidine-1-carboxylate. LCMS: Purity 99.07%. MS calculated for [M] 390.50 and found [M−H]$^+$ 389.26.

e) 4-(piperidin-4-yl)naphthalene-1-sulfonamide Hydrochloride

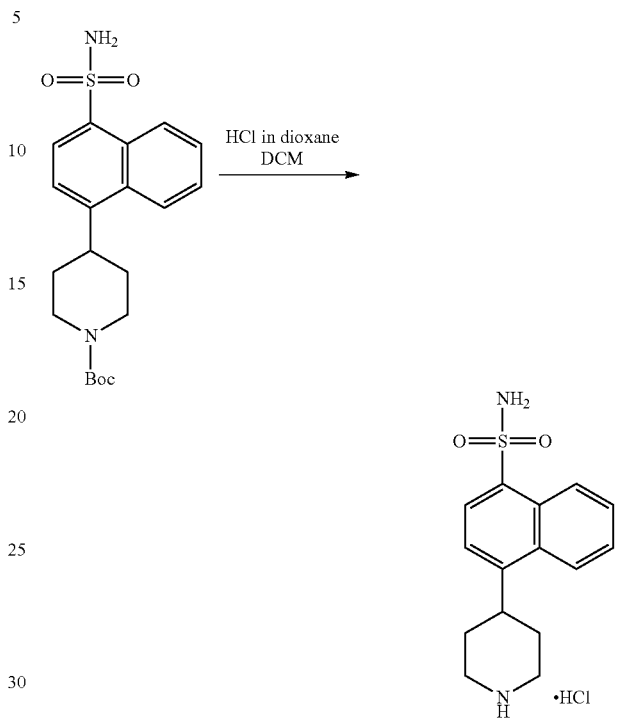

4M HCl in 1,4-dioxane (2 mL) was added dropwise to a solution of tert-butyl 4-(4-sulfamoylnaphthalen-1-yl)piperidine-1-carboxylate (0.2 g, 0.512 mmol, 1.0 eq) in dichloromethane (4 mL) and the mixture was stirred for 1 h at room temperature. Solvents evaporated under reduced pressure, the residue was triturated with diethyl ether followed by pentane and dried under vacuum to afford 4-(piperidin-4-yl)naphthalene-1-sulfonamide hydrochloride. LCMS: Purity 97.61%. RT=3.84 min (Method 1). MS calculated for [M] 290.38 and found [M+H]$^+$ 291.07. $^1$H-NMR (400 MHz, DMSO-$d_6$) δ 8.98 (bs, 1H), 8.80-8.78 (m, 1H), 8.71-8.68 (m, 1H), 8.41-8.12 (m, 1H), 8.13 (d, J=7.68 Hz, 1H), 7.72-7.70 (m, 1H), 7.63 (s, 2H), 7.50 (d, J=6.92 Hz, 1H), 3.82-3.80 (m, 1H), 3.43-3.20 (m, 4H), 2.02-1.93 (m, 4H).

Example 47

8-(Piperidin-4-yl)-5-(trifluoromethyl)quinoline (64)

a) 8-bromo-5-(trifluoromethyl)quinoline

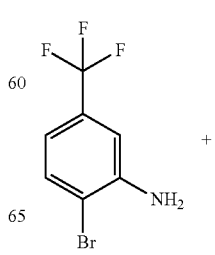

+

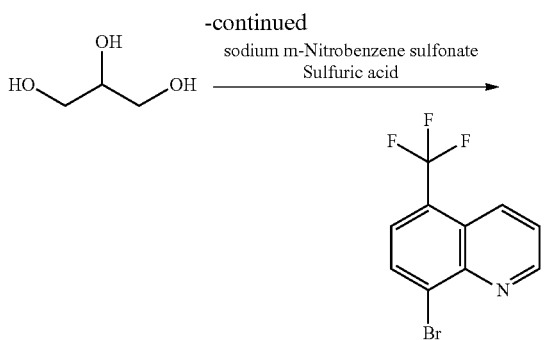

70% Sulfuric acid (18 mL) was added drop-wise to the solution of 2-bromo-5-(trifluoromethyl)aniline (5.0 g, 21.0 mmol, 1.0 eq), propane-1,2,3-triol (3.8 g, 42.0 mmol, 2.0 eq) and sodium m-Nitrobenzene sulfonate (7.3 g, 32.55 mmol, 1.55 eq) at 0° C. and the mixture was stirred under nitrogen atmosphere, at 150° C. for 4 h. After complete consumption of starting material, the mixture was cooled to ambient temperature, poured into chilled water and filtered through a celite bed. The filtrate was neutralized with 2N aqueous NaOH, which led to a precipitate, which was filtered and dried under vacuum to obtain 8-bromo-5-(trifluoromethyl)quinoline. LCMS: Purity 95.13%. MS calculated for [M] 274.96 and found [M+H]+ 276.04.

b) Tert-butyl 4-(5-(trifluoromethyl)quinolin-8-yl)-3,6-dihydropyridine-1(2H)-carboxylate

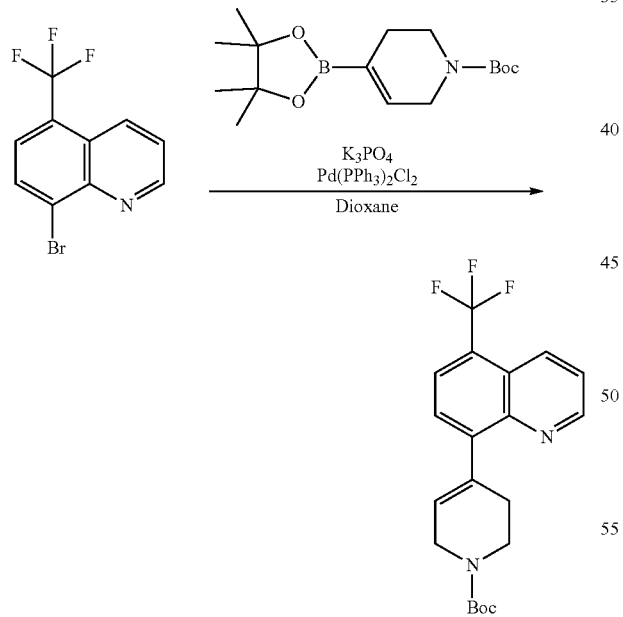

A mixture of 8-bromo-5-(trifluoromethyl)quinoline (1.3 g, 4.71 mmol, 1.0 eq), tert-butyl 4-(4,4,5,5-tetramethyl-1,3,2-dioxaborolan-2-yl)-3,6-dihydropyridine-1(2H)-carboxylate (2.9 g, 9.42 mmol, 2.0 eq) and K₃PO₄ (2.99 g, 14.13 mmol, 3.0 eq) in 1,4-Dioxane (15 mL) was purged with nitrogen for 15 min. Pd(PPh₃)₂Cl₂ (0.33 g, 0.471 mmol, 0.1 eq) was added to the reaction mixture and was stirred under nitrogen atmosphere, at 85° C. for 16 h. After complete consumption of starting material, the mixture was cooled to ambient temperature and partitioned between water and ethyl acetate. The organic extract was separated and the aqueous extract was again extracted with ethyl acetate. The combined organic extract was washed with brine, dried over anhydrous Na₂SO₄, filtered and solvents evaporated from the filtrate under reduced pressure to obtain a crude product, which was purified by flash chromatography on silica gel, 230-400 mesh, using gradient of ethyl acetate in hexanes as eluent to obtain tert-butyl 4-(5-(trifluoromethyl)quinolin-8-yl)-3,6-dihydropyridine-1(2H)-carboxylate. LCMS: Purity 61.96%. MS calculated for [M] 378.40 and found [M+H]+ 379.31.

c) Tert-butyl 4-(5-(trifluoromethyl)quinolin-8-yl)piperidine-1-carboxylate

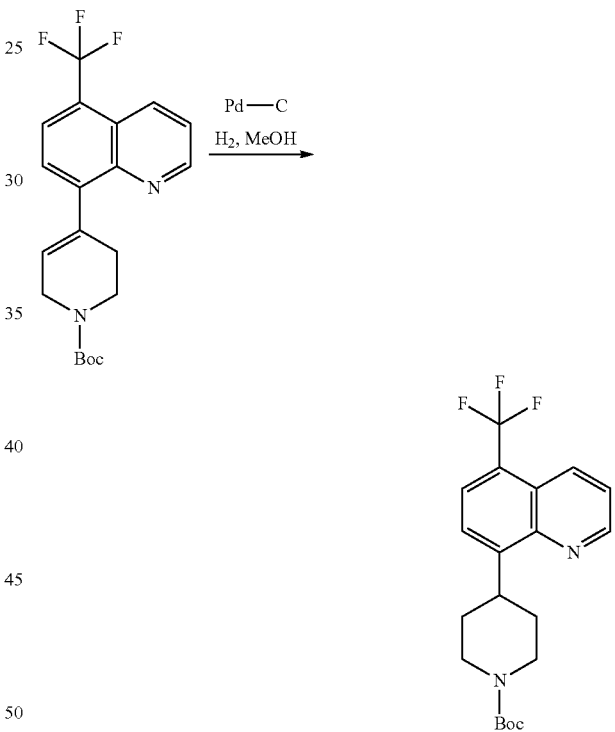

Pd—C (10% w/w, 50% moisture, 0.25 g) was added to the solution of tert-butyl 4-(5-(trifluoromethyl)quinolin-8-yl)-3,6-dihydropyridine-1(2H)-carboxylate (0.5 g, 1.29 mmol, 1.0 eq) in MeOH (7 mL). The reaction was allowed to stir at room temperature under hydrogen atmosphere (balloon pressure) for 1 h. Pd—C was filtered off (through celite) and solvent was evaporated from the filtrate under reduced pressure to obtain a crude product, which was purified by flash chromatography on silica gel, 230-400 mesh, using gradient of ethyl acetate in hexanes as eluent to obtain tert-butyl 4-(5-(trifluoromethyl)quinolin-8-yl)piperidine-1-carboxylate. LCMS: Purity 97.53%. MS calculated for [M] 380.41 and found [M-100+H+]+ 281.15.

d) 8-(piperidin-4-yl)-5-(trifluoromethyl)quinoline Dihydrochloride

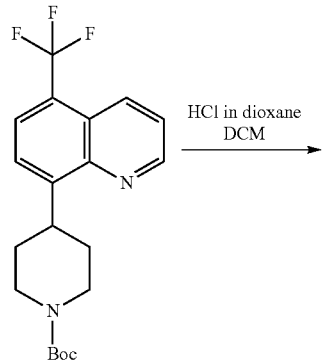

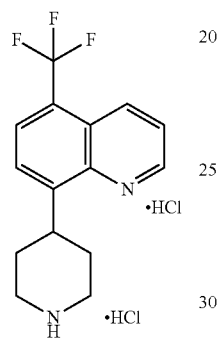

4M HCl in 1,4-dioxane (1.0 mL) was added drop-wise to a solution of tert-butyl 4-(5-(trifluoromethyl)quinolin-8-yl) piperidine-1-carboxylate (0.1 g, 0.262 mmol, 1.0 eq) in dichloromethane (2 mL) and the reaction mixture was stirred at ambient temperature for 2 h. Solvents evaporated under reduced pressure, the residue was triturated with diethyl ether and dried under vacuum to afford 8-(piperidin-4-yl)-5-(trifluoromethyl)quinoline dihydrochloride. LCMS: Purity 98.23%. RT=4.48 min (Method 1). MS calculated for [M] 280.29 and found [M+H]$^+$ 281.29. $^1$H-NMR (400 MHz, DMSO-d$_6$) δ 9.11-9.10 (m, 1H), 9.00 (bs, 1H), 8.51 (d, J=8.56 Hz, 1H), 8.11 (d, J=7.52 Hz, 1H), 7.81-7.78 (m, 1H), 7.74 (d, J=7.44 Hz, 1H), 4.45-4.18 (m, 1H), 3.49-3.43 (m, 2H), 3.25-3.10 (m, 2H), 2.05-2.04 (m, 4H).

Example 48

5-(Piperidin-4-yl)-8-(trifluoromethyl)quinoline (65)

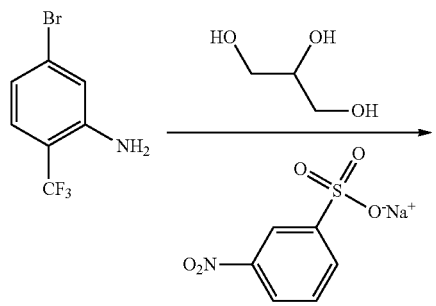

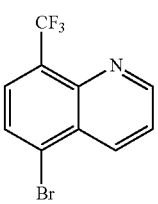
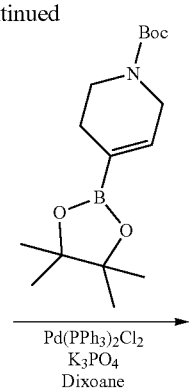

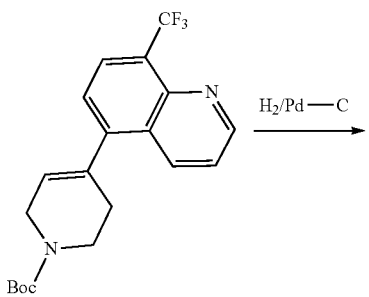

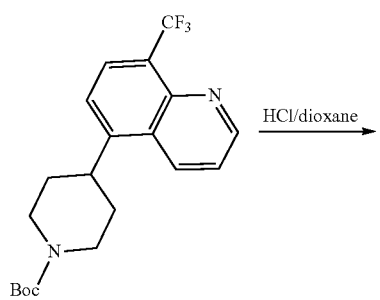

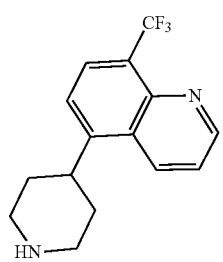

5-(piperidin-4-yl)-8-(trifluoromethyl)quinoline may be prepared by methods similar to those described in Example 47, using 5-bromo-2-(trifluoromethyl)aniline as the arylamine starting material in step 1. LCMS RT=3.87 min, m/z=281.29 [M+H]$^+$ (Method 1).

Example 49

5-(Piperidin-4-yl)-2-naphthamide (66)

a) Methyl 5-bromo-2-naphthoate

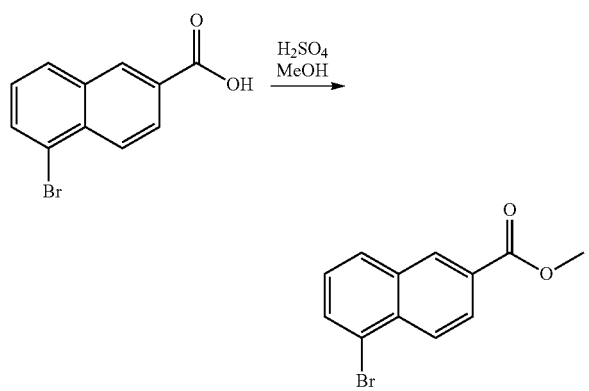

Sulfuric acid (0.2 mL) was added to the solution of 5-bromo-2-naphthoic acid (1.0 g, 3.98 mmol, 1.0 eq) in MeOH (10 mL) at room temperature and the solution was stirred under nitrogen atmosphere, at 80° C. for 16 h. After complete consumption of starting material, the reaction mixture was evaporated under reduced pressure, diluted ethyl acetate and washed with saturated aqueous sodium bicarbonate. The aqueous extract was again extracted with ethyl acetate. The combined organic extract was washed with brine, dried over anhydrous $Na_2SO_4$, filtered and solvents evaporated from the filtrate under reduced pressure to afford methyl 5-bromo-2-naphthoate.

b) Tert-butyl 4-(6-(methoxycarbonyl)naphthalen-1-yl)-3,6-dihydropyridine-1(2H)-carboxylate

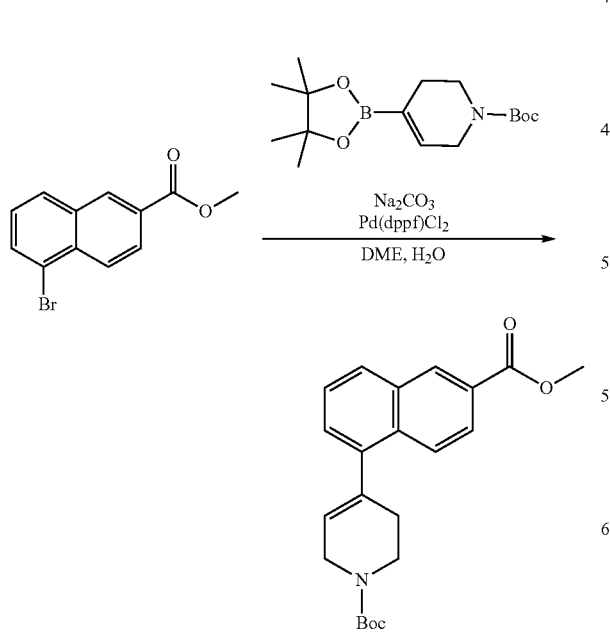

A mixture of methyl 5-bromo-2-naphthoate (0.5 g, 1.88 mmol, 1.0 eq), tert-butyl 4-(4,4,5,5-tetramethyl-1,3,2-dioxaborolan-2-yl)-3,6-dihydropyridine-1(2H)-carboxylate (0.64 g, 2.07 mmol, 1.1 eq) and $Na_2CO_3$ (0.57 g, 5.4 mmol, 3.0 eq) in a mixture of 1,2-DME (5 mL) and water (1 mL) was purged with nitrogen for 15 min. $Pd(dppf)Cl_2 \cdot DCM$ (0.14 g, 0.188 mmol, 0.1 eq) was added to the reaction mixture and the mixture was stirred under nitrogen atmosphere, at 80° C. for 5 h. After complete consumption of starting material, the mixture was cooled to ambient temperature and partitioned between water and ethyl acetate. The organic extract was separated and the aqueous extract was again extracted with ethyl acetate. The combined organic extract was washed with brine, dried over anhydrous $Na_2SO_4$, filtered and solvents evaporated from the filtrate under reduced pressure to obtain a crude product, which was purified by flash chromatography on silica gel, 230-400 mesh, using gradient of ethyl acetate in hexanes as eluent to obtain tert-butyl 4-(6-(methoxycarbonyl)naphthalen-1-yl)-3,6-dihydropyridine-1(2H)-carboxylate. LCMS: Purity 99.14%. MS calculated for [M] 367.45 and found $[M+H]^+$ 368.28.

c) Tert-butyl 4-(6-(methoxycarbonyl)naphthalen-1-yl)piperidine-1-carboxylate

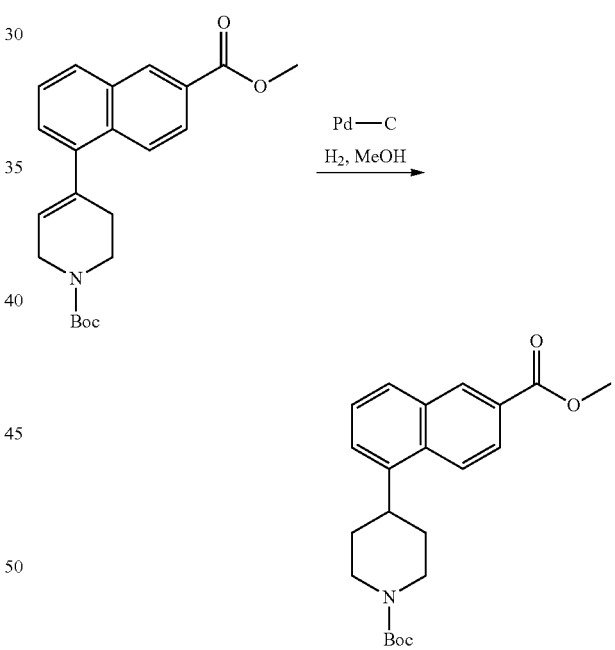

Pd—C (10% w/w, 50% moisture, 0.25 g) was added to the solution of tert-butyl 4-(6-(methoxycarbonyl)naphthalen-1-yl)-3,6-dihydropyridine-1(2H)-carboxylate (0.5 g, 1.36 mmol, 1.0 eq) in MeOH (5 mL) and reaction was allowed to stir at room temperature under hydrogen atmosphere (balloon pressure) for 10 h. Pd—C was filtered off (through celite) and solvent was evaporated from the filtrate under reduced pressure to obtain tert-butyl 4-(6-(methoxycarbonyl)naphthalen-1-yl)piperidine-1-carboxylate. LCMS: Purity 96.12%. MS calculated for [M] 369.46 and found $[M+H]^+$ 370.35.

d) 5-(1-(tert-butoxycarbonyl)piperidin-4-yl)-2-naphthoic Acid

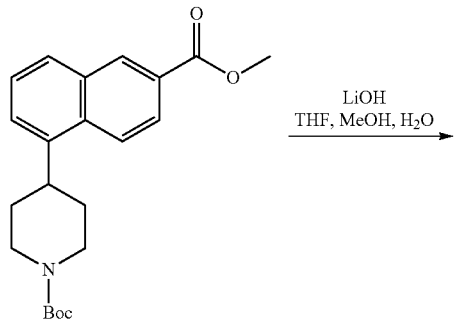

Lithium hydroxide (0.085 g, 2.02 mmol, 1.5 eq) was added to the solution of tert-butyl 4-(6-(methoxycarbonyl)naphthalen-1-yl)piperidine-1-carboxylate (0.3 g, 1.35 mmol, 1.0 eq) in a mixture of THF (2 mL), MeOH (2 mL) and water (2 mL) and the reaction mixture was stirred at room temperature for 4 h. After complete consumption of starting material, the reaction mixture was evaporated under reduced pressure, the residue was dissolved in water, acidified with 10% aqueous citric acid and extracted with ethyl acetate. The combined organic extract was washed with brine, dried over anhydrous Na$_2$SO$_4$, filtered and solvents evaporated from the filtrate under reduced pressure to afford 5-(1-(tert-butoxycarbonyl)piperidin-4-yl)-2-naphthoic acid. LCMS: Purity 96.88%. MS calculated for [M]355.43 and found [M−H]$^+$ 354.34.

e) Tert-butyl 4-(6-carbamoylnaphthalen-1-yl)piperidine-1-carboxylate

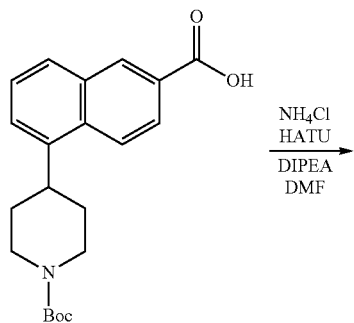

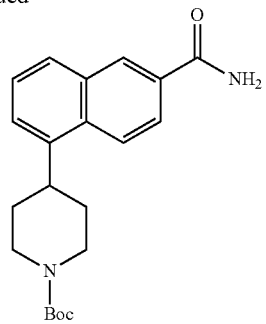

HATU (0.32 g, 0.84 mmol, 1.5 eq) was added to a solution of 5-(1-(tert-butoxycarbonyl)piperidin-4-yl)-2-naphthoic acid (0.2 g, 0.56 mmol, 1.0 eq) and DIPEA (0.32 g, 0.84 mmol, 1.5 eq) in DMF (5 mL) at 0° C. The reaction mixture was stirred at 0° C. for 15 min. Ammonium chloride (0.29 g, 5.6 mmol, 10.0 eq) was added and the reaction mixture was stirred at room temperature for 4 h. After complete consumption of starting material, the reaction mixture was poured into chilled water. The precipitate was filtered, washed with water, pentane and dried under vacuum to afford tert-butyl 4-(6-carbamoylnaphthalen-1-yl)piperidine-1-carboxylate. MS calculated for [M] 354.19 and found [M+H]$^+$ 355.35.

f) (5-(piperidin-4-yl)-2-naphthamide Hydrochloride

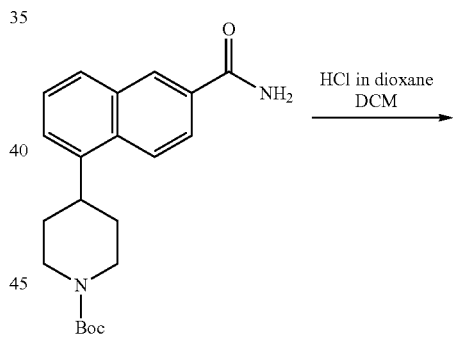

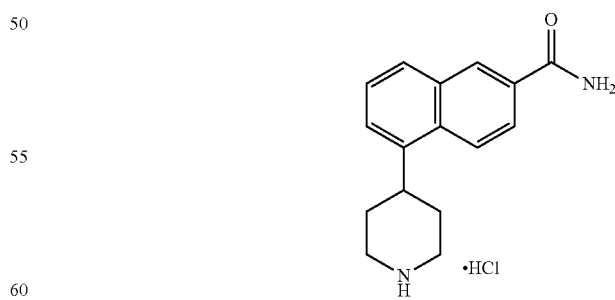

4M HCl in 1,4-dioxane (0.4 mL) was added drop-wise to a solution of tert-butyl 4-(6-carbamoylnaphthalen-1-yl)piperidine-1-carboxylate (0.1 g, 0.28 mmol, 1.0 eq) in dichloromethane (5 mL) at 0° C. The reaction mixture was stirred at ambient temperature for 4 h. Solvents evaporated under reduced pressure, the residue was triturated with diethyl ether, pentane and dried under vacuum to afford 5-(piperidin-4-yl)-2-naphthamide hydrochloride. LCMS: Purity 95.49%. RT=3.74 min (Method 1). MS calculated for [M] 254.33 and found [M+H]+ 255.11. ¹H-NMR (400 MHz, DMSO-d₆) δ 9.03-8.98 (m, 1H), 8.93-8.84 (m, 1H), 8.51 (s, 1H), 8.29 (d, J=9.0 Hz, 1H), 8.17 (bs, 1H), 8.00 (d, J=8.88 Hz, 1H), 7.90 (d, J=8.04 Hz, 1H), 7.57 (t, J=7.6 Hz, 1H), 7.47 (t, J=8.76 Hz, 1H), 3.78-3.71 (m, 1H), 3.40 (d, J=11.76 Hz, 2H), 3.25-3.16 (m, 2H), 2.04-1.95 (m, 4H).

Example 50

5-(Piperidin-4-yl)-1-naphthamide (67)

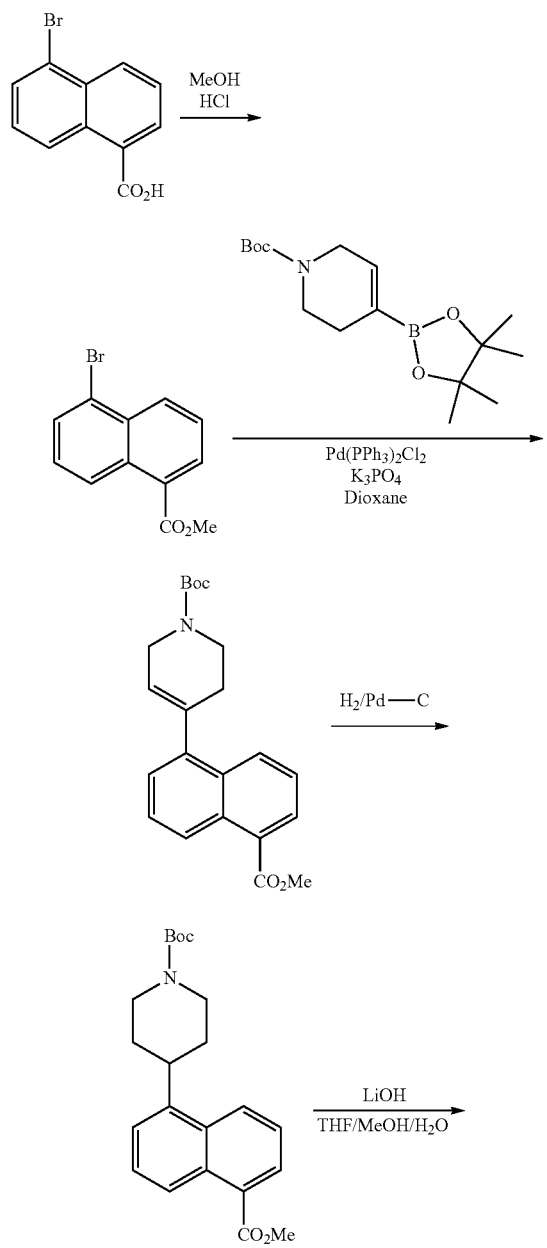

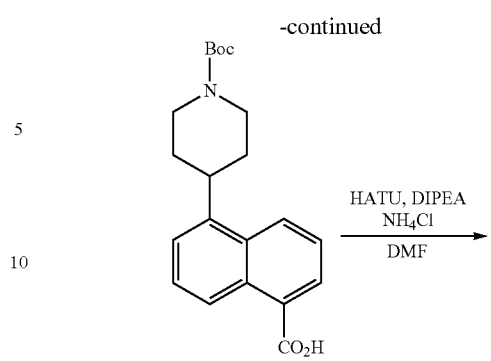

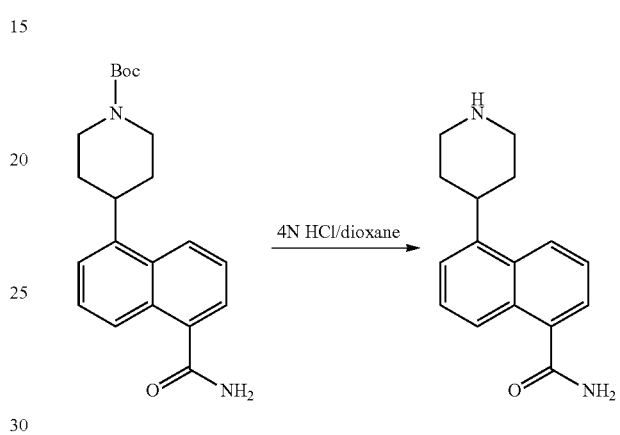

5-(piperidin-4-yl)-1-naphthamide may be prepared by methods similar to those described in Example 49, using 5-bromo-1-naphthoic acid as the starting material. LCMS RT=4.61 min, m/z=255.11 [M+H]+ (Method 2).

Example 51

4-(Piperidin-4-yl)-1-naphthamide (68)

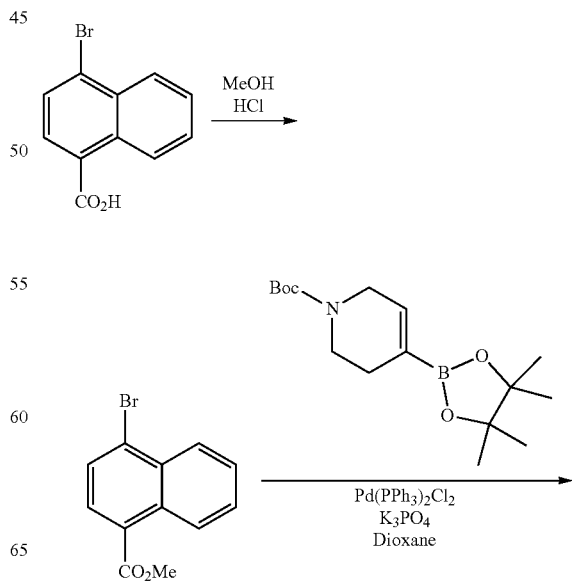

-continued

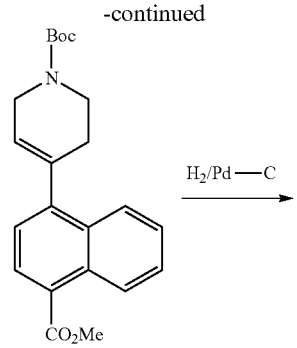

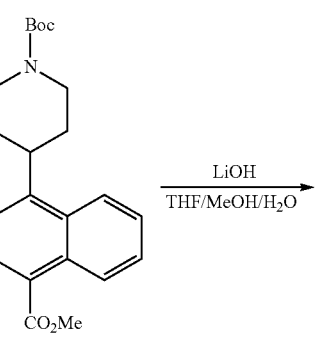

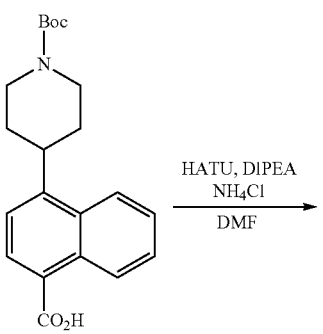

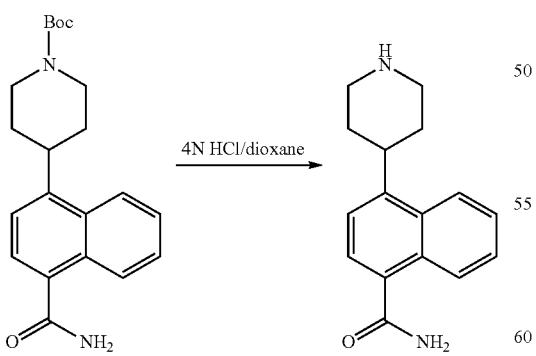

4-(piperidin-4-yl)-1-naphthamide may be prepared by methods similar to those described in Example 49, using 4-bromo-1-naphthoic acid as the starting material. LCMS RT=3.41 min, m/z=255.11 [M+H]+ (Method 1).

Example 52

8-(Naphthalen-1-yl)-1,3-diazaspiro[4.5]decan-2-one (69)

a) [8-(naphthalen-1-yl)-1,3-diazaspiro[4.5]decane-2,4-dione

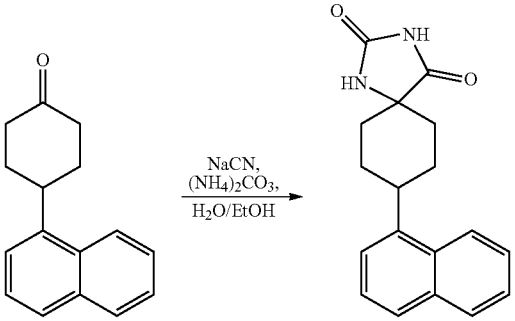 [SMILES: O=C1CCC(c2cccc3ccccc23)CC1 ; "H2O/EtOH" ; "NaCN,(NH4)2CO3," ; O=C1NC(=O)C2(CCC(c3cccc4ccccc34)CC2)N1]

To a stirred solution of ammonium carbonate (3.07 g, 32.00 mmol, 8.0 equiv) and sodium cyanide (784 mg, 16.000 mol, 4.0 equiv) in a solvent mixture of water (10.44 mL, 11.6 vol.) and EtOH (1.04 mL, 1.6 vol.) was added portion wise 4-(naphthalen-1-yl)cyclohexanone (0.9 g, 4.00 mmol, 1.0 eq) at RT. The reaction mixture was slowly heated to 40-50° C. for 3 h and then refluxed for 5 days. The reaction mixture was concentrated under reduced pressure and water was added to the residue to generate a precipitate. The precipitate was isolated by filtration, washed with water (1 mL), and dried under vacuum to give 8-(naphthalen-1-yl)-1,3-diazaspiro[4.5]decane-2,4-dione.

b) [8-(naphthalen-1-yl)-1,3-diazaspiro[4.5]decan-2-one]

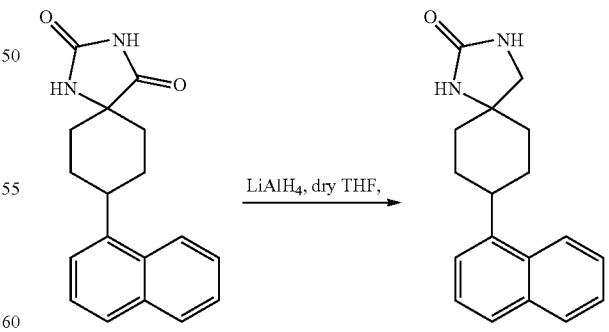

To a solution of 8-(naphthalen-1-yl)-1,3-diazaspiro[4.5]decane-2,4-dione (145 mg, 0.492 mmol, 1.0 equiv) in THF was added portion wise LiAlH$_4$ (55 mg, 1.478 mmol, 3.0 equiv) and then (5×55 mg for a 24 h period) at RT under a N$_2$ atmosphere. The reaction mixture was slowly heated to reflux for 6 days. The reaction mixture was cooled to RT, quenched with a 10% citric acid solution and extracted with DCM (2×10 mL). The aqueous fraction was basified with aq. NH₄OH, and subsequently extracted with DCM (2×5 mL). The combined organic layers were washed with water and brine, and concentrated under reduced pressure. The residue was purified by preparative HPLC to yield 8-(naphthalen-1-yl)-1,3-diazaspiro[4.5]decan-2-one. LCMS: 86.105%, m/z=281.3 [M+H]⁺ (Method 3). ¹H-NMR (400 MHz, DMSO-d₆): δ 8.11 (1H, d), 7.91 (1H, d), 7.74 (1H, d), 7.60-7.41 (4H, m), 5.58 (1H, brs), 4.70 (1H, brs), 3.35 (2H, s), 2.21-2.20 (3H, m), 1.85-1.51 (6H, m).

Example 53

N-(4-(piperidin-4-yl)naphthalen-1-yl)tetrahydro-2H-pyran-4-amine (70)

a) N-(4-bromonaphthalen-1-yl)tetrahydro-2H-pyran-4-amine

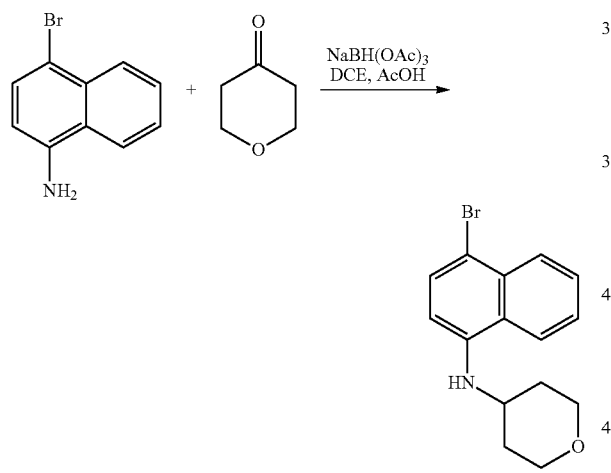

Tetrahydro-4H-pyran-4-one (0.677 g, 6.75 mmol, 1.5 eq) was added to a mixture of 4-bromonaphthalen-1-amine (1.0 g, 4.5 mmol, 1.0 eq) in 1,2-dichloroethane (10 mL). The reaction mixture was stirred at room temperature for 5 min. Acetic acid (0.1 mL) was added to the reaction mixture and was stirred under nitrogen atmosphere, at room temperature for 1 h. A solution of sodium triacetoxyborohydride (1.43 g, 6.75 mmol, 1.5 eq) in 1,2-dichloroethane (10 mL) and was added drop-wise to the above mixture and stirring continued at room temperature for 16 h. After complete consumption of starting material, the mixture was partitioned between water and ethyl acetate. The organic extract was separated and the aqueous extract was again extracted with ethyl acetate. The combined organic extract was washed with brine, dried over anhydrous Na₂SO₄, filtered and solvents evaporated from the filtrate under reduced pressure to obtain N-(4-bromonaphthalen-1-yl)tetrahydro-2H-pyran-4-amine. LCMS: Purity 61.71%. MS calculated for [M] 305.04 and found [M−H⁺] 304.05.

b) Tert-butyl 4-(4-((tetrahydro-2H-pyran-4-yl)amino)naphthalen-1-yl)-3,6-dihydropyridine-1 (2M-carboxylate

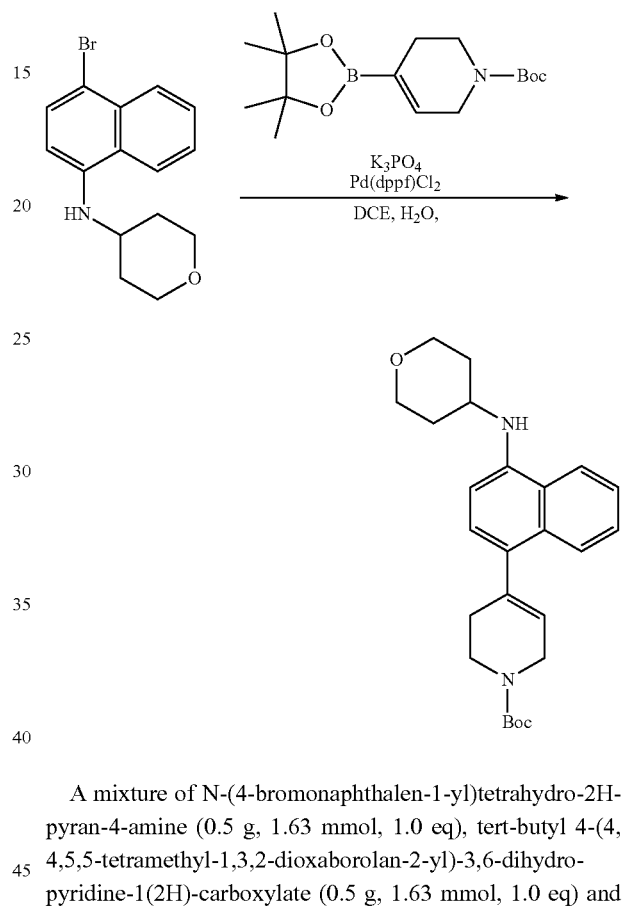

A mixture of N-(4-bromonaphthalen-1-yl)tetrahydro-2H-pyran-4-amine (0.5 g, 1.63 mmol, 1.0 eq), tert-butyl 4-(4,4,5,5-tetramethyl-1,3,2-dioxaborolan-2-yl)-3,6-dihydropyridine-1(2H)-carboxylate (0.5 g, 1.63 mmol, 1.0 eq) and K₃PO₄ (1.03 g, 4.9 mmol, 3.0 eq) in a mixture of 1,2-dichloroethane (5 mL) and water (2 mL) was purged with nitrogen for 15 min. Pd(dppf)Cl₂ (0.133 g, 0.16 mmol, 0.1 eq) was added to the reaction mixture and was stirred under nitrogen atmosphere, at 80° C. for 8 h. After complete consumption of starting material, the mixture was cooled to ambient temperature and partitioned between water and ethyl acetate. The organic extract was separated and the aqueous extract was again extracted with ethyl acetate. The combined organic extract was washed with brine, dried over anhydrous Na₂SO₄, filtered and solvents evaporated from the filtrate under reduced pressure to obtain a crude product, which was purified by flash chromatography on silica gel, 230-400 mesh, using gradient of ethyl acetate in hexanes as eluent to obtain tert-butyl 4-(4-((tetrahydro-2H-pyran-4-yl)amino)naphthalen-1-yl)-3,6-dihydropyridine-1(2H)-carboxylate.

c) Tert-butyl 4-(4-((tetrahydro-2H-pyran-4-yl)amino)naphthalen-1-yl)piperidine-1-carboxylate

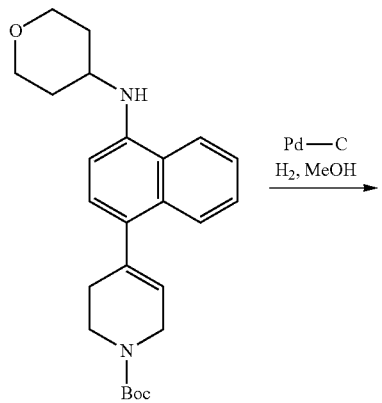

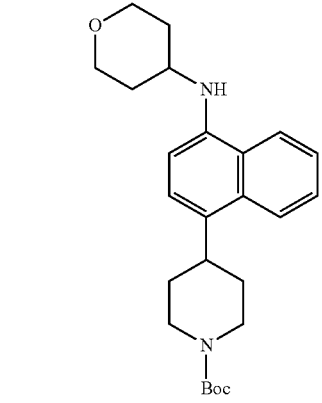

Pd—C (10% w/w, 50% moisture, 0.1 g) was added to the solution of tert-butyl 4-(4-((tetrahydro-2H-pyran-4-yl)amino)naphthalen-1-yl)-3,6-dihydropyridine-1(2H)-carboxylate (0.2 g, 0.489 mmol, 1.0 eq) in MeOH (5 mL) and reaction was allowed to stir at room temperature under hydrogen atmosphere (balloon pressure) for 4 h. Pd—C was filtered off (through celite) and solvent was evaporated from the filtrate under reduced pressure to afford tert-butyl 4-(4-((tetrahydro-2H-pyran-4-yl)amino)naphthalen-1-yl)piperidine-1-carboxylate. LCMS: Purity 98.35%. MS calculated for [M] 410.56 and found [M+H]$^+$ 411.30.

d) N-(4-(piperidin-4-yl)naphthalen-1-yl)tetrahydro-2H-pyran-4-amine dihydrochloride

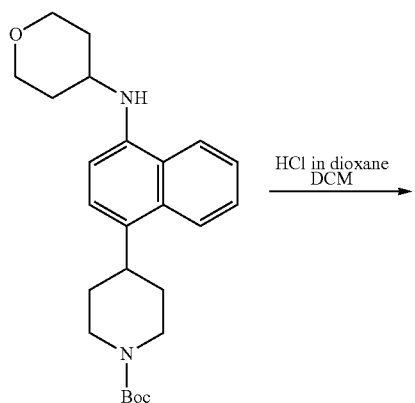

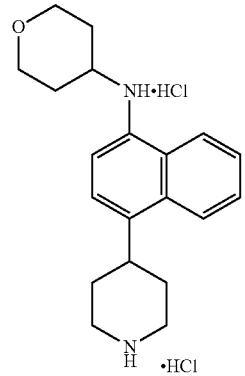

4M HCl in 1,4-dioxane (3 mL) was added dropwise to a solution of tert-butyl 4-(4-((tetrahydro-2H-pyran-4-yl)amino)naphthalen-1-yl)piperidine-1-carboxylate (0.1 g, 0.243 mmol, 1.0 eq) in dichloromethane (5 mL) at 0° C. The reaction mixture was stirred at ambient temperature for 4 h. Solvents evaporated under reduced pressure, the residue was triturated with diethyl ether followed by pentane and dried under vacuum to afford N-(4-(piperidin-4-yl)naphthalen-1-yl)tetrahydro-2H-pyran-4-amine dihydrochloride. LCMS: Purity 99.64%. RT=3.72 min (Method 1). MS calculated for [M] 310.44 and found [M+H]$^+$ 311.16. $^1$H-NMR (400 MHz, DMSO-$d_6$) δ 8.94 (bs, 1H), 8.80-8.78 (m, 1H), 8.26 (d, J=8.24 Hz, 1H), 8.18 (bs, 1H), 7.58-7.57 (m, 2H), 7.31 (bs, 1H), 7.00 (bs, 1H), 3.91-3.60 (m, 6H), 3.41-3.38 (m, 4H), 3.21-3.15 (m, 2H), 1.96-1.91 (m, 6H), 1.71 (bs, 2H).

Example 54

4-(4-((Tetrahydro-2H-pyran-4-yl)oxy)naphthalen-1-yl)piperidine (71)

a) Tetrahydro-2H-pyran-4-yl 4-methylbenzenesulfonate

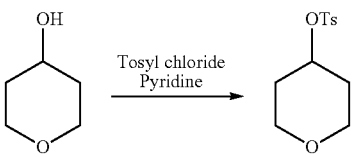 [SMILES: OC1CCOCC1 ; "Tosyl chloridePyridine" ; Cc1ccc(S(=O)(=O)OC2CCOCC2)cc1]

A solution of tosyl chloride (1.4 g, 7.34 mmol, 1.5 eq) in pyridine (5 mL) was added to a solution of tetrahydro-2H-pyran-4-ol (0.5 g, 4.9 mmol, and 1.0 eq) in pyridine (5 mL) at 0° C. The reaction mixture was stirred under nitrogen atmosphere, at room temperature for 4 h. After complete consumption of starting material, 1N aqueous HCl was added, diluted with water and extracted with ethyl acetate. The organic extract was separated and the aqueous extract was again extracted with ethyl acetate. The combined organic extract was washed with brine, dried over anhydrous Na$_2$SO$_4$, filtered and solvents evaporated from the filtrate under reduced pressure to obtain tetrahydro-2H-pyran-4-yl 4-methylbenzenesulfonate.

b) 4-((4-bromonaphthalen-1-yl)oxy)tetrahydro-2H-pyran

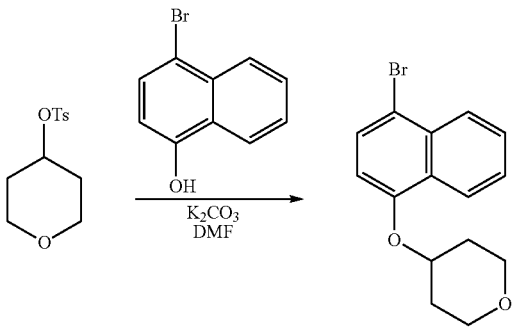

Tetrahydro-2H-pyran-4-yl 4-methylbenzenesulfonate (1.19 g, 4.66 mmol, 1.3 eq) was added to a mixture of 4-bromonaphthalen-1-ol (0.8 g, 3.5 mmol, 1.0 eq) and K₂CO₃ (0.64 g, 4.6 mmol, 1.3 eq) in DMF (10 mL) at ambient temperature and the mixture was stirred under nitrogen atmosphere, at 80° C. for 16 h. After complete consumption of starting material, the mixture was cooled to ambient temperature and partitioned between water and ethyl acetate. The organic extract was separated and the aqueous extract was again extracted with ethyl acetate. The combined organic extract was washed with brine, dried over anhydrous Na₂SO₄, filtered and solvents evaporated from the filtrate under reduced pressure to obtain a crude product, which was purified by flash chromatography on silica gel, 230-400 mesh, using gradient of ethyl acetate in hexanes as eluent to obtain 4-((4-bromonaphthalen-1-yl)oxy)tetrahydro-2H-pyran. LCMS: Purity 90.19%.

c) Tert-butyl 4-(4-((tetrahydro-2H-pyran-4-yl)oxy)naphthalen-1-yl)-3,6-dihydropyridine-1(2H)-carboxylate

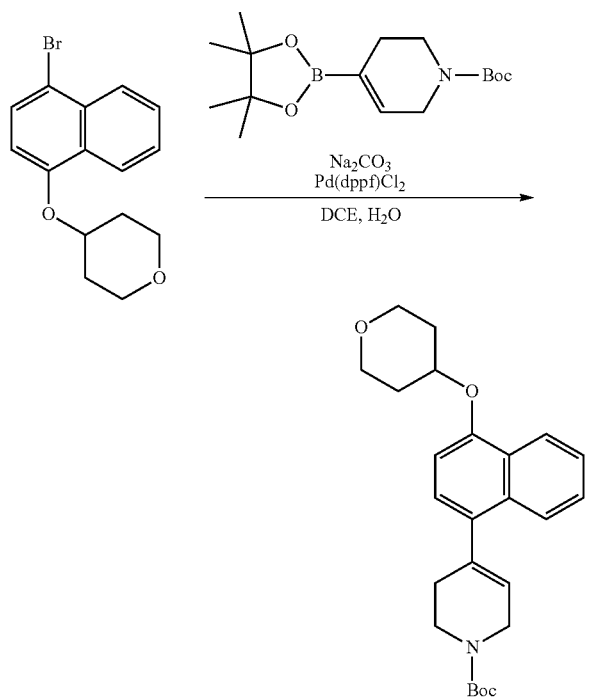

A mixture of 4-((4-bromonaphthalen-1-yl)oxy)tetrahydro-2H-pyran (0.27 g, 0.88 mmol, 1.0 eq), tert-butyl 4-(4,4,5,5-tetramethyl-1,3,2-dioxaborolan-2-yl)-3,6-dihydropyridine-1(2H)-carboxylate (0.27 g, 0.88 mmol, 1.0 eq) and Na₂CO₃ (0.267 g, 2.6 mmol, 3.0 eq) in a mixture of 1,2-DME (5 mL) and water (1 mL) was purged with nitrogen for 15 min. Pd(dppf)Cl₂·DCM (0.071 g, 0.08 mmol, 0.1 eq) was added to the reaction mixture and was stirred under nitrogen atmosphere, at 80° C. for 8 h. After complete consumption of starting material, the mixture was cooled to ambient temperature and partitioned between water and ethyl acetate. The organic extract was separated and the aqueous extract was again extracted with ethyl acetate. The combined organic extract was washed with brine, dried over anhydrous Na₂SO₄, filtered and solvents evaporated from the filtrate under reduced pressure to obtain a crude product, which was purified by flash chromatography on silica gel, 230-400 mesh, using gradient of ethyl acetate in hexanes as eluent to obtain tert-butyl 4-(4-((tetrahydro-2H-pyran-4-yl)oxy)naphthalen-1-yl)-3,6-dihydropyridine-1(2H)-carboxylate. LCMS: Purity 96.36%. MS calculated for [M] 409.53 and found [M+H]⁺ 410.34.

d) Tert-butyl 4-(4-((tetrahydro-2H-pyran-4-yl)oxy)naphthalen-1-yl)piperidine-1-carboxylate

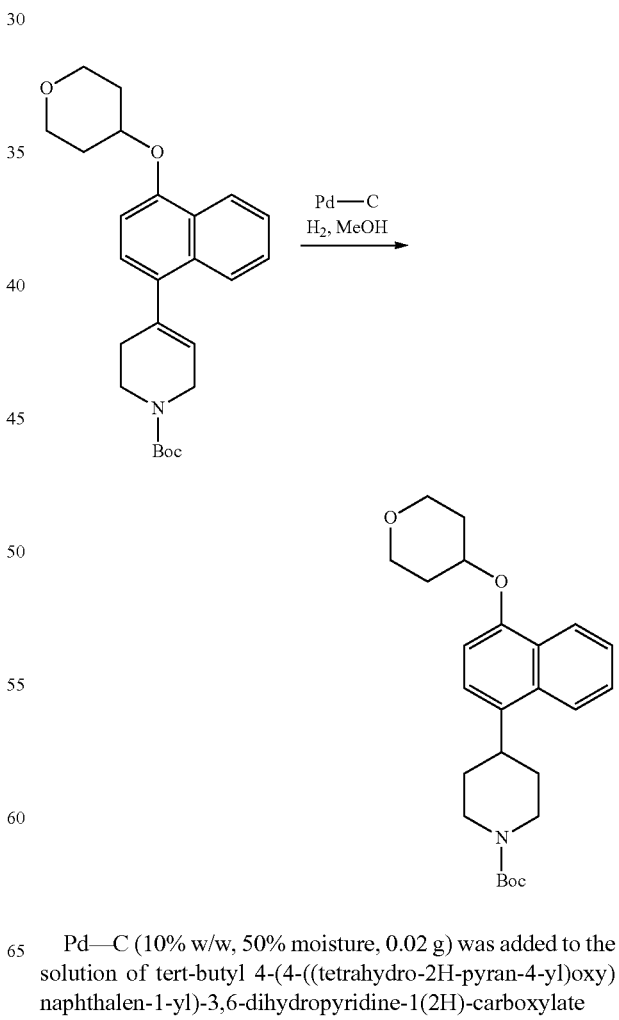

Pd—C (10% w/w, 50% moisture, 0.02 g) was added to the solution of tert-butyl 4-(4-((tetrahydro-2H-pyran-4-yl)oxy)naphthalen-1-yl)-3,6-dihydropyridine-1(2H)-carboxylate (0.06 g, 0.146 mmol, 1.0 eq) in MeOH (5 mL) and reaction was allowed to stir at room temperature under hydrogen atmosphere (balloon pressure) for 2 h. Pd—C was filtered off (through celite) and solvent was evaporated from the filtrate under reduced pressure to afford tert-butyl 4-(4-((tetrahydro-2H-pyran-4-yl)oxy)naphthalen-1-yl)piperidine-1-carboxylate, which was utilized in the next step without purification.

e) 4-(4-((tetrahydro-2H-pyran-4-yl)oxy)naphthalen-1-yl)piperidine Hydrochloride

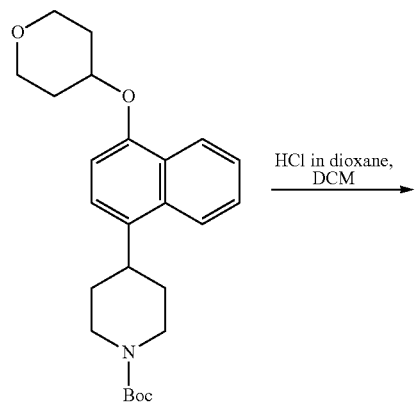

4M HCl in 1,4-dioxane (0.2 mL) was added dropwise to a solution of tert-butyl 4-(4-((tetrahydro-2H-pyran-4-yl)oxy)naphthalen-1-yl)piperidine-1-carboxylate (0.038 g, 0.092 mmol, 1.0 eq) in dichloromethane (5 mL) at 0° C. The reaction mixture was stirred at ambient temperature for 4 h. Solvents evaporated under reduced pressure, the residue was triturated with diethyl ether and pentane, dried under vacuum to afford 4-(4-((tetrahydro-2H-pyran-4-yl)oxy) naphthalen-1-yl)piperidine hydrochloride. LCMS: Purity 99.88%. RT=4.67 min (Method 1). MS calculated for [M] 311.43 and found [M+H]$^+$ 312.20. $^1$H-NMR (400 MHz, DMSO-$d_6$) δ 8.68 (bs, 1H), 8.34 (bs, 1H), 8.27 (d, J=8.16 Hz, 1H), 8.16 (d, J=8.4 Hz, 1H), 7.60-7.51 (m, 2H), 7.24 (d, J=8.16 Hz, 1H), 7.05 (d, J=8.08 Hz, 1H), 4.80-4.77 (m, 1H), 3.91-3.88 (m, 2H), 3.63-3.53 (m, 3H), 3.41-3.18 (m, 4H), 2.06-1.86 (m, 6H), 1.76-1.72 (m, 2H).

Example 55

(4-(Piperazin-1-yl)-N-(5,6,7,8-tetrahydronaphthalen-1-yl)naphthalene-1-sulfonamide) (72)

a) 4-fluoronaphthalene-1-sulfonyl Chloride

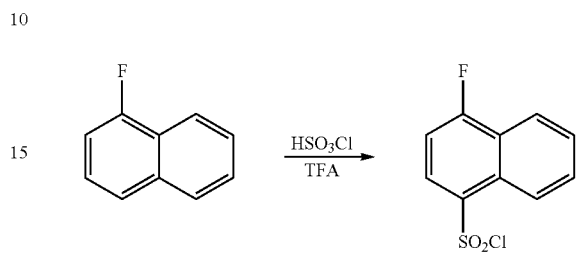

To a stirred solution of 1-fluoronaphthalene (500 mg, 0.342 mmol) was added TFA (2.43 mL) drop wise at 0° C. under an inert atmosphere. The solution was stirred for 10 min. after which HSO$_3$Cl (0.5 ml) was added drop wise to the reaction mixture. The reaction was stirred at 0° C. for 0.5 h and subsequently warmed to room temperature 2 h. The reaction mixture was quenched with ice cold water and the resulting material was isolated by filtration. The hygroscopic solid was dried in a vacuum desiccator containing P$_2$O$_5$ to provide intermediate 4-fluoronaphthalene-1-sulfonyl chloride. LCMS purity: 90.7% b) 4-fluoro-N-(5,6,7,8-tetrahydronaphthalen-1-yl) naphthalene-1-sulfonamide

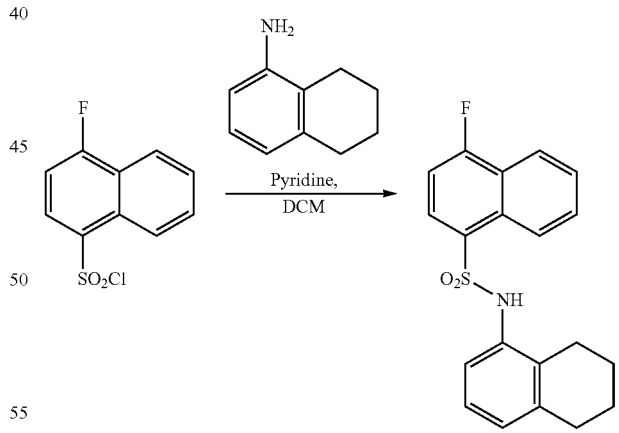

To a stirred solution of 5,6,7,8-tetrahydronaphthalen-1-amine (100 mg, 0.6802 mmol) in pyridine (0.2 ml) was added drop wise a solution of 4-fluoronaphthalene-1-sulfonyl chloride (2) (140 mg, 0.566 mmol) in DCM (3 mL). The resulting mixture was stirred for 1 h after which the reaction mixture was diluted with ethyl acetate and the organic phase was washed with 1M HCl. The collected organic phase was dried over Na$_2$SO$_4$ and was concentrated to obtain 4-fluoro-N-(5,6,7,8-tetrahydronaphthalen-1-yl)naphthalene-1-sulfonamide. LCMS purity: 94.71%.

c) 4-(piperazin-1-yl)-N-(5,6,7,8-tetrahydronaphthalen-1-yl) naphthalene-1-sulfonamide (75)

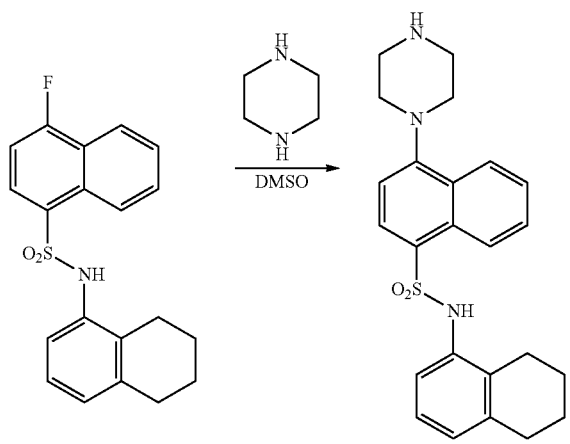

To a stirred solution of 4-fluoro-N-(5,6,7,8-tetrahydronaphthalen-1-yl)naphthalene-1-sulfonamide 3 (150 mg, 0.421 mmol) in DMSO (0.5 mL) was added piperazine (36 mg, 0.421 mmol) at room temperature under an inert atmosphere. The resulting reaction mixture was heated to 100° C. and stirred for 3 h. The reaction mixture was diluted with diethyl ether and the solidified product was isolated by filtration. The solid was washed with a sat. NaHCO₃ solution and then dissolved in 10% MeOH in DCM. The solution was dried over Na₂SO₄, concentrated under vacuum and the crude product was purified by column chromatography (elution of product: 5% MeOH in DCM) to furnish 4-(piperazin-1-yl)-N-(5,6,7,8-tetrahydronaphthalen-1-yl)naphthalene-1-sulfonamide. LCMS purity: 88.2%, RT=5.919 min, m/z=422.3 [M+H]⁺. ¹H-NMR (DMSO-d6): δ 8.65 (1H, d), 8.20 (1H, d), 7.92 (1H, d), 7.92 (1H, d), 7.40-7.72 (4H, m), 7.13 (1H, t), 6.88 (1H, d), 6.80 (1H, d), 6.67 (1H, d), 3.20-2.22 (10H, m), 1.58-1.96 (6H, m).

Example 56

(N-phenyl-4-(piperazin-1-yl)naphthalene-1-sulfonamide) (73)

a) 4-fluoro-N-phenylnaphthalene-1-sulfonamide

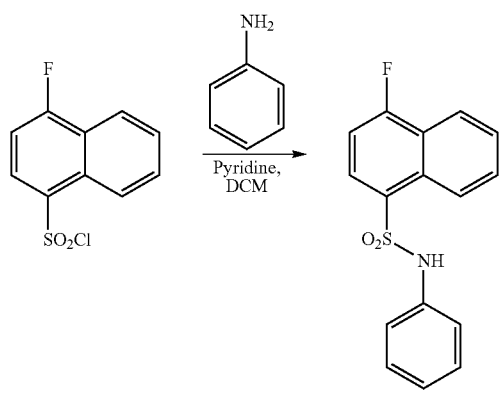

To a stirred solution of 4-fluoronaphthalene-1-sulfonyl chloride (100 mg, 0.409 mol) in DCM (2 mL) were added drop wise pyridine (0.1 mL) and aniline (0.04 mL) under an inert atmosphere. The resulting solution was stirred at room temperature for 3 h. The reaction mixture was diluted with ethyl acetate (10 mL) and then the organic phase was washed with a 1M aqueous HCl solution. The organic fraction was separation, dried over Na₂SO₄, filtered and concentrated under vacuum to obtain intermediate 4-fluoro-N-phenylnaphthalene-1-sulfonamide. LCMS purity: 69.7%.

b) N-phenyl-4-(piperazin-1-yl)naphthalene-1-sulfonamide (73)

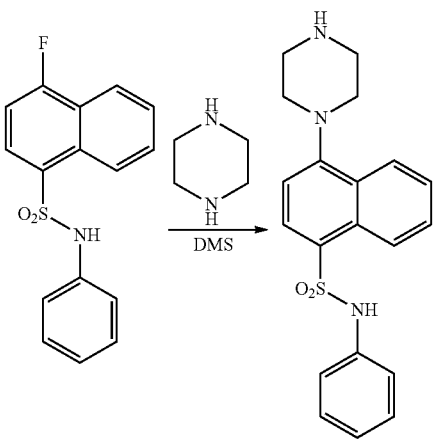

To a stirred solution of 4-fluoro-N-phenylnaphthalene-1-sulfonamide (80 mg, 0.264 mmol) in DMSO (0.5 mL) was added piperazine (113 mg, 1.324 mmol) under an inert atmosphere. The resulting reaction mixture was heated to 100° C. and stirring continued for 3 h. After completion of the reaction the reaction mixture was diluted with diethyl ether and the solidified product was filtered, and washed with a Na₂CO₃ solution. The solid was washed with a sat. NaHCO₃ solution and then dissolved in 10% MeOH in DCM. The solution was dried over Na₂SO₄, concentrated under vacuum and the crude product was purified by column chromatography to furnish N-phenyl-4-(piperazin-1-yl) naphthalene-1-sulfonamide. LCMS purity: 94.6%, RT=5.050 min, m/z=368.3 [M+H]⁺. ¹H-NMR (400 MHz, DMSO-d6): δ 8.71 (1H, d), 8.20-8.01 (2H, m), 7.75-7.50 (2H, m), 718-6.76 (7H, m), 3.12-2.80 (8H, m).

Example 57

(4-(Piperazin-1-yl)naphthalene-1-sulfonamide) (74)

a) 4-fluoronaphthalene-1-sulfonamide

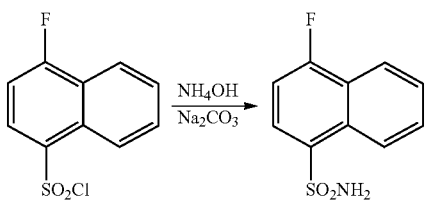

To a stirred solution of 4-fluoronaphthalene-1-sulfonyl chloride (250 mg, 1.024 mmol) in NH₄OH solution (5 mL) was added Na₂CO₃ (543 mg, 5.122 mmol) at room temperature under an inert atmosphere. The resulting reaction mixture was heated to 100° C. and stirring continued for 3 h. The reaction mixture was diluted with water and extracted with EtOAc (2×20 mL). The combined organic layers were dried over Na₂SO₄ and concentrated under vacuum to obtain intermediate 4-fluoronaphthalene-1-sulfonamide. LCMS purity: 91.98%.

b) 4-(piperazin-1-yl)naphthalene-1-sulfonamide (74)

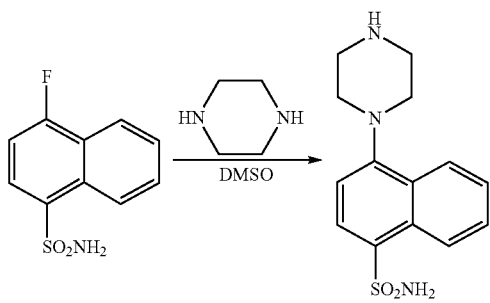

To a stirred solution of 4-fluoronaphthalene-1-sulfonamide (200 mg, 0.888 mmol) in DMSO (0.5 mL) was added piperazine (76 mg, 0.888 mmol) at room temperature under an inert atmosphere. The resulting reaction mixture was heated to 100° C. and stirring was continued for 12 h. The reaction mixture was diluted with diethyl ether and the solidified product mass was filtered, which washed with sat. NaHCO₃ solution. The solid was washed with a sat. NaHCO₃ solution and then dissolved in 10% MeOH in DCM. The solution was dried over Na₂SO₄, concentrated under vacuum and the crude product was purified by column chromatography to furnish 4-(piperazin-1-yl)naphthalene-1-sulfonamide. LCMS purity: 94.7%, RT=3.354 min, m/z=292.2 [M+H]⁺. ¹H-NMR [DMSO-d6]: δ 8.61 (1H, d), 8.22 (1H, d), 8.05 (1H, d), 7.70-7.58 (2H, m), 7.50 (2H, s), 7.15 (1H, d), 3.12-2.90 (8H, m).

Example 58

N-(1-(naphthalen-1-yl)piperidin-4-yl)methanesulfonamide (17)

a) Tert-butyl 1-(naphthalen-1-yl)piperidin-4-ylcarbamate

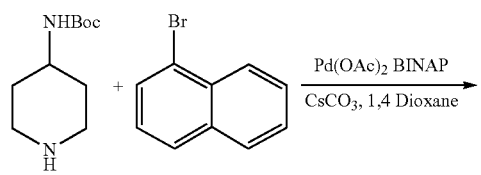

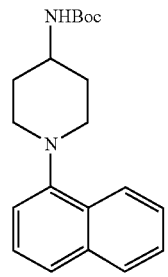

An oven dried Schlenk flask was evacuated and back filled with inert gas. The flask was charged with BINAP (1.2 g, 1.93 mmol) and palladium (II)-acetate (216 mg, 0.96 mmol) in dioxane (10 mL) at room temperature under an inert atmosphere. The resultant reaction mixture was evacuated with stirring for 5 min and then the reaction mixture was heated to 110° C. for 1-2 min to generate a red colored catalyst. 1-Bromonaphthalene (2 g, 9.65 mmol), tert-butyl piperidin-4-ylcarbamate (2.12 g, 10.6 mmol), Cs₂CO₃ (9.44 g, 28.9 mmol) and 30 mL of dioxane were added and the resulting reaction mixture was heated to 110° C. for 12 h. The reaction mixture was filtered through a celite pad and washed with ethyl acetate. The filtrate, was concentrated under reduced pressure and the residue was purified by basic alumina [elution: ethyl acetate/hexane (10:90)] to furnish tert-butyl 1-(naphthalen-1-yl)piperidin-4-ylcarbamate. LCMS purity: 98.363%. ¹H-NMR (400 MHz, DMSO-d₆): δ 8.1 (d, 1H), 7.85 (d, 1H), 7.6-7.35 (m, 4H), 7.1 (d, 1H), 6.9 (d, 1H), 3.5-3.4 (m, 1H), 3.25 (d, 2H), 2.8-2.7 (t, 2H), 2.0-1.85 (d, 2H), 1.8-1.65 (m, 2H), 1.4 (s, 9H).

b) 1-(naphthalen-1-yl)piperidin-4-amine

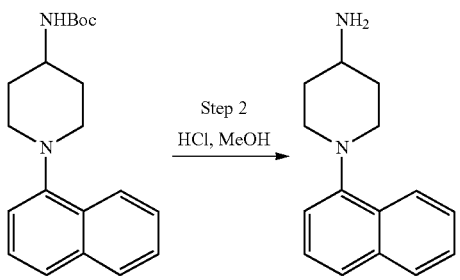 [SMILES: CC(C)(C)OC(=O)NC1CCN(c2cccc3ccccc23)CC1 ; NC1CCN(c2cccc3ccccc23)CC1]

To a stirred solution of tert-butyl 1-(naphthalen-1-yl)piperidin-4-ylcarbamate (2.4 g) in MeOH (10 mL) was added methanolic HCl (10 mL) at 0° C. and the resulting solution was stirred at RT for 1 h under an inert atmosphere. The reaction was concentrated under vacuum and the crude residue was diluted with EtOAc (25 mL) and basified with aq. Na₂CO₃ to pH=8. The organic phase was dried over anhydrous sodium sulfate, filtered and concentrated under reduced pressure. The crude product was purified by basic alumina column chromatography on gradient elution of 3% MeOH in DCM to give 1-(naphthalen-1-yl)piperidin-4-amine. LCMS purity: 96.137%. ¹H-NMR (400 MHz, DMSO-d₆): δ 8.10 (d, 1H), 7.85 (d, 1H), 7.6-7.35 (m, 4H), 7.15 (d, 1H), 3.35-3.28 (m, 2H), 2.80-2.61 (m, 3H), 1.95-1.81 (d, 2H), 1.6-1.45 (m, 2H).

185 c) N-(1-(naphthalen-1-yl)piperidin-4-yl)methane-sulfonamide (17)

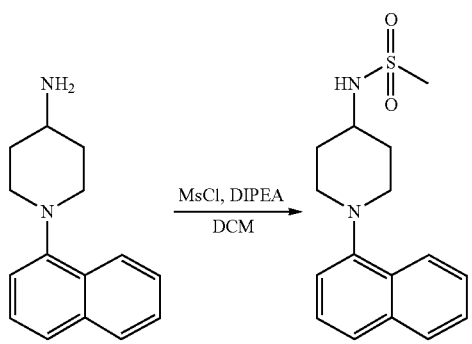 [SMILES: NC1CCN(c2cccc3ccccc23)CC1 ; CS(=O)(=O)NC1CCN(c2cccc3ccccc23)CC1]

To a solution of 1-(naphthalen-1-yl)piperidin-4-amine (200 mg, 0.884 mmol) and DIPEA (0.3 mL, 1.769 mmol) in DCM (8 mL) was added methane sulfonyl Chloride (0.1 mL, 1.1504 mmol) at 0° C. under an inert atmosphere and the resulting mixture was stirred at 0° C. for 2 h. After completion of the reaction H$_2$O (10 mL) was added and the mixture was extracted with DCM (2×10 mL). The combined organic phase was dried over anhydrous sodium sulfate and concentrated under reduced pressure. The crude product was purified by basic alumina column chromatography on gradient elution of using 50% EtoAc in hexane to give N-(1-(naphthalen-1-yl)piperidin-4-yl)methanesulfonamide. LCMS purity: 99.183%, RT=6.823 min, m/z=305.3 [M+H]$^+$ (Method 3). $^1$H-NMR (400 MHz, DMSO-d$_6$): δ 8.10 (d, 1H), 7.85 (d, 1H), 7.61-7.35 (m, 4H), 7.25 (d, 1H), 7.10 (d, 1H), 3.31-3.20 (m, 3H), 3.01 (s, 3H), 2.85-2.75 (t, 2H), 2.05-1.95 (m, 2H), 1.80-1.65 (m, 2H).

Example 59

N-(1-(naphthalen-1-yl)piperidin-4-yl)acetamide (18)

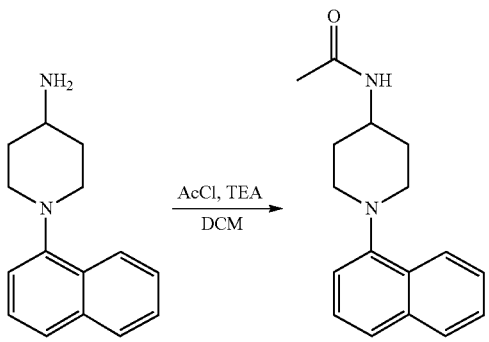 [SMILES: NC1CCN(c2cccc3ccccc23)CC1 ; CC(=O)NC1CCN(c2cccc3ccccc23)CC1]

To a stirred solution of 1-(naphthalen-1-yl)piperidin-4-amine (200 mg, 0.884 mmol) and TEA (0.24 mL, 1.7699 mmol) in DCM (8 mL) was added acetyl chloride (0.082 mL, 1.1504 mmol) at 0° C. under an inert atmosphere and the resulting mixture was stirred at 0° C. for 1 h. After completion of the reaction H$_2$O (10 mL) was added and the mixture was extracted with DCM (2×10 mL). The combined organic phase was dried over anhydrous sodium sulfate and concentrated under reduced pressure. The crude product was purified by basic alumina column chromatography of using 100% DCM to give N-(1-(naphthalen-1-yl)piperidin-4-yl)acetamide. LCMS purity: 97.330%, RT=5.884 min, m/z): 269.3 (M+H)$^+$ (Method 3). $^1$H-NMR (400 MHz, DMSO-d$_6$): δ 8.11 (d, 1H), 8.02-7.85 (m, 2H), 7.60-7.35 (m, 4H), 7.11 (d, 1H), 3.85-3.65 (brs, 1H), 3.30-3.21 (m, 2H), 2.85-2.75 (m, 2H), 2.05-1.9 (m, 2H), 1.8 (s, 3H), 1.80-1.61 (m, 2H).

Example 60

1-(1-(Naphthalen-1-yl)piperidin-4-yl)urea (19)

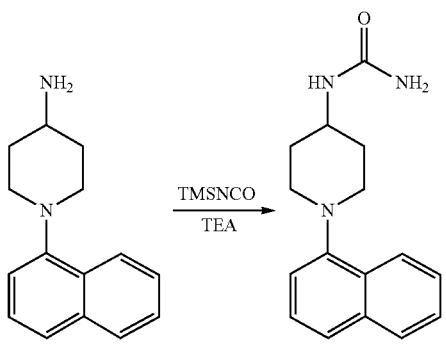 [SMILES: "TMSNCO" ; NC1CCN(c2cccc3ccccc23)CC1 ; NC(=O)NC1CCN(c2cccc3ccccc23)CC1]

To a stirred solution of 1-(naphthalen-1-yl)piperidin-4-amine (200 mg, 0.884 mmol), TEA (0.24 mL, 1.7699 mmol) in DCM (8 mL) was added TMSNCO (0.15 mL, 1.1504 mmol) at room temperature under an inert atmosphere and the resulting mixture was stirred at same temperature for 3 h. The reaction mixture was concentrated under reduced pressure the crude product was purified by flash column chromatography of basic alumina on gradient elution of 6% MeOH in DCM to furnish 1-(1-(naphthalen-1-yl)piperidin-4-yl)urea. LCMS purity: 99.330%, RT=5.351 min, m/z=270.3 [M+H]$^+$ (Method 3). $^1$H-NMR (400 MHz, DMSO-d$_6$): δ 8.10 (d, 1H), 7.91 (d, 1H), 7.60-7.35 (m, 4H), 7.11 (d, 1H), 6.10 (d, 1H), 5.40 (brs, 2H), 3.65-3.45 (brs, 1H), 3.25-3.21 (d, 2H), 2.85-2.71 (m, 2H), 2.01-1.90 (m, 2H), 1.75-1.55 (m, 2H).

Example 61

4-((4-(Piperidin-4-yl)naphthalen-1-yl)sulfonyl)piperidine (23)

a) Tert-butyl 4-((4-bromonaphthalen-1-yl)thio)piperidine-1-carboxylate

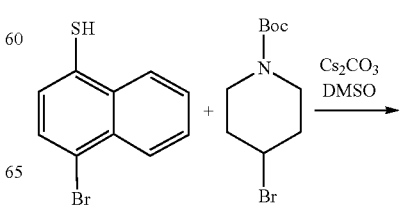

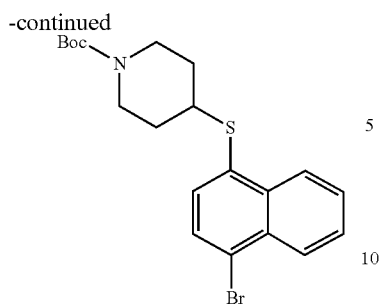

Cs₂CO₃ (1.64 g, 5.0 mmol, 2.0 eq) was added to a solution of 4-bromonaphthalene-1-thiol (0.6 g, 2.50 mmol, 1.0 eq) and tert-butyl 4-bromopiperidine-1-carboxylate (0.795 g, 3.02 mmol, 1.2 eq) in DMSO (5 mL) under nitrogen atmosphere at room temperature. The mixture was stirred at 120° C. for 15 h. After complete consumption of starting material, the reaction mixture was diluted with ethyl acetate and washed with water. The organic extract was then dried over anhydrous sodium sulfate, filtered, and solvent evaporated from the filtrated under reduced pressure to afford tert-butyl 4-((4-bromonaphthalen-1-yl)thio)piperidine-1-carboxylate. LCMS: Purity 95.04%. MS calculated for [M] 421.07 and found [M+H]⁺ 421.99.

b) Tert-butyl 4-((4-bromonaphthalen-1-yl)sulfonyl)piperidine-1-carboxylate

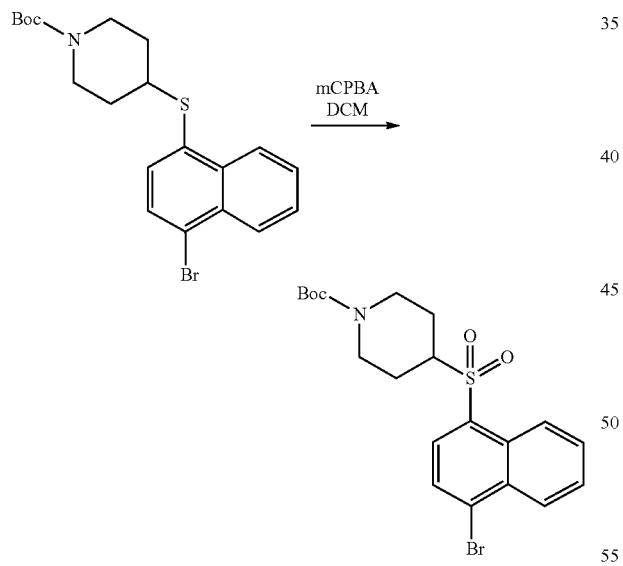

m-CPBA (0.572 g, 3.31 mmol, 2.0 eq) was added to a solution of tert-butyl 44(4-bromonaphthalen-1-yl)thio)piperidine-1-carboxylate (0.7 g, 1.66 mmol, 1.0 eq) in DCM (7 mL) under nitrogen atmosphere at 0° C. The mixture was stirred at RT for 1 h. After complete consumption of starting material, the reaction mixture was diluted with DCM and washed with water. The organic extract was then dried over anhydrous sodium sulfate, filtered, and solvent evaporated from the filtrated under reduced pressure to obtain a crude product, which was purified by flash chromatography on silica gel, 230-400 mesh, using gradient of ethyl acetate in hexanes as eluent to obtain tert-butyl 4-((4-bromonaphthalen-1-yl)sulfonyl)piperidine-1-carboxylate. LCMS: Purity 87.64%. MS calculated for [M] 453.06 and found [M+NH₄⁺] 471.07.

c) Tert-butyl 4-(4-((1-(tert-butoxycarbonyl)piperidin-4-yl)sulfonyl)naphthalen-1-yl)-3,6-dihydropyridine-1(2H)-carboxylate

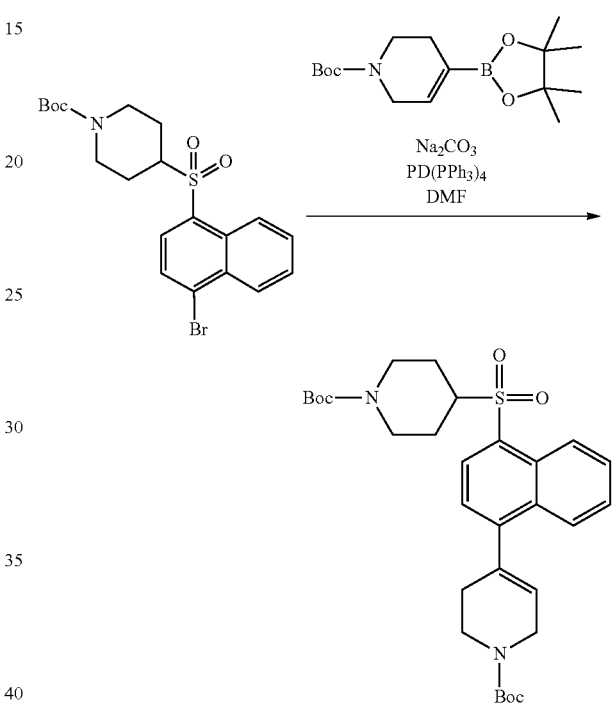

A mixture of tert-butyl 4-((4-bromonaphthalen-1-yl)sulfonyl)piperidine-1-carboxylate (0.78 g, 1.72 mmol, 1.0 eq), tert-butyl 4-(4,4,5,5-tetramethyl-1,3,2-dioxaborolan-2-yl)-3,6-dihydropyridine-1(2H)-carboxylate (0.638 g, 2.06 mmol, 1.2 eq) and Na₂CO₃ (0.545 g, 5.16 mmol, 3.0 eq) in DMF (8 mL) was purged with nitrogen for 15 min. Pd(PPh₃)₄ (0.198 g, 0.171 mmol, 0.1 eq) was added to the reaction mixture and the mixture was then stirred under nitrogen atmosphere, at 80° C. for 4 h. After complete consumption of starting material, the mixture was cooled to ambient temperature and partitioned between water and ethyl acetate. The organic extract was separated and the aqueous extract was again extracted with ethyl acetate. The combined organic extract was washed with brine, dried over anhydrous Na₂SO₄, filtered and solvents evaporated from the filtrate under reduced pressure to obtain a crude product, which was purified by flash chromatography on silica gel, 230-400 mesh, using gradient of ethyl acetate in hexanes as eluent to obtain tert-butyl 4-(4-((1-(tert-butoxycarbonyl)piperidin-4-yl)sulfonyl)naphthalen-1-yl)-3,6-dihydropyridine-1(2H)-carboxylate. LCMS: Purity 97.31%. MS calculated for [M] 556.26 and found [M+H]⁺ 557.27.

d) Tert-butyl 4-((4-(1-(tert-butoxycarbonyl)piperidin-4-yl)naphthalen-1-yl)sulfonyl)piperidine-1-carboxylate

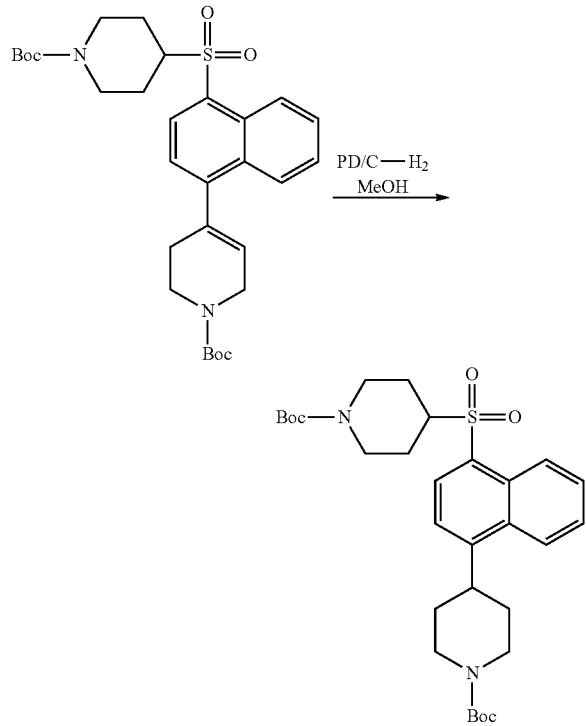

To a solution of tert-butyl 4-(4-((1-(tert-butoxycarbonyl)piperidin-4-yl)sulfonyl)naphthalen-1-yl)-3,6-dihydropyridine-1(2H)-carboxylate (0.47 g, 0.84 mmol, 1.0 eq) in MeOH (20 mL) was added Pd—C (0.2 g, 10% w/w Pd on carbon, 50% moisture) at RT. The mixture was stirred at RT under H₂ atmosphere (balloon pressure) for 16 h. The progress of reaction was monitored by TLC. The mixture was filtered through celite and washed with MeOH. Solvents evaporated from the mixture of filtrate and washings under reduced pressure to obtain tert-butyl 4-((4-(1-(tert-butoxycarbonyl)piperidin-4-yl)naphthalen-1-yl)sulfonyl)piperidine-1-carboxylate. LCMS: Purity 92.14%. MS calculated for [M] 558.28 and found [M+H]⁺ 559.34.

e) 4-((4-(piperidin-4-yl)naphthalen-1-yl)sulfonyl)piperidine Dihydrochloride

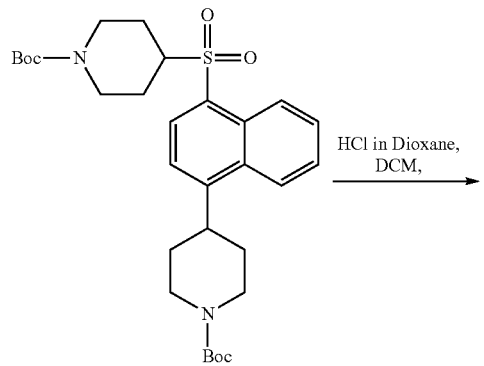

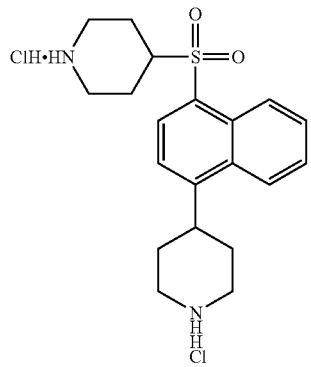

4M HCl in Dioxane (2.0 mL) was added to a solution of tert-butyl 4-((4-(1-(tert-butoxycarbonyl)piperidin-4-yl)naphthalen-1-yl)sulfonyl)piperidine-1-carboxylate (0.45 g, 0.80 mmol, 1.0 eq) in DCM (40 mL) at RT and stirred for 2 h. After complete consumption of starting material, solvents evaporated from the mixture under reduced pressure, the residue was washed with diethyl ether and dried under vacuum to obtain 44(4-(piperidin-4-yl)naphthalen-1-yl)sulfonyl)piperidine dihydrochloride. LCMS: Purity 91.25%. RT=3.32 min (Method 1). MS calculated for [M] 358.17 and found [M+H]⁺ 359.19. ¹H-NMR (400 MHz, DMSO-d₆) δ 9.27 (bs, 1H), 9.18 (bs, 2H), 8.79 (bs, 1H), 8.72 (d, J=8.0 Hz, 1H), 8.49 (d, J=8.0 Hz, 1H), 8.22 (d, J=8.0 Hz, 1H), 7.82-7.78 (m, 2H), 7.64 (d, J=8.0 Hz, 1H), 3.95-3.85 (m, 1H), 3.85-3.75 (m, 1H), 3.43-3.40 (m, 2H), 3.28-3.16 (m, 4H), 2.91-2.79 (m, 2H), 2.11-2.00 (m, 4H), 1.98-1.87 (m, 4H).

Example 62

8-Methoxy-5-(piperidin-4-yl)isoquinoline-3-carboxylic Acid (75)

a) 2-amino-3-(2-bromo-5-hydroxyphenyl)propanoic Acid

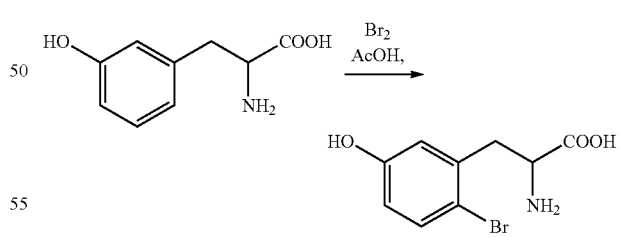

A solution of bromine (13.26 g, 82.97 mmol, 1.02 eq) in AcOH (700 mL) was added to a solution of 2-amino-3-(3-hydroxyphenyl)propanoic acid (14.6 g, 0.08 mmol, 1.0 eq) in AcOH (700 mL) at RT and stirred for 16 h. The precipitate formed in reaction mixture was collected by filtration, washed with diethyl ether and dried under high vacuum to afford 2-amino-3-(2-bromo-5-hydroxyphenyl)propanoic acid. LCMS: Purity 79.11%. MS calculated for [M] 258.98 and found [M+H]⁺ 260.03.

b) 5-bromo-8-hydroxy-1,2,3,4-tetrahydroisoquinoline-3-carboxylic Acid

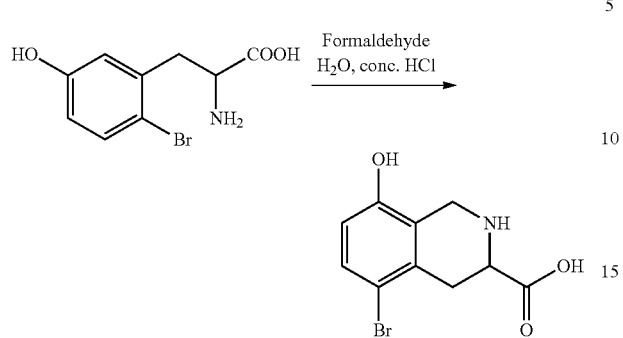

To a solution of 2-amino-3-(2-bromo-5-hydroxyphenyl) propanoic acid (14.0 g, 53.82 mmol, 1.0 eq) in H$_2$O (500 mL) was added 37% formaldehyde (72.5 mL, 807.19 mmol, 15.0 eq) and conc. HCl (44 mL). The mixture was stirred at RT for 1.5 h followed by at 60° C. for 1.5 h. Another lot of conc. HCl (40 mL) was added and stirred at RT for further 30 min. Then the reaction mixture was subjected to heating and stirred at 90° C. for additional 40 min. After complete consumption of starting material, solvent was evaporated to give 5-bromo-8-hydroxy-1,2,3,4-tetrahydroisoquinoline-3-carboxylic acid. LCMS: Purity 79.02%. MS calculated for [M] 270.98 and found [M+H]$^+$ 271.99.

c) Methyl 5-bromo-8-hydroxy-1,2,3,4-tetrahydroisoquinoline-3-carboxylate

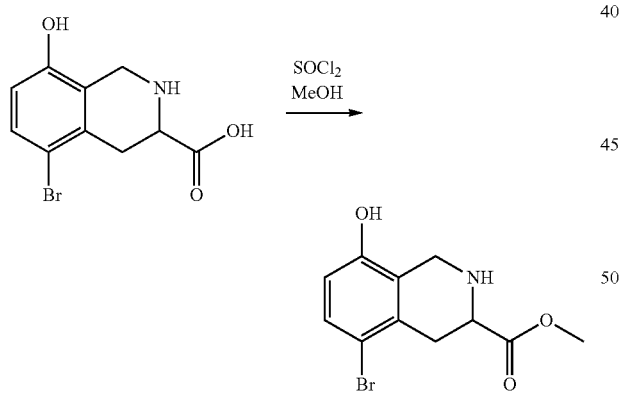

SOCl$_2$ (0.234 g, 66.14 mmol, 2.0 eq) was added to a solution of 5-bromo-8-hydroxy-1,2,3,4-tetrahydroisoquinoline-3-carboxylic acid (9.0 g, 33.07 mmol, 1.0 eq) in MeOH (90 mL) at 0° C. and the mixture was stirred at RT for 1 h. After complete consumption of starting material, solvent evaporated under reduced pressure. The residue was triturated in DCM and filtered to afford methyl 5-bromo-8-hydroxy-1,2,3,4-tetrahydroisoquinoline-3-carboxylate. LCMS: Purity 85.20%. MS calculated for [M] 285.00 and found [M−H]$^+$ 283.99 [M+H]$^+$ 286.01.

d) 2-(tert-butyl) 3-methyl 5-bromo-8-hydroxy-3,4-dihydroisoquinoline-2,3(1H)-dicarboxylate

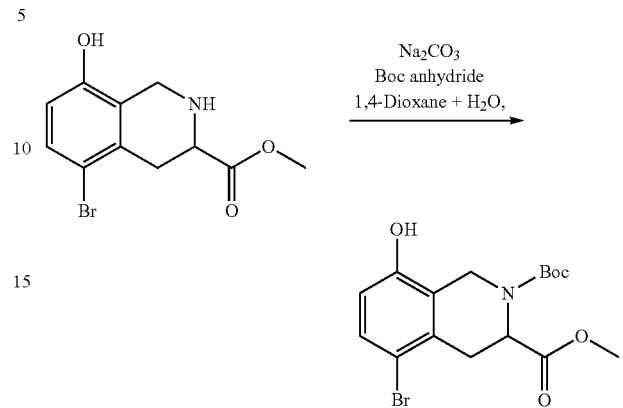

Boc anhydride (6.4 g, 29.3 mmol, 2.0 eq) was added to a solution of methyl 5-bromo-8-hydroxy-1,2,3,4-tetrahydroisoquinoline-3-carboxylate (4.2 g, 14.6 mmol, 1.0 eq) and Na$_2$CO$_3$ (3.11 g, 29.37 mmol, 2.0 eq) in a mixture of 1,4-Dioxane (85 mL) and water (15 mL) at RT and stirred for 3 h. Reaction mixture was then diluted with ethyl acetate and washed with brine. Organic extract was dried over anhydrous Na$_2$SO$_4$, filtered and solvents was evaporated from the filtrate under reduced pressure to afford crude residue, which was subjected to purification by flash chromatography on silica gel, 230-400 mesh, using gradient of ethyl acetate in hexanes as eluent to obtain to 2-(tert-butyl) 3-methyl 5-bromo-8-hydroxy-3,4-dihydroisoquinoline-2,3 (1H)-dicarboxylate. LCMS: Purity 81.83%. MS calculated for [M] 385.05 and found [M+H]$^+$ 386.06.

e) 2-(tert-butyl) 3-methyl 5-bromo-8-methoxy-3,4-dihydroisoquinoline-2,3(1H)-dicarboxylate

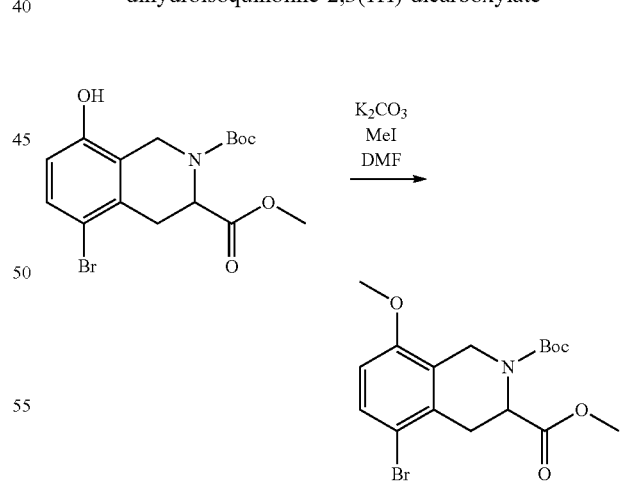

MeI (4.4 g, 31.06 mmol, 1.5 eq) was added to a solution of 2-(tert-butyl) 3-methyl 5-bromo-8-hydroxy-3,4-dihydroisoquinoline-2,3(1H)-dicarboxylate (8.0 g, 20.71 mmol, 1.0 eq) and K$_2$CO$_3$ (4.2 g, 31.06 mmol, 1.5 eq) in DMF (85.0 mL) at RT and stirred at 90° C. for 6 h. The reaction mixture was then cooled to ambient temperature, diluted in ethyl acetate and washed with water followed by brine. The organic extract was dried over anhydrous Na$_2$SO$_4$, filtered and solvents evaporated from the filtrate under reduced pressure to afford 2-(tert-butyl) 3-methyl 5-bromo-8-hydroxy-3,4-dihydroisoquinoline-2,3(1H)-dicarboxylate. LCMS: Purity 73.85%. MS calculated for [M] 399.07 and found [M+H]⁺ 400.12.

f) Methyl 5-bromo-8-methoxy-1,2,3,4-tetrahydroisoquinoline-3-carboxylate Hydrochloride

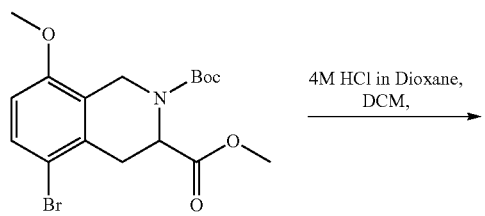

4M HCl in dioxane (8.0 mL) was added to a solution of 2-(tert-butyl) 3-methyl 5-bromo-8-methoxy-3,4-dihydroisoquinoline-2,3(1H)-dicarboxylate (8.0 g, 19.95 mmol, 1.0 eq) in DCM (80 mL) at RT and stirred for 6 h. After complete consumption of starting material, solvent was evaporated under reduced pressure, the residue was washed with diethyl ether and dried under vacuum to afford methyl 5-bromo-8-methoxy-1,2,3,4-tetrahydroisoquinoline-3-carboxylate hydrochloride. LCMS: Purity 83.25%. MS calculated for [M] 299.02 and found [M+H]⁺ 300.04.

g) Methyl 5-bromo-8-methoxyisoquinoline-3-carboxylate

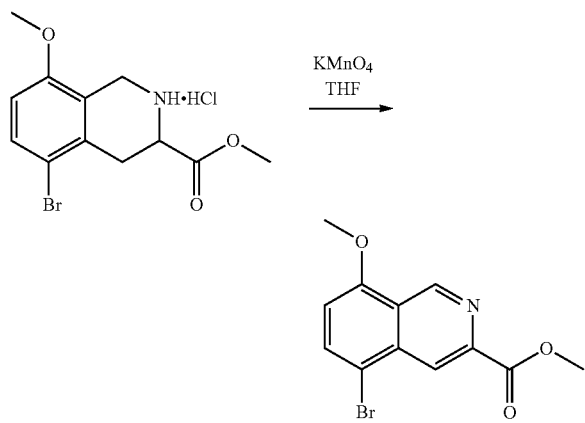

KMnO₄ (13.2 g, 83.6 mmol, 1.0 eq) was added to a solution of methyl 5-bromo-8-methoxy-1,2,3,4-tetrahydroisoquinoline-3-carboxylate (5.0 g, 83.61 mmol, 1.0 eq) in THF (50 mL) at RT and stirred for 6 h. The reaction mixture was diluted in ethyl acetate and washed with water followed by brine. The organic extract was dried over anhydrous Na₂SO₄, filtered and solvents was evaporated from the filtrate under reduced pressure to afford a crude residue, which was purified by flash chromatography on silica gel, 230-400 mesh, using gradient of ethyl acetate in hexanes as eluent to obtain methyl 5-bromo-8-methoxyisoquinoline-3-carboxylate. LCMS: Purity 99.16%. MS calculated for [M] 294.98 and found [M−H]⁺ 295.99.

h) Methyl 5-(1-(tert-butoxycarbonyl)-1,2,3,6-tetrahydropyridin-4-yl)-8-methoxyisoquinoline-3-carboxylate

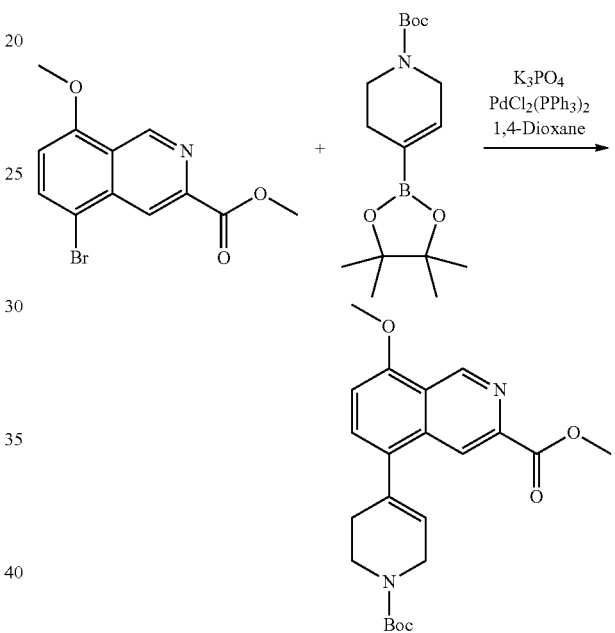

A mixture of methyl 5-bromo-8-methoxyisoquinoline-3-carboxylate (0.32 g, 1.08 mmol, 1.0 eq), tert-butyl 4-(4,4,5,5-tetramethyl-1,3,2-dioxaborolan-2-yl)-3,6-dihydropyridine-1(2H)-carboxylate (0.672 g, 2.16 mmol, 2.0 eq) and K₃PO₄ (0.687 g, 3.24 mmol, 3.0 eq) in 1,4-Dioxane (5 mL) was purged with nitrogen for 15 min. PdCl₂(PPh₃)₂ (0.076 g, 0.108 mmol, 0.1 eq) was added to the reaction mixture and was stirred under nitrogen atmosphere, at 90° C. for 16 h. The mixture was then cooled to ambient temperature and partitioned between water and ethyl acetate. The organic extract was separated and the aqueous extract was again extracted with ethyl acetate. The combined organic extract was washed with brine, dried over anhydrous Na₂SO₄, filtered and solvents evaporated from the filtrate under reduced pressure to obtain a crude product, which was subjected to purification by flash chromatography on silica gel, 230-400 mesh, using gradient of ethyl acetate in hexanes as eluent to obtain methyl 5-(1-(tert-butoxycarbonyl)-1,2,3,6-tetrahydropyridin-4-yl)-8-methoxyisoquinoline-3-carboxylate. LCMS: Purity 78.48%. MS calculated for [M] 398.18 and found [M+H]⁺ 399.28.

i) Methyl 5-(1-(tert-butoxycarbonyl)piperidin-4-yl)-8-methoxyisoquinoline-3-carboxylate

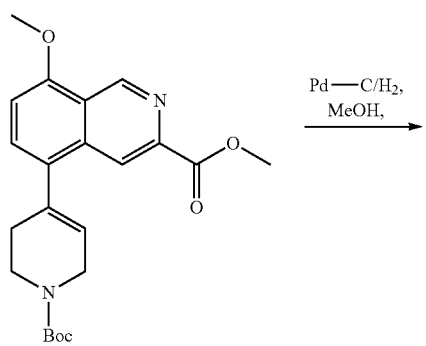

To a solution of methyl 5-(1-(tert-butoxycarbonyl)-1,2,3,6-tetrahydropyridin-4-yl)-8-methoxyisoquinoline-3-carboxylate (0.15 g, 0.376 mmol, 1.0 eq) in MeOH (15 mL) was added Pd—C (0.100 g, 10% w/w Pd on carbon, 50% moisture) at RT. The mixture was stirred at RT under $H_2$ atmosphere (balloon pressure) for 3 h. The progress of reaction was monitored by TLC. The mixture was filtered through celite and washed with MeOH. Solvents evaporated from the mixture of filtrate and washings under reduced pressure to obtain methyl 5-(1-(tert-butoxycarbonyl)piperidin-4-yl)-8-methoxyisoquinoline-3-carboxylate. LCMS: Purity 89.91%. MS calculated for [M] 400.20 and found [M+H]$^+$ 401.29.

j) 5-(1-(tert-butoxycarbonyl)piperidin-4-yl)-8-methoxyisoquinoline-3-carboxylic Acid

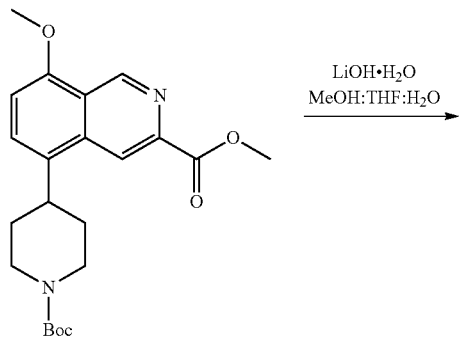

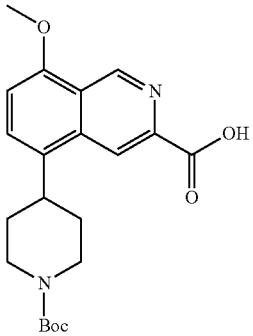

LiOH·H$_2$O (0.034 g, 0.828 mmol, 3.0 eq) was added to a solution of methyl 5-(1-(tert-butoxycarbonyl)piperidin-4-yl)-8-methoxyisoquinoline-3-carboxylate (0.11 g, 0.276 mmol, 1.0 eq) in a mixture of MeOH:THF:H$_2$O (1:1:1; 1.5 mL) at RT and stirred for 2 h. After complete consumption of starting material, the reaction mixture was acidified with saturated aq. citric acid (pH=6), diluted with water and extracted with a mixture of isopropanol:CHCl$_3$ (1:9). The organic extract was dried over anhydrous Na$_2$SO$_4$, filtered and solvents was evaporated from the filtrate under reduced pressure to afford 5-(1-(tert-butoxycarbonyl)piperidin-4-yl)-8-methoxyisoquinoline-3-carboxylic acid. LCMS: Purity 95.78%. MS calculated for [M] 386.18 and found [M+H]$^+$ 387.35.

k) 8-methoxy-5-(piperidin-4-yl)isoquinoline-3-carboxylic Acid Hydrochloride

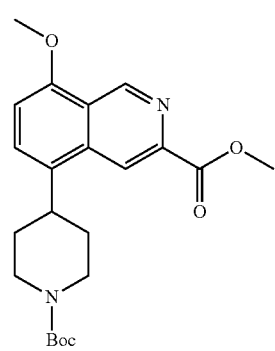

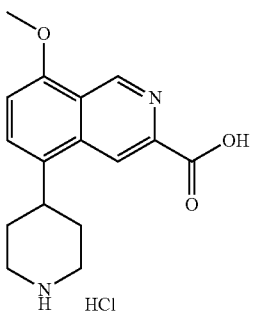

4M HCl in Dioxane (1.0 mL) was added to a solution of 5-(1-(tert-butoxycarbonyl)piperidin-4-yl)-8-methoxyisoquinoline-3-carboxylic acid (0.05 g, 0.129 mmol, 1.0 eq) in DCM (3 mL) at RT and stirred for 2 h. After complete consumption of starting material, solvent was evaporated under reduced pressure, the residue was washed with diethyl ether and dried under vacuum to afford 4-((4-(piperidin-4-yl)naphthalen-1-yl)methyl)piperidine dihydrochloride. LCMS: Purity 98.08%. RT=4.92 min (Method 2). MS calculated for [M] 286.13 and found [M+H]$^+$ 287.31. $^1$H-NMR (400 MHz, DMSO-d6) δ ppm 9.57 (s, 1H), 8.95 (s, 1H), 8.84 (bs, 1H), 8.75 (bs, 1H), 7.70 (d, J=8.0 Hz, 1H), 7.33 (d, J=8.0 Hz 1H), 4.05 (s, 3H), 3.76-3.71 (m, 1H), 3.41-3.38 (m, 2H), 3.24-3.22 (m, 2H), 2.05-1.90 (m, 4H).

Example 63

8-Methoxy-5-(piperidin-4-yl)isoquinoline-3-carboxamide (76)

a) Tert-butyl 4-(3-carbamoyl-8-methoxyisoquinolin-5-yl)piperidine-1-carboxylate

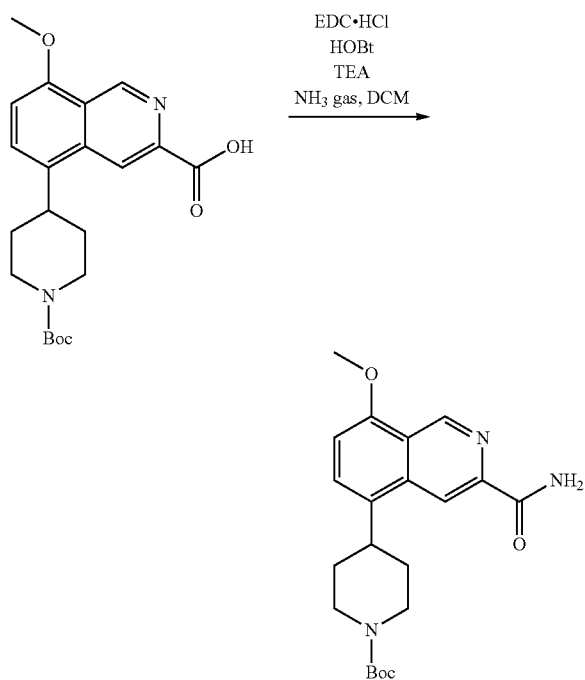

A solution of 5-(1-(tert-butoxycarbonyl)piperidin-4-yl)-8-methoxyisoquinoline-3-carboxylic acid (0.05 g, 0.129 mmol, 1.0 eq), EDC.HCl (0.037 g, 0.193 mmol, 1.5 eq), HOBt (0.026 g, 0.194 mmol, 1.5 eq) and Et$_3$N (0.026 g, 0.259 mmol, 2.0 eq) in DCM (2 mL) was purged with ammonia (gas) at 0° C. and the mixture was stirred for 30 min. The progress of reaction was monitored by TLC. After consumption of starting material, the mixture was partitioned between water and DCM. The organic extract was separated and the aqueous extract was again extracted with DCM. The combined organic extract was washed with brine, dried over anhydrous Na$_2$SO$_4$, filtered and solvents evaporated from the filtrate under reduced pressure to obtain a crude product, which was purified by flash chromatography on silica gel, 230-400 mesh, using gradient of MeOH in DCM as eluent to obtain tert-butyl 4-(3-carbamoyl-8-methoxyisoquinolin-5-yl)piperidine-1-carboxylate. LCMS: Purity 91.81%. MS calculated for [M] 385.20 and found [M+H]$^+$ 386.30.

b) 8-methoxy-5-(piperidin-4-yl)isoquinoline-3-carboxamide

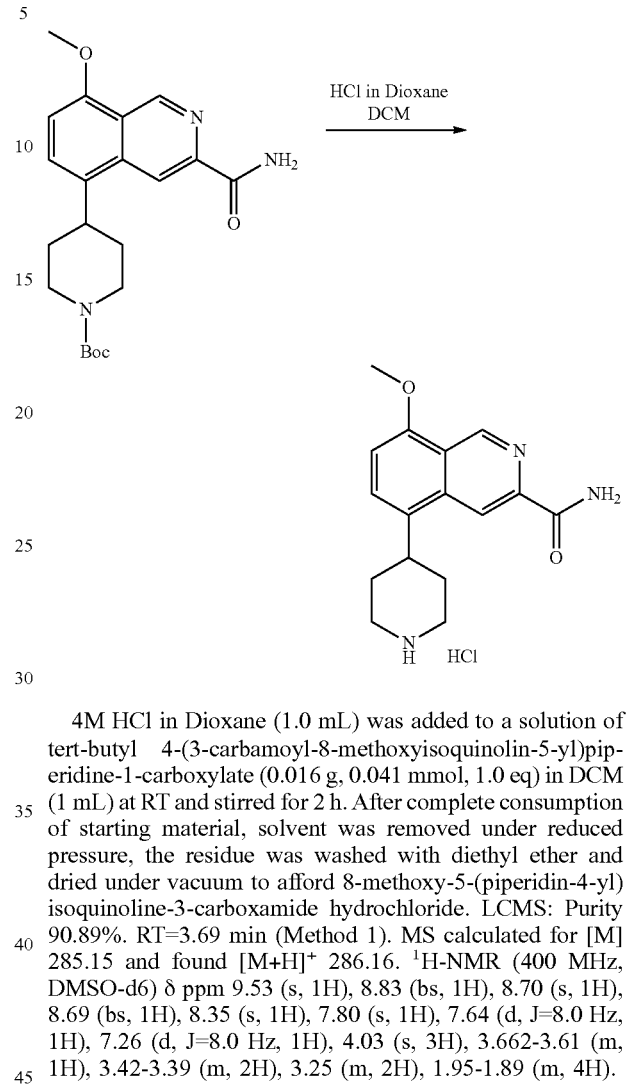

4M HCl in Dioxane (1.0 mL) was added to a solution of tert-butyl 4-(3-carbamoyl-8-methoxyisoquinolin-5-yl)piperidine-1-carboxylate (0.016 g, 0.041 mmol, 1.0 eq) in DCM (1 mL) at RT and stirred for 2 h. After complete consumption of starting material, solvent was removed under reduced pressure, the residue was washed with diethyl ether and dried under vacuum to afford 8-methoxy-5-(piperidin-4-yl)isoquinoline-3-carboxamide hydrochloride. LCMS: Purity 90.89%. RT=3.69 min (Method 1). MS calculated for [M] 285.15 and found [M+H]$^+$ 286.16. $^1$H-NMR (400 MHz, DMSO-d6) δ ppm 9.53 (s, 1H), 8.83 (bs, 1H), 8.70 (s, 1H), 8.69 (bs, 1H), 8.35 (s, 1H), 7.80 (s, 1H), 7.64 (d, J=8.0 Hz, 1H), 7.26 (d, J=8.0 Hz, 1H), 4.03 (s, 3H), 3.662-3.61 (m, 1H), 3.42-3.39 (m, 2H), 3.25 (m, 2H), 1.95-1.89 (m, 4H).

Example 64

4-((4-(Piperidin-4-yl)naphthalen-1-yl)methyl)piperidine (22)

a) 1-bromo-4-(bromomethyl)naphthalene

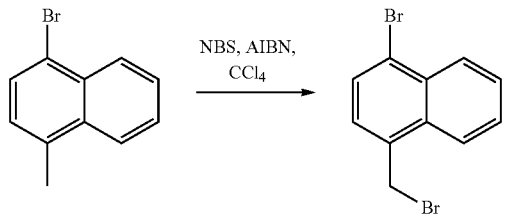

Freshly crystallized NBS (13.84 g, 77.80 mmol, 1.2 eq) was added to the solution of 1-bromo-4-methylnaphthalene (15.0 g, 67.84 mmol, 1.0 eq) and AIBN (1.11 g, 6.78 mmol, 0.1 eq) in carbon tetrachloride (150 mL) and the mixture was stirred at 80° C. for 16 h under nitrogen atmosphere. After complete consumption of starting material, water was added to the reaction mixture and extracted with DCM. The organic layer was washed with water followed by brine, dried over anhydrous sodium sulfate, filtered, and the solvent evaporated from the filtrated under reduced pressure to obtain 1-bromo-4-(bromomethyl)naphthalene. LCMS: Purity 96.83%.

b) Tert-butyl 4-(4-((1-(tert-butoxycarbonyl)-1,2,3,6-tetrahydropyridin-4-yl)methyl)naphthalen-1-yl)-3,6-dihydropyridine-1(2H)-carboxylate

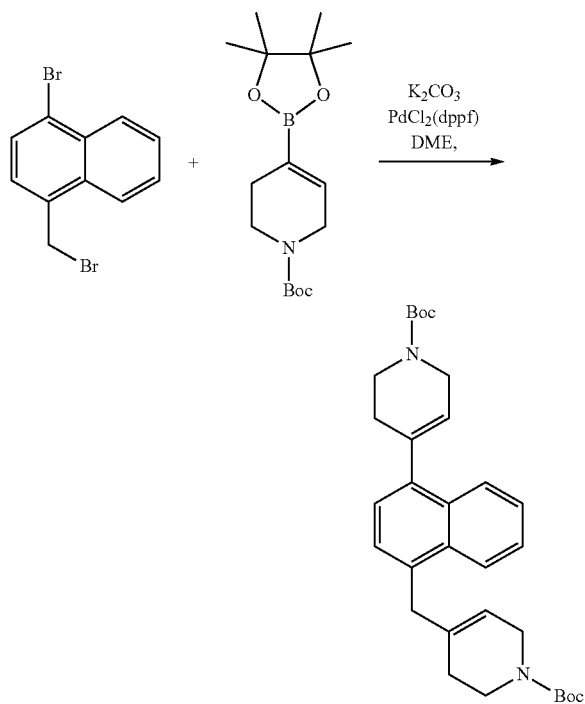

A mixture of 1-bromo-4-(bromomethyl)naphthalene (1.0 g, 3.34 mmol, 1.0 eq), tert-butyl 4-(4,4,5,5-tetramethyl-1,3,2-dioxaborolan-2-yl)-3,6-dihydropyridine-1(2H)-carboxylate (3.10 g, 10.03 mmol, 1.5 eq) and $K_2CO_3$ (2.78 g, 20.07 mmol, 3.0 eq) in 1,2-DME (10 mL) was purged with nitrogen for 15 min. Pd(dppf)Cl$_2$·DCM (0.546 g, 0.669 mmol, 0.1 eq) was added to the reaction mixture and was stirred under nitrogen atmosphere, at 110° C. for 16 h. The mixture was cooled to ambient temperature and partitioned between water and ethyl acetate. The organic extract was separated and the aqueous extract was again extracted with ethyl acetate. The combined organic extract was washed with brine, dried over anhydrous $Na_2SO_4$, filtered and solvents evaporated from the filtrate under reduced pressure to obtain a crude product, which was subjected to purification by flash chromatography on silica gel, 230-400 mesh, using gradient of ethyl acetate in hexanes as eluent to obtain tert-butyl 4-(4-((1-(tert-butoxycarbonyl)-1,2,3,6-tetrahydropyridin-4-yl)methyl)naphthalen-1-yl)-3,6-dihydropyridine-1(2H)-carboxylate. LCMS: Purity 57.36%. MS calculated for [M] 504.30 and found [M+H]$^+$ 505.31.

c) Tert-butyl 4-(4-((1-(tert-butoxycarbonyl)piperidin-4-yl)methyl)naphthalen-1-yl)piperidine-1-carboxylate

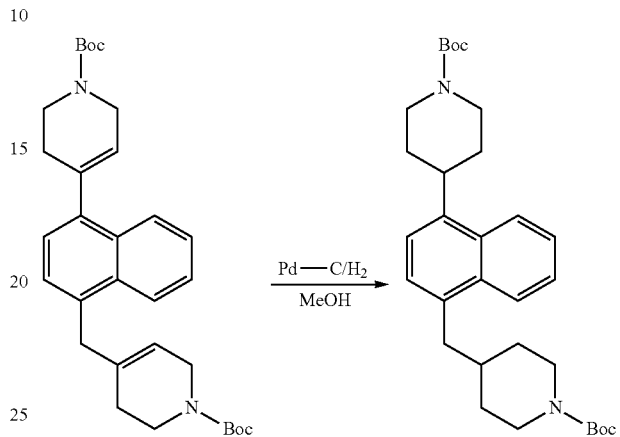

To a solution of tert-butyl 4-(4-((1-(tert-butoxycarbonyl)piperidin-4-ylidene)methyl)naphthalen-1-yl)-3,6-dihydropyridine-1(2H)-carboxylate (0.4 g, 0.792 mmol, 1.0 eq) in MeOH (20 mL) was added Pd—C (0.2 g, 10% w/w Pd on carbon, 50% moisture) at RT. The mixture was stirred at ambient temperature, under hydrogen atmosphere (balloon pressure) for 18 h. The progress of reaction was monitored by TLC. After complete consumption of starting material, the mixture was filtered through celite and washed with MeOH. The mixture of filtrate and washings was evaporated under reduced pressure to obtain tert-butyl 4-(4-((1-(tert-butoxycarbonyl)piperidin-4-yl)methyl)naphthalen-1-yl)piperidine-1-carboxylate. LCMS: Purity 95.56%. MS calculated for [M] 508.33 and found [M−H]$^+$ 509.32.

d) 4-((4-(piperidin-4-yl)naphthalen-1-yl)methyl)piperidine Dihydrochloride

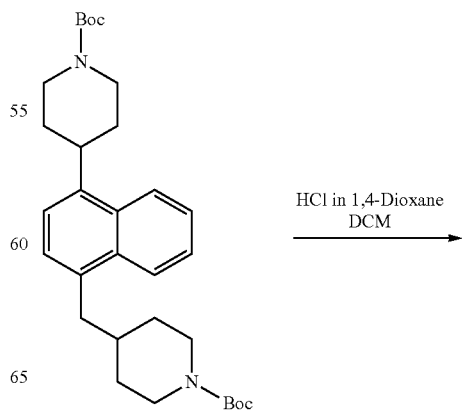

-continued

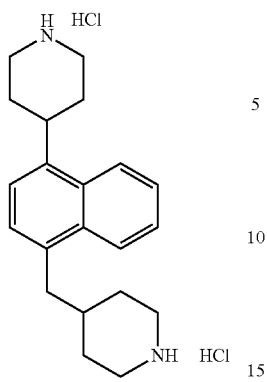

4M HCl in Dioxane (2.0 mL) was added to a solution of tert-butyl 4-(4-((1-(tert-butoxycarbonyl)piperidin-4-yl)methyl)naphthalen-1-yl)piperidine-1-carboxylate (0.17 g, 0.354 mmol, 1.0 eq) in DCM (20 mL) at RT and stirred for 2 h. The solvent was removed under reduced pressure, the residue was washed with diethyl ether and dried under vacuum to obtain 4-((4-(piperidin-4-yl)naphthalen-1-yl)methyl)piperidine dihydrochloride. LCMS: Purity 96.72%. RT=3.95 min (Method 1). MS calculated for [M] 308.23 and found [M+H]$^+$ 309.24. $^1$H-NMR (400 MHz, DMSO-d$_6$) δ 9.06 (bs, 2H), 8.89 (bs, 1H), 8.66 (bs, 1H), 8.27-8.25 (m, 1H), 8.13-8.11 (m, 1H), 7.59-7.56 (m, 2H), 7.33-7.12 (m, 2H), 3.71-3.66 (m, 1H), 3.41-3.38 (m, 2H), 3.21-3.18 (m, 4H), 2.97-2.96 (m, 2H), 2.78-2.70 (m, 2H), 2.01-1.99 (m, 4H), 1.95-1.85 (m, 1H), 1.75-1.72 (m, 2H), 1.50-1.41 (m, 2H).

Example 65

The compounds presented in Table 3 can be synthesized according to the Examples or general schemes described herein.

TABLE 3-continued
| No. | Structure |
|---|---|
| 28 | 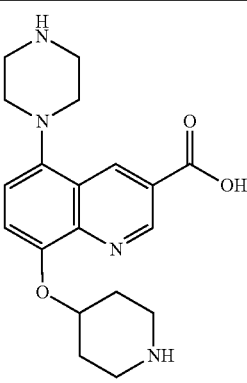 |
| 29 | 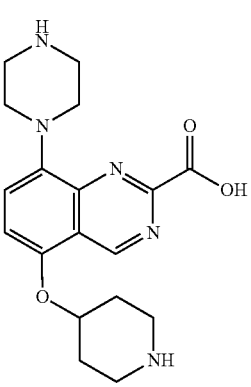 [SMILES: O=C(O)c1ncc2c(OC3CCNCC3)ccc(N3CCNCC3)c2n1] |
| 30 | 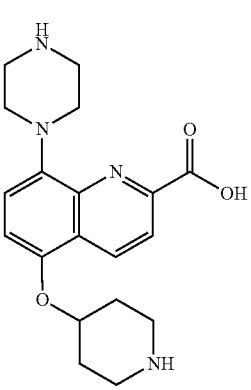 [SMILES: O=C(O)c1ccc2c(OC3CCNCC3)ccc(N3CCNCC3)c2n1] |
| 31 | 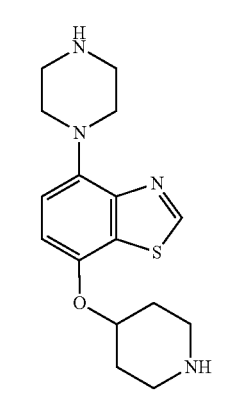 [SMILES: c1nc2c(N3CCNCC3)ccc(OC3CCNCC3)c2s1] |
| 32 | 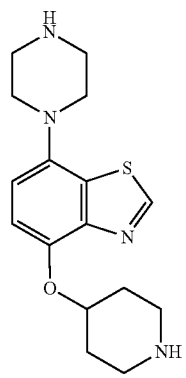 [SMILES: c1nc2c(OC3CCNCC3)ccc(N3CCNCC3)c2s1] |
| 33 | 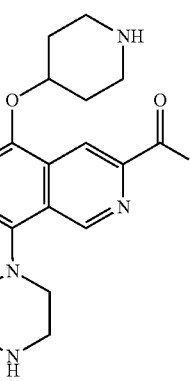 |
| 34 | 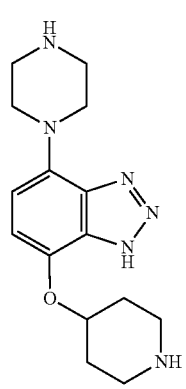 [SMILES: c1cc(OC2CCNCC2)c2[nH]nnc2c1N1CCNCC1] |
| 35 | 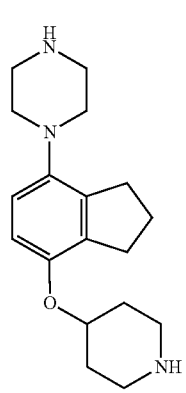 [SMILES: c1cc(N2CCNCC2)c2c(c1OC1CCNCC1)CCC2] |

TABLE 3-continued
| No. | Structure |
|---|---|
| 36 | 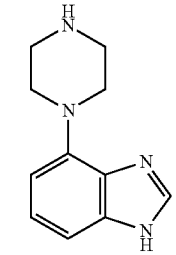 |
| 37 | 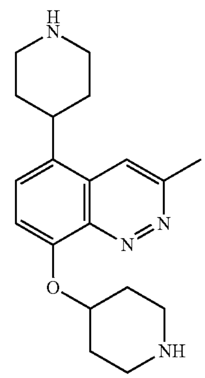 [SMILES: Cc1cc2c(C3CCNCC3)ccc(OC3CCNCC3)c2nn1] |
| 38 | 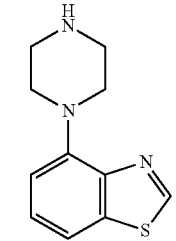 [SMILES: c1cc(N2CCNCC2)c2ncsc2c1] |
| 39 | 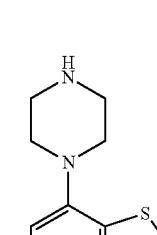 |
| 40 | 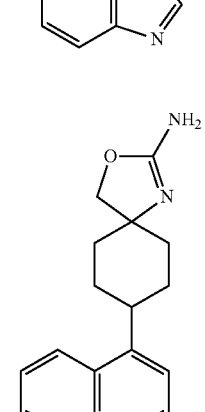 |
| 41 | 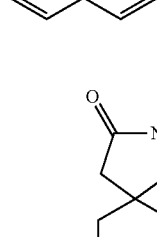 |
| 42 | 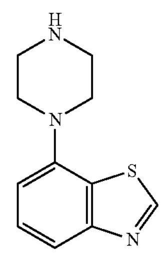 [SMILES: c1cc(N2CCNCC2)c2scnc2c1] |
| 82 | 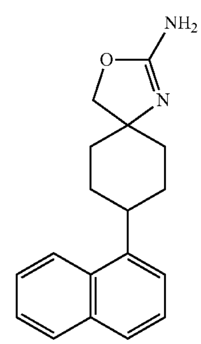 [SMILES: NC1=NC2(CCC(c3cccc4ccccc34)CC2)CO1] |
| 77 | 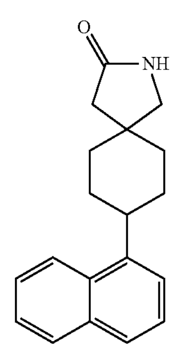 [SMILES: O=C1CC2(CCC(c3cccc4ccccc34)CC2)CN1] |

TABLE 3-continued

| No. | Structure |
|---|---|
| 78 | 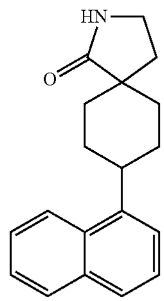 [SMILES: O=C1NCCC12CCC(c1cccc3ccccc13)CC2] |
| 79 | 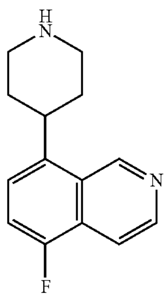 |
| 80 | 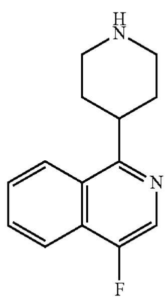 [SMILES: Fc1cnc(C2CCNCC2)c2ccccc12] |
| 81 | 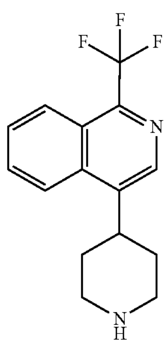 [SMILES: FC(F)(F)c1ncc(C2CCNCC2)c2ccccc12] |
| 82 | 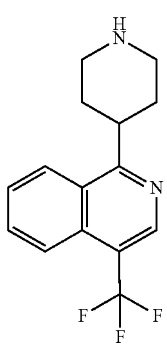 [SMILES: FC(F)(F)c1cnc(C2CCNCC2)c2ccccc12] |

TABLE 3-continued

| No. | Structure |
|---|---|
| 83 | 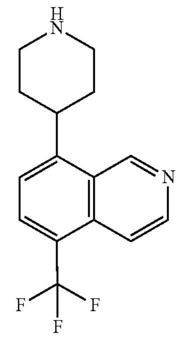 [SMILES: FC(F)(F)c1ccc(C2CCNCC2)c2cnccc12] |
| 84 | 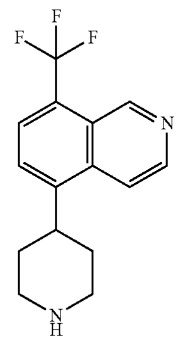 [SMILES: FC(F)(F)c1ccc(C2CCNCC2)c2ccncc12] |
| 85 | 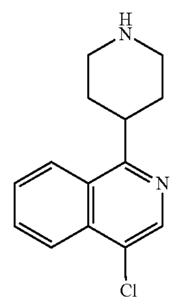 |
| 86 | 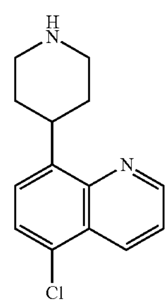 [SMILES: Clc1ccc(C2CCNCC2)c2ncccc12] |
| 87 | 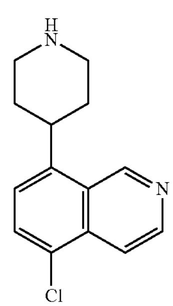 |

TABLE 3-continued
| No. | Structure |
|---|---|
| 88 | 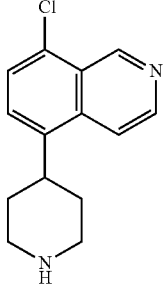 [SMILES: Clc1ccc(C2CCNCC2)c2ccncc12] |
| 89 | 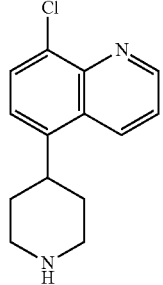 |
| 90 | 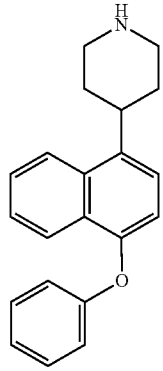 [SMILES: c1ccc(Oc2ccc(C3CCNCC3)c3ccccc23)cc1] |
| 91 | 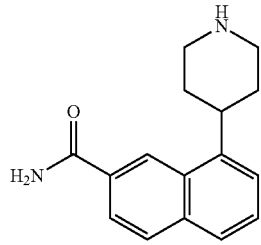 [SMILES: NC(=O)c1ccc2cccc(C3CCNCC3)c2c1] |
| 92 | 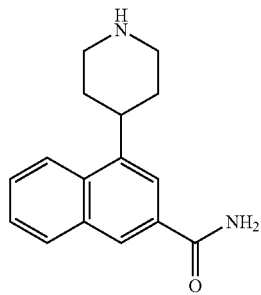 [SMILES: NC(=O)c1cc(C2CCNCC2)c2ccccc2c1] |
| 93 | 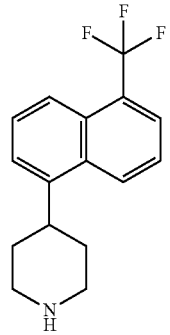 [SMILES: FC(F)(F)c1cccc2c(C3CCNCC3)cccc12] |
| 94 | 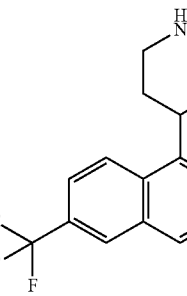 |
| 95 | 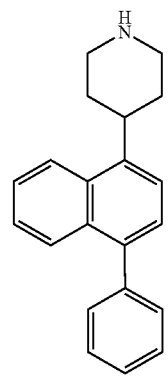 [SMILES: c1ccc(-c2ccc(C3CCNCC3)c3ccccc23)cc1] |
| 96 | 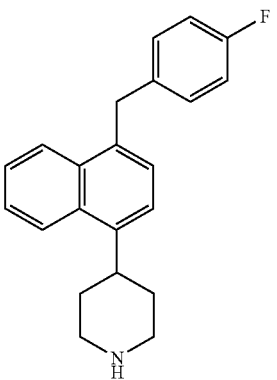 [SMILES: Fc1ccc(Cc2ccc(C3CCNCC3)c3ccccc23)cc1] |

TABLE 3-continued
| No. | Structure |
|---|---|
| 97 | 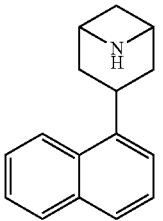 [SMILES: c1ccc2c(C3CC4CC(C3)N4)cccc2c1] |
| 98 | 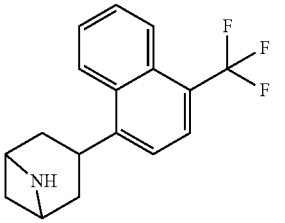 [SMILES: FC(F)(F)c1ccc(C2CC3CC(C2)N3)c2ccccc12] |
| 99 | 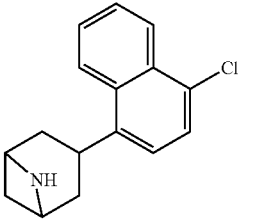 [SMILES: Clc1ccc(C2CC3CC(C2)N3)c2ccccc12] |
| 100 | 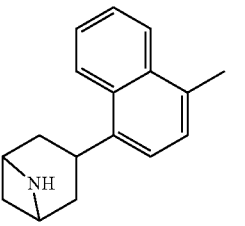 [SMILES: Cc1ccc(C2CC3CC(C2)N3)c2ccccc12] |
| 101 | 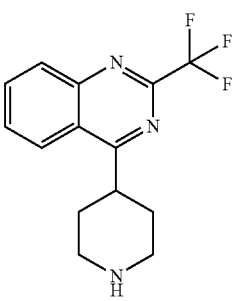 [SMILES: FC(F)(F)c1nc(C2CCNCC2)c2ccccc2n1] |
| 102 | 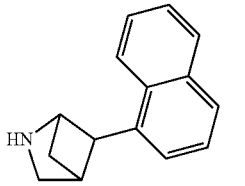 [SMILES: c1ccc2c(C3C4CNC3C4)cccc2c1] |
| 103 | 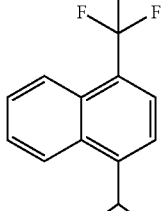 |
| 104 | 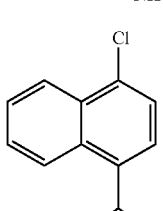 |
| 105 | 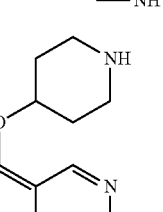 |
| 107 | 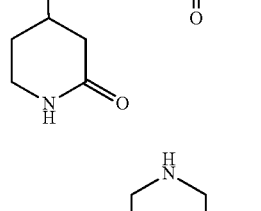 |
| 108 | 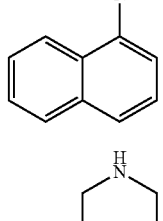 |
Biological Assays
The compounds of the present disclosure may be tested for binding to, inhibition of, and/or modulation of PCSK9 activity according to the following protocols.

Cell Culture

Cells, such as HepG2, HuH7, FL83B, or a cell line transfected with a short-hairpin PCSK9 knockdown sequence (e.g., HepG2/shPCSK9, HuH7/shPCSK9) can be cultured following routine procedures, such as those described by Benjannet et al., "Effects of the prosegment and pH on the activity of PCSK9: evidence for additional processing events" *J Biol Chem.* 285(52): 40965-40978 (2010), which is hereby incorporated by reference in its entirety.

LDLR Flow Cytometric Analysis

LDLR levels can be measured using flow cytometry or fluorescence activated cell sorting (FACS) using protocols adapted from Benjannet et al., "Effects of the prosegment and pH on the activity of PCSK9: evidence for additional processing events" *J Biol Chem.* 285(52): 40965-40978 (2010) and "Composition and Methods of Use of Small Molecules as Binding Ligands for the Modulation of Proprotein Convertase Subtilisin/Kexin Type 9 (PCSK9) Protein Activity" (WO2016029037), which are incorporated by reference in their entirety.

Cells, such as HepG2, HuH7, FL83B, or a cell line transfected with a short-hairpin PCSK9 knockdown sequence such as HepG2/shPCSK9, HuH7/shPCSK9, or FL83B/shPCSK9 are cultured in media composed of complete, high glucose DMEM (Invitrogen) with 10% fetal bovine serum (Life Technologies), supplemented with penicillin-streptomycin (Life Technologies). Cells are plated in a 24-well plate, at 125 k cells/well, and cultured at 37° C. for 12-24 h. Culture media is removed and replaced with fresh culture media or culture media plus a predetermined amount of recombinant PCSK9 (final 5 ug/ml). Wells evaluating test compounds are dosed with concentrations ranging from 0 nM to 100 uM.

Following an incubation period of 4-6 hours at 37° C., the media is removed and the cells are rinsed by adding 0.5 ml of complete D-PBS (i.e., Dulbecco's phosphate buffered saline (D-PBS, Life Technologies) supplemented with 0.5% bovine serum albumin (BSA, Sigma) and 1 g/L glucose (Sigma)). The wash media is carefully aspirated, and cells are released from the plate using 200 uls of TrypLE Express (Life Technologies) by incubating for 5-10 minutes at 37° C. The TyrpLE-Cell suspension is inactivated by adding 100 uls of Fetal Bovine Serum, transferred to a v-bottom plate, and centrifuged at 250× gravity for 5 minutes. Following centrifugation, the supernatant is aspirated and the cell pellet is resuspended in 100 uL of complete D-PBS, and centrifuged at 250× gravity for 5 minutes. Following centrifugation, the supernatant is aspirated and the cell pellet is resuspended in 100 uls of antibody staining solution (600 uls of anti-LDLr-PE in complete D-PBS) and incubated on ice, protected from light, for 30 minutes. The cells are then pelleted by centrifugation, resuspended in 100 uL of 4',6-Diamidino-2-phenylindole (DAPI, Cayman Chemical) or 7-aminoactinomycin D (7AAD, Life Technologies) staining solution to measure cell viability Cells are analyzed for both cell viability marker (dead cells) and LDLR in live cells using a flow cytometer per the manufacturer's operating manual. Cells incubated with small molecule compounds that are inhibitors of PCSK9 will be expected to show increased amounts of LDLR, relative to control (no compound) specimens, and cells incubated with small molecule compounds that are activators of PCSK9 will be expected to show decreased amounts of LDLR relative to control (no compound) specimens.

Cellular DiI-LDL Uptake Analysis

Cellular DiI-LDL uptake can be measured using protocols adapted from Benjannet et al., "Effects of the prosegment and pH on the activity of PCSK9: evidence for additional processing events" *J Biol Chem.* 285(52): 40965-40978 (2010) and "Composition and Methods of Use of Small Molecules as Binding Ligands for the Modulation of Proprotein Convertase Subtilisin/Kexin Type 9 (PCSK9) Protein Activity" (WO2016029037), which are incorporated by reference in their entirety.

Cells, such as HepG2, HuH7, FL83B, or a cell line transfected with a short-hairpin PCSK9 knockdown sequence such as HepG2/shPCSK9, HuH7/shPCSK9, or FL83B/shPCSK9 are plated and cultured at 37° C. for 12-24 h. Culture media is removed and replaced with fresh lipoprotein-depleted culture media supplemented with 5 ug/mL of DiI-LDL (Kalen Biomedical) or lipoprotein-depleted culture media supplemented with 5 ug/mL of DiI-LDL plus a predetermined concentration of recombinant PCSK9, for example a 10 nM final concentration of PCSK9. Lipoprotein-depleted culture media can be composed of DMEM (Invitrogen) with 10% lipoprotein-depleted fetal bovine serum (Kalen Biomedical) and supplemented with penicillin-streptomycin (Life Technologies). Cells are dosed with small molecule test compounds at doses ranging from 0 nM to 100 uM.

Following an incubation period of specified length, such as 16 hours, Hoechst 33342 (AnaSpec) stain is added to the cell media per manufacturer's instructions and incubated for a specified length (e.g., 30 minutes). The lipoprotein-depleted media is removed and cells rinsed three times with phosphate buffered saline. A final volume of phosphate buffered saline is added back to the wells. The DiI fluorescence is measured with a plate reader using an exciting wavelength of 550 nm and the resulting emission at 590 nm is measured. The Hoechst stain fluorescence is measured with a plate reader using an exciting wavelength of 355 nm and the resulting emission at 460 nm is measured.

Cells are analyzed by for both Hoechst stain (DNA content) and DiI-LDL fluorescence. Cells incubated with small molecule compounds that are inhibitors of PCSK9 will be expected to show increased amounts of DiI-LDL fluorescence, relative to control (no compound) specimens, and cells incubated with small molecule compounds that are activators of PCSK9 will be expected to show decreased amounts of DiI-LDL fluorescence relative to control (no compound) specimens.

Results of the LDLR and DiI-LDL uptake assay are set forth in Table 4. As described therein, the percentage recovery in the LDL-R assay at 20 uM concentration is provided as follows: +++=>30% recovery; ++=10-30% recovery; +=0-10% recovery. The percentage uptake of DiI-LDL over the control in the LDL-uptake assay at 20 uM concentration is provided as follows: +++=>150%; ++=100-150%; +=<100%.

TABLE 4

| Compound No. | LDL-R % Recovered | LDL-uptake % of control |
|---|---|---|
| 107 | ++ | +++ |
| 108 | +++ | +++ |

TABLE 4-continued

| Compound No. | LDL-R % Recovered | LDL-uptake % of control |
|---|---|---|
| 11 | + | + |
| 5 | ++ | + |
| 1 | +++ | +++ |
| 23 | + | +++ |
| 62 | +++ | +++ |
| 43 | ++ | +++ |
| 44 | ++ | +++ |
| 73 | + | ++ |
| 7 | + | +++ |
| 8 | + | +++ |
| 4 | + | +++ |
| 46 | + | ++ |

LDL Uptake Cell-Based Assay Kit

LDL uptake and LDLR expression can also be measured in cells, such as HepG2 or HuH7 cells, using a commercial kit (Cayman Chemical Co., Catalog #10011125) and the accompanying protocols provided by the manufacturer.

Fluorescent-LDL Uptake Analysis by Flow Cytometric Analysis

Cells, such as HuH7, FL83B, or a cell line transfected with a short-hairpin PCSK9 knockdown sequence such as HuH7/shPCSK9 or FL83B/shPCSK9 are plated and cultured at 37° C. for 12-24 h. Culture media is removed and replaced with fresh lipoprotein-depleted culture media supplemented with 5 ug/mL of fluorescently labeled LDL or lipoprotein-depleted culture media supplemented with 5 ug/mL of fluorescently labeled LDL plus 10 nM recombinant PCSK9. Examples of fluorescently labeled LDL include: DiI-LDL (Kalen Biomedical), or LDL conjugated to Dylight (e.g., LDL-Dylight 488, or LDL-Dylight 550 (Cayman Chemical, Cat. #10011229)). Lipoprotein-depleted culture media can be composed of DMEM (Invitrogen) with 10% lipoprotein-depleted fetal bovine serum (Kalen Biomedical) and supplemented with penicillin-streptomycin (Life Technologies). Cells are dosed with small molecule test compounds at doses ranging from 0 nM to 100 uM, following a protocol adapted from Benjannet et al., "Effects of the prosegment and pH on the activity of PCSK9: evidence for additional processing events" *J Biol Chem.* 285(52): 40965-40978 (2010), which is incorporated by reference in its entirety.

Following an incubation period of specified length, such as 16 hours, the lipoprotein-depleted media is removed and cells rinsed three times with a rinse solution (Dulbecco's phosphate buffered saline (D-PBS, Life Technologies), supplemented with 0.5% bovine serum albumin (BSA, Sigma) and 1 g/L glucose (Sigma)). The fluid is then removed, and cells are released from the plate using TrypLE Express (Life Technologies) per manufacturer's recommended procedures, such as incubation for 5-10 minutes at 37° C. The TyrpLE-Cell suspension is then transferred to 15 mL conical tubes, volume is increased to 2 mL with D-PBS supplemented with 0.5% BSA, and 1 g/mL glucose, and the tubes are centrifuged at 250× gravity for 10 minutes. Following centrifugation, the supernatant is aspirated and the cell pellet is resuspended in 300 uL PBS and counterstained with 4',6-diamidino-2-phenylindole (DAPI, Cayman Chemical) as a cell viability marker, other cell viability markers such as 7-aminoactinomycin D (7AAD, Life Technologies) have also been described in the art.

Cells are analyzed by for both 7AAD (dead cells) and fluorescent LDL in live cells using a flow cytometer per the manufacturer's operating manual. Cells incubated with small molecule compounds that are inhibitors of PCSK9 will be expected to show increased amounts of LDL fluorescence, relative to control (no compound) specimens, and cells incubated with small molecule compounds that are activators of PCSK9 will be expected to show decreased amounts of LDL fluorescence relative to control (no compound) specimens.

Back-Scattering Interferometry Direct Binding Measurement

Direct binding can be measured using Back-Scattering Interferometry (BSI), which has been previously described in "Interferometric detection system and method" (EP 1210581), "Free solution measurement of molecular interactions by backscattering interferometry" (WO 2009039466), "Temperature-stable interferometer" (WO 2009076372), and "Improved event detection for back-scattering interferometry" (WO 2013158300); each of which are hereby incorporated by reference in their entirety.

Thus, it should be understood that although the present disclosure has been specifically disclosed by exemplary embodiments and optional features, modification, improvement and variation of the disclosed embodiments may be implemented by those skilled in the art, and that such modifications, improvements and variations are considered to be within the scope of the present disclosure and claims. The materials, methods, and examples provided here are representative of preferred embodiments, are exemplary, and are not intended as limitations on the scope of the disclosure nor as limitations on the scope of the appended claims.

All publications, patent applications, patents, and other references mentioned herein are expressly incorporated by reference in their entirety, to the same extent as if each were incorporated by reference individually. In case of conflict, the present specification, including definitions, will control.

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

What is claimed is:

1. A method of treating a disease or condition, wherein the disease or condition is selected from hypocholesterolemia, coronary disease, hypertension, hypercholesterolemia, atherosclerosis, and diabetes, the method comprising administering to a patient in need thereof a compound of Formula (I):

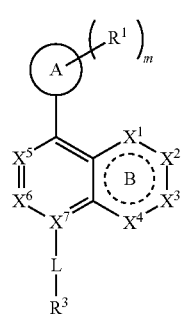

or a pharmaceutically acceptable salt thereof;

wherein:
m is 0, 1, or 2;
$X^1$ is N;
$X^2$, $X^3$, and $X^4$ are each independently $CR^2$ or $CR^2R^2$;
ring B is a six-membered ring comprising one or more double bonds;
$X^5$ and $X^6$ are $CR^2$;
$X^7$ is C;
ring A is:

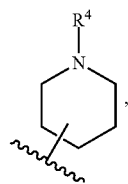

where the wavy line in ring A indicates the point of attachment to

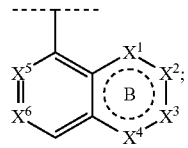

L is a bond;

R$^1$ in each instance is independently halo or C$_{1-6}$ alkyl optionally substituted with halo or hydroxy;

R$^2$ in each instance is independently hydrogen, halo, or C$_{1-6}$ alkyl optionally substituted with halo or hydroxy R$^3$ is halo, C$_{1-6}$ alkyl, C$_{3-6}$ cycloalkyl, or aryl;
wherein each C$_{1-6}$ alkyl, C$_{3-6}$ cycloalkyl, or aryl of R$^3$ is optionally substituted with 1 to 3 substituents independently selected from halo and hydroxy; and R$^4$ is hydrogen or C$_{1-6}$ alkyl;
provided that when A is attached via a carbon atom to the remainder of the molecule and m is other than 0, then R$^1$ is not appended to the same carbon atom.

2. The method of claim 1, wherein the disease or condition is hypocholesterolemia.

3. The method of claim 1, wherein the disease or condition is coronary disease, hypertension, hypercholesterolemia, or atherosclerosis.

4. The method of claim 1, wherein the disease or condition is diabetes.

5. The method of claim 4, wherein the patient has elevated plasma levels of low density lipoprotein cholesterol.

* * * * *